US011072665B2

(12) United States Patent
Silence et al.

(10) Patent No.: US 11,072,665 B2
(45) Date of Patent: Jul. 27, 2021

(54) ANTIBODIES TO CD70

(71) Applicant: argenx BVBA, Zwijnaarde (BE)

(72) Inventors: Karen Silence, Overijse (BE); Peter Ulrichts, Destelbergen (BE); Johannes Joseph Wilhelmus De Haard, NA Oudelande (NL); Torsten Dreier, Sint Martems Latem (BE); Michael John Scott Saunders, Brussels (BE); Harald Wajant, Kist (DE); Sofie Maria Elvire Gabriels, Zottegem (BE); Mahan Moshir, Oostakker (BE)

(73) Assignee: argenx BVBA, Zwijnaarde (BE)

( * ) Notice: Subject to any disclaimer, the term of this patent is extended or adjusted under 35 U.S.C. 154(b) by 866 days.

(21) Appl. No.: 14/626,038

(22) Filed: Feb. 19, 2015

(65) Prior Publication Data

US 2015/0266963 A1 Sep. 24, 2015
US 2017/0369581 A9 Dec. 28, 2017

Related U.S. Application Data

(60) Division of application No. 14/163,752, filed on Jan. 24, 2014, now Pat. No. 9,765,149, and a continuation of application No. 14/005,113, filed on Jan. 24, 2014, now Pat. No. 9,765,148, which is a division of application No. 14/073,462, filed as application No. PCT/EP2012/054733 on Mar. 16, 2012, now Pat. No. 8,834,882.

(60) Provisional application No. 61/503,871, filed on Jul. 1, 2011, provisional application No. 61/453,390, filed on Mar. 16, 2011.

(51) Int. Cl.
*C07K 16/28* (2006.01)
*A61K 39/00* (2006.01)

(52) U.S. Cl.
CPC ...... *C07K 16/2875* (2013.01); *C07K 16/2878* (2013.01); *A61K 2039/505* (2013.01); *C07K 2317/22* (2013.01); *C07K 2317/24* (2013.01); *C07K 2317/34* (2013.01); *C07K 2317/41* (2013.01); *C07K 2317/55* (2013.01); *C07K 2317/56* (2013.01); *C07K 2317/565* (2013.01); *C07K 2317/73* (2013.01); *C07K 2317/732* (2013.01); *C07K 2317/734* (2013.01); *C07K 2317/76* (2013.01); *C07K 2317/77* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | |
|---|---|---|
| 5,573,924 A | 11/1996 | Beckmann et al. |
| 5,859,205 A | 1/1999 | Adair et al. |
| 6,500,633 B1 | 12/2002 | Compton |
| 6,844,422 B1 | 1/2005 | Niehrs et al. |
| 7,261,892 B2 | 8/2007 | Terrett |
| 7,491,390 B2 | 2/2009 | Law et al. |
| 7,641,903 B2 | 1/2010 | Law et al. |
| 7,662,387 B2 | 2/2010 | Law et al. |
| 7,723,477 B2 | 5/2010 | Gurney et al. |
| 7,728,114 B2 | 6/2010 | Mach et al. |
| 7,745,156 B2 | 6/2010 | Terrett |
| 7,745,419 B2 | 6/2010 | Oh et al. |
| 7,982,013 B2 | 7/2011 | Gurney et al. |
| 8,124,738 B2 | 2/2012 | Terret et al. |
| 8,324,361 B2 | 12/2012 | Gurney et al. |
| 8,455,622 B2 | 6/2013 | McDonagh et al. |
| 8,507,442 B2 | 8/2013 | Gurney et al. |
| 8,535,678 B2 | 9/2013 | Law et al. |
| 8,552,156 B2 | 10/2013 | Takayanagi et al. |
| 8,604,052 B2 | 12/2013 | Hood et al. |
| 8,647,623 B2 | 2/2014 | Takayanagi et al. |
| 8,663,642 B2 | 3/2014 | Law et al. |
| 8,765,913 B2 | 7/2014 | Gurney et al. |
| 8,834,882 B2 | 9/2014 | Silence et al. |
| 8,841,418 B2 | 9/2014 | Karsunky et al. |
| 9,556,270 B2 | 1/2017 | Takayanagi et al. |
| 9,605,070 B2 | 3/2017 | Sabatos-Peyton et al. |
| 9,631,026 B2 | 4/2017 | Karsunky et al. |
| 2003/0148321 A1 | 8/2003 | Pecker |
| 2005/0118656 A1 | 6/2005 | Terrett |
| 2006/0115832 A1 | 6/2006 | Hoon |
| 2006/0275844 A1 | 12/2006 | Linke |
| 2007/0072178 A1 | 3/2007 | Haferlach |
| 2008/0025989 A1 | 1/2008 | Law et al. |
| 2008/0138341 A1 | 6/2008 | Law et al. |
| 2008/0280297 A1 | 11/2008 | Dalla-Favera |

(Continued)

FOREIGN PATENT DOCUMENTS

| WO | 94/05691 A1 | 3/1994 |
|---|---|---|
| WO | 03/046581 A2 | 6/2003 |

(Continued)

OTHER PUBLICATIONS

Naresh et al., Leukemia & Lymphoma, Aug. 2004 vol. 45 (8), pp. 1569-1577 (Year: 2004).*
Lens et al. (British Journal of Haematology, 1999, 106, 491-503) (Year: 1999).*
Ranheim et al. (Blood. 1995, pp. 3556-3565) (Year: 1995).*
Jak et al. (Leukemia & Lymphoma, May 2009; 50(5): 788-801) (Year: 2009).*
McEarchern et al. (Clin Cancer Res. Dec. 1, 2008;14(23):7763-72 and Suppl Figs. 1-4 + 2 page Suppl Table). (Year: 2008).*

(Continued)

*Primary Examiner* — Zachary S Skelding
(74) *Attorney, Agent, or Firm* — Lathrop GPM LLP; James H. Velema, Esq.

(57) ABSTRACT

The present invention relates to antibodies and antigen binding fragments thereof which bind to the human CD70 protein with high affinity and display potent inhibition of tumor cell growth.

39 Claims, 19 Drawing Sheets

Specification includes a Sequence Listing.

(56) References Cited

U.S. PATENT DOCUMENTS

| | | |
|---|---|---|
| 2009/0028872 A1 | 1/2009 | Terret et al. |
| 2009/0074772 A1 | 3/2009 | Law et al. |
| 2009/0148942 A1 | 6/2009 | McDonagh et al. |
| 2009/0232806 A1 | 9/2009 | Law et al. |
| 2010/0129362 A1 | 5/2010 | Law et al. |
| 2010/0150925 A1 | 6/2010 | Law et al. |
| 2010/0150950 A1 | 6/2010 | Coccia et al. |
| 2010/0158910 A1 | 6/2010 | Law et al. |
| 2010/0183636 A1 | 7/2010 | Law et al. |
| 2010/0267626 A1 | 10/2010 | Cheung et al. |
| 2010/0278779 A1 | 11/2010 | Zeldis |
| 2011/0190157 A1 | 8/2011 | Kipps |
| 2012/0093805 A1 | 4/2012 | Kubota |
| 2012/0178111 A1 | 7/2012 | Diamandis |
| 2013/0078237 A1 | 3/2013 | Delaney et al. |
| 2013/0243795 A1 | 9/2013 | Chen et al. |
| 2014/0141016 A1 | 5/2014 | Silence et al. |
| 2014/0147450 A1 | 5/2014 | Silence et al. |
| 2014/0235843 A1 | 8/2014 | Silence et al. |
| 2015/0086521 A1 | 3/2015 | Godfrin |

FOREIGN PATENT DOCUMENTS

| | | | |
|---|---|---|---|
| WO | 2004/073656 A2 | 9/2004 | |
| WO | 2006/044643 A2 | 4/2006 | |
| WO | 2006/113909 A2 | 10/2006 | |
| WO | 2007/038637 A2 | 4/2007 | |
| WO | WO 2007/146968 A2 | 12/2007 | |
| WO | 2008/074004 A2 | 6/2008 | |
| WO | 2010/001251 A2 | 1/2010 | |
| WO | WO-2010001251 A2 * | 1/2010 | ............ C07K 16/00 |
| WO | WO 2010/014948 A1 | 2/2010 | |
| WO | WO 2012/098407 A2 | 7/2012 | |
| WO | WO 2012/123586 A1 | 9/2012 | |
| WO | WO 2013/093508 A2 | 6/2013 | |
| WO | WO 2013/177420 A2 | 11/2013 | |
| WO | WO 2013/185353 A1 | 12/2013 | |
| WO | WO 2014/045101 A1 | 3/2014 | |
| WO | WO 2014/100772 A2 | 6/2014 | |
| WO | WO 2015/138600 A2 | 9/2015 | |
| WO | WO 2016/111947 A2 | 7/2016 | |
| WO | WO 2017/021354 A1 | 2/2017 | |
| WO | WO 2017/079116 A1 | 5/2017 | |
| WO | WO 2017/134140 A1 | 8/2017 | |

OTHER PUBLICATIONS

Webster's New World Dictionary, Third College Edition, 1988, see p. 1067 (Year: 1988).*
McKinney, J Neurol Neurosurg Psychiatry 2004;75(Suppl II):ii12-ii17. (Year: 2004).*
Edwards et al. (J. Mol. Biol. (2003) 334, 103-118). (Year: 2003).*
Lloyd et al. (Protein Engineering, Design & Selection vol. 22 No. 3 pp. 159-168, 2009). (Year: 2009).*
Meyer et al. (British Journal of Haematology, 2018, 180, 808-820). (Year: 2018).*
Memorandum, Feb. 22, 2018, Robert W. Bahr, Deputy Commissioner for Patent Examination Policy, pp. 1-2. (Year: 2018).*
Glouchkova et al., J Immunol 2009; 182:718-725. (Year: 2009).*
Ragusa et al., BMC Cancer 2010, 10:377. (Year: 2010).*
Nolte et al., Immunological Reviews 2009, vol. 229: 216-231. (Year: 2009).*
Sandberg et al., Proc Natl Acad Sci USA. Feb. 8, 2005;102(6):2052-7. (Year: 2005).*
Robert Weinberg, the Biology of Cancer, 2007, pp. 536-539. (Year: 2007).*
Sloan et al., American Journal of Pathology, vol. 164, No. 1, Jan. 2004. (Year: 2004).*
Boursalian et al., Adv Exp Med Biol. 2009;647:108-119. (Year: 2009).*
Baba et al., Journal of Virology, Apr. 2008, pp. 3843-3852. (Year: 2008).*

Ranheim et al., Blood. 1995;85(12):3556-3565. (Year: 1995).*
Hishima et al., The American Journal of Surgical Pathology 24(5): 742-746, 2000. (Year: 2000).*
Tesselaar et al. (1997) "Characterization of murine CD70, the ligand of the TNF receptor family member CD27," J. Immunol. 159:4959-4965.
Adam et al: 'CD70 (TNFSF7) is Expressed at High Prevalence in Renal Cell Carcinomas and is Rapidly Internalised on Antibody Binding' British J of Cancer; Aug. 7, 2006, vol. 95, No. 3, pp. 298-306.
French et al: 'Eradication of Lymphoma by CD8 T Cells Following Anti-CD40 Monoclonal Antibody Therapy is Critically Dependant on CD27 Costimulation'. Blood; Jun. 1, 2007, vol. 109, No. 11, pp. 4810-4815.
McEarchern et al 'Preclinical Characterization of SGN-70, a Humanized Antibody Directed against CD70'. Clin Cancer Res; Dec. 1, 2008, vol. 14, No. 23, pp. 7763-7772.
International Search Report, PCT/EP2012/054733, dated Jul. 26, 2012, 5 pages.
International Preliminary Report on Patentability, PCT/EP2012/054733, dated Sep. 17, 2013, 12 pages.
Achour et al. (2008) "Tetrameric and homodimeric camelid IgGs originate from the same IgH locus," J. Immunol. 181:2001-2009.
Brown et al. (1996) "Tolerance of single, but not multiple, amino acid replacements in antibody VH CDR 2: a means of minimizing B cell wastage from somatic hypermutation?" J Immunol. 156(9):3285-3291.
Damschroder et al. (2004) "Analysis of human and primate CD2 molecules by protein sequence and epitope mapping with anti-human CD2 antibodies," Mol. Immunol. 41(10):985-1000.
Groves et al. (2006) "Affinity maturation of phage display antibody populations using ribosome display," Journal of Immunological Methods. 313:129-139.
Harlow et al. (1988) Antibodies, A Laboratory Manual. Cold Spring Harbor laboratory. pp. 37-47.
Padlan (1994) "Anatomy of the antibody molecule," Mol. Immunol. 31(3):169-217.
Portolano et al. (1993) "Lack of promiscuity in autoantigen-specific H and L chain combinations as revealed by human H and L chain 'roulette,'" J. Immunol. 150(3):880-887.
Rudikoff et al. (1982) "Single amino acid substitution altering antigen-binding specificity," Proc. Natl. Acad. Sci. USA. 79:1979-1983.
Ryan et al. (2010) "Targeting pancreatic and ovarian carcinomas using the auristatin-based anti-CD70 antibody-drug conjugate SGN-75," British Journal of Cancer. 103:676-684.
Vajdos et al. (2002) "Comprehensive Functional Maps of the Antigen-binding Site of an Anti-ErbB2 Antibody Obtained with Shotgun Scanning Mutagenesis," J. Mol. Biol. 320(2):415-428.
Zahnd et al. (2010) "Computational analysis of off-rate selection experiments to optimize affinity maturation by directed evolution," Protein Engineering: Design & Selection. 23(4):175-184.
Arroyo Hornero et al., "CD70 expression determines the therapeutic efficacy of expanded human regulatory T cells", Communications Biology, 2020, vol. 3, No. 375, pp. 1-17.
Appel et al (Molecular Diversity, 1996, 2:29-34).
Askmyr et al. (2013) "Selective killing of candidate AML stem cells by antibody targeting of IL1RAP," Blood, 121(18):3709-3713.
Baba et al., "Highly Enhanced Expression of CD70 on Human T-Lymphotropic Virus Type 1-Carrying T-Cell Lines and Adult T-Cell Leukemia Cells", Journal of Virology, April 2008, pp. 3843-3852.
Baccarani et al. (2006) "Evolving concepts in the management of chronic myeloid leukemia: recommendations from an expert panel on behalf of the European LeukemiaNet," Blood 108:1809-1820.
Baxevanis, "Antibody-based cancertherapy", Expert Opinion: Drug Discovery, 2008, vol. 3, No. 4, pp. 441-452.
Belloc et al. (2007) "lmatinib and nilotinib induce apoptosis of chronic myeloid leukemia cells through a Bim-dependant pathway modulated by cytokines," Cancer Biol. Ther. 6:912-919.
Bertrand et al. (2013) "The Costimulatory Molecule CD70 is Regulated by Distinct Molecular Mechanisms and is Associated

(56) References Cited

OTHER PUBLICATIONS with Overall Survival in Diffuse Large B-cell Lymphoma," Genes, Chromosomes and Cancer, 52:764-774.
Bosman et al. (2016) "Constitutive NF-KB activation in AML: Causes and treatment strategies," Critical Reviews in Oncology/Hematology, 98:35-44.
Brugnoni et al., "CD70 expression on T-cell subpopulations: study of normal individuals and patients with chronic immune activation", Immunology Letters, 1997, vol. 55, pp. 99-104.
Caron et al. (1992) "Engineered Humanized Dimeric Forms of IgG Are More Effective Antibodies," J. Exp. Med., 176:1191-1195.
CAS Registry No. 0641571-10-0.
CAS Registry No. 1165740-62-4.
CAS Registry No. 302962-49-8.
CAS Registry No. 379231-04-6.
CAS Registry No. 380843-75-4.
CAS Registry No. 639089-54-6.
CAS Registry No. 664993-53-7.
CAS Registry No. 82115-62-6.
CAS Registry No. 859212-16-1.
CAS Registry No. 943319-70-8.
Chahlavi et al. (2005) "Glioblastomas Induce T-Lymphocyte Death by Two Distinct Pathways Involving Gangliosides and CD70," Cancer Res., 65(12):5428-5438.
Chan et al. (2010) "Therapeutic antibodies for autoimmunity and inflammation," Nature Reviews: Immunology, 10:301-316.
Claus et al. (2012) "CD27 Signaling Increases the Frequency of Regulatory T Cells and Promotes Tumor Growth," Cancer Res., 72(14):3664-3676.
Clevers et al. (2012) "Wnt/β-catenin signaling and disease," Cell. 149:1192-1205.
Clinicaltrials.Gov (First received Dec. 16, 2011) "AMG 172 First in Human Study in Patients With Kidney Cancer," U.S. National Institutes of Health. ClinicalTrials.gov Identifier: NCT01497821.
Clinicaltrials.Gov (First received Dec. 3, 2013) "A Study of Vantictumab (OMP-18R5) in Combination With Nab-Paclitaxel and Gemcitabine in Previously Untreated Stage IV Pancreatic Cancer," U.S. National Institutes of Health. ClinicalTrials.gov Identifier: NCT02005315.
Clinicaltrials.Gov (First received Jul. 17, 2011) "Phase I Clinical Study of CWP232291 in Acute Myeloid Leukemia Patients," U.S. National Institutes of Health. ClinicalTrials.gov Identifier: NCT01398462.
Clinicaltrials.Gov (First received May 4, 2011) "A Study of LGK974 in Patients With Malignancies Dependent on Wnt Ligands," U.S. National Institutes of Health. ClinicalTrials.gov Identifier: NCT01351103. Accessible on the Internet at URL: http://www.ebi.ac.uk/arrayexpress/experiments/E-MEXP-480. [Last Accessed December 15, 2016].
Clinicaltrials.Gov (First received Oct. 25, 2013) "A Study of Vantictumab (OMP-18R5) in Combination With Paclitaxel in Locally Recurrent or Metastatic Breast Cancer," U.S. National Institutes of Health. ClinicalTrials.gov Identifier: NCT01973309.
Clinicaltrials.Gov (First received Sep. 27, 2013) "A Study of Vantictumab (OMP-18R5) in Combination With Docetaxel in Patients With Previously Treated NSCLC," U.S. National Institutes of Health. ClinicalTrials.gov Identifier: NCT01957007.
Colman, "Effects of amino acid sequence changes on antibody-antigen interactions", Research in Immunology, 1994, vol. 145, pp. 33-36.
Colovai et al. (2007) "Expression of Inhibitory Receptor ILT3 on Neoplastic B Cells is Associated with Lymphoid Tissue Involvement Leukemia," Cytometry Part B (Clinical Cytometry) 72B:354-362.
Coluccia et al. (2007) "Bcr-Abl stabilizes β-catenin in chronic myeloid leukemia through its tyrosine phosphorylation," EMBO J. 26:1456-1466.
Corbin et al. (2011) "Human chronic myeloid leukemia stem cells are insensitive to imatinib despite inhibition of BCR-ABL activity," J. Clin. Invest. 121:396-409.

Cortes et al. (Nov. 29, 2012) "Ponatinib in refractory Philadelphia chromosome-positive leukemias," N. Engl. J. Med. 367:2075-2088.
Deininger (2007) "Optimizing therapy of chronic myeloid leukemia," Exp. Hematol. 35:144-154.
Dempke et al. (2017) "Second- and third-generation drugs for immune-oncology treatment—The more the better?," European Journal of Cancer 74(10):55-72.
Denoeud et al., "Role of CD27/CD70 pathway of activation in immunity and tolerance", Journal of Leukocyte Biology, February 2011, vol. 89, pp. 195-203.
Deveraux et al. (1984) "A comprehensive set of sequence analysis programs for the VAX," Nucleic Acids Research, 12(1):387-395.
Diegemann et al. (2006) "Immune Escape for Renal Cell Carcinoma: CD70 Mediates Apoptosis in Lymphocytes," Neoplasia, 8(11):933-938.
Dohner et al. (2017) "Diagnosis and management of AML in adults: 2017 ELN recommendations from an international expert panel," Blood, 129(4): 66 pages.
Druker et al. (2001) "Activity of a Specific Inhibitor of the BCR-ABL Tyrosine Kinase in the Blast Crisis of Chronic Myeloid Leukemia and Acute Lymphoblastic Leukemia with the Philadelphia Chromosome," N. Engl. J. Med. 344:1038-1042.
Druker et al. (2001) "Efficacy and Safety of a Specific Inhibitor of the BCR-ABL Tyrosine Kinase in Chronic Myeloid Leukemia," N. Engl. J. Med. 344:1031-1037.
EMBL-EBI Database [Online] (Last updated May 3, 2014) "E-MEXP-480—Transcription profiling of D34+BCR-ABL+ cells of CML patients in chronic phase or blast crisis to identify differentially expressed stage-specific genes," Accession Number E-MEXP-480. Accessible on the Internet at URL: http://www.ebi.ac.uk/arrayexpress/experiments/E-MEXP-480. "Last Accessed Dec. 15, 2016".
Faderl et al. (1999) "The Biology of Chronic Myeloid Leukemia," N. Engl. J. Med. 341:164-172.
Frank, Immunology and Evolution of Infectious Disease, Chapter 4 "Specificity and Cross-Reactivity," Princeton University Press, 2002.
Genbank Database "Online" (Nov. 2, 2016) "RecName: Full=Proto-oncogene Wnt-1; AltName: Full=Proto-oncogene Int-1 homolog; Flags: Precursor," Accession No. P04628. Accessible on the Internet at URL: https://www.ncbi.nlm.nih.gov/protein/P04628. [Last Accessed Dec. 16, 2016].
Goncalves-Silva et al. (2015) "Differential expression and biochemical activity of the immune receptor Tim-3 in healthy and malignant human myeloid cells," Oncotarget, 6(32):33823-33833.
Goto et al. (2012) "Serum soluble CD27 level is associated with outcome in patients with diffuse large B-cell lymphoma treated with rituximab, cyclophosphamide, doxorubicin, vincristine and prednisolone," Leukemia and Lymphoma, 53(8):1494-1500.
Gregory et al (Cancer Cell, 2010, 18:74-87).
Hamad et al. (Hindawi Publishing Corporation, Stem Cells International, 2013, 12 pages).
Han et al. (2005) "Increased prevalence of activated CD70+ CD4+ T cells in the periphery of patients with systematic lupus erythematosus," Lupus 14:598-606.
Hanekamp et al. (2017) "Leukemic stem cells: identification and clinical application," Int. J. Hematol, 105:549-557.
Harris et al., "Assessing Genetic Heterogeneity in Production Cell Lines: Detection by Peptide Mapping of a Low Level Tyr to Gln Sequence Variant in a Recombinant Antibody", Biotechnology, 1993, vol. 11, pp. 1293-1297.
Held-Feindt et al. (2002) "CD70/CD27 Ligand, a member or the TNF family, is expressed in human brain tumors," Int. J. Cancer, 98:352-356.
Hinton et al. (2006) "An Engineered Human IgG1 Antibody with Longer Serum Half-Life," The Journal of Immunology, 176:346-356.
Holliger et al. (2005) "Engineered antibody fragments and the rise of single domains," Nature Biotechnology, 23(9):1126-1136.
Hsiao et al. (2008) "Tankyrase function at telomeres, spindle poles, and beyond," Biochimie. 90:83-92.
Hu et al (Leukemia, 2009, 23:109-116)
International Search Report and Written Opinion corresponding to International Patent Application No. PCT/EP2018/066144, dated Aug. 17, 2018.

(56) References Cited

OTHER PUBLICATIONS

International Search Report and Written Opinion for International Application No. PCT/EP2019/051058, dated Mar. 21, 2019.
ISRAEL et al. (2005) "Anti-CD70 antibodies: a potential treatment for EBV+ CD70− expressing lymphomas," Mol. Cancer Ther. 4:2037-2044.
Jacobs et al. (2015) "CD70: An emerging target in cancer immunotherapy," Pharmacology and Therapeutics 155:1-10.
Jacobs et al. (2015) "Unlocking the potential of CD70 as a novel immunotherapeutic target for non-small cell lung cancer," Oncotarget, 6(15):13462-13475.
Jan et al. (2011) "Prospective separation of normal and leukemic stem cells based on differential expression of TIM3, a human acute myeloid leukemia stem cell marker," PNAS, 108(12):5009-5014.
Japp et al. (2015) "Dysfunction of PSA-specific CD8+ cells in prostate cancer patients correlates with CD38 and Tim-3 expression," Cancer of Immunol Immunother, 8 pages.
Jaras et al. (2010) "Isolation and killing of candidate chronic myeloid leukemia stem cells by antibodytargeting of IL-1 receptor accessory protein," PNAS, 107(37):16280-16285.
Jilaveanu et al. (2012) "CD70 Expression Patterns in Renal Cell Carcinoma," Human Pathol., 43(9):1394-1399.
Junker et al. (2005) "CD70: A new tumor specific biomarker for renal cell carcinoma," 173:2150-2153.
Kang et al. (2015) "The ITM-containing receptor LAIR1 is essential for acute myeloid leukemia development," Nat. Cell Biol., 17(5):665-677.
Kapinas et al. (2010) "miR-29 modulates Wnt signaling in human osteoblasts through a positive feedback loop," J. Biol. Chem. 285:25221-25231.
KATOH et al. (2007) "WNT signaling pathway and stem cell signaling network," Clin. Cancer Res. 13(14):4042-4045.
Kavalerchik et al. (2008) "Chronic myeloid leukemia stem cells," J. Clin. Oncol. 26:2911-2915.
Kikushige et al. (2010) "TIM-3 is a promising target to selectively kill acute myeloid leukemia stem cells," Cell Stem Cell, 7:708-717.
Kikushige et al. (2013) "TIM-3 as a novel therapeutic target for eradicating acute myelogenous leukemia stem cells," Int. J. Hematol., 98:627-633.
Kikushige et al. (2015) "A TIM-3/Gal-9 Autocrine Stimulatory Loop Drives Self-Renewal of Human Myeloid Leukemia Stem Cells and Leukemic Progression," Cell Stem Cell, 17:341-352.
Koren-Michowitz et al. (Jan. 12, 2012) "lmatinib plasma trough levels in chronic myeloid leukaemia: results of a multicentre study CSTI571AIL11TGLIVEC," Hematol. Oncol. 30:200-205.
Lee et al. (2007) "Unchecked CD70 expression on T cells lowers threshold for T-cell activation in rheumatoid arthritis," J. lmmunol., 179(4):2609-2615.
Li et al. (Feb. 14, 2012) "Activation of p53 by SIRT1 inhibition enhances elimination of CML leukemia stem cells in combination with imatinib," Cancer Cell. 21 :266-281.
Liu et al. (2010) "Sp1/NFκB/HDAC/miR-29b Regulatory Network in KIT-driven Myeloid Leukemia," Cancer Cell. 17:333-347.
Lugo et al. (1990) "Tyrosine kinase activity and transformation potency of bcr-abl oncogene products," Science. 247:1079-1082.
Manocha et al., "Blocking CD27-CD70 Costimulatory Pathway Suppresses Experimental Colitis", The Journal of Immunology, Jul. 1, 2009, 183(1): 270-276.
Natsume et al. (2009) "Improving effector functions of antibodies for cancer treatment: Enhancing ADCC and CDC," Drug Design Development and Therapy, 3:7-16.
Nilsson et al. (2005) "Expression of CD27-CD70 on Early B Cell Progenitors in the Bone Marrow: Implication and Therapy of Childhood ALL," Experimental Hematology, 33:1500-1507.
O'donnell et al. (2017) "Acute Myeloid Leukemia, Version 3," Journal of the National Comprehensive Cancer Network, 15(7):926-957.
O'HARE et al. (2009) "AP24534, a Pan-BCR-ABL Inhibitor for Chronic Myeloid Leukemia, Potently Inhibits the T315I Mutant and Overcomes Mutation-Based Resistance," Cancer Cell. 16:401-412.
O'Hare et al. (2012) Nature Reviews Cancer, 12:513-526.
Oelke et al. (2004) "Overexpression of CD70 and Overstimulation of lgG Synthesis by Lupus T Cells and T Cells Treated with DNA Methylation Inhibitors," Arthritis and Rheumatism, 50(6):1850-1860.
Oflazoglu et al., "Blocking of CD27-CD70 Pathway by Anti-CD70 Antibody Ameliorates Joint Disease in Murine Collagen-Induced Arthritis", Journal of Immunology, 2009, 183(6): 3770-3777.
Ohaegbulam et al. (2015) "Human cancer immunotherapy with antibodies to the PD-1 and PD-L1 pathway," Trends Mol. Med., 21(1):24-33.
Paul, Fundamental Immunology, $3^{rd}$ Edition, 1993, Chapter 9, pages 292-295.
Perna et al. (2017) "Integration Proteomics and Transcriptomics for Systematic Combinatorial Chimeric Antigen Receptor Therapy of AML," Cancer Cell, 32:506-519.
Petrau et al. (2014) "CD70: A potential target in breast cancer?," Journal of Cancer, 5:761-764.
Polakis (2012) "Drugging Wnt signalling in cancer," EMBO J. 31(12):2737-2746.
Pollye et al. (2017) "Therapeutic targeting of acute myeloid leukemia stem cells," Blood, 129(12):1627-1635.
Ponce et al. (2017) "SIRPa-antibody fusion proteins stimulate phagocytosis and promote elimination of acute myeloid leukemia cells," Oncotarget, 8(7):11284-11301.
Presta et al. (2008) "Molecular engineering and design of therapeutic antibodies," Current Opinion in Immunology, 20:460-470.
Richardson et al. (2014) "Epigenetics in 2013: DNA methylation and miRNA- key roles in systematic autoimmunity," Nat. Rev. Rheumatol., 10(2):72-74.
Riether et al. (2017) "CD70/CD27 signaling promotes blast stemness and is a viable therapeutic target in acute myeloid leukemia," J. Exp. Med., 214(2):359-380.
Ring et al. (2017) "Anti-SIRPG antibody immunotherapy enhances neutrophil and macrophage antitumor activity," PNAS, 114(49):E10578-E10585.
Sakuishi et al. (2010) "Targeting Tim-3 and PD-1 pathways to reverse T cell exhaustion and restore anti-tumor immunity," J. Exp. Med., 207(10):2187-2194.
Sandberg et al., "Assessment of tumor characteristic gene expression in cell lines using a tissue similarity index (TSI)", Proc Natl Acad Sci USA, Feb. 8, 2005, vol. 102, No. 6. pp. 2052-2057.
Sawalha et al., "Defective DNA methylation and CD70 overexpression in CD4+ T cells in MRL/LPR lupus-prone mice", European Journal of Immunology, 2007, 37(5): 1407-1413.
Schürch et al. (Feb. 1, 2012) "CD27 signaling on chronic myelogenous leukemia stem cells activates Wnt target genes and promotes disease progression," J. Clin. Invest. 122:624-638.
Shao et al. (2011) "Combination or monoclonal antibodies with DST inhibits accelerated rejection mediated by memory T cells to induce long-lived heart allograft acceptance in mice," Immunology Letters 138:122-128.
Shopes et al. (1992) "A genetically engineered human lgG mutant with enhanced cytolytic activity," The Journal of Immunology, 148:2918-2922.
Shultz et al. (2005) "Human Lymphoid and Myeloid Cell Development in NOD/LtSz-scid IL2Rynull Mice Engrafted with Mobilized Human Hemopoietic Stem Cells," J. Immunol. 174:6477-6489.
Silence et al. (2014) "ARGX-110, a highly potent antibody targeting CD70, eliminates tumors via both enhanced ADCC and immune checkpoint blockade," mAbs, 6(2):523-532.
Tan et al. (Aug. 9, 2013) "Suppression of Wnt Signaling by the miR-29 Family is Mediated by Demethylation of WIF-1 in Non-Small-Cell Lung Cancer," Biochem. Biophys. Res. Commun. 438:673-679.
Tesselaar et al. (2003) "Expression of the murine CD27 ligand CD70 in vitro and in vivo," J. Immunol. 170:33-40.
Theocharides et al. (2012) "Disruption of SlRPα signaling in macrophages eliminates human acute myeloid leukemia stem cells in xenografts," J. Exp. Med., 209(10):1883-1899.

(56) References Cited

OTHER PUBLICATIONS

Uniprot Database [Online] (Feb. 6, 2007) "UniProtKB-A1Z199 (A1Z199_HUMAN)," Accession No. A1Z199. Accessible on the Internet at URL: http://www.uniprot.org/uniprot/A1Z199. [Last Accessed Dec. 16, 2016].
Uniprot Database [Online] (Nov. 1, 1996) "UniProtKB-Q13745 (Q13745_HUMAN)," Accession No. Q13745. Accessible on the Internet at URL: http://www.uniprot.org/uniprot/Q13745. [Last Accessed Dec. 16, 2016].
Vaccaro et al. (2005) "Engineering the FC region of immunoglobulin G to modulate in vivo antibody levels," Nature Biotechnology, 23(10):1283-1288.
Van Doorn et al. (2004) "Aberrant Expression of the Tyrosine Kinase Receptor EphA4 and the Transcription Factor Twist in Sezary Syndrome Identified by Gene Expression Analysis," Cancer Research, 64:5578-5586.
Van Regenmortel (1998) Journal of Immunological Methods, 216:37-48.
Voronkov et al. (2013) "Wnt/beta-catenin signaling and small molecule inhibitors," Current Pharmaceutical Design. 19:634-664.
Waaler et al. (Mar. 22, 2012) "A novel tankyrase inhibitor decreases canonical Wnt signaling in colon carcinoma cells and reduces tumor growth in conditional APC mutant mice," Cancer Res. 72(11):2822-2832.
Wajant, H. (2006) "Therapeutic targeting of CD70 and CD27," Expert Opinion on Therapeutic Targets, 20(8):959-973.
Wang et al. (2007) "Antibody Structure, Instability, and Formulation," Journal of Pharmaceutical Sciences, 96(1):1-26.
Wang et al. (2012) "Distinctive Features of the Differentiated Phenotype and Infiltration of Tumor-reactive Lymphocytes in Clear Cell Renal Cell Carcinoma," Cancer Res., 72(23):6119-6129.
Wang et al. (2017) "Circular RNAs in human cancer," Molecular Cancer, 16(25):8 pages.
Weinberg, "Tumors resemble wound-healing sites" the Biology of Cancer, 2007, Chapter 13.2-13.3, pp. 536-539.
Wischhusen et al. (2002) "Identification of CD70-mediated Apoptosis of Immune Effector Cells as a Novel Immune Escape Pathway of Human Glioblastoma," Cancer Research, 62:2592-2599.
Yamane-Ohnuke et al. (2009) "Production of therapeutic antibodies with controlled fucosylation," mAbs, 1(3):230-236.
Yanagisawa et al., "Effects of anti-CD70 mAb on Theiler's murine encephalomyelitis virus-induced demyelinating disease", Brain Research, 2010, 1317: 236-245.
Yang et al. (2014) "TGF-B upregulates CD70 expression and induces exhaustion of effector memory T cells in B-cell non-Hodgkin's lymphoma," Leukemia, 28(9):1872-1884.
Yeung et al. (2009) "Engineering Human IgG1 Affinity to Human Neonatal Fc Receptor: Impact of Affinity Improvement on Pharmacokinetics in Primates," The Journal of Immunology, 182:7663-7671.
Zalevsky et al. (2010) "Enhanced antibody half-life improves in vivo activity," Nat. Biotechnol., 28(2):157-159.
Zhang et al. (2010) "Effective targeting of quiescent chronic myelogenous leukemia stem cells by histone deacetylase inhibitors in combination with imatinib mesylate," Cancer Cell. 17:427-442.
Zhou et al. (2011) "Histone modifications and methyl-CpG-binding domain protein levels at the TNFSF7 (CD70) promoter in SLE CD4+ T cells," Lupus, 20:1365-1371.

\* cited by examiner

Figure 2
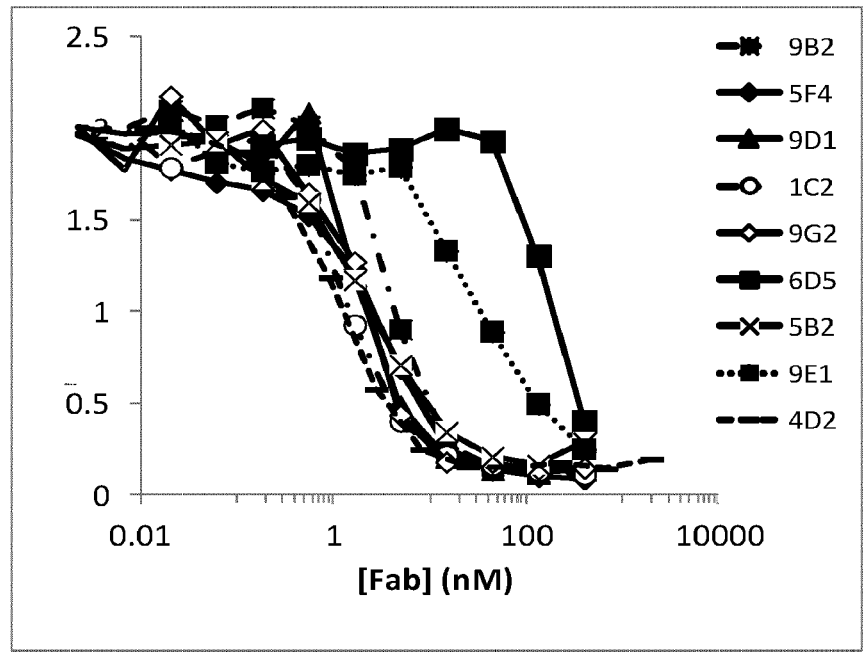
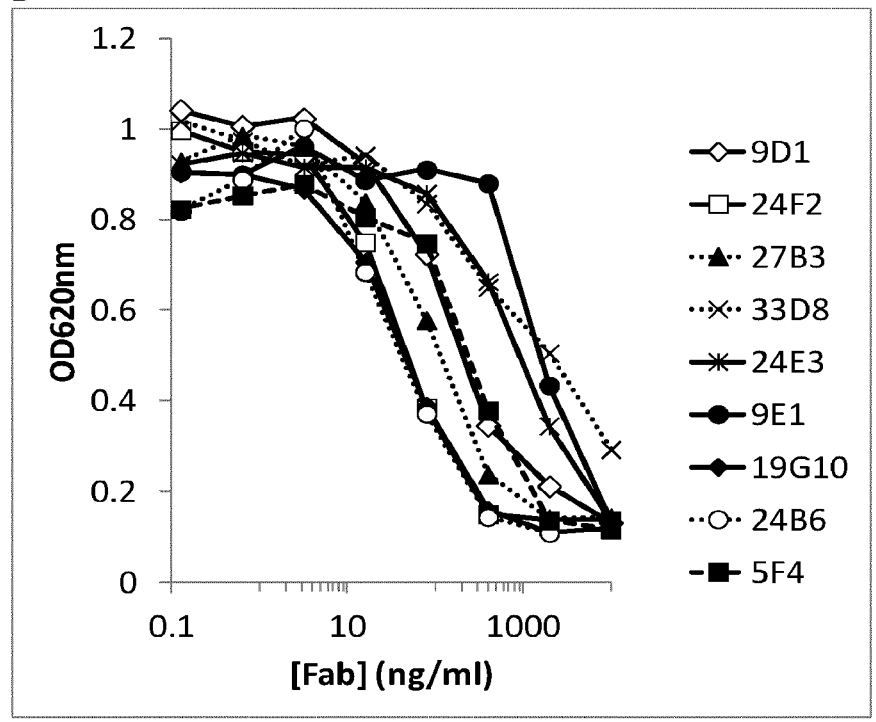

Figure 4
A
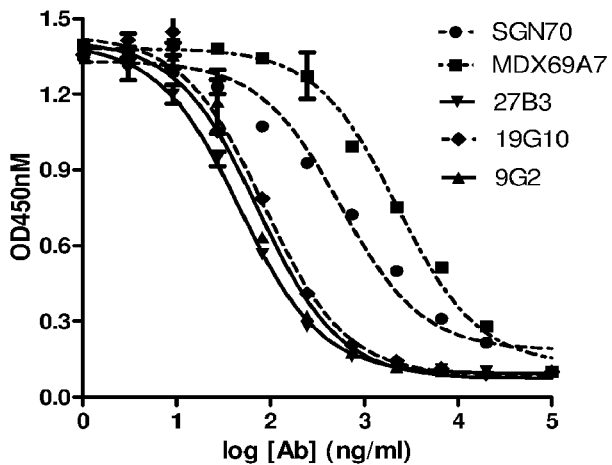
B
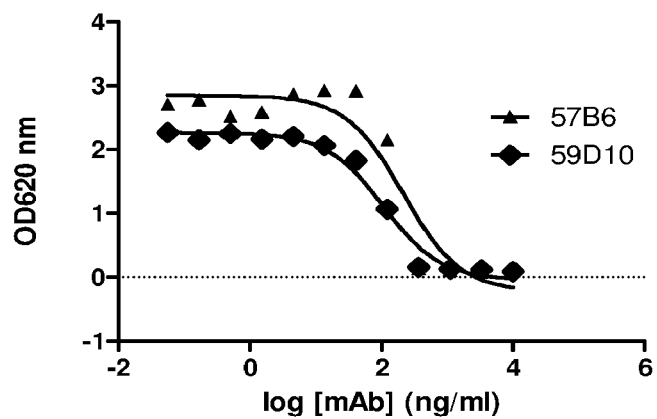
C
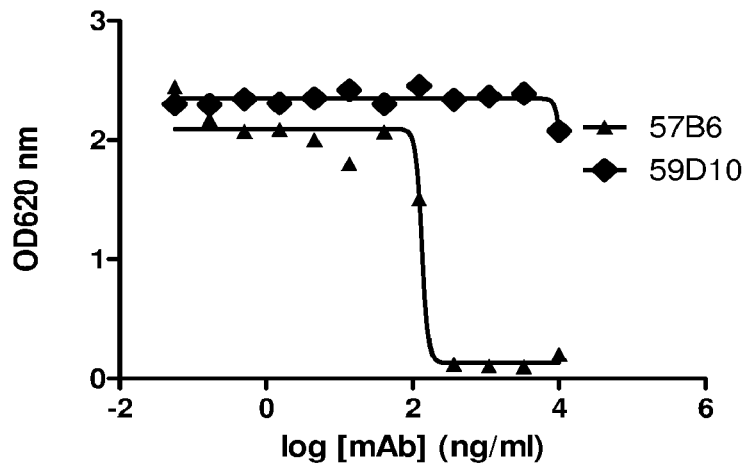

Figure 5
A
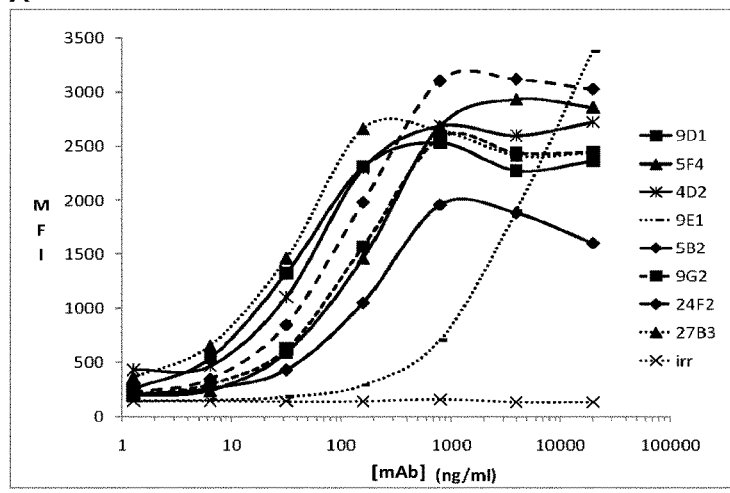
B
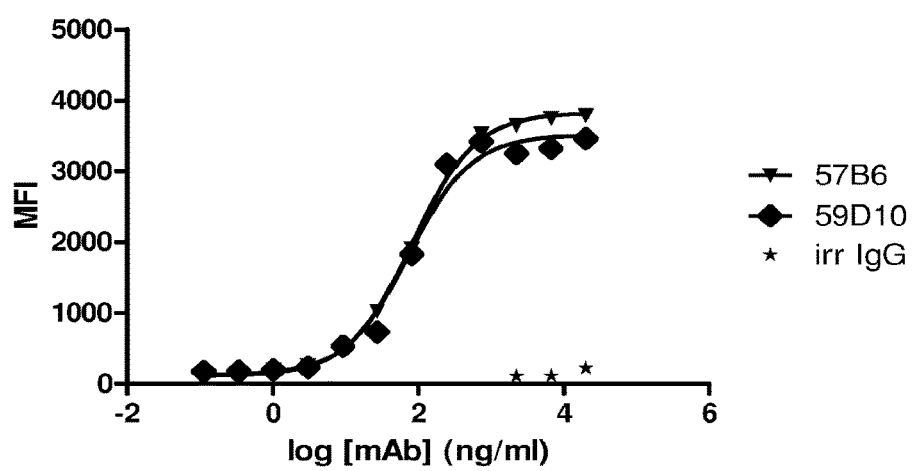

Figure 8
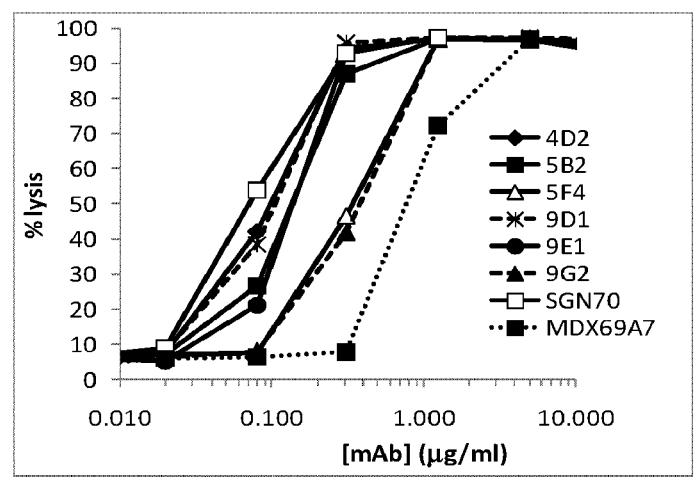
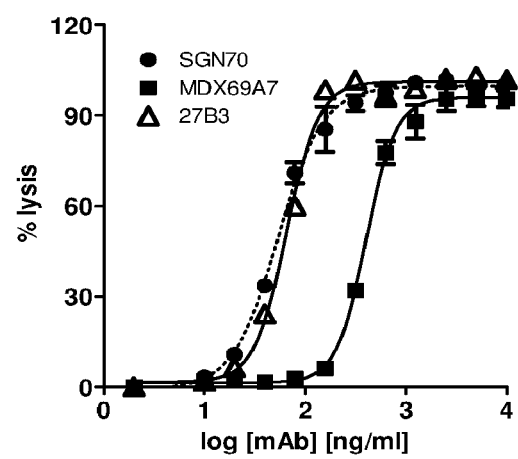

Figure 9
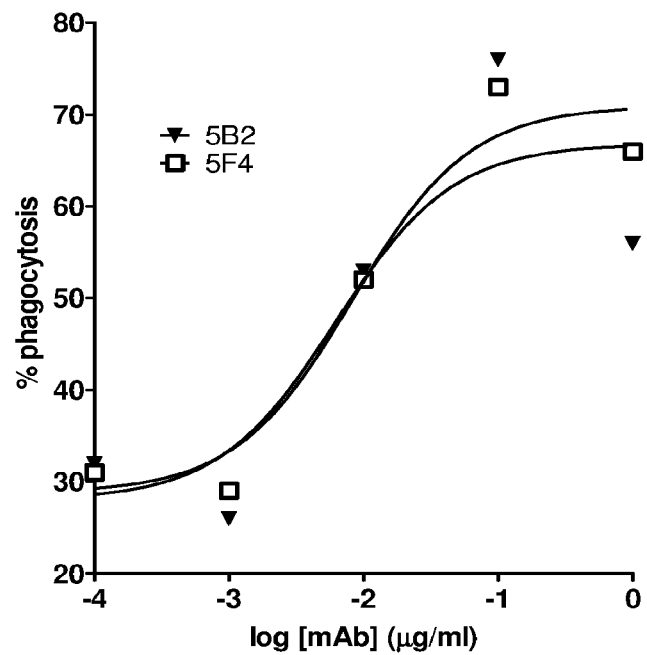
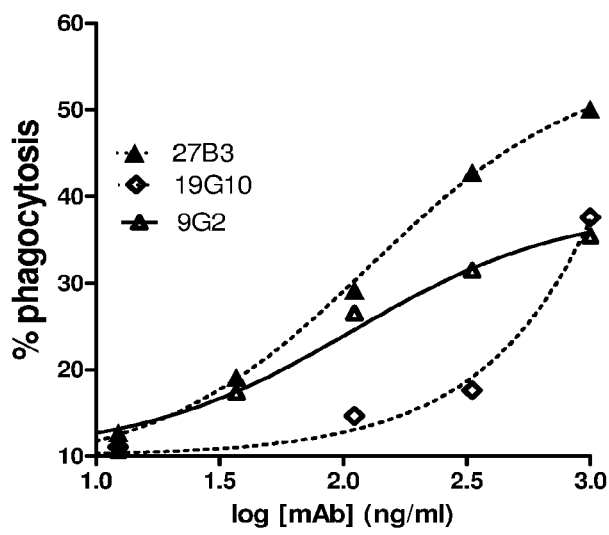

Figure 10
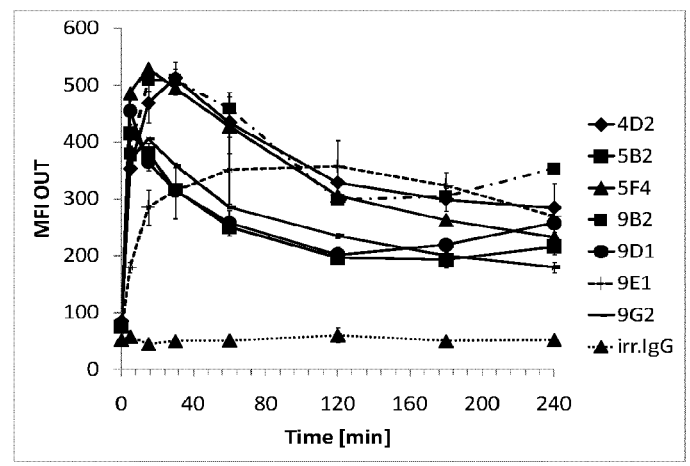
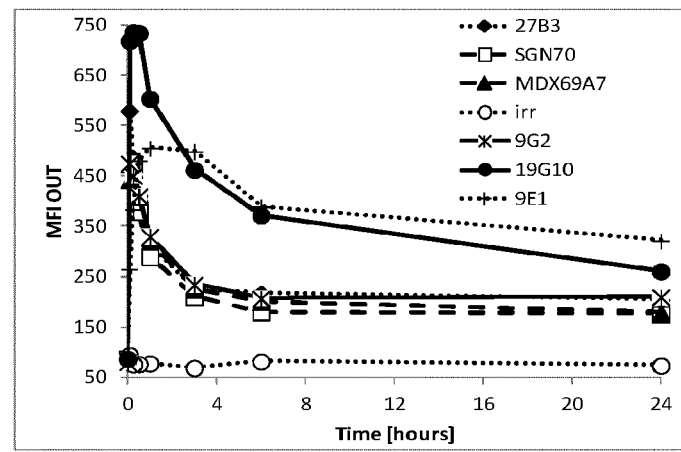

Figure 11

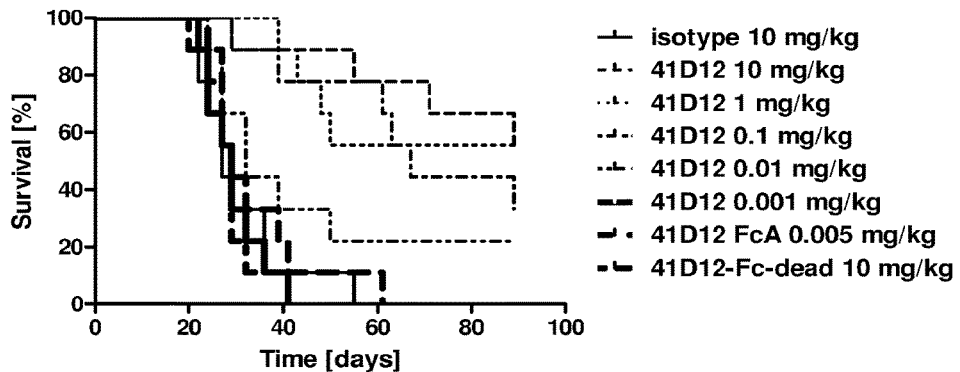

Figure 12

| light chain | FR1 | | CDR1 | | FR2 | |
|---|---|---|---|---|---|---|
| Name | | | | | | |
| Z73650\|IGLV8-61*01 | QTVVTQEPS | FSVSPGGTVTLTC | GLSSGSV | STSYYPS | WYQQTPGQAPRTLIY | |
| 27B3 | QAVVTQEPS | LTVSPGGTVTLTC | GLKSGSV | TSTNFPT | WYQQTPGQAPRLLIY | |

| CDR2 | FR3 | CDR3 | FR4 |
|---|---|---|---|
| ST NTRSS | GVPDRFSGSILG NKAALTITGAQADDESDYYC | VL AV | FGGGTQLTVL |
| NT NTRHS | GVPSRFSGSISE NKAALTITGAQPEDEAEYFC | ALFISNPS VE | FGGGTQLTVL |

| heavy chain | FR1 | CDR1 | FR2 | CDR2 |
|---|---|---|---|---|
| Name | | | | |
| Z12358\|IGHV3-48*03 | EVQLVESGGGLVQPGGSLRLSCAASGFTFS | SYEMN | WVRQAPGKGLEWVS | YISS SGSTIYYADSVKG |
| 27B3 | EVQLVESGGGLVQPGGSLRLSCAASGFTFS | VYYMN | WVRQAPGKGLEWVS | DINN EGGTTYYADSVKG |

| FR3 | CDR3 | FR4 |
|---|---|---|
| RFTISRDNAKNSLYLQMNSLRAEDTAVYYCAR | DS | WGQGTLVTVSS |
| RFTISRDNAKNTLTLQMNSLKPEDTALYYCVR | DAGYSNHVPIF DS | WGQGTQVIVAS |

Figure 18

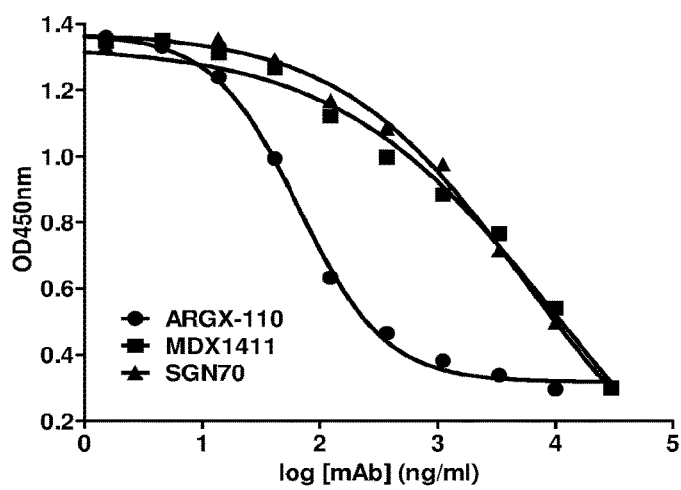

Figure 19

| | |
|---|---|
| HUMAN | QRFAQAQQQLPLESLGWDVAELQLNHTGPQQDPRLYWQGGPALGRSFLHGPELDKGQL |
| CYNO | QRLSRAQQQLPLESLGWDIAELQLNHTGPQQDPRLYWQGGPALGRSFLHGPELDKGQL |
| RHESUS | QRLSRAQQQLPLESLGWDIAELQLNHTGPQQDPRLYWQGGPALGRSFLRGPELDKGQL |
| MOUSE | SGLLSKQQQRLLEHPEPHTAELQLNLTVPRKDPTLRWGAGPALGRSFTHGPELEEGHL |
| RAT | GGHLSKPQHVLLEPPELHVAELQLNLTDPQKDLTLRWGAGPALGRSFTHGPGLEKGNL |
| | |
| HUMAN | RIHRDGIYMVHIQVTLAICSSTTASR HHPTTLAVGICSPASRSISLLR |
| CYNO | RIRRDGIYMVHIQVTLAICSSTSTSRHHHPTTLAVGICSPASRSISLLR |
| RHESUS | RIRRDGIYMVHIQVTLAICSSTSTSRHHHPTTLAVGICSPASRSISLLR |
| MOUSE | RIHQDGLYRLHIQVTLANCSSPGSTL QHRATLAVGICSPAAHGISLLR |
| RAT | RIHQDGIYRLHIQVTLANCSSSGSAL QHRASLVVGICSPAVHIISLLR |
| | |
| HUMAN | LSFHQGCTIASQRLTPLARGDTLCTNLTGTLLPSRNTDETFFGVQWVRP |
| CYNO | LSFHQGCTIASQRLTPLARGDTLCTNLTGTLLPSRNTDETFFGVQWVRP |
| RHESUS | LSFHQGCTIASQRLTPLARGDTLCTNLTGTLLPSRNTDETFFGVQWVRP |
| MOUSE | GRFGQDCTVALQRLTYLVHGDVLCTNLTLPLLPSRNADETFFGVQWICP |
| RAT | RRFGQDCTVSLQRLTPLARGDVLCSNLTQPLLPSRNADETFFGVQRVYPWP |

Figure 23

```
Human           SLGWDVAELQLNHTGPQQDPRLYWQGG
Chimera 1       HPEPHTAELQLNLTVPRKDPTLRWGAG
Chimera 2.1     HPEPHTAELQLNLTVPRKDPTLRWGAG
Chimera 2.2     HPEPHTAELQLNLTVPRKDPTLRWGAG
Chimera 2.3     HPEPHTAELQLNLTVPRKDPTLRWGAG
Chimera 2.4     HPEPHTAELQLNLTVPRKDPTLRWGAG
Chimera 2       HPEPHTAELQLNLTVPRKDPTLRWGAG
Chimera 3       HPEPHTAELQLNLTVPRKDPTLRWGAG
Chimera 4       HPEPHTAELQLNLTVPRKDPTLRWGAG
Mouse           HPEPHTAELQLNLTVPRKDPTLRWGAG Human           PALGRSFLHGPELDKGQLRIHRDGIYMVHIQVTLAICS
Chimera 1       PALGRSFLHGPELDKGQLRIHRDGIYMVHIQVTLAICS
Chimera 2.1     PALGRSFTHGPELDKGQLRIHRDGIYMVHIQVTLAICS
Chimera 2.2     PALGRSFTHGPELEEGHLRIHRDGIYMVHIQVTLAICS
Chimera 2.3     PALGRSFTHGPELEEGHLRIHQDGLYMVHIQVTLAICS
Chimera 2.4     PALGRSFTHGPELEEGHLRIHQDGLYRLHIQVTLAICS
Chimera 2       PALGRSFTHGPELEEGHLRIHQDGLYRLHIQVTLANCS
Chimera 3       PALGRSFTHGPELEEGHLRIHQDGLYRLHIQVTLANCS
Chimera 4       PALGRSFTHGPELEEGHLRIHQDGLYRLHIQVTLANCS
Mouse           PALGRSFTHGPELEEGHLRIHQDGLYRLHIQVTLANCS Human           STTASR HHPTTLAVGICSPASRSISLLRLSFHQGCTIASQRLTPLARGDT
Chimera 1       STTASR HHPTTLAVGICSPASRSISLLRLSFHQGCTIASQRLTPLARGDT
Chimera 2.1     STTASR HHPTTLAVGICSPASRSISLLRLSFHQGCTIASQRLTPLARGDT
Chimera 2.2     STTASR HHPTTLAVGICSPASRSISLLRLSFHQGCTIASQRLTPLARGDT
Chimera 2.3     STTASR HHPTTLAVGICSPASRSISLLRLSFHQGCTIASQRLTPLARGDT
Chimera 2.4     STTASR HHPTTLAVGICSPASRSISLLRLSFHQGCTIASQRLTPLARGDT
Chimera 2       STTASR HHPTTLAVGICSPASRSISLLRLSFHQGCTIASQRLTPLARGDT
Chimera 3       SPGSTL QHRATLAVGICSPASRSISLLRLSFHQGCTIASQRLTPLARGDT
Chimera 4       SPGSTL QHRATLAVGICSPAAHGISLLRGRFGQDCTVALQRLTYLVHGDV
Mouse           SPGSTL QHRATLAVGICSPAAHGISLLRGRFGQDCTVALQRLTYLVHGDV Human           LCTNLTGTLLPSRNTDETFFGVQWVRP
Chimera 1       LCTNLTGTLLPSRNTDETFFGVQWVRP
Chimera 2.1     LCTNLTGTLLPSRNTDETFFGVQWVRP
Chimera 2.2     LCTNLTGTLLPSRNTDETFFGVQWVRP
Chimera 2.3     LCTNLTGTLLPSRNTDETFFGVQWVRP
Chimera 2.4     LCTNLTGTLLPSRNTDETFFGVQWVRP
Chimera 2       LCTNLTGTLLPSRNTDETFFGVQWVRP
Chimera 3       LCTNLTGTLLPSRNTDETFFGVQWVRP
Chimera 4       LCTNLTGTLLPSRNTDETFFGVQWVRP
Mouse           LCTNLTLPLLPSRNADETFFGVQWICP
```

ANTIBODIES TO CD70

REFERENCE TO RELATED APPLICATIONS

This application is a divisional application of U.S. patent application Ser. No. 14/163,752, filed Jan. 24, 2014, which is a divisional application of U.S. patent application Ser. No. 14/073,462, filed Nov. 6, 2013, issued as U.S. Pat. No. 8,834,882, which is a continuation of U.S. patent application Ser. No. 14/005,113, filed Sep. 13, 2013, which is a 371 National Stage of International Patent Application No. PCT/EP2012/054733, filed Mar. 16, 2012, which claims priority to U.S. Provisional Patent Application Ser. No. 61/503,871, filed Jul. 1, 2011, and also claims priority to U.S. Provisional Patent Application Ser. No. 61/453,390, filed Mar. 16, 2011, each of which is incorporated herein by reference in its entirety.

TECHNICAL FIELD

The present invention relates to antibodies and antigen binding fragments thereof which bind to the human CD70 protein with high affinity and display potent inhibition of tumour cell growth.

BACKGROUND

The cytokine receptor CD27 is a member of the tumour necrosis factor receptor (TFNR) superfamily, which play a role in cell growth and differentiation, as well as apoptosis. The ligand for CD27 is CD70, which belongs to the tumour necrosis factor family of ligands. CD70 is a 193 amino acid polypeptide having a 20 amino acid hydrophilic N-terminal domain and a C-terminal domain containing 2 potential N-linked glycosylation sites (Goodwin, R. G. et al. (1993) Cell 73:447-56; Bowman et al. (1994) Immunol 152: 1756-61). Based on these features, CD70 was determined to be a type II transmembrane protein having an extracellular C-terminal portion.

CD70 is transiently found on activated T and B lymphocytes and dendritic cells (Hintzen et al. (1994) *J. Immunol.* 152: 1762-1773; Oshima et al. (1998) *Int. Immunol.* 10:517-26; Tesselaar et al. (2003) *J. Immunol.* 170:33-40). In addition to expression on normal cells, CD70 expression has been reported in different types of cancers including renal cell carcinomas, metastatic breast cancers, brain tumours, leukemias, lymphomas and nasopharyngeal carcinomas (Junker et al. (2005) *J Urol.* 173:2150-3; Sloan et al. (2004) *Am J Pathol.* 164:315-23; Held-Feindt and Mentlein (2002) *Int J Cancer* 98:352-6; Hishima et al. (2000) *Am J Surg Pathol.* 24:742-6; Lens et al. (1999) Br J Haematol. 106: 491-503). The interaction of CD70 with CD27 has also been proposed to play a role in cell-mediated autoimmune disease and the inhibition of TNF-alpha production (Nakajima et al. (2000) *J. Neuroimmunol.* 109:188-96).

Accordingly, CD70 represents a target for the treatment of cancer, autoimmune disorders and a variety of other diseases characterized by CD70 expression.

WO 2006/0044643 describes CD70 antibodies containing an antibody effector domain which can mediate one or more of ADCC, ADCP, CDC or ADC and either exert a cytostatic or cytotoxic effect on a CD70-expressing cancer or exert an immunosuppressive effect on a CD70-expressing immunological disorder in the absence of conjugation to a cytostatic or cytotoxic agent. The antibodies exemplified therein are based on the antigen-binding regions of two monoclonal antibodies, denoted 1F6 and 2F2.

WO 2007/038637 describes fully human monoclonal antibodies that bind to CD70. These antibodies are characterised by binding to human CD70 with a $K_D$ of $1 \times 10^{-7}$ M or less. The antibodies also bind to, and are internalised by, renal cell carcinoma tumor cell lines which express CD70, such as 786-O.

SUMMARY OF THE INVENTION

Provided herein are antibodies, or antigen binding fragments thereof, (referred to herein as CD70 antibodies) which bind to the human CD70 protein and exhibit properties which are different, and generally superior, to CD70 antibodies described in the prior art. The superior properties of these antibodies are advantageous with regard to use in human therapy, particularly treatment of CD70-expressing cancers and also immunological disorders.

The CD70 antibodies described herein are characterised by extremely high binding affinity for human CD70. All preferred embodiments described herein exhibit a binding affinity for recombinant human CD70 (measured by Biacore™ surface plasmon resonance as described herein) which is significantly higher than the most potent prior art CD70 antibodies proposed for human therapy, including prior art CD70 antibodies of "fully human" origin. In addition, all preferred embodiments of the CD70 antibodies described herein exhibit superior (i.e. higher affinity) binding to CD70 expressed on the surface of human cell lines, specifically human cancer cell lines, when compared to prior art CD70 antibodies proposed for human therapy. This superior binding to cell-surface CD70 is particularly marked in regard to human cancer cell lines which express CD70 at "low copy number" and is of direct relevance to use of the antibodies in human therapy. Still further, preferred embodiments of the CD70 antibodies described herein exhibit substantially improved binding to cancer cells isolated from human patients, particularly cancer cells isolated from patients with chronic lymphocytic leukaemia (CLL), when compared to prior art CD70 antibodies proposed for human therapeutic use.

Therefore, in a first aspect of the invention there is provided an antibody, or an antigen binding fragment thereof, which binds to human CD70, said antibody or antigen binding fragment comprising at least one heavy chain variable domain (VH) and at least one light chain variable domain (VL), wherein said VH and VL domain exhibit an off-rate ($k_{off}$ measured by Biacore™) for human CD70 of less than $7 \times 10^{-4}$ s$^{-1}$, when tested as a Fab fragment using the standard Biacore™ protocol described herein.

In a preferred embodiment the antibody or antigen binding fragment comprises at least one heavy chain variable domain (VH) and at least one light chain variable domain (VL), wherein said VH and VL domain exhibit an off-rate for human CD70 of $5 \times 10^{-4}$ s$^{-1}$ or less, or $2 \times 10^{-4}$ s$^{-1}$ or less, or $1 \times 10^{-4}$ s$^{-1}$ or less. Most preferably the CD70 antibody will exhibit an off-rate for CD70 in the range of from $0.4 \times 10^{-4}$ s$^{-1}$ to $4.8 \times 10^{-4}$ s$^{-1}$, when tested as a Fab fragment.

There is also provided an antibody which binds to human CD70, said antibody comprising two Fab regions, wherein each of the Fab regions binds to human CD70 and exhibits an off-rate for human CD70 of $5 \times 10^{-4}$ s$^{-1}$ or less, or $2 \times 10^{-4}$ s$^{-1}$ or less, or $1 \times 10^{-4}$ s$^{-1}$ or less and preferably in the range of from $0.4 \times 10^{-4}$ s$^{-1}$ to $4.8 \times 10^{-4}$ s$^{-1}$, when tested as a Fab fragment. The two Fab regions may be identical or they may differ in terms of binding properties, e.g. affinity for human CD70. The two Fab regions may bind to the same epitope or overlapping epitopes on human CD70 or they may bind to distinct, non-overlapping epitopes on human CD70. The two Fab regions may differ from one another in terms of amino acid sequence within one or both of the VH and VL domains.

Preferred embodiments of the CD70 antibodies provided herein may, in addition to the extremely high binding affinity for CD70, exhibit potent blocking or inhibition of the interaction between CD70 and its ligand CD27. The preferred CD70 antibodies which exhibit both high affinity binding to CD70 and potent blocking of the CD70/CD27 interaction are particularly advantageous as therapeutic agents for treatment of disease indications where blocking of CD70/CD27 signalling enhances therapeutic efficacy (e.g. in addition to cell-killing mediated by the effector functions of the CD70 antibody), for example autoimmune diseases and cancers which co-express CD70 and CD27.

Not all of the CD70 antibodies described herein exhibit potent blocking of the CD70/CD27 interaction in addition to the high affinity binding to CD70. Also described herein are a number of CD70 antibodies which exhibit very high affinity binding to CD70 but do not show significant blocking of the CD70/CD27 interaction. The properties of these antibodies are described elsewhere herein. The availability of high affinity non-blocking CD70 antibodies may enhance/extend the range of therapeutic possibilities.

Preferred embodiments of the CD70 antibodies described herein, exhibiting very high binding affinity for human CD70, are also characterised by a combination of binding properties which is not exhibited by prior art CD70 antibodies proposed for human therapeutic use. Accordingly, the preferred CD70 antibodies described herein are characterised by:
  (a) binding within the amino acid sequence HIQVTLA-ICSS (SEQ ID NO:342) in human CD70;
  (b) cross-reactivity with CD70 homologs of rhesus macaque (*Macaca mulatta*) and *cynomolgus* monkey (*Macaca cynomolgus*);
  (c) binding to both native human CD70 and heat denatured recombinant human CD70.

This combination of binding properties, which is not exhibited by the prior art antibodies proposed for human therapeutic use, indicates binding to a novel epitope on CD70 which is different to the epitopes bound by prior art CD70 antibodies.

The combination of binding properties exhibited by the preferred CD70 antibodies is advantageous in the context of human drug development. In particular, cross-reactivity with simian CD70 homologs enables toxicology studies on CD70 antibodies proposed for human therapeutic use to be carried out in primate models.

The preferred CD70 antibodies described herein still further exhibit favourable properties which are relevant to commercial manufacture as a therapeutic antibody product. As discussed elsewhere herein, the preferred CD70 antibodies provided herein exhibit extremely high level expression in the recombinant expression systems utilised for commercial manufacture of clinical grade therapeutic antibody products. The expression levels achievable with the preferred CD70 antibodies far exceed the levels typically achieved even for "fully human" therapeutic antibody products. In addition, the preferred CD70 antibody products (produced by recombinant expression in a format suitable for human therapeutic use) exhibit outstanding thermal stability, which is superior to typical therapeutic antibody products.

The CD70 antibodies provided herein with superior binding affinity for human CD70 and the other advantageous properties listed above are camelid-derived (for example llama-derived). The camelid-derived CD70 antibodies may be isolated or recombinantly expressed monoclonal antibodies. Preferred embodiments may be a humanised (or germlined) monoclonal antibody (e.g. a humanised variant of a camelid-derived antibody), a chimeric antibody (e.g. a camelid-human chimeric antibody) or a humanised chimeric antibody (e.g. a chimeric antibody comprising humanised variants of camelid VH and VL domains and constant domains of a human antibody).

Camelid-derived CD70 antibodies may comprise at least one hypervariable loop or complementarity determining region obtained from a VH domain or a VL domain of a species in the family Camelidae. In a particular embodiment, the CD70 antibody, or antigen binding fragment thereof, may comprise a heavy chain variable domain (VH) and light chain variable domain (VL), wherein the VH and VL domains, or one or more CDRs thereof, are camelid-derived. In particular embodiments the antibody or antigen binding fragment thereof may comprise llama VH and VL domains, or human germlined variants of llama VH and VL domains. This antibody, or antigen binding fragment, may exhibit "high human homology", as defined herein.

The camelid-derived CD70 antibodies described herein typically exhibit VH and/or VL region amino acid sequences having at least 90% (e.g., 91%, 92%, 93%, 94%, 95%, 96%, 97%, 98%, or 99%) sequence identity the closest matching human antibody germline sequence.

Further preferred embodiments of the invention include humanised (or human germlined) variants of the camelid-derived CD70 antibodies. In particular, the invention provides humanised or human germlined variants of the llama-derived CD70 antibodies described herein.

In a further aspect of invention there is provided a chimeric camelid-human antibody which binds human CD70, wherein the antigen-binding portions of the antibody (e.g. VH and/or VL domains or CDRs thereof) are camelid-derived and the constant regions of the antibody are derived from a human antibody. In particular, the invention provides a chimeric llama-human antibody which binds human CD70.

In a further aspect of invention there is provided a humanised variant of a chimeric camelid-human antibody which binds human CD70, wherein the antigen-binding portions of the antibody (e.g. VH and/or VL domains or CDRs thereof) are humanised variants of camelid-derived sequences and the constant regions of the antibody are derived from a human antibody. In particular, the invention provides a humanised variant of a chimeric llama-human antibody which binds human CD70.

Preferred (but non-limiting) embodiments of the CD70 antibodies, or antigen binding fragments thereof, are defined below by reference to specific structural characteristics, i.e. specified amino acid sequences of either the CDRs (one or more of SEQ ID Nos: 49-59, 262 or 263 (heavy chain CDR3), or SEQ ID Nos: 26-37, 249, 258 or 259 (heavy chain CDR2) or SEQ ID Nos: 10-20, 248, 256 or 257 (heavy chain CDR1) or one of the CDR sequences shown as SEQ ID NOs: 148-168, 271 or 273 (light chain CDR3), or SEQ ID Nos: 109-128 or 270 (light chain CDR2) or SEQ ID Nos:77-95, or 250-253, 267 or 268 (light chain CDR1), or entire variable domains (one or more of SEQ ID NOs: 177-188, 212-223, 274 or 275 (VH) or SEQ ID Nos:189-211, 230-245, 276 or 277 (VL)). All of these antibodies bind to human CD70 with high affinity, exhibiting an off-rate for human CD70 of $5\times10^{-4}$ $s^{-1}$ or less, and typically in the range of from $0.4\times10^{-4}$ $s^{-1}$ to $4.8\times10^{-4}$ $s^{-1}$, when tested as a Fab fragment.

The invention also provides humanised/germlined variants of these antibodies, plus affinity variants and variants containing conservative amino acid substitutions, as defined herein. Specifically provided are chimeric antibodies containing VH and VL domains which are camelid-derived, or human germlined variants thereof, fused to constant domains of human antibodies, in particular human IgG1, IgG2, IgG3 or IgG4. The heavy chain variable domains defined above can be utilised as single domain antibodies, or may be included within a conventional four-chain antibody or other antigen binding proteins, such as for example Fab, Fab', F(ab')2, bi-specific Fab's, and Fv fragments, diabodies, linear antibodies, single-chain antibody molecules, a single chain variable fragment (scFv) and multi specific antibodies.

Preferred embodiments of the CD70 antibodies are antibodies, or antigen binding fragments thereof, comprising a heavy chain variable domain comprising a variable heavy chain CDR3, a variable heavy chain CDR2 and a variable heavy chain CDR1, wherein said variable heavy chain CDR3 comprises an amino acid sequence selected from the group consisting of:
SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:262 and SEQ ID NO:263, and sequence variants of any one of the recited sequences, wherein the sequence variant comprises one, two or three amino acid substitutions in the recited sequence;

said variable heavy chain CDR2 optionally comprises an amino acid sequence selected from the group consisting of: amino acid sequences of SEQ ID NO: 306 [$X_1X_2X_3X_4X_5X_6X_7X_8X_9$YYADSVKX$_{10}$], wherein
$X_1$ is any amino acid, preferably D, T, S or E,
$X_2$ is any amino acid, preferably I,
$X_3$ is any amino acid, preferably N, S, T or Y,
$X_4$ is any amino acid, preferably N, M, S or T,
$X_5$ is any amino acid, preferably E, D, Y or H,
$X_6$ is any amino acid, preferably G, D, S or N,
$X_7$ is any amino acid, preferably G, Y, S, D or M,
$X_8$ is any amino acid, preferably T, E, S, N, Y or R,
$X_9$ is any amino acid, preferably T, A or R, and
$X_{10}$ is any amino acid, preferably G or S,
and the amino acid sequences of SEQ ID NO:30, SEQ ID NO:32, SEQ ID NO:33, SEQ ID NO:34, SEQ ID NO:249, SEQ ID NO:258 and SEQ ID NO:259 and sequence variants of any one of the recited sequences, wherein the sequence variant comprises one, two or three amino acid substitutions in the recited sequence; and said variable heavy chain CDR1 optionally comprises an amino acid sequence selected from the group consisting of: amino acid sequences of SEQ ID NO: 307 [$X_1$YYMN], wherein
$X_1$ is any amino acid, preferably V, G or A, amino acid sequences of SEQ ID NO: 308 [$X_1X_2$AMS], wherein
$X_1$ is any amino acid, preferably D, T, S, N or G and
$X_2$ is any amino acid, preferably Y, S or P,
and the amino acid sequences of SEQ ID NO:10, SEQ ID NO:15, SEQ ID NO:16, SEQ ID NO:248, SEQ ID NO:256 and SEQ ID NO:257 and sequence variants of any one of the recited sequences, wherein the sequence variant comprises one, two or three amino acid substitutions in the recited sequence.

The heavy chain variable domain may comprise any one of the listed variable heavy chain CDR3 sequences (HCDR3) in combination with any one of the variable heavy chain CDR2 sequences (HCDR2) and any one of the variable heavy chain CDR1 sequences (HCDR1). However, certain combinations of HCDR3 and HCDR2 and HCDR1 are particularly preferred, these being the "native" combinations which derive from a single common VH domain. These preferred combinations are listed in Table 6 and Table 14A.

The antibody or antigen binding fragment thereof may additionally comprise a light chain variable domain (VL), which is paired with the VH domain to form an antigen binding domain. Preferred light chain variable domains are those comprising a variable light chain CDR3, a variable light chain CDR2 and a variable light chain CDR1, wherein said variable light chain CDR3 comprises an amino acid sequence selected from the group consisting of: SEQ ID NO:148, SEQ ID NO:149, SEQ ID NO:150, SEQ ID NO:151, SEQ ID NO:152, SEQ ID NO:153, SEQ ID NO:154, SEQ ID NO:155, SEQ ID NO:156, SEQ ID NO:157, SEQ ID NO:158, SEQ ID NO:159, SEQ ID NO:160, SEQ ID NO:161, SEQ ID NO:162, SEQ ID NO:163, SEQ ID NO:164, SEQ ID NO:165, SEQ ID NO:166, SEQ ID NO:166, SEQ ID NO:168, SEQ ID NO:271 and SEQ ID NO:273 and sequence variants of any one of the recited sequences, wherein the sequence variant comprises one, two or three amino acid substitutions in the recited sequence;

said variable light chain CDR2 optionally comprises an amino acid sequence selected from the group consisting of:
(a) amino acid sequences of SEQ ID NO: 310 [$X_1$T$X_2X_3$RHS], wherein
$X_1$ is any amino acid, preferably N or S,
$X_2$ is any amino acid, preferably N, S or A, and
$X_3$ is any amino acid, preferably S, N or T,
(b) amino acid sequences of SEQ ID NO: 311 [YYSDS$X_1X_2X_3$Q$X_4$S], wherein
$X_1$ is any amino acid, preferably Y, V or L,
$X_2$ is any amino acid, preferably K or S,
$X_3$ is any amino acid, preferably H or N, and
$X_4$ is any amino acid, preferably G or S,
(c) amino acid sequences of SEQ ID NO: 312 [$X_1$N$X_2$NRPS], wherein
$X_1$ is any amino acid, preferably V, I or Y, and
$X_2$ is any amino acid, preferably N or T,
(d) amino acid sequences of SEQ ID NO: 313 [GDN$X_1X_2$PL], wherein
$X_1$ is any amino acid, preferably Y, and
$X_2$ is any amino acid, preferably R or M,
(e) amino acid sequences of SEQ ID NO:314 [$X_1$DD$X_2$RPS], wherein
$X_1$ is any amino acid, preferably D or G, and
$X_2$ is any amino acid, preferably S or I,
and the amino acid sequences of SEQ ID NO:113, SEQ ID NO:116, SEQ ID NO:120 and SEQ ID NO:270, and sequence variants of any one of the recited sequences, wherein the sequence variant comprises one, two or three amino acid substitutions in the recited sequence; and said variable light chain CDR1 optionally comprises an amino acid sequence selected from the group consisting of:
(a) amino acid sequences of SEQ ID NO:315 [GL$X_1$SGS$X_2$T$X_3X_4X_5$YP$X_6$], wherein
$X_1$ is any amino acid, preferably S or T,
$X_2$ is any amino acid, preferably V or A,
$X_3$ is any amino acid, preferably S or T,
$X_4$ is any amino acid, preferably S, T or G,
$X_5$ is any amino acid, preferably N or H,
$X_6$ is any amino acid, preferably G, D or E,
(b) amino acid sequences of SEQ ID NO:316 [TL$X_1$S$X_2X_3X_4X_5$G$X_6$YDIS], wherein
$X_1$ is any amino acid, preferably S, N or I, X$_2$ is any amino acid, preferably G or A,
X$_3$ is any amino acid, preferably N or D,
X$_4$ is any amino acid, preferably N or S,
X$_5$ is any amino acid, preferably V or I,
X$_6$ is any amino acid, preferably N or S,
(c) amino acid sequences of SEQ ID NO:317 [QGGNLX$_1$LYGAN], wherein
X$_1$ is any amino acid, preferably G or W,
(d) amino acid sequences of SEQ ID NO:318 [RGDX$_1$LX$_2$X$_3$YX$_4$X$_5$N], wherein
X$_1$ is any amino acid, preferably S or T,
X$_2$ is any amino acid, preferably E or R,
X$_3$ is any amino acid, preferably R or N,
X$_4$ is any amino acid, preferably G or H,
X$_5$ is any amino acid, preferably T or A,
(e) amino acid sequences of SEQ ID NO:319 [GX$_1$X$_2$SGSVTSX$_3$NFPT], wherein
X$_1$ is any amino acid, preferably V or L,
X$_2$ is any amino acid, preferably K or T,
X$_3$ is any amino acid, preferably T or D,
and the amino acid sequences of SEQ ID NO:82, SEQ ID NO:87, SEQ ID NO:88, SEQ ID NO:250, SEQ ID NO:251, SEQ ID NO: 252, SEQ ID NO:253, SEQ ID NO:267 and SEQ ID NO:268 and sequence variants of any one of the recited sequences, wherein the sequence variant comprises one, two or three amino acid substitutions in the recited sequence.

The light chain variable domain may comprise any one of the listed variable light chain CDR3 sequences (LCDR3) in combination with any one of the variable light chain CDR2 sequences (LCDR2) and any one of the variable light chain CDR1 sequences (LCDR1). However, certain combinations of LCDR3 and LCDR2 and LCDR1 are particularly preferred, these being the "native" combinations which derive from a single common VL domain. These preferred combinations are listed in Table 7 and Table 15A.

Any given CD70 antibody or antigen binding fragment thereof comprising a VH domain paired with a VL domain to form a binding site for CD70 antigen will comprise a combination of 6 CDRs: variable heavy chain CDR3 (HCDR3), variable heavy chain CDR2 (HCDR2), variable heavy chain CDR1 (HCDR1), variable light chain CDR3 (LCDR3), variable light chain CDR2 (LCDR2) and variable light chain CDR1 (LCDR1). Although all combinations of 6 CDRs selected from the CDR sequence groups listed above are permissible, and within the scope of the invention, certain combinations of 6 CDRs are particularly preferred; these being the "native" combinations within a single Fab exhibiting high affinity binding to human CD70.

Preferred combinations of 6 CDRs include, but are not limited to, the combinations of variable heavy chain CDR3 (HCDR3), variable heavy chain CDR2 (HCDR2), variable heavy chain CDR1 (HCDR1), variable light chain CDR3 (LCDR3), variable light chain CDR2 (LCDR2) and variable light chain CDR1 (LCDR1) selected from the group consisting of:
(i) HCDR3 comprising SEQ ID NO:50, HCDR2 comprising SEQ ID NO:27, HCDR1 comprising SEQ ID NO:11, LCDR3 comprising SEQ ID NO:160, LCDR2 comprising SEQ ID NO:119, and LCDR1 comprising SEQ ID NO:250;
(ii) HCDR3 comprising SEQ ID NO:49, HCDR2 comprising SEQ ID NO:26, HCDR1 comprising SEQ ID NO:10, LCDR3 comprising SEQ ID NO:148, LCDR2 comprising SEQ ID NO:109, and LCDR1 comprising SEQ ID NO:77;
(iii) HCDR3 comprising SEQ ID NO:50, HCDR2 comprising SEQ ID NO:27, HCDR1 comprising SEQ ID NO:11, LCDR3 comprising SEQ ID NO:149, LCDR2 comprising SEQ ID NO:110, and LCDR1 comprising SEQ ID NO:78;
(iv) HCDR3 comprising SEQ ID NO:50, HCDR2 comprising SEQ ID NO:28, HCDR1 comprising SEQ ID NO:11, LCDR3 comprising SEQ ID NO:150, LCDR2 comprising SEQ ID NO:111, and LCDR1 comprising SEQ ID NO:79;
(v) HCDR3 comprising SEQ ID NO:50, HCDR2 comprising SEQ ID NO:28, HCDR1 comprising SEQ ID NO:11, LCDR3 comprising SEQ ID NO:151, LCDR2 comprising SEQ ID NO:110, and LCDR1 comprising SEQ ID NO:80;
(vi) HCDR3 comprising SEQ ID NO:51, HCDR2 comprising SEQ ID NO:29, HCDR1 comprising SEQ ID NO:12, LCDR3 comprising SEQ ID NO: 152, LCDR2 comprising SEQ ID NO:110, and LCDR1 comprising SEQ ID NO:80;
(vii) HCDR3 comprising SEQ ID NO:52, HCDR2 comprising SEQ ID NO:30, HCDR1 comprising SEQ ID NO:13, LCDR3 comprising SEQ ID NO:153, LCDR2 comprising SEQ ID NO: 112, and LCDR1 comprising SEQ ID NO:81;
(viii) HCDR3 comprising SEQ ID NO:53, HCDR2 comprising SEQ ID NO:31, HCDR1 comprising SEQ ID NO:14, LCDR3 comprising SEQ ID NO:154, LCDR2 comprising SEQ ID NO:113, and LCDR1 comprising SEQ ID NO:82;
(ix) HCDR3 comprising SEQ ID NO:54, HCDR2 comprising SEQ ID NO:32, HCDR1 comprising SEQ ID NO:15, LCDR3 comprising SEQ ID NO:155, LCDR2 comprising SEQ ID NO:114, and LCDR1 comprising SEQ ID NO:83;
(x) HCDR3 comprising SEQ ID NO:55, HCDR2 comprising SEQ ID NO:33, HCDR1 comprising SEQ ID NO:16, LCDR3 comprising SEQ ID NO:156, LCDR2 comprising SEQ ID NO:115, and LCDR1 comprising SEQ ID NO:84;
(xi) HCDR3 comprising SEQ ID NO:56, HCDR2 comprising SEQ ID NO:34, HCDR1 comprising SEQ ID NO:17, LCDR3 comprising SEQ ID NO:157, LCDR2 comprising SEQ ID NO:116, and LCDR1 comprising SEQ ID NO:85;
(xii) HCDR3 comprising SEQ ID NO:57, HCDR2 comprising SEQ ID NO:35, HCDR1 comprising SEQ ID NO: 18, LCDR3 comprising SEQ ID NO:158, LCDR2 comprising SEQ ID NO: 117, and LCDR1 comprising SEQ ID NO: 84;
(xiii) HCDR3 comprising SEQ ID NO: 58, HCDR2 comprising SEQ ID NO: 36, HCDR1 comprising SEQ ID NO: 19, LCDR3 comprising SEQ ID NO: 159, LCDR2 comprising SEQ ID NO: 118, and LCDR1 comprising SEQ ID NO: 86;
(xiv) HCDR3 comprising SEQ ID NO: 50, HCDR2 comprising SEQ ID NO: 27, HCDR1 comprising SEQ ID NO: 11, LCDR3 comprising SEQ ID NO: 161, LCDR2 comprising SEQ ID NO:120, and LCDR1 comprising SEQ ID NO:88;
(xv) HCDR3 comprising SEQ ID NO: 50, HCDR2 comprising SEQ ID NO: 27, HCDR1 comprising SEQ ID NO: 11, LCDR3 comprising SEQ ID NO: 162, LCDR2 comprising SEQ ID NO: 121, and LCDR1 comprising SEQ ID NO: 89;
(xvi) HCDR3 comprising SEQ ID NO: 50, HCDR2 comprising SEQ ID NO: 27, HCDR1 comprising SEQ ID NO: 11, LCDR3 comprising SEQ ID NO: 163, LCDR2 comprising SEQ ID NO: 122, and LCDR1 comprising SEQ ID NO: 90;
(xvii) HCDR3 comprising SEQ ID NO: 51, HCDR2 comprising SEQ ID NO: 29, HCDR1 comprising SEQ ID NO: 12, LCDR3 comprising SEQ ID NO: 164, LCDR2 comprising SEQ ID NO: 123, and LCDR1 comprising SEQ ID NO:91;
(xviii) HCDR3 comprising SEQ ID NO: 51, HCDR2 comprising SEQ ID NO: 29, HCDR1 comprising SEQ ID NO:

12, LCDR3 comprising SEQ ID NO: 164, LCDR2 comprising SEQ ID NO: 124, and LCDR1 comprising SEQ ID NO: 91;
(xix) HCDR3 comprising SEQ ID NO: 59, HCDR2 comprising SEQ ID NO: 37, HCDR1 comprising SEQ ID NO: 12, LCDR3 comprising SEQ ID NO: 165, LCDR2 comprising SEQ ID NO: 125, and LCDR1 comprising SEQ ID NO: 92;
(xx) HCDR3 comprising SEQ ID NO: 59, HCDR2 comprising SEQ ID NO: 37, HCDR1 comprising SEQ ID NO: 20, LCDR3 comprising SEQ ID NO: 165, LCDR2 comprising SEQ ID NO: 126, and LCDR1 comprising SEQ ID NO: 93;
(xxi) HCDR3 comprising SEQ ID NO: 59, HCDR2 comprising SEQ ID NO: 37, HCDR1 comprising SEQ ID NO: 20, LCDR3 comprising SEQ ID NO: 166, LCDR2 comprising SEQ ID NO: 127, and LCDR1 comprising SEQ ID NO: 92;
(xxii) HCDR3 comprising SEQ ID NO:59, HCDR2 comprising SEQ ID NO: 37, HCDR1 comprising SEQ ID NO: 20, LCDR3 comprising SEQ ID NO: 167, LCDR2 comprising SEQ ID NO: 128, and LCDR1 comprising SEQ ID NO: 94;
(xxiii) HCDR3 comprising SEQ ID NO: 59, HCDR2 comprising SEQ ID NO: 37, HCDR1 comprising SEQ ID NO: 20, LCDR3 comprising SEQ ID NO: 168, LCDR2 comprising SEQ ID NO: 110, and LCDR1 comprising SEQ ID NO: 95;
(xxiv) HCDR3 comprising SEQ ID NO: 262, HCDR2 comprising SEQ ID NO: 258, HCDR1 comprising SEQ ID NO: 256, LCDR3 comprising SEQ ID NO: 271, LCDR2 comprising SEQ ID NO: 110, and LCDR1 comprising SEQ ID NO: 267;
(xxv) HCDR3 comprising SEQ ID NO: 263, HCDR2 comprising SEQ ID NO: 259, HCDR1 comprising SEQ ID NO: 257, LCDR3 comprising SEQ ID NO: 273, LCDR2 comprising SEQ ID NO: 270, and LCDR1 comprising SEQ ID NO: 268.

Further preferred CD70 antibodies, exhibiting high affinity binding to human CD70, include isolated antibodies or antigen binding fragments thereof, comprising a heavy chain variable domain having an amino acid sequence selected from the group consisting of: the amino acid sequences of SEQ ID NO:177, SEQ ID NO:178, SEQ ID NO:179, SEQ ID NO:180, SEQ ID NO:181, SEQ ID NO:182, SEQ ID NO:183, SEQ ID NO:184, SEQ ID NO:185, SEQ ID NO:186, SEQ ID NO:187, SEQ ID NO:188, SEQ ID NO:212, SEQ ID NO:213, SEQ ID NO:214, SEQ ID NO:215, SEQ ID NO:216, SEQ ID NO:217, SEQ ID NO:218, SEQ ID NO:219, SEQ ID NO:220, SEQ ID NO:221, SEQ ID NO:222, SEQ ID NO:223, SEQ ID NO:224, SEQ ID NO:225, SEQ ID NO:226, SEQ ID NO:227, SEQ ID NO:228, SEQ ID NO:229, SEQ ID NO:274 and SEQ ID NO:275 and amino acid sequences exhibiting at least 90%, 95%, 97%, 98% or 99% sequence identity to one of the recited sequences, and optionally comprising a light chain variable domain having an amino acid sequence selected from the group consisting of: the amino acid sequences of SEQ ID NO:189, SEQ ID NO:190, SEQ ID NO:191, SEQ ID NO:192, SEQ ID NO:193, SEQ ID NO:194, SEQ ID NO:195, SEQ ID NO:196, SEQ ID NO:197, SEQ ID NO:198, SEQ ID NO:199, SEQ ID NO:200, SEQ ID NO:201, SEQ ID NO:202, SEQ ID NO:203, SEQ ID NO:204, SEQ ID NO:205, SEQ ID NO:206, SEQ ID NO:207, SEQ ID NO:208, SEQ ID NO:209, SEQ ID NO:210, SEQ ID NO:211, SEQ ID NO:223, SEQ ID NO:230, SEQ ID NO:231, SEQ ID NO:232, SEQ ID NO:233, SEQ ID NO:234, SEQ ID NO:234, SEQ ID NO:236, SEQ ID NO:237, SEQ ID NO:238, SEQ ID NO:239, SEQ ID NO:240, SEQ ID NO:241, SEQ ID NO:242, SEQ ID NO:243, SEQ ID NO:244, SEQ ID NO:245, SEQ ID NO:245, SEQ ID NO:247, SEQ ID NO:248, SEQ ID NO:276 and SEQ ID NO:277 and amino acid sequences exhibiting at least 90%, 95%, 97%, 98% or 99% sequence identity to one of the recited sequences.

Although all possible pairings of VH domains and VL domains selected from the VH and VL domain sequence groups listed above are permissible, and within the scope of the invention, certain combinations VH and VL are particularly preferred; these being the "native" combinations within a single Fab exhibiting high affinity binding to human CD70. Accordingly, preferred CD70 antibodies, or antigen binding fragments thereof, exhibiting high affinity CD70 binding are those comprising a combination of a heavy chain variable domain (VH) and a light chain variable domain (VL), wherein the combination is selected from the group consisting of:
(i) a heavy chain variable domain comprising the amino acid sequence of SEQ ID NO:223 and a light chain variable domain comprising the amino acid sequence of SEQ ID NO:241;
(ii) a heavy chain variable domain comprising the amino acid sequence of SEQ ID NO:177 and a light chain variable domain comprising the amino acid sequence of SEQ ID NO:189;
(iii) a heavy chain variable domain comprising the amino acid sequence of SEQ ID NO:178 and a light chain variable domain comprising the amino acid sequence of SEQ ID NO: 190;
(iv) a heavy chain variable domain comprising the amino acid sequence of SEQ ID NO:179 and a light chain variable domain comprising the amino acid sequence of SEQ ID NO:191;
(v) a heavy chain variable domain comprising the amino acid sequence of SEQ ID NO:179 and a light chain variable domain comprising the amino acid sequence of SEQ ID NO:192;
(vi) a heavy chain variable domain comprising the amino acid sequence of SEQ ID NO:180 and a light chain variable domain comprising the amino acid sequence of SEQ ID NO:193;
(vii) a heavy chain variable domain comprising the amino acid sequence of SEQ ID NO:181 and a light chain variable domain comprising the amino acid sequence of SEQ ID NO:194;
(viii) a heavy chain variable domain comprising the amino acid sequence of SEQ ID NO:182 and a light chain variable domain comprising the amino acid sequence of SEQ ID NO:195;
(ix) a heavy chain variable domain comprising the amino acid sequence of SEQ ID NO:183 and a light chain variable domain comprising the amino acid sequence of SEQ ID NO:196;
(x) a heavy chain variable domain comprising the amino acid sequence of SEQ ID NO:184 and a light chain variable domain comprising the amino acid sequence of SEQ ID NO:197;
(xi) a heavy chain variable domain comprising the amino acid sequence of SEQ ID NO:185 and a light chain variable domain comprising the amino acid sequence of SEQ ID NO:198;

(xii) a heavy chain variable domain comprising the amino acid sequence of SEQ ID NO:186 and a light chain variable domain comprising the amino acid sequence of SEQ ID NO:199;
(xiii) a heavy chain variable domain comprising the amino acid sequence of SEQ ID NO:187 and a light chain variable domain comprising the amino acid sequence of SEQ ID NO:200;
(xiv) a heavy chain variable domain comprising the amino acid sequence of SEQ ID NO:178 and a light chain variable domain comprising the amino acid sequence of SEQ ID NO:201;
(xv) a heavy chain variable domain comprising the amino acid sequence of SEQ ID NO:178 and a light chain variable domain comprising the amino acid sequence of SEQ ID NO:202;
(xvi) a heavy chain variable domain comprising the amino acid sequence of SEQ ID NO:178 and a light chain variable domain comprising the amino acid sequence of SEQ ID NO:203;
(xvii) a heavy chain variable domain comprising the amino acid sequence of SEQ ID NO:178 and a light chain variable domain comprising the amino acid sequence of SEQ ID NO:204;
(xviii) a heavy chain variable domain comprising the amino acid sequence of SEQ ID NO:180 and a light chain variable domain comprising the amino acid sequence of SEQ ID NO:205;
(xix) a heavy chain variable domain comprising the amino acid sequence of SEQ ID NO:180 and a light chain variable domain comprising the amino acid sequence of SEQ ID NO:206;
(xx) a heavy chain variable domain comprising the amino acid sequence of SEQ ID NO:188 and a light chain variable domain comprising the amino acid sequence of SEQ ID NO:207;
(xxi) a heavy chain variable domain comprising the amino acid sequence of SEQ ID NO:188 and a light chain variable domain comprising the amino acid sequence of SEQ ID NO:208;
(xxii) a heavy chain variable domain comprising the amino acid sequence of SEQ ID NO:188 and a light chain variable domain comprising the amino acid sequence of SEQ ID NO:209;
(xxiii) a heavy chain variable domain comprising the amino acid sequence of SEQ ID NO:188 and a light chain variable domain comprising the amino acid sequence of SEQ ID NO:210;
(xxiv) a heavy chain variable domain comprising the amino acid sequence of SEQ ID NO:188 and a light chain variable domain comprising the amino acid sequence of SEQ ID NO:211;
(xxv) a heavy chain variable domain comprising the amino acid sequence of SEQ ID NO:274 and a light chain variable domain comprising the amino acid sequence of SEQ ID NO:276;
(xxvi) a heavy chain variable domain comprising the amino acid sequence of SEQ ID NO:275 and a light chain variable domain comprising the amino acid sequence of SEQ ID NO:277.

For each of the specific VH/VL combinations listed above, it is also permissible, and within the scope of the invention, to combine a VH domain having an amino acid sequence at least 90%, 92%, 95%, 97% or 99% identical to the recited VH domain sequence with a VL domain having an amino acid sequence at least 90%, 92%, 95%, 97% or 99% identical to the recited VL domain sequence.

In the preceding paragraph, and elsewhere herein, the structure of the antibodies/antigen binding fragments is defined on the basis of % sequence identity with a recited reference sequence (with a given SEQ ID NO). In this context, % sequence identity between two amino acid sequences may be determined by comparing these two sequences aligned in an optimum manner and in which the amino acid sequence to be compared can comprise additions or deletions with respect to the reference sequence for an optimum alignment between these two sequences. The percentage of identity is calculated by determining the number of identical positions for which the amino acid residue is identical between the two sequences, by dividing this number of identical positions by the total number of positions in the comparison window and by multiplying the result obtained by 100 in order to obtain the percentage of identity between these two sequences. Typically, the comparison window with correspond to the full length of the sequence being compared. For example, it is possible to use the BLAST program, "BLAST 2 sequences" (Tatusova et al, "Blast 2 sequences—a new tool for comparing protein and nucleotide sequences", FEMS Microbiol Lett. 174:247-250) available on the site http://www.ncbi.nlm.nih.gov/gorf/b12.html, the parameters used being those given by default (in particular for the parameters "open gap penalty": 5, and "extension gap penalty": 2; the matrix chosen being, for example, the matrix "BLOSUM 62" proposed by the program), the percentage of identity between the two sequences to be compared being calculated directly by the program.

The most preferred CD70 antibodies provided herein, which exhibit a particularly advantageous combination of properties, including extremely high affinity binding to human CD70, are those based on the antigen-binding portion of the llama-derived Fab denoted 27B3 in the accompanying examples, plus human germlined variants of 27B3, including the germlined variants identified in the accompanying examples. 27B3 and its germlined variants, particularly variants based on the CDRs or complete variable domains of variant 41D12, exhibit an extremely advantageous combination of properties, summarised as follows: high affinity binding to recombinant human CD70, strong binding to cell surface CD70, specifically binding to CD70 expressed on cancer cell lines, particularly cell lines which express CD70 at "low copy number" and strong binding to cancer cells isolated from patient samples (CLL), potent blocking of the CD70/CD27 interaction, potent effector function—particularly when expressed as a chimera with human IgG1 constant regions, and especially when expressed as a non-fucosylated IgG1, cross-reactivity with CD70 homologs of rhesus macaque and *cynomolgus* monkey enabling toxicology studies in primate species, binding to both native (i.e. cell-surface) and heat denatured CD70, partial or low levels of internalisation on certain cancer cell lines. All of these characteristics in combination render 41D12, and indeed other 27B3 variants and the other CD70 antibodies described herein which exhibit similar properties, an outstanding candidate for therapeutic use in the treatment of CD70-associated diseases, specifically CD70-expressing cancers and immunological disorders.

27B3, and its variants, are characterised by the presence of the heavy chain variable CDR3 sequence shown as SEQ ID NO:50 (DAGYSNHVPIFDS).

Accordingly, preferred embodiments of the CD70 antibody, or antigen binding fragments thereof, are those comprising a heavy chain variable domain wherein the variable heavy chain CDR3 comprises or consists of the amino acid sequence of SEQ ID NO:50 or a sequence variant thereof, wherein the sequence variant comprises one, two or three amino acid substitutions in the recited sequence.

More preferred embodiments are antibodies or antigen binding fragments thereof which include the same combination of heavy chain CDRs as 27B3, or human germlined variants of 27B3. Accordingly, the antibody or antigen binding fragment thereof, may comprise a heavy chain variable domain wherein the variable heavy chain CDR3 comprises or consists of the amino acid sequence of SEQ ID NO:50 or a sequence variant thereof;

the variable heavy chain CDR2 comprises or consists of an amino acid sequence selected from the group consisting of: SEQ ID NO:27, SEQ ID NO:249 and sequence variants thereof; and the variable heavy chain CDR1 comprises or consists of an amino acid sequence selected from the group consisting of: SEQ ID NO:11, SEQ ID NO:248 and sequence variants thereof, wherein the sequence variants comprise one, two or three amino acid substitutions (e.g., conservative substitutions, humanising substitutions or affinity variants) in the recited sequence.

Any combination of HCDR3, HCDR2 and HCDR1 from within the recited groups of CDR sequences is permissible, and within the scope of the invention, however certain combinations are particular preferred. Accordingly, in preferred embodiments the antigen or antigen binding fragment thereof may comprise a heavy chain variable domain wherein the combination of HCDR3, HCDR2 and HCDR1 is selected from the following:

(a) the variable heavy chain CDR3 comprises or consists of SEQ ID NO:50 (DAGYSNHVPIFDS) or a sequence variant thereof;
the variable heavy chain CDR2 comprises or consists of SEQ ID NO:27 (DINNEGGTTYYADSVKG) or a sequence variant thereof; and the variable heavy chain CDR1 comprises or consists of SEQ ID NO:11 (VYYMN) or a sequence variant thereof,
wherein the sequence variants comprises one, two or three amino acid substitutions (e.g., conservative substitutions, humanising substitutions or affinity variants) in the recited sequence;

(b) the variable heavy chain CDR3 comprises or consists of SEQ ID NO:50 (RDAGYSNHVPIFDS) or a sequence variant thereof;
the variable heavy chain CDR2 comprises or consists of SEQ ID NO:249 (DINNEGGATYYADSVKG) or a sequence variant thereof; and the variable heavy chain CDR1 comprises or consists of SEQ ID NO:11 (VYYMN) or a sequence variant thereof,
wherein the sequence variants comprises one, two or three amino acid substitutions (e.g., conservative substitutions, humanising substitutions or affinity variants) in the recited sequence.

(c) the variable heavy chain CDR3 comprises or consists of SEQ ID NO:50 (DAGYSNHVPIFDS) or a sequence variant thereof;
the variable heavy chain CDR2 comprises or consists of SEQ ID NO:27 (DINNEGGTTYYADSVKG) or a sequence variant thereof; and
the variable heavy chain CDR1 comprises or consists of SEQ ID NO:248 (GYYMN) or a sequence variant thereof,
wherein the sequence variants comprises one, two or three amino acid substitutions (e.g., conservative substitutions, humanising substitutions or affinity variants) in the recited sequence.

In preferred embodiments, the antibody or antigen binding fragment thereof also includes a light chain variable domain (VL), paired with the heavy chain variable domain, In the preferred light chain variable domains, the variable light chain CDR3 comprises or consists of SEQ ID NO:160 or a sequence variant thereof;

the variable light chain CDR2 comprises or consists of an amino acid sequence selected from the group consisting of: SEQ ID NO:119, SEQ ID NO:110 and sequence variants of the recited sequences; and the variable light chain CDR1 comprises or consists of an amino acid sequence selected from the group consisting of: SEQ ID NO:87, SEQ ID NO:250, SEQ ID NO:251, SEQ ID NO:252, SEQ ID NO:253 and sequence variants of the recited sequences, and wherein the sequence variants comprise one, two or three amino acid substitutions (e.g., conservative substitutions, humanising substitutions or affinity variants) in the recited sequences.

Any combination of LCDR3, LCDR2 and LCDR1 from within the recited groups of light chain CDR sequences is permissible, and within the scope of the invention, however certain combinations are particular preferred. Accordingly, in preferred embodiments the antigen or antigen binding fragment thereof may comprise a light chain variable domain wherein the combination of LCDR3, LCDR2 and LCDR1 is selected from the following:

(a) the variable light chain CDR3 comprises or consists of SEQ ID NO:160 (ALFISNPSVE) or a sequence variant thereof;
the variable light chain CDR2 comprises or consists of SEQ TD NO:119 (NTNTRHS) or a sequence variant thereof; and
the variable light chain CDR1 comprises or consists of SEQ ID NO:250 (GLKSGSVTSDNFPT) or a sequence variant thereof,
wherein the sequence variants comprises one, two or three amino acid substitutions (e.g., conservative substitutions, humanising substitutions or affinity variants) in the recited sequence;

(b) the variable light chain CDR3 comprises or consists of SEQ ID NO:160 (ALFISNPSVE) or a sequence variant thereof;
the variable light chain CDR2 comprises or consists of SEQ ID NO:119 (NTNTRHS) or a sequence variant thereof; and
the variable light chain CDR1 comprises or consists of SEQ ID NO:87 (GLKSGSVTSTNFPT) or a sequence variant thereof,
wherein the sequence variants comprises one, two or three amino acid substitutions (e.g., conservative substitutions, humanising substitutions or affinity variants) in the recited sequence.

Other preferred light chain CDR combinations for human "germlined" variants of 27B3 are given in Table 15A.

The most preferred embodiment of the CD70 antibody or antigen binding fragment thereof comprises a heavy chain variable domain (VH) and a light chain variable domain (VL) wherein the combination of 6 CDRs which forms the binding site for human CD70 is as follows:

the variable heavy chain CDR3 comprises or consists of SEQ ID NO:50 (DAGYSNHVPIFDS) or a sequence variant thereof;

the variable heavy chain CDR2 comprises or consists of SEQ ID NO:27 (DINNEGGTTYYADSVKG) or a sequence variant thereof;

the variable heavy chain CDR1 comprises or consists of SEQ ID NO:11 (VYYMN) or a sequence variant thereof;

the variable light chain CDR3 comprises or consists of SEQ ID NO:160 (ALFISNPSVE) or a sequence variant thereof;

the variable light chain CDR2 comprises or consists of SEQ ID NO:119 (NTNTRHS) or a sequence variant thereof; and the variable light chain CDR1 comprises or consists of SEQ ID NO:250 (GLKSGSVTSDNFPT) or a sequence variant thereof, wherein the sequence variants comprises one, two or three amino acid substitutions (e.g., conservative substitutions, humanising substitutions or affinity variants) in the recited sequence.

Other preferred combinations of 6 CDRs are those "native" combinations which occur in the human germlined variants of 27B3 listed in Tables 14A (heavy chains) and 15A (light chains).

In the foregoing preferred embodiments based on 27B3 and its germlined variants, the antibody preferably includes the CH1 domain, hinge region, CH2 domain and CH3 domain of a human antibody, in particular human IgG1, IgG2, IgG3 or IgG4. The most preferred embodiment is a human IgG1. It is still further preferred for the human IgG1 to be engineering to maximise effector function in one or more of antibody-dependent cellular cytotoxicity (ADCC), complement-dependent cytotoxicity (CDC) or antibody-dependent cellular phagocytosis (ADCP). Particularly preferred is a non-fucosylated human IgG1, e.g. a non-fucosylated IgG1 produced using the Potelligent™ technology of BioWa Inc.

Further preferred CD70 antibodies, exhibiting high affinity binding to human CD70, based on the Fab denoted 27B3 and human germlined variants of 27B3, include isolated antibodies or antigen binding fragments thereof, comprising a heavy chain variable domain having an amino acid sequence selected from the group consisting of: the amino acid sequences of SEQ ID NO:178, SEQ ID NO:212, SEQ ID NO:213, SEQ ID NO:214, SEQ ID NO:215, SEQ ID NO:216, SEQ ID NO:217, SEQ ID NO:218, SEQ ID NO:219, SEQ ID NO:220, SEQ ID NO:221, SEQ ID NO:222, SEQ ID NO:223, SEQ ID NO:224, SEQ ID NO:225, SEQ ID NO:226, SEQ ID NO:227, SEQ ID NO:228, SEQ ID NO:229, SEQ ID NO:274 and SEQ ID NO:275 and amino acid sequences exhibiting at least 90%, 95%, 97%, 98% or 99% sequence identity to one of the recited sequences, and optionally comprising a light chain variable domain having an amino acid sequence selected from the group consisting of: the amino acid sequences of SEQ ID NO:201, SEQ ID NO:230, SEQ ID NO:231, SEQ ID NO:232, SEQ ID NO:233, SEQ ID NO:234, SEQ ID NO:234, SEQ ID NO:236, SEQ ID NO:237, SEQ ID NO:238, SEQ ID NO:239, SEQ ID NO:240, SEQ ID NO:241, SEQ ID NO:242, SEQ ID NO:243, SEQ ID NO:244, SEQ ID NO:245, SEQ ID NO:245, SEQ ID NO:247, SEQ ID NO:248, SEQ ID NO:276 and SEQ ID NO:277 and amino acid sequences exhibiting at least 90%, 95%, 97%, 98% or 99% sequence identity to one of the recited sequences.

Although all possible pairings of VH domains and VL domains selected from the VH and VL domain sequence groups listed above are permissible, and within the scope of the invention, certain combinations VH and VL are particularly preferred; these being the "native" combinations within a single Fab exhibiting high affinity binding to human CD70. In the case of the germlined variants of 27B3 recited in Tables 14B and 15B, it may be preferred to retain the original VH/VL pairing Accordingly, preferred CD70 antibodies, or antigen binding fragments thereof, exhibiting high affinity CD70 binding are those comprising a combination of a heavy chain variable domain and a light chain variable domain, wherein the combination is selected from the group consisting of:

(i) a heavy chain variable domain comprising the amino acid sequence of SEQ ID NO:223 and a light chain variable domain comprising the amino acid sequence of SEQ ID NO:241;

(ii) a heavy chain variable domain comprising the amino acid sequence of SEQ ID NO:178 and a light chain variable domain comprising the amino acid sequence of SEQ ID NO: 190;

(iii) a heavy chain variable domain comprising the amino acid sequence of SEQ ID NO:212 and a light chain variable domain comprising the amino acid sequence of SEQ ID NO: 230

(iv) a heavy chain variable domain comprising the amino acid sequence of SEQ ID NO:213 and a light chain variable domain comprising the amino acid sequence of SEQ ID NO:231;

(v) a heavy chain variable domain comprising the amino acid sequence of SEQ ID NO:214 and a light chain variable domain comprising the amino acid sequence of SEQ ID NO:232;

(vi) a heavy chain variable domain comprising the amino acid sequence of SEQ ID NO:215 and a light chain variable domain comprising the amino acid sequence of SEQ ID NO:235;

(vii) a heavy chain variable domain comprising the amino acid sequence of SEQ ID NO:216 and a light chain variable domain comprising the amino acid sequence of SEQ ID NO:234;

(viii) a heavy chain variable domain comprising the amino acid sequence of SEQ ID NO:217 and a light chain variable domain comprising the amino acid sequence of SEQ ID NO:235;

(ix) a heavy chain variable domain comprising the amino acid sequence of SEQ ID NO:218 and a light chain variable domain comprising the amino acid sequence of SEQ ID NO:236;

(x) a heavy chain variable domain comprising the amino acid sequence of SEQ ID NO:219 and a light chain variable domain comprising the amino acid sequence of SEQ ID NO:237;

(xi) a heavy chain variable domain comprising the amino acid sequence of SEQ ID NO:220 and a light chain variable domain comprising the amino acid sequence of SEQ ID NO:238;

(xii) a heavy chain variable domain comprising the amino acid sequence of SEQ ID NO:221 and a light chain variable domain comprising the amino acid sequence of SEQ ID NO:239;

(xiii) a heavy chain variable domain comprising the amino acid sequence of SEQ ID NO:222 and a light chain variable domain comprising the amino acid sequence of SEQ ID NO:240;

(xiv) a heavy chain variable domain comprising the amino acid sequence of SEQ ID NO:224 and a light chain variable domain comprising the amino acid sequence of SEQ ID NO:242;

(xv) a heavy chain variable domain comprising the amino acid sequence of SEQ ID NO:225 and a light chain variable domain comprising the amino acid sequence of SEQ ID NO:243;

(xvi) a heavy chain variable domain comprising the amino acid sequence of SEQ ID NO:226 and a light chain variable domain comprising the amino acid sequence of SEQ ID NO:244;

(xvii) a heavy chain variable domain comprising the amino acid sequence of SEQ ID NO:227 and a light chain variable domain comprising the amino acid sequence of SEQ ID NO:245;

(xviii) a heavy chain variable domain comprising the amino acid sequence of SEQ ID NO:228 and a light chain variable domain comprising the amino acid sequence of SEQ ID NO:246;

(xix) a heavy chain variable domain comprising the amino acid sequence of SEQ ID NO:229 and a light chain variable domain comprising the amino acid sequence of SEQ ID NO:247;

(xx) a heavy chain variable domain comprising the amino acid sequence of SEQ ID NO:223 and a light chain variable domain comprising the amino acid sequence of SEQ ID NO:244;

(xxi) a heavy chain variable domain comprising the amino acid sequence of SEQ ID NO:223 and a light chain variable domain comprising the amino acid sequence of SEQ ID NO:245.

For each of the specific VH/VL combinations listed above, it is also permissible, and within the scope of the invention, to combine a VH domain having an amino acid sequence at least 90%, 92%, 95%, 97% or 99% identical to the recited VH domain sequence with a VL domain having an amino acid sequence at least 90%, 92%, 95%, 97% or 99% identical to the recited VL domain sequence.

The most preferred embodiment is a CD70 antibody or antigen binding fragment thereof based on the native VH/VL combination of the human germlined variant denoted 41D12. Accordingly, there is also provided herein an antibody or antigen binding fragment thereof comprising a heavy chain variable domain (VH) comprising or consisting of an amino acid sequence selected from the group consisting of: the amino acid sequence shown as SEQ ID NO:223, germlined variants and affinity variants thereof and amino acid sequences at least 90%, 95%, 97%, 98% or 99% identical thereto, and a light chain variable domain (VL) comprising or consisting of an amino acid sequence selected from the group consisting of: the amino acid sequence shown as SEQ ID NO:241, germlined variants and affinity variants thereof and amino acid sequences at least 90%, 95%, 97%, 98% or 99% identical thereto.

Embodiments wherein the amino acid sequence of the VH domain exhibits less than 100% sequence identity with the sequence shown as SEQ ID NO: 223 may nevertheless comprise heavy chain CDRs which are identical to HCDR1, HCDR2 and HCDR3 of SEQ ID NO:223 (SEQ ID NOs:11, 27 and 50, respectively) whilst exhibiting amino acid sequence variation within the framework regions. Likewise, embodiments wherein the amino acid sequence of the VL domain exhibits less than 100% sequence identity with the sequence shown as SEQ ID NO: 241 may nevertheless comprise heavy chain CDRs which are identical to LCDR1, LCDR2 and LCDR3 of SEQ ID NO:241 (SEQ ID NOs:250, 116 and 160, respectively) whilst exhibiting amino acid sequence variation within the framework regions.

In the foregoing preferred embodiments based on the VH and VL domains of 41D12, or variants thereof, the antibody preferably includes the CH1 domain, hinge region, CH2 domain and CH3 domain of a human antibody, in particular human IgG1, IgG2, IgG3 or IgG4. The most preferred embodiment is a human IgG1. It is still further preferred for the human IgG1 to be engineering to maximise effector function in one or more of ADCC, CDC or ADCP. Particularly preferred is a de-fucosylated human IgG1, preferably prepared using the Potelligent™ expression system.

Another advantageous embodiment is an antibody or antigen binding fragment thereof comprising a heavy chain variable domain (VH) comprising or consisting of an amino acid sequence selected from the group consisting of: the amino acid sequence shown as SEQ ID NO:225, germlined variants and affinity variants thereof and amino acid sequences at least 90%, 95%, 97%, 98% or 99% identical thereto, and a light chain variable domain (VL) comprising or consisting of an amino acid sequence selected from the group consisting of: the amino acid sequence shown as SEQ ID NO:243, germlined variants and affinity variants thereof and amino acid sequences at least 90%, 95%, 97%, 98% or 99% identical thereto; or Another advantageous embodiment is an antibody or antigen binding fragment thereof comprising a heavy chain variable domain (VH) comprising or consisting of an amino acid sequence selected from the group consisting of: the amino acid sequence shown as SEQ ID NO:226, germlined variants and affinity variants thereof and amino acid sequences at least 90%, 95%, 97%, 98% or 99% identical thereto, and a light chain variable domain (VL) comprising or consisting of an amino acid sequence selected from the group consisting of: the amino acid sequence shown as SEQ ID NO:244, germlined variants and affinity variants thereof and amino acid sequences at least 90%, 95%, 97%, 98% or 99% identical thereto.

Features/Properties of CD70 Antibodies

In the aforementioned aspects and embodiments, the CD70 antibodies, or antigen binding fragments thereof, may each exhibit one or more, or any combination, of the following properties or features:

The antibody or antigen binding fragment may bind to human CD70 with high affinity, exhibiting an off-rate for human CD70 of $7\times10^{-4}$ $s^{-1}$ or less, preferably $5\times10^{-4}$ $s^{-1}$ or less, and typically in the range of from $0.4\times10^{-4}$ $s^{-1}$ to $4.8\times10^{-4}$ $s^{-1}$, when tested as a Fab fragment.

The antibody or antigen binding fragment may bind to human CD70 with high affinity and inhibit the interaction between CD70 and CD27. Alternatively, the antibody or antigen binding fragment may bind to human CD70 but not inhibit the interaction between CD70 and CD27.

The antibody or antigen binding fragment may bind with high affinity to human CD70 on the surface of CD70-expressing cells.

The antibody or antigen binding fragment may bind to human CD70 on the surface of CD70-expressing cells and be slowly or only partially internalised. A key aspect of the invention is the observation that the CD70 antibodies are in fact very poorly internalised on a large number of CD70-expressing cell-lines, including many CD70-expressing cancer cell lines. This observation is in direct contrast to previous published reports that CD70 antibodies are rapidly internalised following binding to renal cell carcinoma cell lines (see Adam et al., British Journal of Cancer (2006) 95: 298-306; and WO 2007/038637) and has direct implications for therapeutic use of the antibodies. The observation that the CD70 antibodies are very poorly internalised following binding to cancer cells strongly supports the conclusion that therapeutic strategies for treatment of many CD70-expressing cancers, and indeed CD70-associated immunological diseases, should be based on extreme high affinity binding to CD70, coupled with antibody effector function, in particular any one or more of ADCC, CDC or ADCP, and not on the use of immunoconjugates in which the CD70 antibody is linked to a therapeutic agent, e.g. a cytotoxic or cytostatic drug moiety.

The antibody or antigen binding fragment may bind within the amino acid sequence HIQVTLAICSS (SEQ ID NO:342) in human CD70;

The antibody or antigen binding fragment may exhibit cross-reactivity with CD70 of simian origin, specifically the CD70 homologs of rhesus macaque (*Macaca mulatta*) and *cynomolgus* monkey (*Macaca cynomolgus*).

The antibody or antigen binding fragment may bind to both native human CD70 (e.g. CD70 expressed on the surface of a cell, such as a cell line or a CD70-expressing cell isolated from a human patient) and heat denatured recombinant human CD70.

The antibody or antigen binding fragment may provide very high production yields (>4 g/L) in recombinant antibody expression systems, such as for example the CHK1SV cell line (proprietary to BioWa/Lonza), as compared to a 1-2 g/L historical average for therapeutic antibody products, resulting in a substantial reduction in production costs.

The antibody or antigen binding fragment may be highly stable under 37° C. storage conditions and in freeze-thaw cycles, which is also a major cost reduction factor.

The antibody may exhibit one or more effector functions selected from antibody-dependent cell-mediated cytotoxicity (ADCC), complement dependent cytotoxicity (CDC) and antibody-dependent cell-mediated phagocytosis (ADCP) against cells expressing human CD70 protein on the cell surface.

The antibody may exhibit ADCC against CD70-expressing cells, e.g. cancer cells or other malignant cells, or immune cells.

The antibody may exhibit enhanced ADCC function in comparison to a reference antibody which is an equivalent antibody comprising a native human Fc domain. In a non-limiting embodiment, the ADCC function may be at least 10× enhanced in comparison to the reference antibody comprising a native human Fc domain. In this context "equivalent" may be taken to mean that the antibody with enhanced ADCC function displays substantially identical antigen-binding specificity and/or shares identical amino acid sequence with the reference antibody, except for any modifications made (relative to native human Fc) for the purposes of enhancing ADCC.

The antibody or antigen binding fragment may inhibit tumour growth in an in vivo tumour xenograft model, in the absence of conjugation to a cytotoxic or cytostatic agent. In a non-limiting embodiment, the inhibition of tumour growth function may be at least 10 fold enhanced in comparison to the reference antibody SGN70.

The antibody or antigen binding fragment may induce apoptosis of CD70-expressing cells.

The antibody may contain the hinge region, CH2 domain and CH3 domain of a human IgG, most preferably human IgG1, IgG2, IgG3 or IgG4.

The antibody may include modifications in the Fc region, such as modifications which enhance antibody effector function as explained elsewhere herein. In particular, the antibody may be a non-fucosylated IgG.

In further aspects, the invention also provides polynucleotide molecules which encode the above-listed CD70 antibodies and antigen binding fragments thereof, in addition to expression vectors comprising the polynucleotides, host cells containing the vectors and methods of recombinant expression/production of the CD70 antibodies.

In a still further aspect, the invention provides a pharmaceutical composition comprising any one of the CD70 antibodies described above and a pharmaceutically acceptable carrier or excipient.

A still further aspect of the invention concerns methods of medical treatment using the above-listed CD70 antibodies, particularly in the treatment of cancer.

BRIEF DESCRIPTION OF THE DRAWINGS

The invention will be further understood with reference to the following experimental examples and the accompanying Figures in which:

FIG. 2: illustrates inhibition of binding of CD27 to CD70 by llama-derived CD70 Fabs and reference CD70 Fabs, measured by ELISA.

FIG. 4: illustrates inhibition of binding of CD27 to human CD70 (A&B) or rhesus CD70 (C) by chimeric llama-human CD70 mAbs and reference CD70 mAbs measured by ELISA.

FIG. 5: shows binding of chimeric llama-human CD70 mAbs to 786-O cells (A) or MHH-PREB-1 cells (B) as demonstrated by FACS analysis.

FIG. 8: shows the results of CDC assay on U266 cells in the presence of 9% human serum.

FIG. 9: demonstrates the efficacy of chimeric llama-human CD70 mAbs in a ADCP assay on 786-O cells FIG. 10. illustrates antibody internalisation, assessed as MFI OUT for different chimeric llama-human CD70 mAbs as a function of time on 786-O cells in two independent experiments.

FIG. 11: demonstrates survival of mice in a Raji Xenograft model after treatment with chimeric llama-human CD70 mAb 41D12, isotype control and Fc-dead control.

FIG. 12: depicts alignments of the VH and VL amino acid sequences of clone 27B3 with the amino acid sequences of human germline gene segments VH3-38 and VL8-61, respectively.

FIG. 18: shows inhibition of binding of CD27 to CD70 by CD70 mAbs, measured by ELISA.

FIG. 19: shows an alignment of CD70 sequences from different species.

FIG. 23: shows CD70 chimeric sequences used for epitope mapping.

DEFINITIONS

Figure 1:
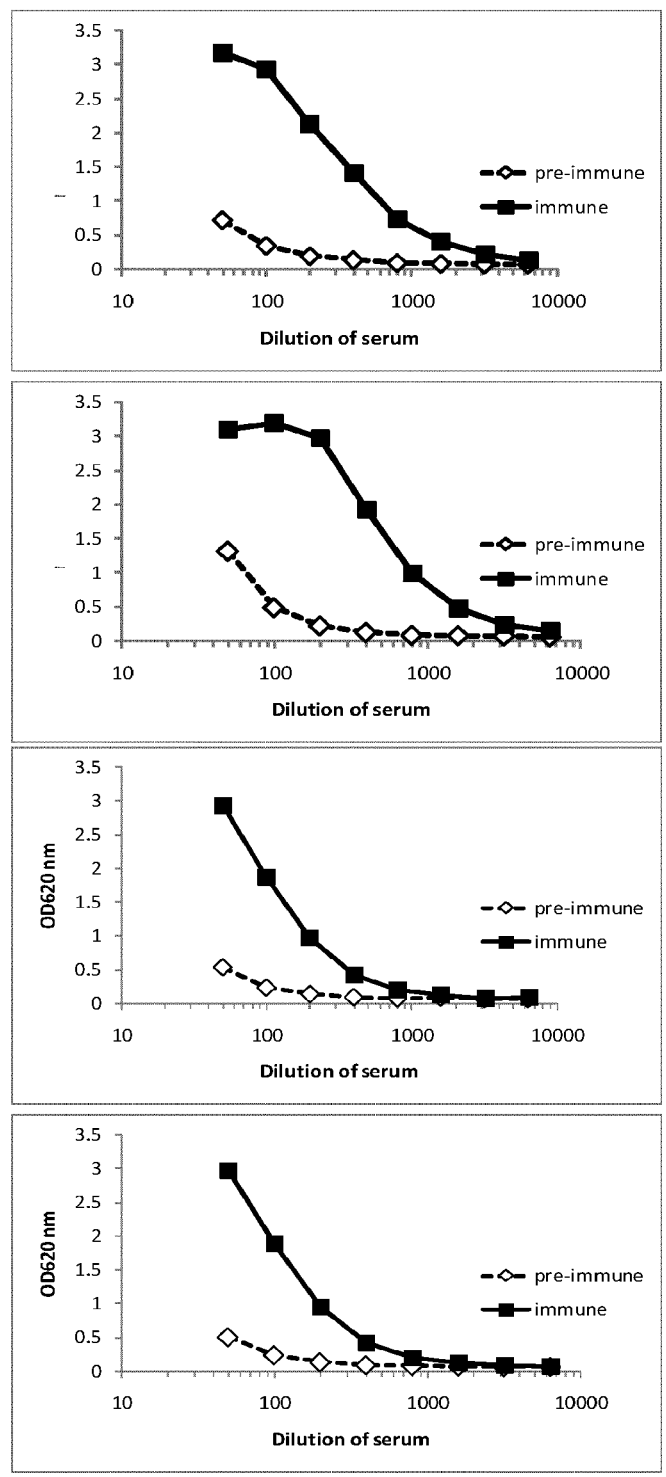
FIG. 1: Shows the immune response tested in ELISA on recombinant CD70 for llamas immunised with 786-O cells (top) and with Raji cells (bottom).

"Antibody" or "Immunoglobulin"—As used herein, the term "immunoglobulin" includes a polypeptide having a combination of two heavy and two light chains whether or not it possesses any relevant specific immunoreactivity. "Antibodies" refers to such assemblies which have significant known specific immunoreactive activity to an antigen of interest (e.g. human CD70). The term "CD70 antibodies" is used herein to refer to antibodies which exhibit immunological specificity for human CD70 protein. As explained elsewhere herein, "specificity" for human CD70 does not exclude cross-reaction with species homologues of CD70. Antibodies and immunoglobulins comprise light and heavy chains, with or without an interchain covalent linkage between them. Basic immunoglobulin structures in vertebrate systems are relatively well understood.

The generic term "immunoglobulin" comprises five distinct classes of antibody that can be distinguished biochemically. All five classes of antibodies are within the scope of the present invention, the following discussion will generally be directed to the IgG class of immunoglobulin molecules. With regard to IgG, immunoglobulins comprise two identical light polypeptide chains of molecular weight approximately 23,000 Daltons, and two identical heavy chains of molecular weight 53,000-70,000. The four chains are joined by disulfide bonds in a "Y" configuration wherein the light chains bracket the heavy chains starting at the mouth of the "Y" and continuing through the variable region.

The light chains of an antibody are classified as either kappa or lambda (κ, λ). Each heavy chain class may be hound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain. Those skilled in the art will appreciate that heavy chains are classified as gamma, mu, alpha, delta, or epsilon, (γ, μ, α, δ, ε) with some subclasses among them (e.g., γ1-γ4). It is the nature of this chain that determines the "class" of the antibody as IgG, IgM, IgA, IgD or IgE, respectively. The immunoglobulin subclasses (isotypes) e.g., IgG1, IgG2, IgG3, IgG4, IgA1, etc. are well characterized and are known to confer functional specialization. Modified versions of each of these classes and isotypes are readily discernable to the skilled artisan in view of the instant disclosure and, accordingly, are within the scope of the instant invention.

As indicated above, the variable region of an antibody allows the antibody to selectively recognize and specifically bind epitopes on antigens. That is, the VL domain and VH domain of an antibody combine to form the variable region that defines a three dimensional antigen binding site. This quaternary antibody structure forms the antigen binding site present at the end of each arm of the Y. More specifically, the antigen binding site is defined by three complementary determining regions (CDRs) on each of the VH and VL chains.

"CD70 protein" or "CD70 antigen"—As used herein, the terms "CD70 protein" or "CD70 antigen" or "CD70" are used interchangeably and refer to a member of the TNF ligand family which is a ligand for TNFRSF27/CD27. The terms "human CD70 protein" or "human CD70 antigen" or "human CD70" are used interchangeably to refer specifically to the human homolog, including the native human CD70 protein naturally expressed in the human body and/or on the surface of cultured human cell lines, as well as recombinant forms and fragments thereof. Specific examples of human CD70 include the polypeptide having the amino acid sequence shown under NCBI Reference Sequence Accession No. NP_001243, or the extracellular domain thereof.

"Binding Site"—As used herein, the term "binding site" comprises a region of a polypeptide which is responsible for selectively binding to a target antigen of interest (e.g. human CD70). Binding domains comprise at least one binding site. Exemplary binding domains include an antibody variable domain. The antibody molecules of the invention may comprise a single binding site or multiple (e.g., two, three or four) binding sites.

"Derived From"—As used herein the term "derived from" a designated protein (e.g. a CD70 antibody or antigen-binding fragment thereof) refers to the origin of the polypeptide. In one embodiment, the polypeptide or amino acid sequence which is derived from a particular starting polypeptide is a CDR sequence or sequence related thereto. In one embodiment, the amino acid sequence which is derived from a particular starting polypeptide is not contiguous. For example, in one embodiment, one, two, three, four, five, or six CDRs are derived from a starting antibody. In one embodiment, the polypeptide or amino acid sequence which is derived from a particular starting polypeptide or amino acid sequence has an amino acid sequence that is essentially identical to that of the starting sequence, or a portion thereof wherein the portion consists of at least of at least 3-5 amino acids, 5-10 amino acids, at least 10-20 amino acids, at least 20-30 amino acids, or at least 30-50 amino acids, or which is otherwise identifiable to one of ordinary skill in the art as having its origin in the starting sequence. In one embodiment, the one or more CDR sequences derived from the starting antibody are altered to produce variant CDR sequences, e.g. affinity variants, wherein the variant CDR sequences maintain CD70 binding activity.

"Camelid-Derived"—In certain preferred embodiments, the CD70 antibody molecules of the invention comprise framework amino acid sequences and/or CDR amino acid sequences derived from a camelid conventional antibody raised by active immunisation of a camelid with CD70 antigen. However, CD70 antibodies comprising camelid-derived amino acid sequences may be engineered to comprise framework and/or constant region sequences derived from a human amino acid sequence (i.e. a human antibody) or other non-camelid mammalian species. For example, a human or non-human primate framework region, heavy chain portion, and/or hinge portion may be included in the subject CD70 antibodies. In one embodiment, one or more non-camelid amino acids may be present in the framework region of a "camelid-derived" CD70 antibody, e.g., a camelid framework amino acid sequence may comprise one or more amino acid mutations in which the corresponding human or non-human primate amino acid residue is present. Moreover, camelid-derived VH and VL domains, or humanised variants thereof, may be linked to the constant domains of human antibodies to produce a chimeric molecule, as extensively described elsewhere herein.

"Conservative amino acid substitution"—A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a non-essential amino acid residue in an immunoglobulin polypeptide may be replaced with another amino acid residue from the same side chain family. In another embodiment, a string of amino acids can be replaced with a structurally similar string that differs in order and/or composition of side chain family members.

"Heavy chain portion"—As used herein, the term "heavy chain portion" includes amino acid sequences derived from the constant domains of an immunoglobulin heavy chain. A polypeptide comprising a heavy chain portion comprises at least one of: a CH1 domain, a hinge (e.g., upper, middle, and/or lower hinge region) domain, a CH2 domain, a CH3 domain, or a variant or fragment thereof. In one embodiment, an antibody or antigen binding fragment of the invention may comprise the Fc portion of an immunoglobulin heavy chain (e.g., a hinge portion, a CH2 domain, and a CH3 domain). In another embodiment, an antibody or antigen binding fragment of the invention may lack at least a portion of a constant domain (e.g., all or part of a CH2 domain). In certain embodiments, at least one, and preferably all, of the constant domains are derived from a human immunoglobulin heavy chain. For example, in one preferred embodiment, the heavy chain portion comprises a fully human hinge domain. In other preferred embodiments, the heavy chain portion comprising a fully human Fc portion (e.g., hinge, CH2 and CH3 domain sequences from a human immunoglobulin).

In certain embodiments, the constituent constant domains of the heavy chain portion are from different immunoglobulin molecules. For example, a heavy chain portion of a polypeptide may comprise a CH2 domain derived from an IgG1 molecule and a hinge region derived from an IgG3 or IgG4 molecule. In other embodiments, the constant domains are chimeric domains comprising portions of different immunoglobulin molecules. For example, a hinge may comprise a first portion from an IgG1 molecule and a second portion from an IgG3 or IgG4 molecule. As set forth above, it will be understood by one of ordinary skill in the art that the constant domains of the heavy chain portion may be modified such that they vary in amino acid sequence from the naturally occurring (wild-type) immunoglobulin molecule. That is, the polypeptides of the invention disclosed herein may comprise alterations or modifications to one or more of the heavy chain constant domains (CH1, hinge, CH2 or CH3) and/or to the light chain constant region domain (CL). Exemplary modifications include additions, deletions or substitutions of one or more amino acids in one or more domains.

"Chimeric"—A "chimeric" protein comprises a first amino acid sequence linked to a second amino acid sequence with which it is not naturally linked in nature. The amino acid sequences may normally exist in separate proteins that are brought together in the fusion polypeptide or they may normally exist in the same protein but are placed in a new arrangement in the fusion polypeptide. A chimeric protein may be created, for example, by chemical synthesis, or by creating and translating a polynucleotide in which the peptide regions are encoded in the desired relationship. Exemplary chimeric CD70 antibodies include fusion proteins comprising camelid-derived VH and VL domains, or humanised variants thereof, fused to the constant domains of a human antibody, e.g. human IgG1, IgG2, IgG3 or IgG4.

"Variable region" or "variable domain"—The terms "variable region" and "variable domain" are used herein interchangeable and are intended to have equivalent meaning. The term "variable" refers to the fact that certain portions of the variable domains VH and VL differ extensively in sequence among antibodies and are used in the binding and specificity of each particular antibody for its target antigen. However, the variability is not evenly distributed throughout the variable domains of antibodies. It is concentrated in three segments called "hypervariable loops" in each of the VL domain and the VH domain which form part of the antigen binding site. The first, second and third hypervariable loops of the VLambda light chain domain are referred to herein as L1($\lambda$), L2($\lambda$) and L3($\lambda$) and may be defined as comprising residues 24-33 (L1($\lambda$), consisting of 9, 10 or 11 amino acid residues), 49-53 (L2($\lambda$), consisting of 3 residues) and 90-96 (L3($\lambda$), consisting of 5 residues) in the VL domain (Morea et al., Methods 20:267-279 (2000)). The first, second and third hypervariable loops of the VKappa light chain domain are referred to herein as L1($\kappa$), L2($\kappa$) and L3($\kappa$) and may be defined as comprising residues 25-33 (L1($\kappa$), consisting of 6, 7, 8, 11, 12 or 13 residues), 49-53 (L2($\kappa$), consisting of 3 residues) and 90-97 (L3($\kappa$), consisting of 6 residues) in the VL domain (Morea et al., Methods 20:267-279 (2000)). The first, second and third hypervariable loops of the VH domain are referred to herein as H1, H2 and H3 and may be defined as comprising residues 25-33 (H1, consisting of 7, 8 or 9 residues), 52-56 (H2, consisting of 3 or 4 residues) and 91-105 (H3, highly variable in length) in the VH domain (Morea et al., Methods 20:267-279 (2000)).

Unless otherwise indicated, the terms L1, L2 and L3 respectively refer to the first, second and third hypervariable loops of a VL domain, and encompass hypervariable loops obtained from both Vkappa and Vlambda isotypes. The terms H1, H2 and H3 respectively refer to the first, second and third hypervariable loops of the VH domain, and encompass hypervariable loops obtained from any of the known heavy chain isotypes, including $\gamma$, $\epsilon$, $\delta$, $\alpha$ or $\mu$.

The hypervariable loops L1, L2, L3, H1, H2 and H3 may each comprise part of a "complementarity determining region" or "CDR", as defined below. The terms "hypervariable loop" and "complementarity determining region" are not strictly synonymous, since the hypervariable loops (HVs) are defined on the basis of structure, whereas complementarity determining regions (CDRs) are defined based on sequence variability (Kabat et al., Sequences of Proteins of Immunological Interest, 5th Ed. Public Health Service, National Institutes of Health, Bethesda, Md., 1983) and the limits of the HVs and the CDRs may be different in some VH and VL domains.

The CDRs of the VL and VH domains can typically be defined as comprising the following amino acids: residues 24-34 (CDRL1), 50-56 (CDRL2) and 89-97 (CDRL3) in the light chain variable domain, and residues 31-35 or 31-35b (CDRH1), 50-65 (CDRH2) and 95-102 (CDRH3) in the heavy chain variable domain; (Kabat et al., Sequences of Proteins of Immunological Interest, 5th Ed. Public Health Service, National Institutes of Health, Bethesda, Md. (1991)). Thus, the HVs may be comprised within the corresponding CDRs and references herein to the "hypervariable loops" of VH and VL domains should be interpreted as also encompassing the corresponding CDRs, and vice versa, unless otherwise indicated.

The more highly conserved portions of variable domains are called the framework region (FR), as defined below. The variable domains of native heavy and light chains each comprise four FRs (FR1, FR2, FR3 and FR4, respectively), largely adopting a β-sheet configuration, connected by the three hypervariable loops. The hypervariable loops in each chain are held together in close proximity by the FRs and, with the hypervariable loops from the other chain, contribute to the formation of the antigen-binding site of antibodies. Structural analysis of antibodies revealed the relationship between the sequence and the shape of the binding site formed by the complementarity determining regions (Chothia et al., J. Mol. Biol. 227: 799-817 (1992)); Tramontano et al., J. Mol. Biol, 215:175-182 (1990)). Despite their high sequence variability, five of the six loops adopt just a small repertoire of main-chain conformations, called "canonical structures". These conformations are first of all determined by the length of the loops and secondly by the presence of key residues at certain positions in the loops and in the framework regions that determine the conformation through their packing, hydrogen bonding or the ability to assume unusual main-chain conformations.

"CDR"—As used herein, the term "CDR" or "complementarity determining region" means the non-contiguous antigen combining sites found within the variable region of both heavy and light chain polypeptides. These particular regions have been described by Kabat et al., J. Biol. Chem. 252, 6609-6616 (1977) and Kabat et al., Sequences of protein of immunological interest. (1991), and by Chothia et al., J. Mol. Biol. 196:901-917 (1987) and by MacCallum et al., J. Mol. Biol. 262:732-745 (1996) where the definitions include overlapping or subsets of amino acid residues when compared against each other. The amino acid residues which encompass the CDRs as defined by each of the above cited references are set forth for comparison. Preferably, the term "CDR" is a CDR as defined by Kabat based on sequence comparisons.

TABLE 1

CDR definitions

| | CDR Definitions | | |
|---|---|---|---|
| | Kabat[1] | Chothia[2] | MacCallum[3] |
| $V_H$ CDR1 | 31-35 | 26-32 | 30-35 |
| $V_H$ CDR2 | 50-65 | 53-55 | 47-58 |
| $V_H$ CDR3 | 95-102 | 96-101 | 93-101 |
| $V_L$ CDR1 | 24-34 | 26-32 | 30-36 |

TABLE 1-continued

CDR definitions

| | CDR Definitions | | |
|---|---|---|---|
| | Kabat[1] | Chothia[2] | MacCallum[3] |
| $V_L$ CDR2 | 50-56 | 50-52 | 46-55 |
| $V_L$ CDR3 | 89-97 | 91-96 | 89-96 |

[1]Residue numbering follows the nomenclature of Kabat et al., supra
[2]Residue numbering follows the nomenclature of Chothia et al., supra
[3]Residue numbering follows the nomenclature of MacCallum et al., supra "Framework region"—The term "framework region" or "FR region" as used herein, includes the amino acid residues that are part of the variable region, but are not part of the CDRs (e.g., using the Kabat definition of CDRs). Therefore, a variable region framework is between about 100-120 amino acids in length but includes only those amino acids outside of the CDRs. For the specific example of a heavy chain variable domain and for the CDRs as defined by Kabat et al., framework region 1 corresponds to the domain of the variable region encompassing amino acids 1-30; framework region 2 corresponds to the domain of the variable region encompassing amino acids 36-49; framework region 3 corresponds to the domain of the variable region encompassing amino acids 66-94, and framework region 4 corresponds to the domain of the variable region from amino acids 103 to the end of the variable region. The framework regions for the light chain are similarly separated by each of the light claim variable region CDRs. Similarly, using the definition of CDRs by Chothia et al. or McCallum et al. the framework region boundaries are separated by the respective CDR termini as described above. In preferred embodiments the CDRs are as defined by Kabat.

In naturally occurring antibodies, the six CDRs present on each monomeric antibody are short, non-contiguous sequences of amino acids that are specifically positioned to form the antigen binding site as the antibody assumes its three dimensional configuration in an aqueous environment. The remainder of the heavy and light variable domains show less inter-molecular variability in amino acid sequence and are termed the framework regions. The framework regions largely adopt a β-sheet conformation and the CDRs form loops which connect, and in some cases form part of, the β-sheet structure. Thus, these framework regions act to form a scaffold that provides for positioning the six CDRs in correct orientation by inter-chain, non-covalent interactions. The antigen binding site formed by the positioned CDRs defines a surface complementary to the epitope on the immunoreactive antigen. This complementary surface promotes the non-covalent binding of the antibody to the immunoreactive antigen epitope. The position of CDRs can be readily identified by one of ordinary skill in the art.

"Hinge region"—As used herein, the term "hinge region" includes the portion of a heavy chain molecule that joins the CH1 domain to the CH2 domain. This hinge region comprises approximately 25 residues and is flexible, thus allowing the two N-terminal antigen binding regions to move independently. Hinge regions can be subdivided into three distinct domains: upper, middle, and lower hinge domains (Roux et al. J. Immunol. 1998 161:4083). CD70 antibodies comprising a "fully human" hinge region may contain one of the hinge region sequences shown in Table 2 below.

TABLE 2

| IgG | Upper hinge | Middle hinge | Lower hinge |
|---|---|---|---|
| | | human hinge sequences | |
| IgG1 | EPKSCDKTHT (SEQ ID NO: 320) | CPRCP (SEQ ID NO: 321) | APELLGGP (SEQ ID NO: 322) |
| IgG3 | ELKTPLGDTTHT (SEQ ID NO: 323) | CPRCP (EPKSCDTPPPCPRCP)$_3$ (SEQ ID NO: 324) | APELLGGP (SEQ ID NO: 325) |
| IgG4 | ESKYGPP (SEQ ID NO: 326) | CPSCP (SEQ ID NO: 327) | APEFLGGP (SEQ ID NO: 328) |
| IgG42 | ERK (SEQ ID NO: 329) | CCVECPPPCP (SEQ ID NO: 330) | APPVAGP (SEQ ID NO: 331) |

"CH2 domain"—As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system, Kabat E A et al. Sequences of Proteins of Immunological Interest. Bethesda, US Department of Health and Human Services, NIH. 1991). The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

"Fragment"—The term "fragment" refers to a part or portion of an antibody or antibody chain comprising fewer amino acid residues than an intact or complete antibody or antibody chain. The term "antigen-binding fragment" refers to a polypeptide fragment of an immunoglobulin or antibody that binds antigen or competes with intact antibody (i.e., with the intact antibody from which they were derived) for antigen binding (i.e., specific binding to human CD70). As used herein, the term "fragment" of an antibody molecule includes antigen-binding fragments of antibodies, for example, an antibody light chain variable domain (VL), an antibody heavy chain variable domain (VH), a single chain antibody (scFv), a F(ab')2 fragment, a Fab fragment, an Fd fragment, an Fv fragment, and a single domain antibody fragment (DAb). Fragments can be obtained, e.g., via chemical or enzymatic treatment of an intact or complete antibody or antibody chain or by recombinant means.

"Valency"—As used herein the term "valency" refers to the number of potential target binding sites in a polypeptide. Each target binding site specifically binds one target molecule or specific site on a target molecule. When a polypeptide comprises more than one target binding site, each target binding site may specifically bind the same or different molecules (e.g., may bind to different ligands or different antigens, or different epitopes on the same antigen). The subject binding molecules have at least one binding site specific for a human CD70 molecule.

"Specificity"—The term "specificity" refers to the ability to bind (e.g., immunoreact with) a given target, e.g., CD70. A polypeptide may be monospecific and contain one or more binding sites which specifically bind a target or a polypeptide may be multispecific and contain two or more binding sites which specifically bind the same or different targets. In one embodiment, an antibody of the invention is specific for more than one target. For example, in one embodiment, a multispecific binding molecule of the invention binds to CD70 and a second molecule expressed on a tumor cell. Exemplary antibodies which comprise antigen binding sites that bind to antigens expressed on tumor cells are known in the art and one or more CDRs from such antibodies can be included in an antibody of the invention.

"Synthetic"—As used herein the term "synthetic" with respect to polypeptides includes polypeptides which comprise an amino acid sequence that is not naturally occurring. For example, non-naturally occurring polypeptides which are modified forms of naturally occurring polypeptides (e.g., comprising a mutation such as an addition, substitution or deletion) or which comprise a first amino acid sequence (which may or may not be naturally occurring) that is linked in a linear sequence of amino acids to a second amino acid sequence (which may or may not be naturally occurring) to which it is not naturally linked in nature.

"Engineered"—As used herein the term "engineered" includes manipulation of nucleic acid or polypeptide molecules by synthetic means (e.g. by recombinant techniques, in vitro peptide synthesis, by enzymatic or chemical coupling of peptides or some combination of these techniques). Preferably, the antibodies of the invention are engineered, including for example, humanized and/or chimeric antibodies, and antibodies which have been engineered to improve one or more properties, such as antigen binding, stability/half-life or effector function.

"Modified antibody"—As used herein, the term "modified antibody" includes synthetic forms of antibodies which are altered such that they are not naturally occurring, e.g., antibodies that comprise at least two heavy chain portions but not two complete heavy chains (such as, domain deleted antibodies or minibodies); multispecific forms of antibodies (e.g., bispecific, trispecific, etc.) altered to bind to two or more different antigens or to different epitopes on a single antigen); heavy chain molecules joined to scFv molecules and the like. ScFv molecules are known in the art and are described, e.g., in U.S. Pat. No. 5,892,019. In addition, the term "modified antibody" includes multivalent forms of antibodies (e.g., trivalent, tetravalent, etc., antibodies that bind to three or more copies of the same antigen). In another embodiment, a modified antibody of the invention is a fusion protein comprising at least one heavy chain portion lacking a CH2 domain and comprising a binding domain of a polypeptide comprising the binding portion of one member of a receptor ligand pair.

The term "modified antibody" may also be used herein to refer to amino acid sequence variants of a CD70 antibody. It will be understood by one of ordinary skill in the art that a CD70 antibody may be modified to produce a variant CD70 antibody which varies in amino acid sequence in comparison to the CD70 antibody from which it was derived. For example, nucleotide or amino acid substitutions leading to conservative substitutions or changes at "non-essential" amino acid residues may be made (e.g., in CDR and/or framework residues). Amino acid substitutions can include replacement of one or more amino acids with a naturally occurring or non-natural amino acid.

"Humanising substitutions"—As used herein, the term "humanising substitutions" refers to amino acid substitutions in which the amino acid residue present at a particular position in the VH or VL domain of a CD70 antibody (for example a camelid-derived CD70 antibody) is replaced with an amino acid residue which occurs at an equivalent position in a reference human VH or VL domain. The reference human VH or VL domain may be a VH or VL domain encoded by the human germline. Humanising substitutions may be made in the framework regions and/or the CDRs of a CD70 antibody, defined herein.

"Humanised variants"—As used herein the term "humanised variant" refers to a variant antibody which contains one or more "humanising substitutions" compared to a reference CD70 antibody, wherein a portion of the reference antibody (e.g. the VH domain and/or the VL domain or parts thereof containing at least one CDR) has an amino derived from a non-human species, and the "humanising substitutions" occur within the amino acid sequence derived from a non-human species.

"Germlined variants"—The term "germlined variant" is used herein to refer specifically to "humanised variants" in which the "humanising substitutions" result in replacement of one or more amino acid residues present at a particular position (s) in the VH or VL domain of a CD70 antibody (for example a camelid-derived CD70 antibody) with an amino acid residue which occurs at an equivalent position in a reference human VH or VL domain encoded by the human germline. It is typical that for any given "germlined variant", the replacement amino acid residues substituted into the germlined variant are taken exclusively, or predominantly, from a single human germline-encoded VH or VL domain. The terms "humanised variant" and "germlined variant" are often used interchangeably herein. Introduction of one or more "humanising substitutions" into a camelid-derived (e.g. llama derived) VH or VL domain results in production of a "humanised variant" of the camelid (llama)-derived VH or VL domain. If the amino acid residues substituted in are derived predominantly or exclusively from a single human germline-encoded VH or VL domain sequence, then the result may be a "human germlined variant" of the camelid (llama)-derived VH or VL domain.

"Affinity variants"—As used herein, the term "affinity variant" refers to a variant antibody which exhibits one or more changes in amino acid sequence compared to a reference CD70 antibody, wherein the affinity variant exhibits an altered affinity for the human CD70 protein in comparison to the reference antibody. Typically, affinity variants will exhibit a changed affinity for human CD70, as compared to the reference CD70 antibody. Preferably the affinity variant will exhibit improved affinity for human CD70, as compared to the reference CD70 antibody. The improvement may be apparent as a lower $K_D$, for human CD70, or a slower off-rate for human CD70 or an alteration in the pattern of cross-reactivity with non-human CD70 homologues. Affinity variants typically exhibit one or more changes in amino acid sequence in the CDRs, as compared to the reference CD70 antibody. Such substitutions may result in replacement of the original amino acid present at a given position in the CDRs with a different amino acid residue, which may be a naturally occurring amino acid residue or a non-naturally occurring amino acid residue. The amino acid substitutions may be conservative or non-conservative.

"High human homology"—An antibody comprising a heavy chain variable domain (VH) and a light chain variable domain (VL) will be considered as having high human homology if the VH domains and the VL domains, taken together, exhibit at least 90% amino acid sequence identity to the closest matching human germline VH and VL sequences. Antibodies having high human homology may include antibodies comprising VH and VL domains of native non-human antibodies which exhibit sufficiently high % sequence identity to human germline sequences, including for example antibodies comprising VH and VL domains of camelid conventional antibodies, as well as engineered, especially humanised or germlined, variants of such antibodies and also "fully human" antibodies.

In one embodiment the VH domain of the antibody with high human homology may exhibit an amino acid sequence identity or sequence homology of 80% or greater with one or more human VH domains across the framework regions FR1, FR2, FR3 and FR4. In other embodiments the amino acid sequence identity or sequence homology between the VH domain of the polypeptide of the invention and the closest matching human germline VH domain sequence may be 85% or greater, 90% or greater, 95% or greater, 97% or greater, or up to 99% or even 100%.

In one embodiment the VH domain of the antibody with high human homology may contain one or more (e.g. 1 to 10) amino acid sequence mis-matches across the framework regions FR1, FR2, FR3 and FR4, in comparison to the closest matched human VH sequence.

In another embodiment the VL domain of the antibody with high human homology may exhibit a sequence identity or sequence homology of 80% or greater with one or more human VL domains across the framework regions FR1, FR2, FR3 and FR4. In other embodiments the amino acid sequence identity or sequence homology between the VL domain of the polypeptide of the invention and the closest matching human germline VL domain sequence may be 85% or greater 90% or greater, 95% or greater, 97% or greater, or up to 99% or even 100%.

In one embodiment the VL domain of the antibody with high human homology may contain one or more (e.g. 1 to 10) amino acid sequence mis-matches across the framework regions FR1, FR2, FR3 and FR4, in comparison to the closest matched human VL sequence.

Before analyzing the percentage sequence identity between the antibody with high human homology and human germline VH and VL, the canonical folds may be determined, which allows the identification of the family of human germline segments with the identical combination of canonical folds for H1 and H2 or L1 and L2 (and L3). Subsequently the human germline family member that has the highest degree of sequence homology with the variable region of the antibody of interest is chosen for scoring the sequence homology. The determination of Chothia canonical classes of hypervariable loops L1, L2, L3, H1 and H2 can be performed with the bioinformatics tools publicly available on webpage www.bioinf.org.uk/abs/chothia.html.page. The output of the program shows the key residue requirements in a datafile. In these datafiles, the key residue positions are shown with the allowed amino acids at each position. The sequence of the variable region of the antibody of interest is given as input and is first aligned with a consensus antibody sequence to assign the Kabat numbering scheme. The analysis of the canonical folds uses a set of key residue templates derived by an automated method developed by Martin and Thornton (Martin et al., J. Mol. Biol. 263:800-815 (1996)).

With the particular human germline V segment known, which uses the same combination of canonical folds for H1 and H2 or L1 and L2 (and L3), the best matching family member in terms of sequence homology can be determined. With bioinformatics tools the percentage sequence identity between the VH and VL domain framework amino acid sequences of the antibody of interest and corresponding sequences encoded by the human germline can be determined, but actually manual alignment of the sequences can be applied as well. Human immunoglobulin sequences can be identified from several protein data bases, such as VBase (http://vbase.mrc-cpe.cam.ac.uk/) or the Pluckthun/Honegger database (http://www.bioc.unizh.ch/antibody/Sequences/Germlines. To compare the human sequences to the V regions of VH or VL domains in an antibody of interest a sequence alignment algorithm such as available via websites like www.expasy.ch/tools/#align can be used, but also manual alignment with the limited set of sequences can be performed. Human germline light and heavy chain sequences of the families with the same combinations of canonical folds and with the highest degree of homology with the framework regions 1, 2, and 3 of each chain are selected and compared with the variable region of interest; also the FR4 is checked against the human germline JH and JK or JL regions.

Note that in the calculation of overall percent sequence homology the residues of FR1, FR2 and FR3 are evaluated using the closest match sequence from the human germline family with the identical combination of canonical folds. Only residues different from the closest match or other members of the same family with the same combination of canonical folds are scored (NB—excluding any primer-encoded differences). However, for the purposes of humanization, residues in framework regions identical to members of other human germline families, which do not have the same combination of canonical folds, can be considered "human", despite the fact that these are scored "negative" according to the stringent conditions described above. This assumption is based on the "mix and match" approach for humanization, in which each of FR1, FR2, FR3 and FR4 is separately compared to its closest matching human germline sequence and the humanized molecule therefore contains a combination of different FRs as was done by Qu and colleagues (Qu et la., Clin. Cancer Res. 5:3095-3100 (1999)) and Ono and colleagues (Ono et al., Mol. Immunol. 36:387-395 (1999)). The boundaries of the individual framework regions may be assigned using the IMGT numbering scheme, which is an adaptation of the numbering scheme of Chothia (Lefranc et al., NAR 27: 209-212 (1999); imgt.cines.fr).

Antibodies with high human homology may comprise hypervariable loops or CDRs having human or human-like canonical folds, as discussed in detail below. In one embodiment at least one hypervariable loop or CDR in either the VH domain or the VL domain of the antibody with high human homology may be obtained or derived from a VH or VL domain of a non-human antibody, for example a conventional antibody from a species of Camelidae, yet exhibit a predicted or actual canonical fold structure which is substantially identical to a canonical fold structure which occurs in human antibodies.

It is well established in the art that although the primary amino acid sequences of hypervariable loops present in both VH domains and VL domains encoded by the human germline are, by definition, highly variable, all hypervariable loops, except CDR H3 of the VH domain, adopt only a few distinct structural conformations, termed canonical folds (Chothia et al., J. Mol. Biol. 196:901-917 (1987); Tramontano et al. Proteins 6:382-94 (1989)), which depend on both the length of the hypervariable loop and presence of the so-called canonical amino acid residues (Chothia et al., J. Mol. Biol. 196:901-917 (1987)). Actual canonical structures of the hypervariable loops in intact VH or VL domains can be determined by structural analysis (e.g. X-ray crystallography), but it is also possible to predict canonical structure on the basis of key amino acid residues which are characteristic of a particular structure (discussed further below). In essence, the specific pattern of residues that determines each canonical structure forms a "signature" which enables the canonical structure to be recognised in hypervariable loops of a VH or VL domain of unknown structure; canonical structures can therefore be predicted on the basis of primary amino acid sequence alone.

The predicted canonical fold structures for the hypervariable loops of any given VH or VL sequence in an antibody with high human homology can be analysed using algorithms which are publicly available from www.bioinf.org.uk/abs/chothia.html, www.biochem.ucl.ac.uk/~martin/antibodies.html and www.bioc.unizh.ch/antibody/Sequences/Germlines/Vbase_hVk.html. These tools permit query VH or VL sequences to be aligned against human VH or VL domain sequences of known canonical structure, and a prediction of canonical structure made for the hypervariable loops of the query sequence.

In the case of the VH domain, H1 and H2 loops may be scored as having a canonical fold structure "substantially identical" to a canonical fold structure known to occur in human antibodies if at least the first, and preferable both, of the following criteria are fulfilled:
1. An identical length, determined by the number of residues, to the closest matching human canonical structural class.
2. At least 33% identity, preferably at least 50% identity with the key amino acid residues described for the corresponding human H1 and H2 canonical structural classes.
(note for the purposes of the foregoing analysis the H1 and H2 loops are treated separately and each compared against its closest matching human canonical structural class)

The foregoing analysis relies on prediction of the canonical structure of the H1 and H2 loops of the antibody of interest. If the actual structures of the H1 and H2 loops in the antibody of interest are known, for example based on X-ray crystallography, then the H1 and H2 loops in the antibody of interest may also be scored as having a canonical fold structure "substantially identical" to a canonical fold structure known to occur in human antibodies if the length of the loop differs from that of the closest matching human canonical structural class (typically by ±1 or ±2 amino acids) but the actual structure of the H1 and H2 loops in the antibody of interest matches the structure of a human canonical fold.

Key amino acid residues found in the human canonical structural classes for the first and second hypervariable loops of human VH domains (H1 and H2) are described by Chothia et al., J. Mol. Biol. 227:799-817 (1992), the contents of which are incorporated herein in their entirety by reference. In particular, Table 3 on page 802 of Chothia et al., which is specifically incorporated herein by reference, lists preferred amino acid residues at key sites for H1 canonical structures found in the human germline, whereas Table 4 on page 803, also specifically incorporated by reference, lists preferred amino acid residues at key sites for CDR H2 canonical structures found in the human germline.

In one embodiment, both H1 and H2 in the VH domain of the antibody with high human homology exhibit a predicted or actual canonical fold structure which is substantially identical to a canonical fold structure which occurs in human antibodies.

Antibodies with high human homology may comprise a VH domain in which the hypervariable loops H1 and H2 form a combination of canonical fold structures which is identical to a combination of canonical structures known to occur in at least one human germline VH domain. It has been observed that only certain combinations of canonical fold structures at H1 and H2 actually occur in VH domains encoded by the human germline. In an embodiment H1 and H2 in the VH domain of the antibody with high human homology may be obtained from a VH domain of a non-human species, e.g. a Camelidae species, yet form a combination of predicted or actual canonical fold structures which is identical to a combination of canonical fold structures known to occur in a human germline or somatically mutated VH domain. In non-limiting embodiments H1 and H2 in the VH domain of the antibody with high human homology may be obtained from a VH domain of a non-human species, e.g. a Camelidae species, and form one of the following canonical fold combinations: 1-1, 1-2, 1-3, 1-6, 1-4, 2-1, 3-1 and 3-5.

An antibody with high human homology may contain a VH domain which exhibits both high sequence identity/ sequence homology with human VH, and which contains hypervariable loops exhibiting structural homology with human VH.

It may be advantageous for the canonical folds present at H1 and H2 in the VH domain of the antibody with high human homology, and the combination thereof, to be "correct" for the human VH germline sequence which represents the closest match with the VH domain of the antibody with high human homology in terms of overall primary amino acid sequence identity. By way of example, if the closest sequence match is with a human germline VH3 domain, then it may be advantageous for H1 and H2 to form a combination of canonical folds which also occurs naturally in a human VH3 domain. This may be particularly important in the case of antibodies with high human homology which are derived from non-human species, e.g. antibodies containing VH and VL domains which are derived from camelid conventional antibodies, especially antibodies containing humanised camelid VH and VL domains.

Thus, in one embodiment the VH domain of the CD70 antibody with high human homology may exhibit a sequence identity or sequence homology of 80% or greater, 85% or greater, 90% or greater, 95% or greater, 97% or greater, or up to 99% or even 100% with a human VH domain across the framework regions FR1, FR2, FR3 and FR4, and in addition H1 and H2 in the same antibody are obtained from a non-human VH domain (e.g. derived from a Camelidae species), but form a combination of predicted or actual canonical fold structures which is the same as a canonical fold combination known to occur naturally in the same human VH domain.

In other embodiments, L1 and L2 in the VL domain of the antibody with high human homology are each obtained from a VL domain of a non-human species (e.g. a camelid-derived VL domain), and each exhibits a predicted or actual canonical fold structure which is substantially identical to a canonical fold structure which occurs in human antibodies.

As with the VH domains, the hypervariable loops of VL domains of both VLambda and VKappa types can adopt a limited number of conformations or canonical structures, determined in part by length and also by the presence of key amino acid residues at certain canonical positions.

Within an antibody of interest having high human homology, L1, L2 and L3 loops obtained from a VL domain of a non-human species, e.g. a Camelidae species, may be scored as having a canonical fold structure "substantially identical" to a canonical fold structure known to occur in human antibodies if at least the first, and preferable both, of the following criteria are fulfilled:

1. An identical length, determined by the number of residues, to the closest matching human structural class.
2. At least 33% identity, preferably at least 50% identity with the key amino acid residues described for the corresponding human L1 or L2 canonical structural classes, from either the VLambda or the VKappa repertoire.

(note for the purposes of the foregoing analysis the L1 and L2 loops are treated separately and each compared against its closest matching human canonical structural class)

The foregoing analysis relies on prediction of the canonical structure of the L1, L2 and L3 loops in the VL domain of the antibody of interest. If the actual structure of the L1, L2 and L3 loops is known, for example based on X-ray crystallography, then L1, L2 or L3 loops derived from the antibody of interest may also be scored as having a canonical fold structure "substantially identical" to a canonical fold structure known to occur in human antibodies if the length of the loop differs from that of the closest matching human canonical structural class (typically by ±1 or ±2 amino acids) but the actual structure of the Camelidae loops matches a human canonical fold.

Key amino acid residues found in the human canonical structural classes for the CDRs of human VLambda and VKappa domains are described by Morea et al. Methods, 20: 267-279 (2000) and Martin et al., J. Mol. Biol., 263:800-815 (1996). The structural repertoire of the human VKappa domain is also described by Tomlinson et al. EMBO J. 14:4628-4638 (1995), and that of the VLambda domain by Williams et al. J. Mol. Biol., 264:220-232 (1996). The contents of all these documents are to be incorporated herein by reference.

L1 and L2 in the VL domain of an antibody with high human homology may form a combination of predicted or actual canonical fold structures which is identical to a combination of canonical fold structures known to occur in a human germline VL domain. In non-limiting embodiments L1 and L2 in the VLambda domain of an antibody with high human homology (e.g. an antibody containing a camelid-derived VL domain or a humanised variant thereof) may form one of the following canonical fold combinations: 11-7, 13-7(A,B,C), 14-7(A,B), 12-11, 14-11 and 12-12 (as defined in Williams et al. J. Mol. Biol. 264:220-32 (1996) and as shown on http://www.bioc.uzh.ch/antibody/Sequences/Germlines/VBase_hVL.html). In non-limiting embodiments L1 and L2 in the Vkappa domain may form one of the following canonical fold combinations: 2-1, 3-1, 4-1 and 6-1 (as defined in Tomlinson et al. EMBO J. 14:4628-38 (1995) and as shown on http://www.bioc.uzh.ch/antibody/Sequences/Germlines/VBase_hVK.html).

In a further embodiment, all three of L1, L2 and L3 in the VL domain of an antibody with high human homology may exhibit a substantially human structure. It is preferred that the VL domain of the antibody with high human homology exhibits both high sequence identity/sequence homology with human VL, and also that the hypervariable loops in the VL domain exhibit structural homology with human VL.

In one embodiment, the VL domain of a CD70 antibody with high human homology may exhibit a sequence identity of 80% or greater, 85% or greater, 90% or greater, 95% or greater, 97% or greater, or up to 99% or even 100% with a human VL domain across the framework regions FR1, FR2, FR3 and FR4, and in addition hypervariable loop L1 and hypervariable loop L2 may form a combination of predicted or actual canonical fold structures which is the same as a canonical fold combination known to occur naturally in the same human VL domain.

It is, of course, envisaged that VH domains exhibiting high sequence identity/sequence homology with human VH, and also structural homology with hypervariable loops of human VH will be combined with VL domains exhibiting high sequence identity/sequence homology with human VL, and also structural homology with hypervariable loops of human VL to provide antibodies with high human homology containing VH/VL pairings (e.g camelid-derived VH/V1 pairings) with maximal sequence and structural homology to human-encoded VH/VL pairings.

As summarised above, the invention relates, at least in part, to antibodies, and antigen binding fragments thereof, that bind to human CD70 with high affinity. The properties and characteristics of the CD70 antibodies, and antibody fragments, according to the invention will now be described in further detail.

CD70 Binding and Affinity

In certain aspects, the antibodies, and antigen binding fragments thereof, provided herein bind to human CD70 with high affinity. Antibodies, or antigen binding fragments thereof, which bind to human CD70 with high affinity may exhibit a binding affinity ($K_D$) for human CD70, and more particularly the extracellular domain of human CD70, of about 10 nM or less, or 1 nM or less, or 0.1 nM or less, or 10 pM or less.

The CD70 antibody (or antigen binding fragment) may comprise VH and VL domains which, when the VH and VL domains are expressed in the form of a Fab, exhibit a dissociation off-rate for human CD70 binding of less than $7 \times 10^{-4}$ $s^{-1}$, preferably less than $5 \times 10^{-4}$ $s^{-1}$, or less than $2 \times 10^{-4}$ $s^{-1}$, less than $1 \times 10^{-4}$ $s^{-1}$. Typically the off rate will fall in the range of from $0.4 \times 10^{-4}$ $s^{-1}$ to $4.8 \times 10^{-4}$ $s^{-1}$. Binding affinity ($K_D$) and dissociation rate ($K_{off}$) can be measured using standard techniques well known to persons skilled in the art, such as for example surface plasmon resonance (BIAcore), as described in the accompanying examples. In brief, 50 µl of sample to be tested is added to 200 µl PBS+0.02% Tween, and diluted 1/400 as follows: 5 µl of sample (1 mg/ml)+195 µl HBS-EP+ (Biacore buffer), further diluted 10 µl+90 µl HVS-EP+=2.5 µg/ml. Biacore analysis is performed at room temperature using a highly CD70 coated CM5 chip (4000 RU) using the manufacturer's supplied protocol.

In this regard, it should be noted that although the off-rate is measured for VH and VL combinations in the form of Fabs, this does not mean that the VH and VL domains contribute equally to CD70 binding. For many VH/VL combinations, it is the VH domain which mainly contributes to CD70 binding, with the VL domain contributing to solubility and/or stability of the VH/VL pairing.

Binding of the CD70 antibodies described herein, or Fab fragments thereof, to recombinant human CD70 may also be assessed by ELISA.

The CD70 antibodies described herein may further exhibit binding to CD70 expressed on the surface of intact cells, e.g. 786-O renal carcinoma cells and other cancer cell lines. Binding of CD70 antibodies to CD70-expressing cells may be assessed by flow cytometry. The results presented in the accompanying examples demonstrate that preferred CD70 antibodies, including variant 41D12 (when expressed as non-fucosylated IgG1 ARGX-110), exhibit very strong binding to cell-surface CD70. Indeed, for many cell lines ARGX-110 exhibits stronger binding than comparator prior art antibody SGN70.

It is particularly noteworthy that ARGX-110 exhibits strong binding to cell lines which express CD70 at low copy number, including inter alia the cell lines Raji, SU-DHL-6, MHHPREB1, Mino, Mec1, JVM-2, HH and EBC-1, and also to cancer cells isolated from patients (e.g. CLL patients), in both cases the binding of ARGX-110 is markedly stronger than SGN70. The "improved" binding to low copy number cell lines and CLL patient materials may in large part reflect the extremely high affinity of ARGX-110 for recombinant CD70. These binding characteristics are supportive of a particular utility of ARGX-110 (based on 41D12) and other CD70 antibodies described herein with similar properties in cancer treatment, particularly when utilised as an IgG exhibiting potent effector function (e.g. non-fucosylated IgG1) rather than as an immunoconjugate linked to a cytotoxic or cytostatic moiety. The significance of high affinity binding (i.e. higher affinity than can be achieved with prior art CD70 antibodies) to recombinant CD70 and cell surface CD70 with regard to clinical utility of the antibodies is demonstrated in the accompanying examples by experiments in which PBMC samples are "spiked" with cancer cell lines and then treated with CD70 antibodies. In this system treatment with ARGX-110 produced significantly more lysis of the target cancer cells than the comparator CD70 antibodies MDX1411 and SGN70.

The CD70 antibodies described herein exhibit high affinity binding to human CD70, and more specifically the extracellular domain of human CD70, but cross-reactivity with non-human homologues of CD70 is not excluded. Indeed, it is an advantageous feature of many of the CD70 antibodies described herein, including 27B3 and its germlined variants, particularly 41D12, that in addition to high affinity binding to human CD70 they also cross-react with simian CD70 homologs, specifically the CD70 homologs of rhesus macaque and *cynomolgus* monkey.

In this regard, a CD70 antibody can be considered to exhibit cross-reactivity with a simian CD70 homolog, for example the CD70 homologs of rhesus macaque and *cynomolgus* monkey, if the difference in IC50 for human versus simian (rhesus or *cynomolgus* monkey) CD70 in a CD70-CD27 inhibition ELISA, such as that described in the accompanying example 20.2, is less than 5-fold, preferably less than 3-fold or less than 2-fold. The binding affinity, and therefore blocking potency, for human and simian CD70 should be broadly comparable.

Interaction Between CD70 and CD27

In certain aspects, the CD70 antibodies, or antigen binding fragments thereof, provided herein may bind to human CD70 with high affinity and block the interaction between CD70 and CD27.

The ability of CD70 antibodies, or antigen binding fragments thereof, to block binding of CD70 to CD27 may be assessed by Elisa using either captured recombinant CD70 (Flag-TNC-CD70) or directed coated CD70 and recombinant CD27-Fc. The CD70 antibodies described herein may inhibit the interaction between CD70 and CD27 with an IC50 of 300 ng/ml or less, or 200 ng/ml or less, or 110 ng/ml or less, or 70 ng/ml or less, or 50 ng/ml or less.

The ability of CD70 antibodies, or antigen binding fragments thereof, to block binding of CD70 to CD27 may also be assessed in an assay based on co-culture of Raji cells (human B cell lymphoma) and HT1080-CD27 cells (human epithelial cell line transfected with CD27), as described in the accompanying examples. The CD70 antibodies described which inhibit the interaction between CD70 and CD27 may exhibit an IC50 in this co-culture assay of 500 ng/ml or less, or 300 ng/ml or less, or 100 ng/ml or less, or 50 ng/ml or less, or 30 ng/ml or less.

The preferred CD70 antibodies based on 27B3 and germlined variants thereof, including 41D12 (ARGX-110) exhibit potent blocking of the CD70/CD27 interaction in the Elisa system. Indeed, ARGX-110 is significantly more potent in blocking CD70/CD27 interactions than comparator antibodies SGN70 and MDX1411. The interaction between CD70 and CD27 may contribute to tumour cell survival, proliferation and/or immune suppression within the tumour microenvironment. Accordingly, potent inhibition of the CD70/CD27 interaction, in addition to high affinity binding to CD70, may contribute to improved clinical outcome in the treatment of certain CD70-expressing cancers or immunological disorders, for example autoimmune diseases and cancers which co-express CD70 and CD27.

In other embodiments, the CD70 antibodies, or antigen binding fragments thereof, may bind to human CD70 but not inhibit the interaction between CD70 and CD27. CD70 antibodies which bind CD70 but do not inhibit the interaction between CD70 and CD27 can be assessed based on Elisa using either captured recombinant CD70 (Flag-TNC-CD70) or directed coated CD70 and recombinant CD27-Fc. As demonstrated in the accompanying examples, a number of Fabs have been identified which bind CD70 but do not inhibit the CD70/CD27 interaction to a significant extent. In particular, the Fab clone identified herein as 59D10 exhibits strong binding to recombinant CD70 as measured by Biacore but does not block the CD70/CD27 interaction to a significant extent, when assessed by ELISA. CD70 antibodies described herein which bind CD70 but do not inhibit the interaction between CD70 and CD27 may still possess intact antibody effector functions, i.e. one or more of ADCC, CDC, ADCP or ADC and inhibit tumour cell growth in vivo. CD70 antibodies which bind CD70 with high affinity but are non-blocking may be advantageously utilised as "one-armed" antibodies, or PEGylated Fab products or in any other antibody format which provides a strict monovalent interaction with a target cell expressing CD70.

CD70 Epitopes

In certain aspects, the CD70 antibodies described herein bind to epitopes within the extracellular domain of human CD70.

The term "epitope" refers to the portion(s) of an antigen (e.g. human CD70) that contact an antibody. Epitopes can be linear, i.e., involving binding to a single sequence of amino acids, or conformational, i.e., involving binding to two or more sequences of amino acids in various regions of the antigen that may not necessarily be contiguous.

The CD70 antibodies provided herein may bind to different (overlapping or non-overlapping) epitopes within the extracellular domain of the human CD70 protein. For example, the Fabs denoted 1C2 and 9E1 in the accompanying examples clearly bind to different, non-overlapping epitopes on human CD70.

As noted elsewhere herein, the preferred CD70 antibody 41D12 (ARGX-110) exhibits a particularly useful combination of binding characteristics which is not exhibited by any known prior art CD70 antibody, namely:

(a) binding within the amino acid sequence HIQVTLAICSS (SEQ ID NO:342) in human CD70;
(b) cross-reactivity with CD70 homologs of rhesus macaque (*Macaca mulatta*) and cynomolgus monkey (*Macaca cynomolgus*);
(c) binding to native human CD70 and heat denatured recombinant human CD70.

For any given CD70 antibody, the ability to bind human CD70 within the amino acid sequence HIQVTLAICSS (SEQ ID NO:342) can be readily determined by a person of ordinary skill in the art, for example using the mouse-human chimeric CD70 binding analysis described in the accompanying example 20.4.

Cross-reactivity with simian CD70 homologs can also be readily determined by a person of ordinary skill in the art, for example by FACs analysis, surface plasmon resonance (Biacore™) or using a CD70-CD27 inhibition ELISA. In this regard, a CD70 antibody can be considered to exhibit cross-reactivity with a simian CD70 homolog, for example the CD70 homologs of rhesus macaque and cynomolgus monkey, if the difference in IC50 for human versus simian (rhesus or cynomolgus monkey) CD70 in a CD70-CD27 inhibition ELISA, such as that described in the accompanying example 20.2, is less than 5-fold, preferably less than 3-fold or less than 2-fold.

The CD70 antibodies described herein may also demonstrate the ability to bind both native human CD70 and heat denatured recombinant human CD70. In this connection, binding to "native" human CD70 is indicated by binding to CD70 expressed on the surface of a CD70-expressing cell, such as any of the CD70+ cell lines described in the accompanying examples, or even natural CD70-expressing cells isolated from patient material (e.g. cells isolated from CLL patients as in the accompanying examples), activated T cells, etc. Binding to "native" human CD70 can thus be easily tested by a person of ordinary skill in the art.

Binding to heat denatured recombinant human CD70 can be tested as described in the accompanying example 20.3. It is preferred that the CD70 antibody should exhibit an OD at 620 nm of 0.6 or greater in this assay, in order to demonstrate significant binding to heat denatured recombinant human CD70.

Partial or Slow Internalisation

The CD70 antibodies described herein, including the preferred CD70 antibody 41D12 (ARGX-110), exhibit partial internalisation in renal carcinoma cell lines, meaning that when antibody internalisation is tested in 786-O renal carcinoma cells a substantial proportion of the bound antibody, i.e. at least 30-40%, remains external after 6 hours, and even after 24 hours, incubation at 37° C. In addition, the CD70 antibodies may also exhibit a slow rate of internalisation. In this regard, a CD70 antibody is considered to exhibit slow internalisation if it is internalised at a slower rate than a reference CD70 antibody 9D1 (VH SEQ ID NO:178; VL SEQ ID NO:190).

As demonstrated in the accompanying examples, different cancer cell lines exhibit significant differences in the degree of internalisation of CD70 antibodies. It is particularly significant that the majority of cancer cell lines exhibit less than 30%, and even less than 10%, internalisation of bound CD70 antibody, even after 6 hours incubation with ARGX-110. These results are clearly supportive of the utility of CD70 antibodies with potent effector function (including variants engineered for enhanced effector function) in the treatment of CD70-expressing cancers. It has previously been reported in the scientific literature that CD70 is an "internalising" target; hence it has been proposed to develop CD70 antibody-drug immunoconjugates for treatment of both CD70-expressing cancers and immunological diseases. Therefore, the results presented herein, which conclusively demonstrate that internalisation of cell-surface bound CD70 antibodies is a rare event and that the majority of CD70-expressing cell lines do not internalise bound CD70 antibody to a significant extent, are extremely surprising.

Camelid-Derived CD70 Antibodies

In yet other aspects, the antibodies or antigen binding fragments thereof described herein may comprise at least one hypervariable loop or complementarity determining region obtained from a VH domain or a VL domain of a species in the family Camelidae. In particular, the antibody or antigen binding fragment may comprise VH and/or VL domains, or CDRs thereof, obtained by active immunisation of outbred camelids, e.g. llamas, with a human CD70 antigen.

By "hypervariable loop or complementarity determining region obtained from a VH domain or a VL domain of a species in the family Camelidae" is meant that that hypervariable loop (HV) or CDR has an amino acid sequence which is identical, or substantially identical, to the amino acid sequence of a hypervariable loop or CDR which is encoded by a Camelidae immunoglobulin gene. In this context "immunoglobulin gene" includes germline genes, immunoglobulin genes which have undergone rearrangement, and also somatically mutated genes. Thus, the amino acid sequence of the HV or CDR obtained from a VH or VL domain of a Camelidae species may be identical to the amino acid sequence of a HV or CDR present in a mature Camelidae conventional antibody. The term "obtained from" in this context implies a structural relationship, in the sense that the HVs or CDRs of the CD70 antibody embody an amino acid sequence (or minor variants thereof) which was originally encoded by a Camelidae immunoglobulin gene. However, this does not necessarily imply a particular relationship in terms of the production process used to prepare the CD70 antibody.

Camelid-derived CD70 antibodies may be derived from any camelid species, including inter alia, llama, dromedary, alpaca, vicuna, guanaco or camel.

CD70 antibodies comprising camelid-derived VH and VL domains, or CDRs thereof, are typically recombinantly expressed polypeptides, and may be chimeric polypeptides. The term "chimeric polypeptide" refers to an artificial (non-naturally occurring) polypeptide which is created by juxtaposition of two or more peptide fragments which do not otherwise occur contiguously. Included within this definition are "species" chimeric polypeptides created by juxtaposition of peptide fragments encoded by two or more species, e.g. camelid and human.

Camelid-derived CDRs may comprise one of the CDR sequences shown as SEQ ID Nos: 49-59, 262 or 263 (heavy chain CDR3), or SEQ ID Nos: 26-37, 249, 258 or 259 (heavy chain CDR2) or SEQ ID Nos: 10-20, 248, 256 or 257 (heavy chain CDR1) or one of the CDR sequences shown as SEQ ID NOs: 148-168, 271 or 273 (light chain CDR3), or SEQ ID Nos: 109-128 or 270 (light chain CDR2) or SEQ ID Nos:77-95, or 250-253, 267 and 268 (light chain CDR1).

In one embodiment the entire VH domain and/or the entire VL domain may be obtained from a species in the family Camelidae. In specific embodiments, the camelid-derived VH domain may comprise the amino acid sequence shown as SEQ ID NOs: 177-188, 212-223, 274 or 275, whereas the camelid-derived VL domain may comprise the amino acid sequence show as SEQ ID Nos:189-211, 230-245, 276 or 277 (VL). The camelid-derived VH domain and/or the camelid-derived VL domain may then be subject to protein engineering, in which one or more amino acid substitutions, insertions or deletions are introduced into the camelid amino acid sequence. These engineered changes preferably include amino acid substitutions relative to the camelid sequence. Such changes include "humanisation" or "germlining" wherein one or more amino acid residues in a camelid-encoded VH or VL domain are replaced with equivalent residues from a homologous human-encoded VH or VL domain.

Isolated camelid VH and VL domains obtained by active immunisation of a camelid (e.g. llama) with a human CD70 antigen can be used as a basis for engineering antigen binding polypeptides according to the invention. Starting from intact camelid VH and VL domains, it is possible to engineer one or more amino acid substitutions, insertions or deletions which depart from the starting camelid sequence. In certain embodiments, such substitutions, insertions or deletions may be present in the framework regions of the VH domain and/or the VL domain. The purpose of such changes in primary amino acid sequence may be to reduce presumably unfavourable properties (e.g. immunogenicity in a human host (so-called humanization), sites of potential product heterogeneity and or instability (glycosylation, deamidation, isomerisation, etc.) or to enhance some other favourable property of the molecule (e.g. solubility, stability, bioavailability, etc.). In other embodiments, changes in primary amino acid sequence can be engineered in one or more of the hypervariable loops (or CDRs) of a Camelidae VH and/or VL domain obtained by active immunisation. Such changes may be introduced in order to enhance antigen binding affinity and/or specificity, or to reduce presumably unfavourable properties, e.g. immunogenicity in a human host (so-called humanization), sites of potential product heterogeneity and or instability, glycosylation, deamidation, isomerisation, etc., or to enhance some other favourable property of the molecule, e.g. solubility, stability, bioavailability, etc.

Thus, in one embodiment, the invention provides a variant CD70 antibody which contains at least one amino acid substitution in at least one framework or CDR region of either the VH domain or the VL domain in comparison to a camelid-derived VH or VL domain, examples of which include but are not limited to the camelid VH domains comprising the amino acid sequences shown as SEQ ID NO: 177-188, 212-223, 274 or 275, and the camelid VL domains comprising the amino acid sequences show as SEQ ID NO: 189-211, 230-245, 276 or 277.

In other embodiments, there are provided "chimeric" antibody molecules comprising camelid-derived VH and VL domains (or engineered variants thereof) and one or more constant domains from a non-camelid antibody, for example human-encoded constant domains (or engineered variants thereof). In such embodiments it is preferred that both the VH domain and the VL domain are obtained from the same species of camelid, for example both VH and VL may be from *Lama glama* or both VH and VL may be from *Lama pacos* (prior to introduction of engineered amino acid sequence variation). In such embodiments both the VH and the VL domain may be derived from a single animal, particularly a single animal which has been actively immunised with a human CD70 antigen.

As an alternative to engineering changes in the primary amino acid sequence of Camelidae VH and/or VL domains, individual camelid-derived hypervariable loops or CDRs, or combinations thereof, can be isolated from camelid VH/VL domains and transferred to an alternative (i.e. non-Camelidae) framework, e.g. a human VH/VL framework, by CDR grafting. In particular, non-limiting, embodiments the camelid-derived CDRs may be selected from CDRs having the amino acid sequences shown as SEQ ID NOs: 49-59 (heavy chain CDR3), or SEQ ID Nos: 26-37 (heavy chain CDR2) or SEQ ID Nos: 10-20 (heavy chain CDR1) or one of the CDR sequences shown as SEQ ID NOs: 148-168 (light chain CDR3), or SEQ ID Nos: 109-128 (light chain CDR2) or SEQ ID Nos:77-95 (light chain CDR1).

CD70 antibodies comprising camelid-derived VH and VL domains, or CDRs thereof, can take various different embodiments in which both a VH domain and a VL domain are present. The term "antibody" herein is used in the broadest sense and encompasses, but is not limited to, monoclonal antibodies (including full length monoclonal antibodies), polyclonal antibodies, multispecific antibodies (e.g., bispecific antibodies), so long as they exhibit the appropriate immunological specificity for a human CD70 protein. The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes) on the antigen, each monoclonal antibody is directed against a single determinant or epitope on the antigen.

"Antibody fragments" comprise a portion of a full length antibody, generally the antigen binding or variable domain thereof. Examples of antibody fragments include Fab, Fab', F(ab')2, bi-specific Fab's, and Fv fragments, diabodies, linear antibodies, single-chain antibody molecules, a single chain variable fragment (scFv) and multispecific antibodies formed from antibody fragments (see Holliger and Hudson, Nature Biotechnol. 23:1126-36 (2005), the contents of which are incorporated herein by reference).

In non-limiting embodiments, CD70 antibodies comprising camelid-derived VH and VL domains, or CDRs thereof, may comprise CH1 domains and/or CL domains, the amino acid sequence of which is fully or substantially human. Where the antigen binding polypeptide of the invention is an antibody intended for human therapeutic use, it is typical for the entire constant region of the antibody, or at least a part thereof, to have fully or substantially human amino acid sequence. Therefore, one or more or any combination of the CH1 domain, hinge region, CH2 domain, CH3 domain and CL domain (and CH4 domain if present) may be fully or substantially human with respect to it's amino acid sequence.

Advantageously, the CH1 domain, hinge region, CH2 domain, CH3 domain and CL domain (and CH4 domain if present) may all have fully or substantially human amino acid sequence. In the context of the constant region of a humanised or chimeric antibody, or an antibody fragment, the term "substantially human" refers to an amino acid sequence identity of at least 90%, or at least 92%, or at least 95%, or at least 97%, or at least 99% with a human constant region. The term "human amino acid sequence" in this context refers to an amino acid sequence which is encoded by a human immunoglobulin gene, which includes germline, rearranged and somatically mutated genes. The invention also contemplates polypeptides comprising constant domains of "human" sequence which have been altered, by one or more amino acid additions, deletions or substitutions with respect to the human sequence, excepting those embodiments where the presence of a "fully human" hinge region is expressly required.

The presence of a "fully human" hinge region in the CD70 antibodies of the invention may be beneficial both to minimise immunogenicity and to optimise stability of the antibody.

As discussed elsewhere herein, it is contemplated that one or more amino acid substitutions, insertions or deletions may be made within the constant region of the heavy and/or the light chain, particularly within the Fc region. Amino acid substitutions may result in replacement of the substituted amino acid with a different naturally occurring amino acid, or with a non-natural or modified amino acid. Other structural modifications are also permitted, such as for example changes in glycosylation pattern (e.g. by addition or deletion of N- or O-linked glycosylation sites). Depending on the intended use of the antibody, it may be desirable to modify the antibody of the invention with respect to its binding properties to Fc receptors, for example to modulate effector function. For example cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., J. Exp. Med. 176:1191-1195 (1992) and Shopes, B. J. Immunol. 148:2918-2922 (1992). Alternatively, a CD70 antibody can be engineered which has dual Fc regions and may thereby have enhanced complement lysis and ADCC capabilities. See Stevenson et al., Anti-Cancer Drug Design 3:219-230 (1989). The invention also contemplates immunoconjugates comprising an antibody as described herein conjugated to a cytotoxic agent such as a chemotherapeutic agent, toxin (e.g., an enzymatically active toxin of bacterial, fungal, plant or animal origin, or fragments thereof), or a radioactive isotope (i.e., a radioconjugate). Fc regions may also be engineered for half-life extension, as described by Chan and Carter, Nature Reviews: Immunology, Vol. 10, pp 301-316, 2010, incorporated herein by reference.

In yet another embodiment, the Fc region is modified to increase the ability of the antibody to mediate antibody dependent cellular cytotoxicity (ADCC) and/or to increase the affinity of the antibody for an Fcγ receptor by modifying one or more amino acids.

In still another embodiment, the glycosylation of an antibody is modified. For example, an aglycoslated antibody can be made (i.e., the antibody lacks glycosylation). Glycosylation can be altered to, for example, increase the affinity of the antibody for the CD70 target antigen. Such carbohydrate modifications can be accomplished by; for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen.

Also envisaged are variant CD70 antibodies having an altered type of glycosylation, such as a hypofucosylated antibody having reduced amounts of fucosyl residues or a non-fucosylated antibody (as described by Natsume et al., Drug Design Development and Therapy, Vol. 3, pp 7-16, 2009) or an antibody having increased bisecting GlcNac structures. Such altered glycosylation patterns have been demonstrated to increase the ADCC activity of antibodies, producing typically 10-fold enhancement of ADCC relative to an equivalent antibody comprising a "native" human Fc domain. Such carbohydrate modifications can be accomplished by, for example, expressing the antibody in a host cell with altered glycosylation enzymatic machinery (as described by Yamane-Ohnuki and Satoh, mAbs 1:3, 230-236, 2009). Examples of non-fucosylated antibodies with enhanced ADCC function are those produced using the Potelligent™ technology of BioWa Inc.

The invention can, in certain embodiments, encompass chimeric Camelidae/human antibodies, and in particular chimeric antibodies in which the VH and VL domains are of fully camelid sequence (e.g. Llama or alpaca) and the remainder of the antibody is of fully human sequence. CD70 antibodies can include antibodies comprising "humanised" or "germlined" variants of camelid-derived VH and VL domains, or CDRs thereof, and camelid/human chimeric antibodies, in which the VH and VL domains contain one or more amino acid substitutions in the framework regions in comparison to camelid VH and VL domains obtained by active immunisation of a camelid with a human CD70 antigen. Such "humanisation" increases the % sequence identity with human germline VH or VL domains by replacing mis-matched amino acid residues in a starting Camelidae VH or VL domain with the equivalent residue found in a human germline-encoded VH or VL domain.

CD70 antibodies may also be CDR-grafted antibodies in which CDRs (or hypervariable loops) derived from a camelid antibody, for example an camelid CD70 antibody raised by active immunisation with human CD70 protein, or otherwise encoded by a camelid gene, are grafted onto a human VH and VL framework, with the remainder of the antibody also being of fully human origin. Such CDR-grafted CD70 antibodies may contain CDRs having the amino acid sequences shown as SEQ ID Nos: 49-59, 262 or 263 (heavy chain CDR3), or SEQ ID Nos: 26-37, 249, 258 or 259 (heavy chain CDR2) or SEQ ID Nos: 10-20, 248, 256 or 257 (heavy chain CDR1) or one of the CDR sequences shown as SEQ ID NOs: 148-168, 271 or 273 (light chain CDR3), or SEQ ID Nos: 109-128 or 270 (light chain CDR2) or SEQ ID Nos:77-95, or 250-253, 267 and 268 (light chain CDR1).

Humanised, chimeric and CDR-grafted CD70 antibodies as described above, particularly antibodies comprising hypervariable loops or CDRs derived from active immunisation of camelids with a human CD70 antigen, can be readily produced using conventional recombinant DNA manipulation and expression techniques, making use of prokaryotic and eukaryotic host cells engineered to produce the polypeptide of interest and including but not limited to bacterial cells, yeast cells, mammalian cells, insect cells, plant cells, some of them as described herein and illustrated in the accompanying examples.

Camelid-derived CD70 antibodies include variants wherein the hypervariable loop(s) or CDR(s) of the VH domain and/or the VL domain are obtained from a conventional camelid antibody raised against human CD70, but wherein at least one of said (camelid-derived) hypervariable loops or CDRs has been engineered to include one or more amino acid substitutions, additions or deletions relative to the camelid-encoded sequence. Such changes include "humanisation" of the hypervariable loops/CDRs. Camelid-derived HVs/CDRs which have been engineered in this manner may still exhibit an amino acid sequence which is "substantially identical" to the amino acid sequence of a camelid-encoded HV/CDR. In this context, "substantial identity" may permit no more than one, or no more than two amino acid sequence mis-matches with the camelid-encoded HV/CDR. Particular embodiments of the CD70 antibody may contain humanised variants of the CDR sequences shown as SEQ ID Nos: 49-59, 262 or 263 (heavy chain CDR3), or SEQ ID Nos: 26-37, 249, 258 or 259 (heavy chain CDR2) or SEQ ID Nos: 10-20, 248, 256 or 257 (heavy chain CDR1) or one of the CDR sequences shown as SEQ ID NOs: 148-168, 271 or 273 (light chain CDR3), or SEQ ID Nos: 109-128 or 270 (light chain CDR2) or SEQ ID Nos:77-95, or 250-253, 267 and 268 (light chain CDR1).

The camelid-derived CD70 antibodies provided herein may be of any isotype. Antibodies intended for human therapeutic use will typically be of the IgA, IgD, IgE IgG, IgM type, often of the IgG type, in which case they can belong to any of the four sub-classes IgG1, IgG2a and b, IgG3 or IgG4. Within each of these sub-classes it is permitted to make one or more amino acid substitutions, insertions or deletions within the Fc portion, or to make other structural modifications, for example to enhance or reduce Fc-dependent functionalities.

Humanisation of Camelid-Derived VH and VL Domains

Camelid conventional antibodies provide an advantageous starting point for the preparation of antibodies with utility as human therapeutic agents due to the following factors, discussed in U.S. Ser. No. 12/497,239 which is incorporated herein by reference:

1) High % sequence homology between camelid VH and VL domains and their human counterparts;
2) High degree of structural homology between CDRs of camelid VH and VL domains and their human counterparts (i.e. human-like canonical fold structures and human-like combinations of canonical folds).

The camelid (e.g. llama) platform also provides a significant advantage in terms of the functional diversity of the CD70 antibodies which can be obtained.

The utility of CD70 antibodies comprising camelid VH and/or camelid VL domains for human therapy can be improved still further by "humanisation" of natural camelid VH and VL domains, for example to render them less immunogenic in a human host. The overall aim of humanisation is to produce a molecule in which the VH and VL domains exhibit minimal immunogenicity when introduced into a human subject, whilst retaining the specificity and affinity of the antigen binding site formed by the parental VH and VL domains.

One approach to humanisation, so-called "germlining", involves engineering changes in the amino acid sequence of a camelid VH or VL domain to bring it closer to the germline sequence of a human VH or VL domain.

Determination of homology between a camelid VH (or VL) domain and human VH (or VL) domains is a critical step in the humanisation process, both for selection of camelid amino acid residues to be changed (in a given VH or VL domain) and for selecting the appropriate replacement amino acid residue(s).

An approach to humanisation of camelid conventional antibodies has been developed based on alignment of a large number of novel camelid VH (and VL) domain sequences, typically somatically mutated VH (or VL) domains which are known to bind a target antigen, with human germline VH (or VL) sequences, human VH (and VL) consensus sequences, as well as germline sequence information available for llama pacos. The following passages outline the principles which can be applied to (i) select "camelid" amino acid residues for replacement in a camelid-derived VH or VL domain or a CDR thereof, and (ii) select replacement "human" amino acid residues to substitute in, when humanising any given camelid VH (or VL) domain. This approach can be used to prepare humanised variants of camelid-derived CDRs having the amino acid sequences shown as SEQ ID Nos: 49-59, 262 or 263 (heavy chain CDR3), or SEQ ID Nos: 26-37, 249, 258 or 259 (heavy chain CDR2) or SEQ ID Nos: 10-20, 248, 256 or 257 (heavy chain CDR1) or one of the CDR sequences shown as SEQ ID NOs: 148-168, 271 or 273 (light chain CDR3), or SEQ ID Nos: 109-128 or 270 (light chain CDR2) or SEQ ID Nos:77-95, or 250-253, 267 or 268 (light chain CDR1), and also for humanisation of camelid-derived VH domains having the sequences shown as SEQ ID NOs: 177-188, 212-223, 274 or 275 and of camelid-derived VL domains having the sequences shown as SEQ ID Nos:189-211, 230-245, 276 or 277.

Step 1. Select human (germline) family and member of this family that shows highest homology/identity to the mature camelid sequence to be humanised. A general procedure for identifying the closest matching human germline for any given camelid VH (or VL) domain is outlined below.

Step 2. Select specific human germline family member used to germline against. Preferably this is the germline with the highest homology or another germline family member from the same family.

Step 3. Identify the preferred positions considered for germlining on the basis of the table of amino acid utilisation for the camelid germline that is closest to the selected human germline.

Step 4. Try to change amino acids in the camelid germline that deviate from the closest human germline; germlining of FR residues is preferred over CDR residues.

a. Preferred are positions that are deviating from the selected human germline used to germline against, for which the amino acid found in the camelid sequence does not match with the selected germline and is not found in other germlines of the same subclass (both for V as well as for J encoded FR amino acids).

b. Positions that are deviating from the selected human germline family member but which are used in other germlines of the same family may also be addressed in the germlining process.

c. Additional mismatches (e.g. due to additional somatic mutations) towards the selected human germline may also be addressed.

The following approach may be used to determine the closest matching human germline for a given camelid VH (or VL) domain:

Before analyzing the percentage sequence identity between Camelidae and human germline VH and VL, the canonical folds may first be determined, which allows the identification of the family of human germline segments with the identical combination of canonical folds for H1 and H2 or L1 and L2 (and L3). Subsequently the human germline family member that has the highest degree of sequence homology with the Camelidae variable region of interest may be chosen for scoring sequence homology. The determination of Chothia canonical classes of hypervariable loops L1, L2, L3, H1 and H2 can be performed with the bioinformatics tools publicly available on webpage www.bioinf.org.uk/abs/chothia.html.page. The output of the program shows the key residue requirements in a datafile. In these datafiles, the key residue positions are shown with the allowed amino acids at each position. The sequence of the variable region of the antibody is given as input and is first aligned with a consensus antibody sequence to assign the Kabat numbering scheme. The analysis of the canonical folds uses a set of key residue templates derived by an automated method developed by Martin and Thornton (Martin et al., J. Mol. Biol. 263:800-815 (1996)). The boundaries of the individual framework regions may be assigned using the IMGT numbering scheme, which is an adaptation of the numbering scheme of Chothia (Lefranc et al., NAR 27: 209-212 (1999); http://imgt.cines.fr).

With the particular human germline V segment known, which uses the same combination of canonical folds for H1 and H2 or L1 and L2 (and L3), the best matching family member in terms of sequence homology can be determined. The percentage sequence identity between Camelidae VH and VL domain framework amino acid sequences and corresponding sequences encoded by the human germline can be determined using bioinformatic tools, but manual alignment of the sequences could also be used. Human immunoglobulin sequences can be identified from several protein data bases, such as VBase (http://vbase.mrc-cpe.cam.ac.uk/) or the Pluckthun/Honegger database (http://www.bioc.unizh.ch/antibody/Sequences/Germlines. To compare the human sequences to the V regions of Camelidae VH or VL domains a sequence alignment algorithm such as available via websites like www.expasy.ch/tools/#align can be used, but also manual alignment can also be performed with a limited set of sequences. Human germline light and heavy chain sequences of the families with the same combinations of canonical folds and with the highest degree of homology with the framework regions 1, 2, and 3 of each chain may be selected and compared with the Camelidae variable region of interest; also the FR4 is checked against the human germline JH and JK or JL regions.

Note that in the calculation of overall percent sequence homology the residues of FR1, FR2 and FR3 are evaluated using the closest match sequence from the human germline family with the identical combination of canonical folds. Only residues different from the closest match or other members of the same family with the same combination of canonical folds are scored (NB—excluding any primer-encoded differences). However, for the purposes of humanization, residues in framework regions identical to members of other human germline families, which do not have the same combination of canonical folds, can be considered for humanization, despite the fact that these are scored "negative" according to the stringent conditions described above. This assumption is based on the "mix and match" approach for humanization, in which each of FR1, FR2, FR3 and FR4 is separately compared to its closest matching human germline sequence and the humanized molecule therefore contains a combination of different FRs as was done by Qu and colleagues (Qu et al., Clin. Cancer Res. 5:3095-3100 (1999)) and Ono and colleagues (Ono et al., Mol. Immunol. 36:387-395 (1999)).

Cross-Competing Antibodies

Monoclonal antibodies or antigen-binding fragments thereof that "cross-compete" with the molecules disclosed herein are those that bind human CD70 at site(s) that are identical to, or overlapping with, the site(s) at which the present CD70 antibodies bind. Competing monoclonal antibodies or antigen-binding fragments thereof can be identified, for example, via an antibody competition assay. For example, a sample of purified or partially purified human CD70 can be hound to a solid support. Then, an antibody compound or antigen binding fragment thereof of the present invention and a monoclonal antibody or antigen-binding fragment thereof suspected of being able to compete with such invention antibody compound are added. One of the two molecules is labelled. If the labelled compound and the unlabeled compound bind to separate and discrete sites on CD70, the labelled compound will bind to the same level whether or not the suspected competing compound is present. However, if the sites of interaction are identical or overlapping, the unlabeled compound will compete, and the amount of labelled compound bound to the antigen will be lowered. If the unlabeled compound is present in excess, very little, if any, labelled compound will bind. For purposes of the present invention, competing monoclonal antibodies or antigen-binding fragments thereof are those that decrease the binding of the present antibody compounds to CD70 by about 50%, about 60%, about 70%, about 80%, about 85%, about 90%, about 95%, or about 99%. Details of procedures for carrying out such competition assays are well known in the art and can be found, for example, in Harlow and Lane (1988) Antibodies, A Laboratory Manual, Cold Spring Harbor Laboratory Press, Cold Spring Harbor, N.Y., pages 567-569, ISBN 0-87969-314-2. Such assays can be made quantitative by using purified antibodies. A standard curve is established by titrating one antibody against itself, i.e., the same antibody is used for both the label and the competitor. The capacity of an unlabeled competing monoclonal antibody or antigen-binding fragment thereof to inhibit the binding of the labelled molecule to the plate is titrated. The results are plotted, and the concentrations necessary to achieve the desired degree of binding inhibition are compared.

Preferred embodiments are antibodies which cross-compete for binding to human CD70 with antibodies comprising the llama-derived Fab 27B3, and its germlined variants, including in particular 41D12 (ARGX-110) and which exhibit the same combination of binding characteristics, namely:

(a) binding within the amino acid sequence HIQVTLA-ICSS (SEQ ID NO:342) in human CD70;
(b) cross-reactivity with CD70 homologs of rhesus macaque (*Macaca mulatta*) and *cynomolgus* monkey (*Macaca cynomolgus*);
(c) binding to native and heat denatured recombinant human CD70.

Polynucleotides Encoding CD70 Antibodies

The invention also provides polynucleotide molecules encoding the CD70 antibodies of the invention, also expression vectors containing a nucleotide sequences which encode the CD70 antibodies of the invention operably linked to regulatory sequences which permit expression of the antigen binding polypeptide in a host cell or cell-free expression system, and a host cell or cell-free expression system containing this expression vector.

Polynucleotide molecules encoding the CD70 antibodies of the invention include, for example, recombinant DNA molecules. The terms "nucleic acid", "polynucleotide" or a "polynucleotide molecule" as used herein interchangeably and refer to any DNA or RNA molecule, either single- or double-stranded and, if single-stranded, the molecule of its complementary sequence. In discussing nucleic acid molecules, a sequence or structure of a particular nucleic acid molecule may be described herein according to the normal convention of providing the sequence in the 5' to 3' direction. In some embodiments of the invention, nucleic acids or polynucleotides are "isolated." This term, when applied to a nucleic acid molecule, refers to a nucleic acid molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or non-human host organism. When applied to RNA, the term "isolated polynucleotide" refers primarily to an RNA molecule encoded by an isolated DNA molecule as defined above. Alternatively, the term may refer to an RNA molecule that has been purified/separated from other nucleic acids with which it would be associated in its natural state (i.e., in cells or tissues). An isolated polynucleotide (either DNA or RNA) may further represent a molecule produced directly by biological or synthetic means and separated from other components present during its production.

In one embodiment, the invention provides nucleotide sequences which encode the VH domain and VL domain of the germlined llama-derived Fab denoted herein 41D12, wherein the VH domain has the amino acid sequence shown as SEQ ID NO:223 and the VH domain has the amino acid sequence shown as SEQ ID NO:241. In a preferred embodiment the nucleotide sequence encoding the VH domain having the amino acid sequence shown as SEQ ID NO:223 comprises the nucleotide sequence shown as SEQ ID NO:344, and the nucleotide sequence encoding the VL domain having the amino acid sequence shown as SEQ ID NO:241 comprises the nucleotide sequence shown as SEQ ID NO:345.

In one embodiment, the invention provides nucleotide sequences which encode the VH domain and VL domain of the germlined llama-derived Fab denoted herein 57B6, wherein the VH domain has the amino acid sequence shown as SEQ ID NO:274 and the VH domain has the amino acid sequence shown as SEQ ID NO:276. In a preferred embodiment the nucleotide sequence encoding the VH domain having the amino acid sequence shown as SEQ ID NO:274 comprises the nucleotide sequence shown as SEQ ID NO:346, and the nucleotide sequence encoding the VL domain having the amino acid sequence shown as SEQ ID NO:276 comprises the nucleotide sequence shown as SEQ ID NO:347.

In one embodiment, the invention provides nucleotide sequences which encode the VH domain and VL domain of the germlined llama-derived Fab denoted herein 59D10, wherein the VH domain has the amino acid sequence shown as SEQ ID NO:275 and the VH domain has the amino acid sequence shown as SEQ ID NO:277. In a preferred embodiment the nucleotide sequence encoding the VH domain having the amino acid sequence shown as SEQ ID NO:275 comprises the nucleotide sequence shown as SEQ ID NO:348, and the nucleotide sequence encoding the VL domain having the amino acid sequence shown as SEQ ID NO:277 comprises the nucleotide sequence shown as SEQ ID NO:349.

For recombinant production of a CD70 antibody according to the invention, a recombinant polynucleotide encoding it may be prepared (using standard molecular biology techniques) and inserted into a replicable vector for expression in a chosen host cell, or a cell-free expression system. Suitable host cells may be prokaryote, yeast, or higher eukaryote cells, specifically mammalian cells. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen. Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); mouse myeloma cells SP2/0-AG14 (ATCC CRL 1581; ATCC CRL 8287) or NS0 (HPA culture collections no. 85110503); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2), as well as DSM's PERC-6 cell line. Expression vectors suitable for use in each of these host cells are also generally known in the art.

It should be noted that the term "host cell" generally refers to a cultured cell line. Whole human beings into which an expression vector encoding an antigen binding polypeptide according to the invention has been introduced are explicitly excluded from the definition of a "host cell".

Antibody Production

In an important aspect, the invention also provides a method of producing a CD70 antibody of the invention which comprises culturing a host cell (or cell free expression system) containing polynucleotide (e.g. an expression vector) encoding the CD70 antibody under conditions which permit expression of the CD70 antibody, and recovering the expressed CD70 antibody. This recombinant expression process can be used for large scale production of CD70 antibodies according to the invention, including monoclonal antibodies intended for human therapeutic use. Suitable vectors, cell lines and production processes for large scale manufacture of recombinant antibodies suitable for in vivo therapeutic use are generally available in the art and will be well known to the skilled person.

As noted elsewhere, the CD70 antibodies provided herein, including in particular antibodies based on the Fab 27B3 and its germlined variants such as 41D12 (ARGX-110) display characteristics which are particularly beneficial for large-scale commercial manufacture. Specifically, the extremely high production yield (>4 g/L) achievable in a commercial scale recombinant expression system will dramatically reduce production costs.

Preferred embodiments also exhibit thermal stability when tested at 37° C. and also over several freeze-thaw cycles, which is again extremely beneficial for commercial manufacture and storage of a clinical product. Surprisingly, several of the human germlined variants of Fab 27B3, including 41D12 and 40F1, exhibit improved thermal stability compared to 27B3 itself.

Accordingly, in a further aspect the invention provides an isolated antibody or antigen binding fragment thereof which binds to human CD70, said antibody or fragment comprising a heavy chain variable domain corresponding to the amino acid sequence set forth in SEQ ID NO:178, provided that at least one amino acid at a Kabat position selected from the group consisting of H6, H18, H24, H31, H56, H74, H74, H77, H79, H83, H84, H89, H93, H94, H108, H110, and H112 is substituted with another amino acid.

This antibody, or antigen binding fragment thereof, may exhibit greater thermal stability than an antibody, or antigen binding fragment thereof, comprising a heavy chain variable domain with the amino acid sequence set forth in SEQ ID NO:178.

In a further embodiment there is provided a CD70 antibody or antigen binding fragment which comprises a light chain variable domain corresponding to the amino acid sequence set forth in SEQ ID NO:201, provided that at least one amino acid at a Kabat position selected from the group consisting of L2, L11, L12, L25, L26, L30, L46, L53, L60, L61, L67, L68, L76, L80, L81, L85, and L87 is substituted with another amino acid.

This antibody, or antigen binding fragment thereof, may exhibit greater thermal stability than an antibody, or antigen binding fragment thereof, comprising a heavy chain variable domain with the amino acid sequence set forth in SEQ ID NO:201.

In a particular embodiment, the CD70 antibody, or antigen binding fragment thereof may comprise:

a) a heavy chain variable domain with the amino acid sequence set forth in SEQ ID NO:178 comprising one or more amino acid substitutions at Kabat positions selected from the group consisting of H6, H18, H24, H31, H56, H74, H74, H77, H79, H83, H84, H89, H93, H94, H108, H110, and H112; and b) a light chain variable domain with the amino acid sequence set forth in SEQ ID NO:201 comprising one or more amino acid substitutions at Kabat positions selected from the group consisting of L2, L11, L12, L25, L26, L30, L46, L53, L60, L61, L67, L68, L76, L80, L81, L85, and L87.

This antibody, or antigen binding fragment thereof, of claim 24, may exhibit greater thermal stability than an antibody, or antigen binding fragment thereof, comprising a heavy chain variable domain with the amino acid sequence set forth in SEQ ID NO:178 and a light chain variable domain with the amino acid sequence set forth in SEQ ID NO:201.

Therapeutic Utility of CD70 Antibodies

The CD70 antibodies, or antigen binding fragments thereof, provided herein can be used to inhibit the growth of cancerous tumour cells in vivo and are therefore useful in the treatment of CD70-expressing cancers.

Accordingly, further aspects of the invention relate to methods of inhibiting tumour cell growth in a human patient, and also methods of treating or preventing cancer, which comprise administering to a patient in need thereof a therapeutically effective amount of a CD70 antibody or antigen binding fragment as described herein.

Another aspect of the invention provides a CD70 antibody or antigen binding fragment as described herein for use inhibiting the growth of CD70-expressing tumour cells in a human patient.

A still further aspect of the invention provides a CD70 antibody or antigen binding fragment as described herein for use treating or preventing cancer in a human patient.

Preferred cancers whose growth may be inhibited using the CD70 antibodies described herein include renal cancer (e.g., renal cell carcinoma), breast cancer, brain tumors, chronic or acute leukemias including acute myeloid leukemia, chronic myeloid leukemia, acute lymphoblastic leukemia, chronic lymphocytic leukemia, lymphomas (e.g., Hodgkin's and non-Hodgkin's lymphoma, lymphocytic lymphoma, primary CNS lymphoma, T-cell lymphoma), nasopharyngeal carcinomas, melanoma {e.g., metastatic malignant melanoma), prostate cancer, colon cancer, lung cancer, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, solid tumors of childhood, cancer of the bladder, cancer of the kidney or ureter, carcinoma of the renal pelvis, neoplasm of the central nervous system (CNS), tumor angiogenesis, spinal axis tumor, brain stem glioma, pituitary adenoma, Kaposi's sarcoma, epidermoid cancer, squamous cell cancer, mesothelioma.

The CD70 antibodies described herein can also be used to treat a subject with a tumorigenic disorder characterized by the presence of tumor cells expressing CD70 including, for example, renal cell carcinomas (RCC), such as clear cell RCC, glioblastoma, breast cancer, brain tumors, nasopharangeal carcinomas, non-Hodgkin's lymphoma (NHL), acute lymphocytic leukemia (ALL), chronic lymphocytic leukemia (CLL), Burkitt's lymphoma, anaplastic large-cell lymphomas (ALCL), multiple myeloma, cutaneous T-cell lymphomas, nodular small cleaved-cell lymphomas, lymphocytic lymphomas, peripheral T-cell lymphomas, Lennert's lymphomas, immunoblastic lymphomas, T-cell leukemia/lymphomas (ATLL), adult T-cell leukemia (T-ALL), entroblastic/centrocytic (cb/cc) follicular lymphomas cancers, diffuse large cell lymphomas of B lineage, angioimmunoblastic lymphadenopathy (AILD)-like T cell lymphoma, HIV associated body cavity based lymphomas, embryonal carcinomas, undifferentiated carcinomas of the rhino-pharynx (e.g., Schmincke's tumor), Castleman's disease, Kaposi's Sarcoma, multiple myeloma, Waldenstrom's macroglobulinemia, Mantle cell lymphoma and other B-cell lymphomas.

Specific embodiments relate to treatment of any one of the above-listed cancers with an antibody comprising the llama-derived Fab 27B3, or one of its germlined variants, including in particular 41D12 (ARGX-110). In particular, any one of the above-listed cancers may be treated using an antibody comprising the Fab regions of 41D12 (germlined variant of 27B3) fused to the constant regions of human IgG1. In the latter embodiment, the human IgG1 constant region may be further engineered in order to maximise antibody effector functions (e.g. by addition of point mutations), or the 41D12-IgG1 antibody may be non-fucosylated, again to enhance antibody effector function.

As noted elsewhere, the CD70 antibodies described herein, particularly 27B3 and its germlined variants, exhibit particularly strong binding to human cancer cell lines which express cell-surface CD70 at low copy number, such as for example the large B cell lymphoma cell line SU-DHL-6, the chronic lymphocytic leukemia cell line JVM-2, the cutaneous T cell lymphoma cell line HH, the gastric carcinoma cell line MKN-45, the lung carcinoma cell lines A549 and EBC-1, the melanoma cell lines WM852 and WM793, the glioblastoma cell line GaMG and the ovarian carcinoma cell lines OAW-42, SKOv3 and OVCAR3. Indeed, the affinity of 41D12 (ARGX-110) for these low copy-number cancer cell lines is significantly higher than comparator prior art antibodies, such as SGN70 and MDX1411.

The "improved" affinity for low copy-number cancer cell lines is of direct relevance for clinical treatment of the corresponding cancers, as demonstrated by the cell spiking experiments in the accompanying examples. When cells of a low copy-number cell line (e.g. the diffuse large B cell lymphoma cell line SU-DHL-6) are spiked into freshly isolated PBMCs from healthy donors, cells of the cancer cell line are preferentially depleted by the example CD70 antibody ARGX-110.

Accordingly, a further aspect of the invention relates to a method of treating or preventing cancer, which comprises administering to a patient in need thereof a therapeutically effective amount of a CD70 antibody or antigen binding fragment as described herein, wherein the cancer is a cancer which exhibits low copy-number expression of CD70.

The invention also provides a CD70 antibody or antigen binding fragment as described herein for use treating or preventing cancer in a human patient, wherein the cancer is a cancer which exhibits low copy-number expression of CD70.

In each of these aspects the low copy-number cancer is preferably selected from the group consisting of: large B cell lymphoma, chronic lymphocytic leukaemia, cutaneous T cell lymphoma, gastric cancer, lung cancer, melanoma, glioblastoma and ovarian cancer.

Specific embodiments relate to treatment of low copy-number cancers with an antibody comprising the llama-derived Fab 27B3, or one of its germlined variants, including in particular 41D12 (ARGX-110). In particular, any one of the above-listed low copy-number cancers may be treated using an antibody comprising the Fab regions of 41D12 (germlined variant of 27B3) fused to the constant regions of human IgG1.

The CD70 antibodies described herein are also useful for the treatment of immunological disorders characterised by expression of CD70. Specific examples of such immunological disorders include the following: rheumatoid arthritis, autoimmune demyelinative diseases (e.g., multiple sclerosis, allergic encephalomyelitis), endocrine ophthalmopathy, uveoretinitis, systemic lupus erythematosus, myasthenia gravis, Grave's disease, glomerulonephritis, autoimmune hepatological disorder, inflammatory bowel disease (e.g., Crohn's disease, ulcerative colitis, Celiac disease), anaphylaxis, allergic reaction, Sjogren's syndrome, type I diabetes mellitus, primary biliary cirrhosis, Wegener's granulomatosis, fibromyalgia, polymyositis, dermatomyositis, multiple endocrine failure, Schmidt's syndrome, autoimmune uveitis, Addison's disease, adrenalitis, thyroiditis, Hashimoto's thyroiditis, autoimmune thyroid disease, pernicious anemia, gastric atrophy, chronic hepatitis, lupoid hepatitis, atherosclerosis, subacute cutaneous lupus erythematosus, hypoparathyroidism, Dressier's syndrome, autoimmune thrombocytopenia, idiopathic thrombocytopenic purpura, hemolytic anemia, pemphigus vulgaris, pemphigus, dermatitis herpetiformis, alopecia areata, pemphigoid, scleroderma, progressive systemic sclerosis, CREST syndrome (calcinosis, Raynaud's phenomenon, esophageal dysmotility, sclerodactyly, and telangiectasia), male and female autoimmune infertility, ankylosing spondolytis, ulcerative colitis, mixed connective tissue disease, polyarteritis nedosa, systemic necrotizing vasculitis, atopic dermatitis, atopic rhinitis, Goodpasture's syndrome, Chagas' disease, sarcoidosis, rheumatic fever, asthma, recurrent abortion, anti-phospholipid syndrome, farmer's lung, erythema multiforme, post cardiotomy syndrome, Gushing's syndrome, autoimmune chronic active hepatitis, bird-fancier's lung, toxic epidermal necrolysis, Alport's syndrome, alveolitis, allergic alveolitis, fibrosing alveolitis, interstitial lung disease, erythema nodosum, pyoderma gangrenosum, transfusion reaction, Takayasu's arteritis, polymyalgia rheumatica, temporal arteritis, schistosomiasis, giant cell arteritis, ascariasis, aspergillosis, Sampler's syndrome, eczema, lymphomatoid granulomatosis, Behcet's disease, Caplan's syndrome, Kawasaki's disease, dengue, encephalomyelitis, endocarditis, endomyocardial fibrosis, endophthalmitis, erythema elevatum et diutinum, psoriasis, erythroblastosis fetalis, eosinophilic faciitis, Shulman's syndrome, Felty's syndrome, filariasis, cyclitis, chronic cyclitis, heterochronic cyclitis, Fuch's cyclitis, IgA nephropathy, Henoch-Schonlein purpura, graft versus host disease, transplantation rejection, cardiomyopathy, Eaton-Lambert syndrome, relapsing polychondritis, cryoglobulinemia, Evan's syndrome, and autoimmune gonadal failure, disorders of B lymphocytes (e.g., systemic lupus erythematosus, Goodpasture's syndrome, rheumatoid arthritis, and type I diabetes), Th1-lymphocytes (e.g., rheumatoid arthritis, multiple sclerosis, psoriasis, Sjorgren's syndrome, Hashimoto's thyroiditis, Grave's disease, primary biliary cirrhosis, Wegener's granulomatosis, tuberculosis, or graft versus host disease), or Th2-lymphocytes (e.g., atopic dermatitis, systemic lupus erythematosus, atopic asthma, rhinoconjunctivitis, allergic rhinitis, Omenn's syndrome, systemic sclerosis, or chronic graft versus host disease), Churg Strauss syndrome, microscopic polyangiitis and Takayasu's arteritis.

Specific embodiments relate to treatment of any one of the above-listed immunological disorders with an antibody comprising the llama-derived Fab 27B3, or one of its germlined variants, including in particular 41D12 (ARGX-110). In particular, any one of the above-listed cancers may be treated using an antibody comprising the Fab regions of 41D12 (germlined variant of 27B3) fused to the constant regions of human IgG1. In the latter embodiment, the human IgG1 constant region may be further engineered in order to maximise antibody effector functions (e.g. by addition of point mutations), or the 41D12-IgG1 antibody may be non-fucosylated, again to enhance antibody effector function.

As used herein, the term "treating" or "treatment" means slowing, interrupting, arresting, controlling, ameliorating, stopping, reducing severity of a symptom, disorder, condition or disease, but does not necessarily involve a total elimination of all disease-related symptoms, conditions or disorders.

For human therapeutic use the CD70 antibodies described herein may be administered to a human subject in need of treatment in an "effective amount". The term "effective amount" refers to the amount or dose of a CD70 antibody which, upon single or multiple dose administration to a human patient, provides therapeutic efficacy in the treatment of disease. Therapeutically effective amounts of the CD70 antibody can comprise an amount in the range of from about 0.1 mg/kg to about 20 mg/kg per single dose. A therapeutic effective amount for any individual patient can be determined by the healthcare professional by monitoring the effect of the CD70 antibody on a biomarker, such as cell surface CD70 in tumour tissues, or a symptom such as tumour regression, etc. The amount of antibody administered at any given time point may be varied so that optimal amounts of CD70 antibody, whether employed alone or in combination with any other therapeutic agent, are administered during the course of treatment.

It is also contemplated to administer the CD70 antibodies described herein, or pharmaceutical compositions comprising such antibodies, in combination with any other cancer treatment, as a combination therapy.

Use of Antibodies which are Poorly Internalised to Deplete CD70-Expressing Cells A surprising finding described herein is that CD70 antibodies bound to CD70 expressed on the surface of cancer cell lines are poorly internalised. This is a surprising result, since the prior art has previously described CD70 as an "internalising target". Although there is variation between different cancer cell types in the precise degree of internalisation of bound CD70 antibodies, no cancer cell type is observed to "fully internalise" the bound CD70 antibody. For example, renal cancer cell lines previously described as rapidly internalising in fact are shown to internalise a maximum of about 70% of bound antibody ARGX-110. Many other cancer cell lines internalise less than 30%, less than 20% or even less than 10% of bound ARGX-110.

The variation in degree of internalisation between different cancer cell lines is largely disease-indication dependent, with similar results being observed using different CD70 antibodies. However, the poor internalisation in certain cell lines is particularly apparent when using the antibody ARGX-110. The observed low degree of internalisation on many cancer cells provides a rationale for the use of CD70 antibodies with strong effector function in order to deplete (e.g. kill or inhibit the growth of) cancer cells in vivo. Since bound CD70 antibodies are relatively poorly internalised on many cancer cells, the antibody will remain hound to the cell surface and can thereby trigger effector functions (ADCC, CDC, ADCP) by interactions with the immune system of a human patient.

Accordingly, a further important aspect of the invention relates to a method of depleting CD70-expressing cells in a human patient, comprising administering to said patient an effective amount of an antibody which binds to human CD70, wherein said CD70-expressing cells exhibit 30% or less, 25% or less, 20% or less, 15% or less, 10% or less or 5% or less internalisation of said antibody after a period of 6 hours, and wherein said antibody exhibits at least one effector function selected from the group consisting of ADCC, CDC and ADCP.

In this method, the CD70 antibody (with active effector functions) is used to deplete CD70 expressing cells. This depletion of CD70-expressing cells may form the basis of therapeutic or prophylactic treatment, e.g. for treatment of prevention of CD70-expressing cancers, or for treatment of prevention of CD70-associated immunological disorders. The precise mechanism by which CD70-expressing antibodies are depleted may depend on the type of effector functions exhibited by the CD70 antibody, but will be dependent on strong (high affinity) binding of the CD70 antibody to cell-surface CD70, coupled with poor internalisation of the bound antibody.

In certain embodiments the CD70-expressing cells are CD70-expressing cancer cells. In particular, the CD70-expressing cancer cells may be of a cancer type selected from the group consisting of: Burkitt lymphoma, large B cell lymphoma, Hodgkin lymphoma, non-Hodgkin lymphoma, mantle cell lymphoma, chronic lymphocytic leukemia, pancreatic carcinoma, gastric carcinoma, glioblastoma and lung carcinoma. Cell lines derived from each of these cancers have been demonstrated to internalise 30% or less of bound CD70 antibody over a period of 6 hours. In a further embodiment CD70-expressing cancer cells may be of a cancer type selected from the group consisting of: Burkitt lymphoma, large B cell lymphoma, Hodgkin lymphoma, non-Hodgkin lymphoma, mantle cell lymphoma, chronic lymphocytic leukemia, gastric carcinoma, glioblastoma and lung carcinoma. Cell lines derived from each of these cancers have been demonstrated to internalise 20% or less of bound CD70 antibody over a period of 6 hours. In a further embodiment CD70-expressing cancer cells may be of a cancer type selected from the group consisting of: Burkitt lymphoma, large B cell lymphoma, mantle cell lymphoma, chronic lymphocytic leukemia, gastric carcinoma and lung carcinoma. Cell lines derived from each of these cancers have been demonstrated to internalise 10% or less of bound CD70 antibody over a period of 6 hours.

In other embodiments the CD70-expressing cells may be CD70-expressing activated T cells, which do not exhibit any detectable internalisation of bound CD70 antibodies (specifically no internalisation of ARGX-110 is observed over a period of 6 hours. This observation that bound CD70 antibodies are not internalised by CD70+ activated T cells is strongly supportive of the use of CD70 antibodies with strong effector function (ADCC, CDC or ADCP), including but not limited to ARGX-110, in the treatment of immunological diseases mediated by CD70+ activated T cells, including autoimmune disorders such as for example rheumatoid arthritis, psoriasis, SLE, etc.

The above-listed embodiments can utilise essentially any CD70 antibody. In specific embodiments the antibody can be any CD70 antibody which has been shown experimentally to exhibit 30% or less, 25% or less, 20% or less, 15% or less, 10% or less or 5% or less internalisation after a period of 6 hours in a CD70-expressing cancer cell line selected from the group consisting of Raji, SU-DHL-6, MHHPREB1, Mino, Mec1, JVM-2, MKN-45, A549, U87MG, PANC-1, PANC-89, L428, Granta 519, Rec-1 and EBC-1. In effect, the cell line internalisation assay described in the accompanying examples can be used as a screen both to determine whether particular disease indications should be targeted with CD70 antibodies having strong effector function, or with CD antibody-drug conjugates (discussed below), and also to identify suitable CD70 antibodies for use in treating particular disease indications.

Accordingly, the invention also provides a method of depleting CD70-expressing cancer cells in a human patient, comprising administering to said patient an effective amount of an antibody which binds to human CD70, wherein said antibody exhibits 30% or less internalisation after a period of 6 hours in a CD70-expressing cancer cell line selected from the group consisting of Raji, SU-DHL-6, MHH-PREB1, Mino, Mec1, JVM-2, MKN-45, A549, U87MG, PANC-1, PANC-89, L428, Granta 519, Rec-1 and EBC-1, and wherein said antibody exhibits at least one effector function selected from the group consisting of ADCC, CDC and ADCP. In one embodiment the antibody to be used to deplete CD70-expressing cancer cells in a human patient may be an antibody which exhibits 10% or less internalisation over a period of 6 hours in a CD70-expressing cancer cell line selected from the group consisting of Raji, SU-DHL-6, Granta 519, Rec-1, Mec1, JVM-2, MKN-45, A549 and EBC-1, and also exhibits at least one effector function selected from the group consisting of ADCC, CDC and ADCP.

Specific embodiments of this aspect of the invention may utilise any of the CD70 antibodies described herein, which bind human CD70 with extremely high affinity. Preferred embodiments may utilise an antibody comprising the llama-derived Fab 27B3, or one of its germlined variants, including in particular 41D12 (ARGX-110). Particularly preferred embodiments utilise an antibody comprising the Fab regions of 41D12 (germlined variant of 27B3) fused to the constant regions of human IgG1. In the latter embodiment, the human IgG1 constant region may be further engineered in order to maximise antibody effector functions (e.g. by addition of point mutations), or the 41D12-IgG1 antibody may be non-fucosylated, again to enhance antibody effector function.

Since the rationale behind the use of poorly internalising CD70 antibodies to deplete CD70-expressing cells relies on antibody effector functions, it is preferred that the antibodies used in this aspect of the invention are not immunoconjugates in which the CD70 antibody is linked to a pharmaceutical agent, cytotoxic agent, cytostatic agent, drug moiety, etc. Indeed, a particular advantage of this aspect of the invention is avoidance of the need to use antibody-drug conjugates, which is desirable both from a patient-safety perspective (avoids administration of potentially toxic agents) and an economic perspective (avoids costly synthesis of antibody-drug conjugates).

Use of Antibody-Drug Conjugates to Kill Cells with Significant Internalisation CD70 Antibodies It is demonstrated in the present examples that there are significant cell-to-cell differences in the degree of internalisation of CD70 antibodies, and that these differences are largely dependent on cell type, rather than the nature of the CD70 antibody (although differences are particularly marked when using the antibody ARGX-110). For those cell types which exhibit a significant degree of internalisation of bound CD70 antibody, i.e. 30% or more, preferably 40% or more, more preferably 50% or more, or even 60% or more internalisation after 6 hours, an alternative therapeutic strategy may be based on the use of CD70 antibody-drug conjugates.

Accordingly, a further important aspect of the invention relates to a method of depleting CD70-expressing cells in a human patient, comprising administering to said patient an effective amount of an antibody-drug conjugate comprising an antibody which binds to human CD70 and a cytotoxic or cytostatic drug moiety, wherein said CD70-expressing cells exhibit 30% or more, 40% or more, 50% or more, or 60% or more internalisation of said antibody which binds to human CD70 after a period of 6 hours.

In specific embodiments the CD70-expressing cells may internalise between 40% and 70%, preferably between 50% and 70% of the CD70 antibody which forms the basis of the antibody-drug conjugate within a period of 6 hours.

In this method, the CD70 antibody-drug conjugate is used to deplete CD70 expressing cells. This depletion of CD70-expressing cells may form the basis of therapeutic or prophylactic treatment, e.g. for treatment of prevention of CD70-expressing cancers, or for treatment of prevention of CD70-associated immunological disorders. The precise mechanism by which CD70-expressing antibodies are depleted may depend on the nature of the antibody-drug conjugate, i.e. whether the "drug" moiety is cytotoxic or cytostatic, but will be dependent on strong (high affinity) binding of the CD70 antibody to cell-surface CD70, coupled with significant internalisation of the bound antibody.

In certain embodiments the CD70-expressing cells are CD70-expressing cancer cells. In particular, the CD70-expressing cancer cells may be of a cancer type selected from the group consisting of: cutaneous T cell lymphoma, multiple myeloma, renal cell carcinoma, astrocytoma, melanoma and ovarian carcinoma. Cell lines derived from each of these cancers have been demonstrated to internalise more than 30% of bound CD70 antibody over a period of 6 hours. In a further embodiment, the CD70-expressing cancer cells may be of a cancer type selected from the group consisting of: renal cell carcinoma, astrocytoma, melanoma and ovarian carcinoma. Cell lines derived from each of these cancers have been demonstrated to internalise more than 50% of bound CD70 antibody over a period of 6 hours.

In specific embodiments of this aspect of the invention, the antibody-drug conjugate may be based on any of the CD70 antibodies described herein, which bind human CD70 with extremely high affinity. In preferred embodiments the antibody-drug conjugate may be based on an antibody comprising the llama-derived Fab 27B3, or one of its germlined variants, including in particular 41D12. The features of antibody-drug conjugates intended for human therapeutic use are generally known in the art, particularly with regard to the nature of the "drug" moiety, e.g. a cytotoxic or cytostatic agent, and means of conjugation of the drug moiety to the CD70 antibody moiety. Examples of CD70 antibody-drug conjugates are given, for example, in WO 2004/073656.

Pharmaceutical Compositions

The scope of the invention includes pharmaceutical compositions, containing one or a combination of CD70 antibodies of the invention, or antigen-binding fragments thereof, formulated with one or more a pharmaceutically acceptable carriers or excipients. Such compositions may include one or a combination of (e.g., two or more different) CD70 antibodies.

Techniques for formulating antibodies for human therapeutic use are well known in the art and are reviewed, for example, in Wang et al., Journal of Pharmaceutical Sciences, Vol. 96, pp 1-26, 2007.

Incorporation by Reference

Various publications are cited in the foregoing description and throughout the following examples, each of which is incorporated by reference herein in its entirety.

EXAMPLES

The invention will be further understood with reference to the following non-limiting experimental examples.

Example 1: Immunization of Llamas

Immunizations of llamas and harvesting of peripheral blood lymphocytes (PBLs) as well as the subsequent extraction of RNA and amplification of antibody fragments were performed as described by De Haard and colleagues (De Haard H, et al., J. Bact. 187:4531-4541, 2005). Two llamas were immunized with CD70-expressing 786-O cells (ATCC-CRL-1932) and two llamas with CD70-expressing Raji cells (ATCC-CCL-86). Cells were prepared freshly for each immunization and were verified for CD70 expression by FACS analysis. The llamas were immunized with approximately $10^7$ live cells injected intramuscularly in the neck, once per week for six weeks. Freund's Incomplete Adjuvant was injected in the neck muscles a few centimeters away from the site of cellular immunization.

Blood samples of 10 ml were collected pre- and post immunization to investigate the immune response. The sera from the llamas were tested for the presence of antibodies against recombinant CD70 (Flag-TNC-CD70) by ELISA prior to (day 0) and after (day 55 or 69) immunization. It should be noted that as detection antibody the goat anti-llama IgG1/2 (Bethyl, A160-100P) was used that does not discriminate between conventional and heavy chain antibodies, meaning that the measured CD70 response is from the total IgG. The results are shown in FIG. 1.

Three-to-four days after the last immunization, 400 ml blood was collected for extraction of total RNA from the PBLs using a Ficoll-Paque gradient to isolate PBLs and the method described by Chomczynski P, et al., Anal. Biochem. 162: 156-159, 1987 to prepare the RNA. In average, RNA yields of 450 μg were achieved, of which an 80 μg aliquot was used for random cDNA synthesis and subsequent amplification of VHCH1, VλCλ and VκCκ gene segments.

Example 2: Library Construction

Independent VλCλ, and VκCκ libraries were constructed using a two step PCR, in which 25 cycles with non tagged primers was done followed by 10 cycles using tagged version of these primers (De Haard H, et al., Biol. Chem. 274, 1999). The VHCH1 libraries were built in parallel using the same approach. The sizes of the individual libraries were between $10^7$ and $10^{10}$ cfu. Next, the light chain from the VλCλ and VκCκ libraries were re-cloned separately in the VHCH1-expressing vector to create the "Lambda" and "Kappa" llama Fab-library respectively. Alternatively the digested VHCH1 amplicons were directly cloned into the VκCκ and VλCλ libraries avoiding the construction of a separate VHCH1 library. As light chain shuffling generally delivers better affinity variants than heavy chain shuffling does, we chose to generate precloned light chain libraries and directly clone the heavy chain amplicons in these primary repertoires.

The final phage display libraries were between $5 \times 10^8$ and $2 \times 10^9$ cfu. Quality control of the libraries by analysis of percentage of full length Fab containing clones was routinely performed using PCR.

Example 3: Selections and Screening

Two-to-three rounds of phage selections were done on either captured recombinant CD70 (Flag-TNC-CD70) or on directly coated CD70 using standard protocols. Elution of bound phage was done with trypsin.

Figure 3:
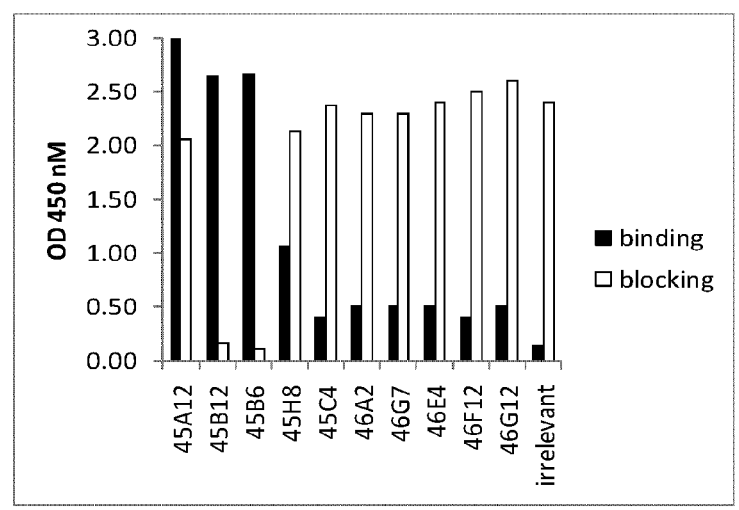
FIG. 3: is a graphical representation of the signal for llama-derived Fabs tested in a binding Elisa (black) or in an inhibition Elisa (white).

From selected phage transfected into TG1, individual colonies were picked randomly for growth in 96 well plates. After IPTG induction according to standard protocols periplasmic fractions (penis) containing Fabs were prepared. In all selections and for all four llamas, several clones were found that were able to express Fabs capable in inhibiting the interaction between CD27 and CD70 as determined by the inhibition ELISA (FIGS. 2 and 3). In this assay, Flag-TNC-CD70 is captured by an anti-Flag mAb and binding of CD27-Fc is detected via a biotinylated anti-CD27 mAb and strep-HRP in the absence or presence of CD70 Fabs (FIGS. 2 and 3) or CD70 mAbs (FIG. 4). In FIG. 2B it can be seen that 27B3, which has an identical VH as 9D1, but contains a somewhat different light chain, seems to block binding of CD27 to CD70 more efficiently, which was in line with the better off rate of this Fab as measured on Biacore (data not shown). Table 3 indicates the blocking potency (expressed as IC50) for the various llama-human chimeric mAbs tested in the CD70 inhibition ELISA. Fab 27B3 has an IC50 of around 0.4 nM, which even seems to improve upon formatting into a chimeric llama-human IgG1 yielding an IC 50 of 0.25 nM, whereas mAb 9D1 with the other light chain is 3-fold less potent (0.73 nM). FIG. 3 is a composite of an experiment testing llama CD70 Fabs for blocking activity (in the inhibition ELISA, see white bars) and for CD70 binding (binding ELISA, black bars). For the binding ELISA, Flag-TNC-CD70 is captured by an anti-Flag mAb and binding of the Fabs is detected using an anti-myc-HRP mAb, which recognizes the MYC tag fused to the C-terminus of the Fd fragment. For comparison purposes, known monoclonal antibodies to CD70 (SGN70 described in US 2010/0129362 A1, clone 1F6; and MDX69A7 described in WO2008/074004 FIGS. 5A and 5B) were tested in parallel. Many llama-derived Fab clones were identified that demonstrate pure binding in ELISA and are non-blocking (see FIG. 3—for example Fab clones 45H8, 45C4, 46A2, 46G7, 46E4, 46F12 and 46G12). Of interest is clone 59D10, which as Fab has no blocking activity, but when converted into a chimeric IgG was antagonistic (see Table 3). Amino acid sequences of the VH and VL domains of binding and blocking llama-derived Fab clones are shown elsewhere herein (Tables 6-9).

TABLE 3

Blocking potency expressed as IC50 (ng/ml) for individual SIMPLE antibodies (mAbs) and benchmarks SGN70 and MDX69A7 as measured in the CD70 inhibition ELISA using recombinant human CD70.

| mAb | IC50 (ng/ml) |
|---|---|
| SGN70 | 330 |
| MDX69A7 | 4038 |
| 9D1 | 109 |
| 5F4 | 296 |
| 9E1 | 1400 |
| 9G2 | 40 |
| 5B2 | 92 |
| 9B2 | 126 |
| 4D2 | 254 |
| 24D4 | 84 |
| 24B6 | 420 |
| 27B3 | 38 |
| 19G10 | 75 |
| 57B6 | 154 |
| 59D10 | 107 | mAbs 27B3 and 57B6 was also tested for their ability to inhibit the interaction between rhesus recombinant CD70 (FLAG-TNC-rhesus CD70) and CD27. The IC50 value determined by the inhibition ELISA described above was 150 and 135 ng/ml, respectively.

Example 4: Affinity for Human and Rhesus CD70

Off-rates of the purified llama-derived anti-CD70 blocking Fabs were determined using the Biacore. Recombinant human CD70 was immobilized on a CM5 Biacore chip. The immobilization was performed in accordance with a method provided by Biacore and by using the NHS/EDC kit (Biacore AB): after activation of the chip, a solution of 50 μg/ml of recombinant CD70 in 10 mM acetate buffer with pH of 5 was prepared and 1 μl of this solution (50 ng) was injected resulting in a surface density of approximately 1000 RU.

Fabs for the CD70 mAbs ARGX-110, MDX2H5 and SGN70 were prepared by trypsin digestion (SGN70 and MDX69A7 are described elsewhere herein, MDX2H5, also referred to as MDX1411, is described in WO2008/074004 FIGS. 1A and 1B). Fabs, at a concentration of approximately 100-400 μg/ml, were diluted 6-fold in hepes-buffered saline (0.1M Hepes, 1.5M NaCl, 30 mM EDTA, 0.5% v/v surfactant P20). They were injected (30 μl) and passed through the flow cells at a flow rate of 30 μl/min. After binding of the Fab to CD70, the off-rate was monitored for a period of 10 minutes. After the dissociation, the flow cell surfaces were regenerated by injecting 5 μl of 10 mM NaOH. Sometimes multiple injections of NaOH were needed to regenerate the surfaces depending on the affinity of the Fabs. Off-rate analysis was done by applying the BIAevaluation software. First, the sensogram of the blank runs were subtracted from those obtained with the coated flow cell. Then the off-rate was determined for a time range of 10 minutes using the Fit kinetics application and the $K_d$ value was calculated. Moreover, the off-rate of CD27 for CD70 was determined as well. The off rates are summarized in Table 4.

All llama-derived Fabs tested bind with apparent very low off-rates (i.e. high affinity) to human recombinant CD70 and to rhesus recombinant CD70 based on Biacore off rates in the range of $0.4\text{-}4.8 \times 10^{-4}$ $s^{-1}$. The off-rates of the llama-derived Fabs for human CD70 are much better than for the reference mAb derived Fabs ($7\text{-}30 \times 10^{-4}$ $s^{-1}$). The llama-derived Fabs with the best off-rates were shown to have comparable off-rates to that of CD27 for its interaction with CD70 ($0.8 \times 10^{-4}$ $s^{-1}$). It should be noted that the lower limit for measurement of off-rates using Biacore is around $0.4 \times 10^{-4}$ $s^{-1}$. Hence the llama-derived Fabs with off-rates falling close to this limit as assessed by Biacore may in fact exhibit even a higher affinity for CD70.

TABLE 4

Off rates of llama-derived Fabs and reference Fabs for human or rhesus CD70

| Fab tested | $k_{off}$ $(s^{-1}) \times E^{-4}$ human CD70 | $k_{off}$ $(s^{-1}) \times E^{-4}$ rhesus CD70 |
|---|---|---|
| SGN70-Fab | 7.0 | |
| MDX2H5-Fab | 17 | No binding |
| MDX69A7-Fab | 30 | |
| CD27 | 0.8 | |
| 1C2 | 0.4 | 3.2 |
| 9D1 | 4.8 | 2.0 |
| 9G2 | 1.8 | 1.8 |
| 5F4 | 0.8 | 5.0 |
| 9E1 | 1.9 | 2.0 |
| 9B2 | 2.8 | 6.1 |
| 4D2 | 3.3 | 2.9 |
| 27B3 | 0.8 | |
| 24E3 | 0.8 | |
| 33D8 | 4.5 | |
| 24F2 | 1.6 | |
| 24B6 | 1.0 | |
| 19G10 | 0.8 | |
| 8B12 | 3.6 | |
| 45B12 | 2.1 | |
| 45D9 | 2.1 | |
| 45F8 | 2.0 | |
| 57B6 | 1.0 | 0.4 |
| 59D10 | 13.9 | No binding |

Example 5: Binding of Chimeric Llama-Human CD70 mAbs to CD70 Positive Cells

The VH and VL of interesting llama-derived Fab clones were fused to constant regions of human IgG1 and to human Cλ (all variable light chain regions are of lambda origin) and produced as bivalent chimeric monoclonal antibodies in the system described in patent application WO 2009/145606. The chimeric llama-human mAbs were purified on Protein A followed by gel filtration.

786-O cells were incubated with a 1/5 dilution series of chimeric llama-human CD70 inhibiting mAbs (20 μg/ml-0.25 ng/ml) and binding of the mAbs to the cells was detected using an anti-human Fc-FITC antibody (1/500 diluted conjugate AF006 from supplier Binding Site). Fluorescence of 10,000 cells/condition was measured using a flow cytometer and the median fluorescence was plotted. The results are shown in FIG. 5. Most of the mAbs bind with high affinity to 786-O cells. SIMPLE antibody 1C2, which as Fab showed to have the best off rate and blocking potency, was not able to recognize cell surface expressed CD70 (data not shown) and therefore was not studied furthermore. SIMPLE antibody 27B3 has the best affinity for cell bound receptor with an EC50 of 0.24 nM.

In a further experiment, NHL-derived MHH-PREB-1 cells ($10^5$ cells) were incubated with a concentration gradient of chimeric llama-human CD70 inhibiting mAbs (20 μg/ml-0.25 ng/ml) and binding of the mAbs to the cells was detected using anti-human IgG-FITC antibody. The results are shown in FIG. 5B. The EC50 values for 57B6 and 59D10 were 83 and 74 ng/ml, respectively.

Example 6: Inhibition in Co-Culture Experiments by Chimeric Llama-Human CD70 mAbs In order to determine the blocking potency in a cell based assay the system described by Wyzgol and colleagues was used (J Immunol (2009) 183: 1851-1861). Fibrosarcoma cell line HT1080 transfected with human CD27 secretes IL-8 upon ligation with trimeric recombinant CD70 and blocking of this interaction with a neutralizing mAb can be measured by reduced cytokine levels. A modified version of the assay was applied in which the B cell lymphoma Raji cell line served as source of CD70, although the molecule is expressed on the cell surface and therefore is more relevant than soluble CD70.

Figure 6:
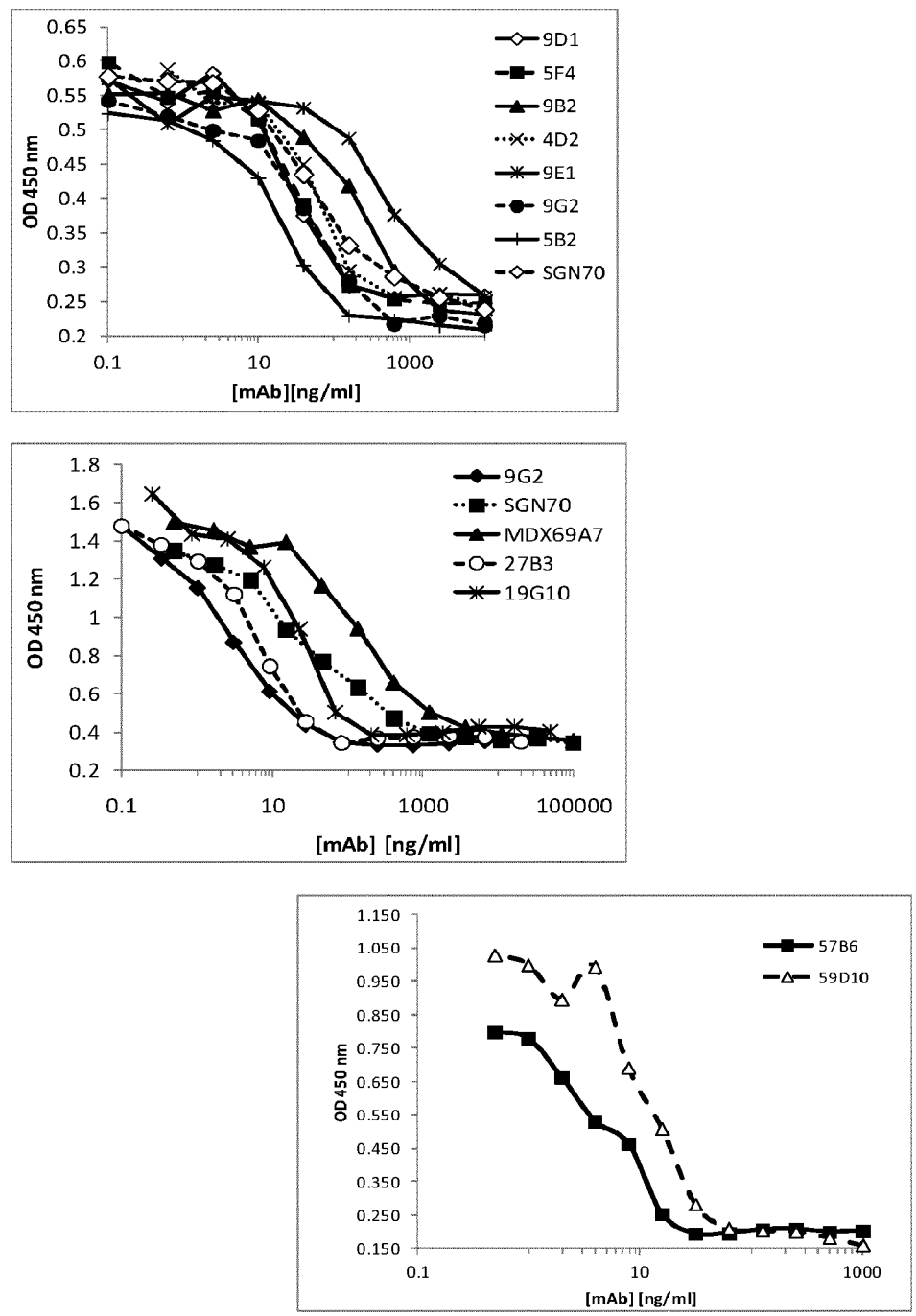
FIG. 6: shows inhibition by CD70 specific chimeric llama-human mAbs in a Raji cell based co-culture potency assay.

Raji cells were cultured and checked for CD70 expression by FACS analysis. Cells were then mixed in a 96-well tissue culture plate (50,000 cells/well) with the anti-CD70 mAbs and incubated at RT for 1 hour. HT1080-CD27 cells were added (10,000 cells/well) and thoroughly mixed. Co-cultures were transferred to the incubator and grown overnight at 37° C. Supernatants were collected and analyzed for their IL-8 content by ELISA. The results for the SIMPLE antibodies are shown in FIG. 6 and are compared to reference CD70 mAbs. IC50 values for the chimeric llama-human CD70 mAbs are between 3 and 517 ng/ml as compared to 42 ng/ml for SGN70 and 143 ng/ml for MDX69A7 (see table 5). SIMPLE antibodies 27B3 (IC50 of 33 pM) and 9G2 (IC50 of 20 pM) are 10 to 20 fold more potent than benchmark SGN70 (IC50 of 370 pM) that again is 3 fold more potent than benchmark MDX69A7 (1 nM). It can therefore be concluded that the chimeric llama-human mAbs are extremely potent in blocking the interaction between CD27 and CD70 and outperform the benchmark antibodies in this highly relevant bioassay.

TABLE 5

Neutralizing potency expressed as IC50 value (ng/ml) of chimeric llama-human CD70 mAbs and reference mAbs tested in Raji-based co-culture assay

| mAb | IC50 (ng/ml) |
| --- | --- |
| 9D1 | 29 |
| 5F4 | 32 |
| 9B2 | 213 |
| 4D2 | 54 |
| 9E1 | 517 |
| 5B2 | 19 |
| SGN70 | 55 |
| MDX69A7 | 143 |
| 27B3 | 5 |
| 19G10 | 16 |
| 9G2 | 3 |
| 57B6 | 5 |
| 59D10 | 10 |

Example 7: Antibody Dependent Cellular Cytotoxicity Activity

Antibody Dependent Cellular Cytotoxicity (ADCC) was measured using the standard $Cr^{51}$-release assay, which was described by McEarchern et al. (Blood (2007) 109: 1185-1192). Human peripheral blood mononuclear cells (PBMC) were purified from heparinized whole blood by standard ficoll separation and were used as source of NK cells (i.e. effector cells). Blood from several independent donors was used. The cells were suspended at $2 \times 10^6$/ml in media containing 200 U/ml of human IL-2 (for stimulation of NK cells) and incubated overnight at 37° C. The following day, adherent and non-adherent cells were collected and washed once in culture media. The target cells were 786-O cells (RCC) and were labeled with $Cr^{51}$. Target to effector cell ratio was 1:20 and the incubation was performed for 2 hours with the antibody present at different concentrations in the culture medium. Chimeric llama-human mAbs as well as the benchmark antibodies were tested for ADCC activity on 786-O cells at different concentrations.

The percent lysis was determined by the equation:

% Lysis=(sample CPM−spontaneous release CPM)/ (maximum release CPM−spontaneous release CPM)×100.

Figure 7:
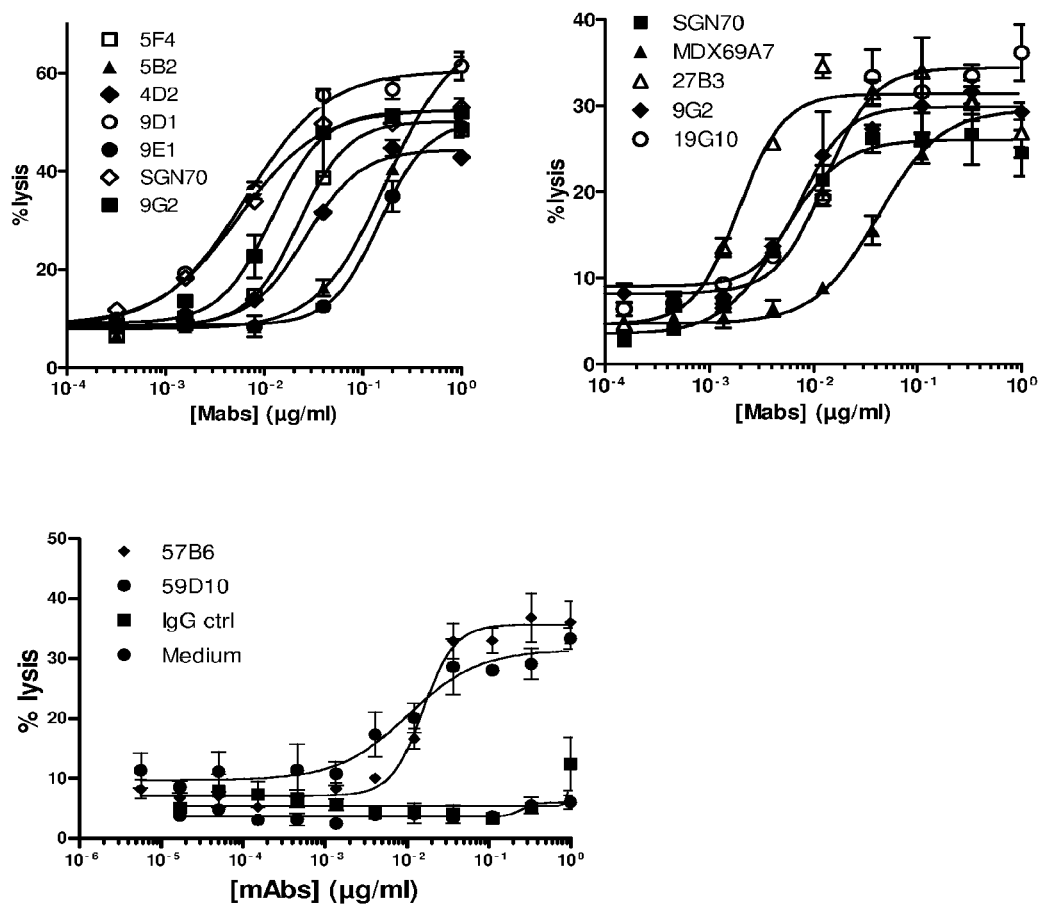
FIG. 7: shows the results of standard $Cr^{51}$ release ADCC assay on 786-O cells.

The results demonstrate that all of the chimeric llama-human mAbs induce lysis of target cells via ADCC activity (FIG. 7). SIMPLE mAb 27B3 has a potency of around 1 µg/ml and therefore is 10 fold more potent than the affinity variant 9D1 that has a comparable IC50 as benchmark SGN70, which again is 2.5 fold more potent in ADCC than benchmark MDX69A7. SIMPLE antibody 27B3 combines best in class receptor-ligand blocking potency with superior ADCC potency and therefore has a favourable therapeutic profile.

Example 8: Complement Dependent Cytoxicity Potency of CD70 Specific mAbs

Complement Dependent Cytotoxicity (CDC) properties of the antibodies were determined in the standard assay described by McEarchern et al. (Blood (2007) 109: 1185-1192). In a first control experiment, U266 (MM) and MHH-PREB1 (NHL) cells were tested for the presence of CD70 antigen by FACS analysis. In a next experiment, a chimeric llama-human CD70 mAb was tested for CDC activity on both cell lines at 3 different concentrations and in the presence of 3, 6 or 9% human serum (as a source of human complement). It was concluded that the U266 cells give the best signal/noise ratio in the presence of 9% serum.

In a next experiment, U266 cells were mixed with chimeric llama-human mAbs (FIG. 8, upper panel) or the reference CD70 mAbs (FIG. 8, lower panel) at 0.001-20 µg/ml in the absence or presence of 9% human serum and incubated for 2 h at 37° C. Cells were spun down and Propidium Iodide was added to determine the number of dead cells. Cell lysis was measured in FACS. CDC activity was demonstrated for all chimeric llama-human mAbs on U266 cells in the presence of 9% human serum. SIMPLE antibody 27B3 has a similar IC50 as benchmark SGN70, while again MDX69A7 is 10 fold less potent.

Example 9: Antibody Dependent Cellular Phagocytosis Potency

To analyze Antibody Dependent Cellular Phagocytosis (ADCP) properties of the SIMPLE mAbs the assay described by McEarchern et al. (Blood (2007) 109: 1185-1192) was implemented. In this assay human peripheral blood mononuclear cells (PBMC) were purified from heparinized whole blood by standard ficoll separation. Blood from different donors were used. Cells were incubated in RPMI containing 10% FCS in tissue culture flask overnight at 37° C. Non-adherent cells were removed and adherent cells were cultured for 15 days in 75mlX-VIVO 15 medium containing 500 U/ml rhGM-CSF (7.5 µg/75 ml). After 15 days, adherent cells were harvested (monocyte derived macrophages (MDM).

$8.0 \times 10^4$ target cells (786-O cells) loaded with the red dye PKH26 were incubated with mAb for 30 minutes on ice in a V-bottom 96 well plate. Next, 2.0×10⁴ MDM cells were added (target to effector (786-O to MDM) ratio of 4:1) and after 1 hour of incubation at 37° C., the cells were centrifuged, resuspended in 100 µl PBS 1% BSA and transferred to a V-bottom 96 well plate. Anti-CD11b monoclonal antibody (FITC conjugated) for staining of macrophages was added for 30 min while keeping the plates on ice, cells were then washed two times with PBS and fixed with 1% paraformaldehyde (in PBS). Samples were analysed by FACS, where phagocytosis was scored on double stained cells. The results are shown in FIG. 9 and these demonstrate that all chimeric llama-human mAbs tested are potent in inducing ADCP. SIMPLE antibody 27B3 induces phagocytosis of up to 50% of the labelled tumour cells by macrophages at concentrations of 1 µg/ml with an IC50 of around 100 ng/ml (0.4 nM).

Example 10: Internalization of Anti-CD70 mAbs on Tumor Cell Line 786-O

It has been demonstrated that binding of CD70 antibodies to the renal carcinoma derived cell line 786-O results in the rapid (within 1 hour) internalization of the antibody-receptor complex (Adam et al., Br J Cancer (2006) 95:298-306). In order to test for internalization of SIMPLE antibodies and benchmark mAbs directed against CD70, 786-O cells were cultured in a 96-well microtiter plate and incubated overnight at 37° C. 2.5 µg/ml mAb was added and incubated with the cells for 0-24 hours at 37° C. Plates were washed 3 times 5' with stripping buffer (150 mM NaCl, 100 mM Glycine, pH=2.5; coded "IN" representing the amount of mAb internalized via CD70) or PBS (coded "OUT" and representing the amount of mAb bound to the receptor at the outside of the cell). Subsequently, cells were fixed with 4% paraformaldehyde for 30' at RT, washed with PBS, and incubated 5' with 0.2% Triton-X-100 ("IN") or PBS ("OUT"). Next, cells were washed twice and incubated at RT for 10' with 100 mM glycine followed by a 30' incubation with PBS-1% BSA. Finally cells were stained with goat anti-human Fc (Jackson immunoresearch 109-005-098) and anti-goat IRDYE800 (Li-cor 926-32214) before analysis on the Li-Cor Odyssey infrared scanner. The antibody remaining at the outside of the cell, i.e. non-internalized, is scored as mean MFI OUT in FIG. 10. The results demonstrate that several mAbs remain longer at the surface of the cells than the other mAbs (higher signal). However, none of the mAbs internalizes completely: initially (between 0 and 2 hours), mAb internalization goes very fast, but then it seems that a steady state is reached where 30-40% of the mAb remains at the outside of the cell, even after 24 hours of incubation at 37° C. SIMPLE antibody 27B3 internalizes as rapidly as benchmark antibodies SGN70 and MDX69A7. It is interesting to observe that SIMPLE antibodies 9E1 and 19G10, but also other, remain at high levels at the outside of the cells, even after 24 hours of incubation (lower panel of FIG. 10). In order to effectively induce ADCC, CDC and ADCP effects it is important that high levels of CD70 specific antibodies remain on the outside of the targeted cancer cells in order to recruit the effector immune cells that are responsible for cell killing. On the other hand rapidly internalizing antibodies have potential as Antibody Drug Conjugates (ADC).

Example 11: In Vivo Efficacy of Chimeric Llama-Human mAbs in a Tumour Xenograft Model To establish disseminated disease, 10⁶ Raji cells in 0.2 mL PBS were injected into the lateral tail vein of C.B.-17 severe combined immunodeficient (SCID) mice (Harlan, Indianapolis, Ind.). After injection, all of the mice were pooled and then placed randomly into the various treatment groups, with 9 mice per group. Antibodies were administered in 0.5 ml at day 1, 4, 8, 11, 15 after the cell implantation by intraperitoneal injection. Mice were monitored at least twice per week and were sacrificed when they exhibited signs of disease, including weight loss of 15% to 20%, hunched posture, lethargy, cranial swelling, or dehydration. Mice received treatment with 41D12 mAb in a dose response. Additionally, a Fc-dead version of 41D12 was tested at 10 mg/kg. This Fc-dead version has been described before in the literature and has no ADCC and CDC activity and much lower ADCP activity (McEarchern et al., Clin Cancer Res (2008) 14(23):7763-72). Results are shown as survival curves in FIG. 11. These data show that the median survival time for the control mice is 27 days. Median survival time was prolonged to at least 67 days when doses equal to or higher than 0.1 mg/kg of 41D12 were administered. The dose of 0.01 mg/kg is still efficacious. The Fc-dead version of 41D12 has no potency in vivo, illustrating the important of ADCC, CDC and ADCP in this model.

Example 12: Expression of Non-Fucosylated mAbs

Antibodies with reduced amounts of fucosyl residues have been demonstrated to increase ADCC by 10-1000 fold (Iida et al., Clin Cancer Res. (2006) 12(9): 2879-2887). The CHO cell line Ms704-PF and MS705, which lack the fucosyltransferase gene (FUT8, BioWa, Inc.) was electroporated with a eukaryotic expression vector encoding the heavy and light chain of the chimeric llama-human CD70 mAbs. Drug resistant clones were selected by growth in Excell 325-PF CHO medium. Clones were screened for IgG production by a standard CD70 binding ELISA.

TABLE 6

| sequence of CD70 specific llama-derived VH | | | | |
|---|---|---|---|---|
| Fab | Framework 1 | SEQ ID | CDR1 | SEQ ID |
| 1C2 | ELQVVESGGGLVQPGGSLRLSCAASGFTLS | 1 | NYWMH | 10 |
| 9D1 | EVQLVESGGGLVQPGGSLRLSCAASGFTFS | 2 | VYYMN | 11 |
| 8B12 | EVQLVESGGGLVQPGGSLRLSCAASGFTFS | 2 | VYYMN | 11 |
| 8C12 | EVQLVESGGGLVQPGGSLRLSCAASGFTFS | 2 | VYYMN | 11 |
| 9E1 | EVQLQESGGGVVQPGGSLRLSCAASGFTFD | 3 | DYAMS | 12 |
| 5F4 | EVQVQESGGGLVHPGGSLKLSCAASGFTFD | 4 | TYAMS | 13 |

TABLE 6-continued

| Fab | sequence of CD70 specific llama-derived VH | SEQ ID | CDR1 | SEQ ID |
|---|---|---|---|---|
| 5B2 | QVQLVESGGDLVQPGGSLRLSCAASGFTVS | 5 | NPAMS | 14 |
| 6D5 | EVQLVQPGAELRKPGASVKVSCKASGYTFT | 6 | SYYID | 15 |
| 4D2 | QVQLQESGPGLVKPSQTLSLACTVSGGSIT | 7 | TSYYYWS | 16 |
| 9A1 | EVQLVESGGGLVQPGGSLRLSCAASGFTFS | 2 | SYAMS | 17 |
| 9G2 | QVQLVESGGGLMQPGGSLRLSCAASGFTFS | 8 | SSAMS | 18 |
| 9B2 | QLQVVESGGGLMQPGGSLRLSCAASGFTFS | 9 | GSAMS | 19 |
| 27B3 | EVQLVESGGGLVQPGGSLRLSCAASGFTFS | 2 | VYYMN | 11 |
| 24E3 | EVQLVESGGGLVQPGGSLRLSCAASGFTFS | 2 | VYYMN | 11 |
| 33D8 | EVQLVESGGGLVQPGGSLRLSCAASGFTFS | 2 | VYYMN | 11 |
| 24F2 | EVQLVESGGGLVQPGGSLRLSCAASGFTFS | 2 | VYYMN | 11 |
| 24B6 | EVQLQESGGGVVQPGGSLRLSCAASGFTFD | 3 | DYAMS | 12 |
| 19G10 | EVQLQESGGGVVQPGGSLRLSCAASGFTFD | 3 | DYAMS | 12 |
| 45B12 | EVQLVESGGGLVQPGGSLRLSCAASGFTFS | 2 | AYYMN | 20 |
| 45D9 | EVQLVESGGGLVQPGGSLRLSCAASGFTFS | 2 | AYYMN | 20 |
| 45F8 | EVQLVESGGGLVQPGGSLRLSCAASGFTFS | 2 | AYYMN | 20 |
| 45A12 | EVQLVESGGGLVQPGGSLRLSCAASGFTFS | 2 | AYYMN | 20 |
| 45B6 | EVQLVESGGGLVQPGGSLRLSCAASGFTFS | 2 | AYYMN | 20 |
| 57B6 | QLQLVESGGGLVQPGGSLRLSCAASGFSFS | 254 | HYAMS | 256 |
| 59D10 | EVQLVESGGGLVQPGGSLRLSCAASELSFS | 255 | ISEMT | 257 |

| Fab | Framework 2 | SEQ ID | CDR2 | SEQ ID |
|---|---|---|---|---|
| 1C2 | WVRQAPRKGLEWVS | 21 | TISTDNSRTYYADSVKG | 26 |
| 9D1 | WVRQAPGKGLEWVS | 22 | DINNEGGTTYYADSVKG | 27 |
| 8B12 | WVRQAPGKGLEWVS | 22 | DINNEGDTTYYADSVKG | 28 |
| 8C12 | WVRQAPGKGLEWVS | 22 | DINNEGDTTYYADSVKG | 28 |
| 9E1 | WVRQAPGKGLEWVS | 22 | SIYMDSSTYYADSVKG | 29 |
| 5F4 | WVRQAPGKGLEWVS | 22 | AISWSGGETFYAESMKG | 30 |
| 5B2 | WVRQAPGKGLEWVS | 22 | EITNYGYNRYYADSVKG | 31 |
| 6D5 | WVRQAPGQGLEWMG | 23 | RIDPEDGGTKYAQKFQG | 32 |
| 4D2 | WIRQPPGKGLEWMG | 24 | AIGSRGSTYYSPSLKT | 33 |
| 9A1 | WVRQAPGKGLEWVS | 22 | DINSGGGSTKYNDSVKG | 34 |
| 9G2 | WVRQAPGKGLEWVS | 22 | SIYSDSSYTYYADSVKS | 35 |
| 9B2 | WVRQAPGKGLEWVS | 22 | SIYSHSMYTYYADSVKS | 36 |
| 27B3 | WVRQAPGKGLEWVS | 22 | DINNEGGTTYYADSVKG | 27 |
| 24E3 | WVRQAPGKGLEWVS | 22 | DINNEGGTTYYADSVKG | 27 |
| 33D8 | WVRQAPGKGLEWVS | 22 | DINNEGGTTYYADSVKG | 27 |
| 24F2 | WVRQAPGKGLEWVS | 22 | DINNEGGTTYYADSVKG | 27 |
| 24B6 | WVRQAPGKGLEWVS | 22 | SIYMDSSTYYADSVKG | 29 |
| 19G10 | WVRQAPGKGLEWVS | 22 | SIYMDSSTYYADSVKG | 29 |
| 45B12 | WVRQAPGKGLEWIS | 25 | DINNEGYETYYADSVKG | 37 |

TABLE 6-continued sequence of CD70 specific llama-derived VH

| | | | | |
|---|---|---|---|---|
| 45D9 | WVRQAPGKGLEWIS | 25 | DINNEGYETYYADSVKG | 37 |
| 45F8 | WVRQAPGKGLEWIS | 25 | DINNEGYETYYADSVKG | 37 |
| 45A12 | WVRQAPGKGLEWIS | 25 | DINNEGYETYYADSVKG | 37 |
| 45B6 | WVRQAPGKGLEWIS | 25 | DINNEGYETYYADSVKG | 37 |
| 57B6 | WVRQAPGKGLEWVS | 22 | GDNTYDGGTRYQDSVKG | 258 |
| 59D10 | WVRQAPGKGLEWVS | 22 | GISGVTGGSSTSYADSVKG | 259 |

| Fab | Framework 3 | SEQ ID | CDR3 | SEQ ID |
|---|---|---|---|---|
| 1C2 | RFTISRDHAKNTLILQMNSLKSEDTAVYYCIR | 38 | GSDYEH | 49 |
| 9D1 | RFTISRDNAKNTLTLQMNSLKPEDTALYYCVR | 39 | DAGYSNHVPIFDS | 50 |
| 8B12 | RFTISRDNAKNTLTLQMDSLKPEDTALYYCVR | 40 | DAGYSNHVPIFDS | 50 |
| 8C12 | RFTISRDNAKNTLTLQMDSLKPEDTALYYCVR | 40 | DAGYSNHVPIFDS | 50 |
| 9E1 | RFTISTDNAKNTVYLQMNSLKSEDTAVYYCAK | 41 | DINRSYGSSWSHFGPIFSS | 51 |
| 5F4 | RFTISRNNAKNTLYLQMNSLKSEDTAVYYCAR | 42 | GMGLAEGLTD | 52 |
| 5B2 | RFTISTDNAKNTLYLQMNSLRSEDSAVYYCTA | 43 | SLGLEYGYGD | 53 |
| 6D5 | RVTFTADASTSTAYVELSSLRSEDTAVYYCAS | 44 | RRRDFDY | 54 |
| 4D2 | RTSISRDTSKNQFTLQLSSVTPEDTAVYYCAR | 45 | VTGEITYNSGSYYYTLNLFDY | 55 |
| 9A1 | RFAISRDNAKNTLYLQMNSLKPEDTAVYYCAK | 46 | EGGSGRYWTNEYDY | 56 |
| 9G2 | RFTISTDNAKNTLYLQMNSLKPDDTAVYYCAG | 47 | SSDYEGSFAS | 57 |
| 9B2 | RFTISTDNAKNTLYLQMNSLKPDDTAVYYCAA | 342 | SSDYEGLFVS | 58 |
| 27B3 | RFTISRDNAKNTLTLQMNSLKPEDTALYYCVR | 39 | DAGYSNHVPIFDS | 50 |
| 24E3 | RFTISRDNAKNTLTLQMNSLKPEDTALYYCVR | 39 | DAGYSNHVPIFDS | 50 |
| 33D8 | RFTISRDNAKNTLTLQMNSLKPEDTALYYCVR | 39 | DAGYSNHVPIFDS | 50 |
| 24F2 | RFTISRDNAKNTLTLQMNSLKPEDTALYYCVR | 39 | DAGYSNHVPIFDS | 50 |
| 24B6 | RFTISTDNAKNTVYLQMNSLKSEDTAVYYCAK | 41 | DINRSYGSSWSHFGPIFSS | 51 |
| 19G10 | RFTISTDNAKNTVYLQMNSLKSEDTAVYYCAK | 41 | DINRSYGSSWSHFGPIFSS | 51 |
| 45B12 | RFTISRDNAKNTLTLQMDSLKPEDTARYYCVR | 48 | DAGYSNHVQIFDS | 59 |
| 45D9 | RFTISRDNAKNTLTLQMDSLKPEDTARYYCVR | 48 | DAGYSNHVQIFDS | 59 |
| 45F8 | RFTISRDNAKNTLTLQMDSLKPEDTARYYCVR | 48 | DAGYSNHVQIFDS | 59 |

TABLE 6-continued sequence of CD70 specific llama-derived VH

| | | | | | |
|---|---|---|---|---|---|
| 45A12 | RFTISRDNAKNTLTLQMD SLKPEDTARYYCVR | 48 | DAGYSNHVQIFDS | | 59 |
| 45B6 | RFTISRDNAKNTLTLQMD SLKPEDTARYYCVR | 48 | DAGYSNHVQIFDS | | 59 |
| 57B6 | RFTISRDNGKNTLYLQMN SLKPEDTAVYYCAK | 260 | DTGRGIMGEYGMDY | | 262 |
| 59D10 | RFTISRDNGKNTLYLQMN SLIPEDTAVYYCAT | 261 | TSGTYYFIPEYEY | | 263 |

| Fab | FRAMEWORK 4 | SEQ ID |
|---|---|---|
| 1C2 | WGQGTQVTVSS | 60 |
| 9D1 | WGQGTQVIVAS | 61 |
| 8B12 | WGQGTQVIVAS | 61 |
| 8C12 | WGQGTQVIVAS | 61 |
| 9E1 | WGQGTQVTVSS | 60 |
| 5F4 | WGQGTQVTVSS | 60 |
| 5B2 | WGQGTQVTVSS | 60 |
| 6D5 | WGQGTQVTVSS | 60 |
| 4D2 | WGQGTQVTVSS | 60 |
| 9A1 | WGQGTQVTVSS | 60 |
| 9G2 | WGQGTQVTVSS | 60 |
| 9B2 | WGQGTQVTVSS | 60 |
| 27B3 | WGQGTQVIVAS | 61 |
| 24E3 | WGQGTQVIVAS | 61 |
| 33D8 | WGQGTQVIVAS | 61 |
| 24F2 | WGQGTQVIVAS | 61 |
| 24B6 | WGQGTQVTVSS | 60 |
| 19G10 | WGQGTQVTVSS | 60 |
| 45B12 | WGQGTQVIVAS | 61 |
| 45D9 | WGQGTQVIVAS | 61 |
| 45F8 | WGQGTQVIVAS | 61 |
| 45A12 | WGQGTQVIVAS | 61 |
| 45B6 | WGQGTQVIVAS | 61 |
| 57B6 | WGKGTLVTVSS | 264 |
| 59D10 | WGQGTQVTVSS | 60 |

TABLE 7 sequence of CD70 specific llama-derived VL
(Q in bold encoded by amber STOP codon)

| Fab | Framework 1 | SEQ ID | CDR1 | SEQ ID |
|---|---|---|---|---|
| 1C2 | QTVVTQEPSLSVSPGGTVTLTC | 62 | GLSSGSVTTTNYPG | 77 |
| 9D1 | QAVVTQEPSLSVSPGGTVTLTC | 63 | GLSSGSVTSSHYPG | 78 |

TABLE 7-continued sequence of CD70 specific llama-derived VL
(Q in bold encoded by amber STOP codon)

| Fab | | SEQ ID | | SEQ ID |
|---|---|---|---|---|
| 8B12 | QTVVTQEPSLSVSPGGTVTLTC | 62 | GLSSGSVTSSNYPG | 79 |
| 8C12 | QAVVTQEPSLSVSPGGTVTLTC | 63 | GLTSGSVTSSNYPD | 80 |
| 9E1 | QAVVTQEPSLSVSPGGTVTLTC | 63 | GLTSGSVTSSNYPD | 80 |
| 5F4 | QAVVTHPPSLSASPGSSVRLTC | 64 | TLISGDNIGGYDIS | 81 |
| 5B2 | QSALTQPPSVSGTLGKTLTISC | 65 | AGTSSDVGYGNYVS | 82 |
| 6D5 | QSALTQPSAVSVSLGQTARITC | 66 | QGGNARFSSFA | 83 |
| 4D2 | QSVLTQPPSLSASPGSSVRLTC | 67 | TLSSGNSVGNYDIS | 84 |
| 9A1 | QSALTQPSALSVTLGQTAKITC | 68 | QGGRLGSSYAH | 85 |
| 9G2 | QSVVTQPPSLSASPGSSVRLTC | 69 | TLSSGNSVGNYDIS | 84 |
| 9B2 | QAVLTQPPSLSASPGSSVRLTC | 70 | TLNSANSVGSYDIS | 86 |
| 27B3 | QAVVTQEPSLTVSPGGTVTLTC | 71 | GLKSGSVTSTNFPT | 87 |
| 24E3 | QAVVTQEPSLSVSPGGTVTLTC | 63 | GLTSGSVTSDNFPV | 88 |
| 33D8 | QSALTQPSTVSVSLGQTARITC | 72 | RGDSLERYGTN | 89 |
| 24F2 | QSALTQPSAVSVSLGQTARITC | 66 | RGDTLRNYHAN | 90 |
| 24B6 | QPVLTQPSAVSVSLGQTARITC | 73 | QGGYYTH | 91 |
| 19G10 | NFMLTQPSAVSVSLGQTARITC | 74 | QGGYYTH | 91 |
| 45B12 | QAVLTQPSSVSVSLGQTAKITC | 75 | QGGNLGLYGAN | 92 |
| 45D9 | QAVLTQPSSVSVSLGQTAKITC | 75 | QGGNLWLYGAN | 93 |
| 45F8 | QAVLTQPSSVSVSLGQTANITC | 76 | QGGNLGLYGAN | 92 |
| 45A12 | QAVVTQEPSLSVSPGGTVTLTC | 63 | GLSSGSATSGNYPE | 94 |
| 45B6 | QAVVTQEPSLSVSPGGTVTLTC | 63 | GLSSGSVTSSNYPD | 95 |
| 57B6 | QTVVTQEPSLSVSPGGTVTLTC | 265 | GLKSGSVTSSNYPA | 267 |
| 59D10 | QSVLTQPPSVSGSPGKTVTISC | 266 | AGTSSDVGYGYYVS | 268 |

| Fab | Framework 2 | SEQ ID | CDR2 | SEQ ID |
|---|---|---|---|---|
| 1C2 | WFQQTPGQAPRTLIY | 96 | STSSRHS | 109 |
| 9D1 | WYQQTPGQAPRLLIF | 97 | NTNSRHS | 110 |
| 8B12 | WYQQTPGQAPRVLIY | 98 | NTNNRHS | 111 |
| 8C12 | WYQQTPGQAPRLLIY | 99 | NTNSRHS | 110 |
| 9E1 | WYQQTPGQAPRLLIY | 99 | NTNSRHS | 110 |
| 5F4 | WYQQKTGSPPRYLLY | 100 | YYSDSYKHQSS | 112 |
| 5B2 | WYQQLPGTAPKLLIY | 101 | RVSTRAS | 113 |
| 6D5 | WYQQKPGQAPVQVIY | 102 | YNTNRPS | 114 |
| 4D2 | WYQQKAGSPPRYLLY | 103 | YYSDSYKNQGS | 115 |
| 9A1 | WYQQKPGQAPVLVIY | 104 | GNNYRPS | 116 |
| 9G2 | WYQQKAGSPPRYLLY | 103 | YYSDSVKHQGS | 117 |
| 9B2 | WYQQKAGSPPRYLLY | 103 | YYSDSLSHQGS | 118 |
| 27B3 | WYQQTPGQAPRLLIY | 99 | NTNTRHS | 119 |
| 24E3 | WYQQTPGQAPRLLIY | 99 | TINSRHS | 120 |
| 33D8 | WYQQKPGQAPVLVIY | 104 | DDDSRPS | 121 |

TABLE 7-continued sequence of CD70 specific llama-derived VL
(Q in bold encoded by amber STOP codon)

| Fab | | SEQ ID | | SEQ ID |
|---|---|---|---|---|
| 24F2 | WYRQKPGQAPVLVIY | 105 | GDDIRPS | 122 |
| 24B6 | WYQQKPGQAPVLVIY | 104 | INNNRPS | 123 |
| 19G10 | WYQQKPGQAPVLVIY | 104 | VNNNRPS | 124 |
| 45B12 | WYQQNPGRAPILLIY | 106 | GDNYRPL | 125 |
| 45D9 | WYQQNPGRAPILLIY | 106 | GDNQRPL | 126 |
| 45F8 | WYQQNPGRAPILLFY | 107 | GDNYMPL | 127 |
| 45A12 | WYQQTPGQAPRLIIY | 108 | NTASRHS | 128 |
| 45B6 | WYQQTPGQAPRLLIY | 99 | NTNSRHS | 110 |
| 57B6 | WYQQTPGQAPRLLIY | 99 | NTNSRHS | 110 |
| 59D10 | WYQQFPGMAPKLLIY | 269 | DVNKRAS | 270 |

| Fab | Framework 3 | SEQ ID | CDR3 | SEQ ID |
|---|---|---|---|---|
| 1C2 | GVPSRFSGSISGNKAALTITGAQPEDEADYYC | 129 | ALEEIGSYTM | 148 |
| 9D1 | GVPSRFSGSISGNKAALTITGAQPEDEADYYC | 129 | ALLNIDDGSTM | 149 |
| 8B12 | GVPSRYSGSISGNKAALTITGAEPEDEADYYC | 130 | NLHLGSYTPM | 150 |
| 8C12 | GVPSRFSGSISGNKAALTITGAQPEDEADYYC | 131 | ALYWGYGTNVDV | 151 |
| 9E1 | GVPSRFSGSISGNKAALTITGAQPEDEADYYC | 129 | NLYMGSGGSKV | 152 |
| 5F4 | GVPSRFSGSKDASANAGLLLISGLQSEDEADYYC | 132 | SAYKSGSYKAPV | 153 |
| 5B2 | GMPDRFSGSKSGNTASLTISGLQSEDEADYYC | 133 | ASYTTNNKPV | 154 |
| 6D5 | GIPARFSGSSSGGAATLTISGAQAEDEADYYC | 134 | QSYESGNYV | 155 |
| 4D2 | GVPSRFSGSKDPSANAGLLLISGLQAEDEADYYC | 135 | SVSNSGTYKPV | 156 |
| 9A1 | GIPERFSGSSSGDTATLTISGAQAEDEAVYYC | 136 | QSGSSNTNVM | 157 |
| 9G2 | GVPSRFSGSSDASANAGLLLISGLQPEDEADYYC | 137 | SAYKSGSHV | 158 |
| 9B2 | GVPSRFSGSTDASANAGLLLISGLQPEDEADYYC | 138 | SAYNRGSHV | 159 |
| 27B3 | GVPSRFSGSISENKAALTITGAQPEDEAEYFC | 139 | ALFISNPSVE | 160 |
| 24E3 | GVPSRFSGSITGNKAILTITGAQPEDEADYYC | 140 | ALYLENFANE | 161 |
| 33D8 | GIPERFSGSSSGATAALTISGAQAEDEGDYYC | 141 | QSADSSGNAV | 162 |
| 24F2 | GIPERFSGSRLGGTATLTVSGAQAEDEADYYC | 142 | QSSDSSGYRVV | 163 |
| 24B6 | GIPERFSGSISGNTATLTISGAQVEDEADYYC | 143 | QSGSSSTIPV | 164 |
| 19G10 | GIPERFSGSSSGNTATLTISGAQAEDEAAYYC | 144 | QSGSSSTIPV | 164 |

TABLE 7-continued sequence of CD70 specific llama-derived VL
(Q in bold encoded by amber STOP codon)

| Fab | | | | | |
|---|---|---|---|---|---|
| 45B12 | GIPERFTISKSGGTATLTIDGAQAEDESDYYC | 145 | QSADYSGNSV | 165 | |
| 45D9 | GIPERFTISKSGGTATLTIDGAQAEDESDYYC | 145 | QSADYSGNSV | 165 | |
| 45F8 | GIPERFTISKSGGTATLTIDGAQAENESDYYC | 146 | QSSDYPGNSV | 166 | |
| 45A12 | GVPGRFSGSISGNKAALTITGAQPEDEADYYC | 147 | LLYMGGSDFNFV | 167 | |
| 45B6 | GVPSRFSGSISGNKAALTITGAQPEDEADYYC | 129 | ALYMGSGSNNVV | 168 | |
| 57B6 | GVPSRFSGSISGNKAALTITGAQPEDEADYYC | 129 | ALYMGSGSANAM | 271 | |
| 59D10 | GIADRFSGSKAGNTASLTISGLQSEDEADYYC | 272 | ASYRSSANAV | 273 | |

| Fab | Framework 4 | SEQ ID |
|---|---|---|
| 1C2 | FGGGTHLTVLG | 169 |
| 9D1 | FGGGTHLTVLG | 169 |
| 8B12 | FGGGTKLTVLG | 170 |
| 8C12 | FGGGTKLTVLG | 170 |
| 9E1 | FGGGTKLTVLG | 170 |
| 5F4 | FGGGTHLTVLG | 169 |
| 5B2 | FGGGTHLTVLG | 169 |
| 6D5 | FGGGTTLTVLG | 171 |
| 4D2 | FGGGSKLTVLG | 172 |
| 9A1 | FGGGTHLTVLS | 173 |
| 9G2 | FGGGTKLTVLG | 170 |
| 9B2 | FGGGTKLTVLG | 170 |
| 27B3 | FGGGTQLTVLS | 174 |
| 24E3 | FGGGTRLTVLG | 175 |
| 33D8 | FGGGTHLTVLG | 169 |
| 24F2 | FGGGTKLTVLG | 170 |
| 24B6 | FGGGTKLTVLG | 170 |
| 19G10 | FGGGTKLTVLG | 170 |
| 45B12 | FGGGTKLTVLG | 170 |
| 45D9 | FGGGTKLTVLG | 170 |
| 45F8 | FGGGTKLTVLG | 170 |
| 45A12 | FGGGTKLTVLG | 170 |
| 45B6 | FGGGTELTVLG | 176 |
| 57B6 | FGGGTHLTVLG | 169 |
| 59D10 | FGGGTHLTVLG | 169 |

TABLE 8

| Fab | Full Length Sequence of VH domain | SEQ ID |
|---|---|---|
| 1C2 | ELQVVESGGGLVQPGGSLRLSCAASGFTLSNMMHWVRQAPRKG LEWVSTISTDNSRTYYADSVKGRFTISRDHAKNTLILQMNSLKSEDT AVYYCIRGSDYEHWGQGTQVTVSS | 177 |
| 9D1 | EVQLVESGGGLVQPGGSLRLSCAASGFTFSVYYMNWVRQAPGKG LEWVSDINNEGGTTYYADSVKGRFTISRDNAKNTLTLQMNSLKPED TALYYCVRDAGYSNHVPIFDSWGQGTQVIVAS | 178 |
| 8B12 | EVQLVESGGGLVQPGGSLRLSCAASGFTFSVYYMNWVRQAPGKG LEWVSDINNEGDTTYYADSVKGRFTISRDNAKNTLTLQMDSLKPED TALYYCVRDAGYSNHVPIFDSWGQGTQVIVAS | 179 |
| 8C12 | EVQLVESGGGLVQPGGSLRLSCAASGFTFSVYYMNWVRQAPGKG LEWVSDINNEGDTTYYADSVKGRFTISRDNAKNTLTLQMDSLKPED TALYYCVRDAGYSNHVPIFDSWGQGTQVIVAS | 179 |
| 9E1 | EVQLQESGGGVVQPGGSLRLSCAASGFTFDDYAMSWVRQAPGKG LEWVSSIYMYDSSTYYADSVKGRFTISTDNAKNTVYLQMNSLKSED TAVYYCAKDINRSYGSSWSHFGPIFSSWGQGTQVTVSS | 180 |
| 5F4 | EVQVQESGGGLVHPGGSLKLSCAASGFTFDTYAMSWVRQAPGKG LEWVSAISWSGGETFYAESMKGRFTISRNNAKNTLYLQMNSLKSED TAVYYCARGMGLAEGLTDWGQGTQVTVSS | 181 |
| 5B2 | QVQLVESGGDLVQPGGSLRLSCAASGFTVSNPAMSWVRQAPGKG LEWVSEITNYGYNRYYADSVKGRFTISTDNAKNTLYLQMNSLRSED SAVYYCTASLGLEYGYGDWGQGTQVTVSS | 182 |
| 6D5 | EVQLVQPGAELRKPGASVKVSCKASGYTFTSYYIDWVRQAPGQGL EWMGRIDPEDGGTKYAQKFQGRVTFTADASTSTAYVELSSLRSED TAVYYCASRRRDFDYWGQGTQVTVSS | 183 |
| 4D2 | QVQLQESGPGLVKPSQTLSLACTVSGGSITTSYYYWSWIRQPPGK GLEWMGAIGSRGSTYYSPSLKTRTSISRDTSKNQFTLQLSSVTPED TAVYYCARVTGEITYNSGSYYYTLNLFDYWGQGTQVTVSS | 184 |
| 9A1 | EVQLVESGGGLVQPGGSLRLSCAASGFTFSSYAMSWVRQAPGKG LEWVSDINSGGGSTKYNDSVKGRFAISRDNAKNTLYLQMNSLKPED TAVYYCAKEGGSGRYWTNEYDYWGQGTQVTVSS | 185 |
| 9G2 | QVQLVESGGGLMQPGGSLRLSCAASGFTFSSSAMSWVRQAPGKG LEWVSSIYSDSSYTYYADSVKSRFTISTDNAKNTLYLQMNSLKPDDT AVYYCAGSSDYEGSFASWGQGTQVTVSS | 186 |
| 9B2 | QLQVVESGGGLMQPGGSLRLSCAASGFTFSGSAMSWVRQAPGK GLEWVSSIYSHSMYTYYADSVKSRFTISTDNAKNTLYLQMNSLKPD DTAVYYCAASSDYEGLFVSWGQGTQVTVSS | 187 |
| 27B3 | EVQLVESGGGLVQPGGSLRLSCAASGFTFSVYYMNWVRQAPGKG LEWVSDINNEGGTTYYADSVKGRFTISRDNAKNTLTLQMNSLKPED TALYYCVRDAGYSNHVPIFDSWGQGTQVIVAS | 178 |
| 24E3 | EVQLVESGGGLVQPGGSLRLSCAASGFTFSVYYMNWVRQAPGKG LEWVSDINNEGGTTYYADSVKGRFTISRDNAKNTLTLQMNSLKPED TALYYCVRDAGYSNHVPIFDSWGQGTQVIVAS | 178 |
| 33D8 | EVQLVESGGGLVQPGGSLRLSCAASGFTFSVYYMNWVRQAPGKG LEWVSDINNEGGTTYYADSVKGRFTISRDNAKNTLTLQMNSLKPED TALYYCVRDAGYSNHVPIFDSWGQGTQVIVAS | 178 |
| 24F2 | EVQLVESGGGLVQPGGSLRLSCAASGFTFSVYYMNWVRQAPGKG LEWVSDINNEGGTTYYADSVKGRFTISRDNAKNTLTLQMNSLKPED TALYYCVRDAGYSNHVPIFDSWGQGTQVIVAS | 178 |
| 24B6 | EVQLQESGGGVVQPGGSLRLSCAASGFTFDDYAMSWVRQAPGKG LEWVSSIYMYDSSTYYADSVKGRFTISTDNAKNTVYLQMNSLKSED TAVYYCAKDINRSYGSSWSHFGPIFSSWGQGTQVTVSS | 180 |
| 19G10 | EVQLQESGGGVVQPGGSLRLSCAASGFTFDDYAMSWVRQAPGKG LEWVSSIYMYDSSTYYADSVKGRFTISTDNAKNTVYLQMNSLKSED TAVYYCAKDINRSYGSSWSHFGPIFSSWGQGTQVTVSS | 180 |
| 45B12 | EVQLVESGGGLVQPGGSLRLSCAASGFTFSAYYMNWVRQAPGKG LEWISDINNEGYETYYADSVKGRFTISRDNAKNTLTLQMDSLKPEDT ARYYCVRDAGYSNHVQIFDSWGQGTQVIVAS | 188 |

TABLE 8-continued

Full Length llama-derived VH

| Fab | Full Length Sequence of VH domain | SEQ ID |
|---|---|---|
| 45D9 | EVQLVESGGGLVQPGGSLRLSCAASGFTFSAYYMNWVRQAPGKG LEWISDINNEGYETYYADSVKGRFTISRDNAKNTLTLQMDSLKPEDT ARYYCVRDAGYSNHVQIFDSWGQGTQVIVAS | 188 |
| 45F8 | EVQLVESGGGLVQPGGSLRLSCAASGFTFSAYYMNWVRQAPGKG LEWISDINNEGYETYYADSVKGRFTISRDNAKNTLTLQMDSLKPEDT ARYYCVRDAGYSNHVQIFDSWGQGTQVIVAS | 188 |
| 45A12 | EVQLVESGGGLVQPGGSLRLSCAASGFTFSAYYMNWVRQAPGKG LEWISDINNEGYETYYADSVKGRFTISRDNAKNTLTLQMDSLKPEDT ARYYCVRDAGYSNHVQIFDSWGQGTQVIVAS | 188 |
| 45B6 | EVQLVESGGGLVQPGGSLRLSCAASGFTFSAYYMNWVRQAPGKG LEWISDINNEGYETYYADSVKGRFTISRDNAKNTLTLQMDSLKPEDT ARYYCVRDAGYSNHVQIFDSWGQGTQVIVAS | 188 |
| 57B6 | QLQLVESGGGLVQPGGSLRLSCAASGFSFSHYAMSWVRQAPGKG LEWVSGDNTYDGGTRYQDSVKGRFTISRDNGKNTLYLQMNSLKPE DTAVYYCAKDTGRGIMGEYGMDYWGKGTLVTVSS | 274 |
| 59D10 | EVQLVESGGGLVQPGGSLRLSCAASELSFSISEMTWVRQAPGKGL EWVSGISGVTGGSSTSYADSVKGRFTISRDNDKNTLYLQMNSLIPE DTAVYYCATTSGTYYFIPEYEYWGQGTQVTVSS | 275 |

TABLE 9

Full Length llama-derived VL
(Q in bold encoded by amber STOP codon)

| Fab | Full Length Sequence | SEQ ID |
|---|---|---|
| 1C2 | QTVVTQEPSLSVSPGGTVTLTCGLSSGSVTTTNYPGWFQQTPGQA PRTLIYSTSSRHSGVPSRFSGSISGNKAALTITGAQPEDEADYYCAL EEIGSYTYMFGGGTHLTVLG | 189 |
| 9D1 | QAVVTQEPSLSVSPGGTVTLTCGLSSGSVTSSHYPGWYQQTPGQ APRLLIFNTSRHSGVPSRFSGSISGNKAALTITGAQPEDEADYYCA LLNIDDGSTMFGGGTHLTVLG | 190 |
| 8B12 | QTVVTQEPSLSVSPGGTVTLTCGLSSGSVTSSNYPGWYQQTPGQA PRVLIYNTNNRHSGVPSRYSGSISGNKAALTITGAEPEDEADYYCNL HLGSYTPMFGGGTKLTVLG | 191 |
| 8C12 | QAVVTQEPSLSVSPGGTVTLTCGLTSGSVTSSNYPDWYQQTPGQA PRLLIYNTNSRHSGVPSRFSGSISGNKAALTITGAQPEDEADYYCAL YWGYGTNVDVFGGGTKLTVLG | 192 |
| 9E1 | QAVVTQEPSLSVSPGGTVTLTCGLTSGSVTSSNYPDWYQQTPGQA PRLLIYNTNSRHSGVPSRFSGSISGNKAALTITGAQPEDEADYYCNL YMGSGGSKVFGGGTKLTVLG | 193 |
| 5F4 | QAVVTHPPSLSASPGSSVRLTCTLISGDNIGGYDISWYQQKTGSPP RYLLYYYSDSYKHQSSGVPSRFSGSKDASANAGLLLISGLQSEDEA DYYCSAYKSGSYKAPVFGGGTHLTVLG | 194 |
| 5B2 | QSALTQPPSVSGTLGKILTISCAGTSSDVGYGNYVSWYQQLPGTA PKLLIYRVSTRASGMPDRFSGSKSGNTASLTISGLQSEDEADYYCA SYTTNNKPVFGGGTHLTVLG | 195 |
| 6D5 | QSALTQPSAVSVSLGQTARITCQGGNARFSSFAWYQQKPGQAPV QVIYYNTNRPSGIPARFSGSSSGGAATLTISGAQAEDEADYYCQSY ESGNYVFGGGTTLTVLG | 196 |
| 4D2 | QSVLTQPPSLSASPGSSVRLTCTLSSGNSVGNYDISWYQQKAGSP PRYLLYYYSDSYKNQGSGVPSRFSGSKDPSANAGLLLISGLQAEDE ADYYCSVSNSGTYKPVFGGGSKLTVLG | 197 |
| 9A1 | QSALTQPSALSVTLGQTAKITCQGGRLGSSYAHWYQQKPGQAPVL VIYGNNYRPSGIPERFSGSSSGDTATLTISGAQAEDEAVYYCQSGS SNTNVMFGGGTHLTVLS | 198 |

TABLE 9-continued

Full Length llama-derived VL
(Q in bold encoded by amber STOP codon)

| Fab | Full Length Sequence | SEQ ID |
|---|---|---|
| 9G2 | QSVVTQPPSLSASPGSSVRLTCTLSSGNSVGNYDISWYQQKAGSP PRYLLYYYSDSVKHQGSGVPSRFSGSSDASANAGLLLISGLQPEDE ADYYCSAYKSGSHVFGGGTKLTVLG | 199 |
| 9B2 | QAVLTQPPSLSASPGSSVRLTCTLNSANSVGSYDISWYQQKAGSP PRYLLYYYSDSLSHQGSGVPSRFSGSTDASANAGLLLISGLQPEDE ADYYCSAYNRGSHVFGGGTKLTVLG | 200 |
| 27B3 | QAVVTQEPSLTVSPGGTVTLTCGLKSGSVTSTNFPTWYQQTPGQA PRLLIYNTNTRHSGVPSRFSGSISENKAALTITGAQPEDEAEYFCAL FISNPSVEFGGGTQLTVLS | 201 |
| 24E3 | QAVVTQEPSLSVSPGGTVTLTCGLTSGSVTSDNFPVWYQQTPGQA PRLLIYTINSRHSGVPSRFSGSITGNKAILTITGAQPEDEADYYCALY LENFANEFGGGTRLTVLG | 202 |
| 33D8 | QSALTQPSTVSVSLGQTARITCRGDSLERYGTNWYQQKPGQAPVL VIYDDDSRPSGIPERFSGSSSGATAALTISGAQAEDEGDYYCQSAD SSGNAVFGGGTHLTVLG | 203 |
| 24F2 | QSALTQPSAVSVSLGQTARITCRGDTLRNYHANWYRQKPGQAPVL VIYGDDIRPSGIPERFSGSRLGGTATLTVSGAQAEDEADYYCQSSD SSGYRVVFGGGTKLTVLG | 204 |
| 24B6 | QPVLTQPSAVSVSLGQTARITCQGGYYTHWYQQKPGQAPVLVIYIN NNRPSGIPERFSGSISGNTATLTISGAQVEDEADYYCQSGSSSTIPV FGGGTKLTVLG | 205 |
| 19G10 | NFMLTQPSAVSVSLGQTARITCQGGYYTHWYQQKPGQAPVLVIYV NNNRPSGIPERFSGSSSGNTATLTISGAQAEDEAAYYCQSGSSSTI PVFGGGTKLTVLG | 206 |
| 45B12 | QAVLTQPSSVSVSLGQTAKITCQGGNLGLYGANWYQQNPGRAPIL LIYGDNYRPLGIPERFTISKSGGTATLTIDGAQAEDESDYYCQSADY SGNSVFGGGTKLTVLG | 207 |
| 45D9 | QAVLTQPSSVSVSLGQTAKITCQGGNLWLYGANWYQQNPGRAPIL LIYGDNQRPLGIPERFTISKSGGTATLTIDGAQAEDESDYYCQSADY SGNSVFGGGTKLTVLG | 208 |
| 45F8 | QAVLTQPSSVSVSLGQTANITCQGGNLGLYGANWYQQNPGRAPIL LFYGDNYMPLGIPERFTISKSGGTATLTIDGAQAENESDYYCQSSDY PGNSVFGGGTKLTVLG | 209 |
| 45A12 | QAVVTQEPSLSVSPGGTVTLTCGLSSGSATSGNYPEWYQQTPGQ APRLIIYNTASRHSGVPGRFSGSISGNKAALTITGAQPEDEADYYCL LYMGGSDFNFVFGGGTKLTVLG | 210 |
| 45B6 | QAVVTQEPSLSVSPGGTVTLTCGLSSGSVTSSNYPDWYQQTPGQA PRLLIYNTNSRHSGVPSRFSGSISGNKAALTITGAQPEDEADYYCAL YMGSGSNNVVFGGGTELTVLG | 211 |
| 57B6 | QTVVTQEPSLSVSPGGTVTLTCGLKSGSVTSSNYPAWYQQTPGQA PRLLIYNTNSRHSGVPSRFSGSISGNKAALTITGAQPEDEADYYCAL YMGSGSANAMFGGGTHLTVLG | 276 |
| 59D10 | QSVLTQPPSVSGSPGKTVTISCAGTSSDVGYGYYVSWYQQFPGMA PKLLIYDVNKRASGIADRFSGSKAGNTASLTISGLQSEDEADYYCAS YRSSANAVFGGGTHLTVLG | 277 |

Example 13: Germlining of Anti-CD70 mAb 27B3

Human germline genes segments with the same canonical fold structure and the highest amino acid sequence identity to the VH and VL regions of mAb 27B3 were identified by comparison with known human germline gene sequences. The closest human VH and VL regions to mAb 27B3 was human VH3-48 (89.7% FR identity) and human VL8-61 (86.1% FR identity), respectively. The closest human germline JH and JL human germline gene segment sequences were JH5 and JL7, respectively. Sequence alignment of the VH and VL regions of mAb 27B3 with the closest human germline VH and VL sequences are set forth in FIG. 12. Comparison of the V regions of SIMPLE antibody 27B3 and human germline sequences identified 12 candidate humanizing mutations in the VH region and 13 in the VL region (2 in CDR1 and 1 in CDR2). An overview of the humanizing mutations in the VH and VL sequences of the 27B3, together with the needed library sizes to cover the introduced diversity, is set forth in Table 10 and 11.

TABLE 10

Targeted mutations in the 27B3 VH amino acid sequence.

Mutations included in library

| Kabat Position | Camelid aa | Human germline aa option 1 | Human germline aa option 2 | Human germline aa option 3 | Probability |
|---|---|---|---|---|---|
| 46 | E | V | | | 0.50 |
| 74 | A | S | | | 0.50 |
| 77 | T | S | | | 0.50 |
| 79 | T | Y | | | 0.50 |
| 83/84 | KP | KT | RA | | 0.33 |
| 89 | L | V | | | 0.50 |
| 93/94 | AR | AK | VR | | 0.33 |
| 108 | Q | L | T | M | 0.25 |
| 110 | I | T | | | 0.50 |
| 112 | A | S | | | 0.50 |
| | | | | | 4608¶ |

¶denotes the library size needed to cover all potential mutants.

TABLE 11

Targeted mutations in the 27B3 VL amino acid sequence.

| Kabat Position | Camelid aa | Human germline aa option 1 | Human germline aa option 2 | Human germline aa option 3 | Probability |
|---|---|---|---|---|---|
| 2 | A | T | | | 0.50 |
| 11-12 | LT | FS | | | 0.50 |
| 26* | K | T | | | 0.50 |
| 30* | T | D | | | 0.50 |
| 46 | L | T | | | 0.50 |
| 53* | T | S | | | 0.50 |
| 60 | S | D | | | 0.50 |
| 61 | R | C | | | 0.50 |
| 67/68 | SE | LG | | | 0.50 |
| 80/81/84/85 | PEDEAE | PEDESD | ADDESD | ADDEAE | 0.25 |
| 87 | F | Y | | | 0.50 |
| | | | | | 4096¶ |

¶denotes the library size needed to cover all potential mutants.
*denotes mutations in the CDR1 or CDR2 regions.

Germlined libraries of VH_27B3 and VL_27B3 encompassing all combinations of humanizing mutations were created by PCR based assembly (see e.g., Stemmer et al., Gene (1995) 164: 49-53). Overlapping oligonucleotides with specific mutations on certain positions were assembled by PCR. The library contained both human and llama amino acids at each mutated position to prevent complete loss of binding in the event that the wild type llama residue was critical for high affinity binding (see e.g., Baca et al., J. Biol. Chem. (1997) 272: 10678-10684; Tsurushita et al., J. Immunol. Methods (2004) 295: 9-19). The VH library contained about $1 \times 10^{10}$ clones and the VL library about $8 \times 10^9$ clones. The VH and VL libraries were combined and reformatted into a single Fab library with a size of $1 \times 10^{10}$ clones (91% with full length Fab insert) suitable for phage display screening. To required diversity to cover all possible mutations as mentioned in tables 10 and 11 was exceeded in the primary heavy chain and light chain libraries, but also the combined Fab library was large enough to cover all possible permutations ($1.89 \times 10^7$).

Example 14: Selection of Germlined 27B3 Fabs with High Human FR Identity

Phage display was used to select for germlined 27B3 Fabs with both a high affinity for CD70 and high human FR identity. Specifically, Flag-TNC-CD70 was biotinylated and was incubated at various concentrations with different amounts of Fab expressing phage. Complexes of phage and Flag-TNC-CD70 were then captured on a streptavidin-coated microtiter plate and washed with non-biotinylated Flag-TNC-CD70 at 37° C. Phage were eluted with Trypsin and used for infection of TG1 cells. Five rounds of selection were performed, with the wash stringency increased in each round. Details of the conditions used for each round of selection are set forth in Table 12.

TABLE 12

Conditions for selection of germlined 27B3 Fabs

| Round | Phage input (μl) | Antigen [pM] | Washing time | Wash temperature | Washing antigen |
|---|---|---|---|---|---|
| 1 | 10 | 24000-2400-240 | 1 hour | RT | PBS |
| 2 | 1 | 2400-240-24 | ON | 37° C. | 24 nM CD70 |
| 3 | 0.1 | 240-24-2.4 | ON | 37° C. | 2.4 nM CD70 |
| 4 | 0.01 | 24-2.4-0.24 | 3 days | 37° C. | 240 pM CD70 |
| 5 | 0.1 | 2.4-0.24-0.024 | 6 days | 37° C. | 24 pM CD70 |

Phage eluted from rounds 3, 4 and 5 of selection were transfected into TG1 and plated clonally; individual clones were picked randomly for further analysis. Periplasmic fractions containing Fabs were prepared from IPTG induced small scale cultures the off rate of each Fab was determined using a CD70 coated CM5 chip in a Biacore binding assay. Clones with Fab having off rates similar to that of 27B3 were sequenced. Off rates for clones with a total human FR sequence identity above 94% are set forth in Table 13, along with the percentage human FR identity of the individual clone (VH, VL and total).

The complete amino acid sequences of the sequenced Fab clones are set forth in tables 14 and 15 and CDR amino acid sequence variants of 27B3 are set forth in table 16. Inspection of these sequences reveals that framework 1 of the light chain often has extra (non human) mutations in the primer region at amino acid 2 (A instead of T). Variants of clones 35G3, 40F1 and 39C3 (clones 53C1, 53B1 and 53E1, respectively) were made that have the corresponding human amino acid at position 2. Moreover, clone 41D12 was further germlined by combining the heavy chain of 41D12 with the light chain of 40F1 (53A2) or with the light chain of 53B1 (53H1).

TABLE 13

Off rate of germlined 27B3 Fab clones with more than 94% total human FR identity.

| Fab Clone | % FR identity for VL | % FR identity for VH | Total % FR identity | Isolation frequency | Off rate [$10^{-4}$ $s^{-1}$] |
|---|---|---|---|---|---|
| 27B3 | 86.0 | 89.5 | 87.9 | | 1.4 |
| 36A9 | 97.5 | 92.0 | 94.5 | 1 | 1.3 |
| 53F1 | 97.5 | 92.0 | 94.5 | 1 | 2.3 |
| 36D6 | 94.9 | 94.3 | 94.6 | 2 | 1.4 |
| 53G1 | 96.2 | 94.0 | 95.0 | 1 | 2.0 |
| 35G3 | 94.9 | 95.4 | 95.2 | 1 | 1.7 |
| 35F6 | 94.9 | 95.4 | 95.2 | 1 | ND |
| 36G2 | 93.6 | 96.6 | 95.2 | 7 | 1.1 |
| 39D5 | 93.7 | 96.6 | 95.2 | 2 | 1.2 |
| 42D12 | 93.7 | 96.6 | 95.2 | 2 | 1.6 |
| 35G1 | 97.5 | 94.3 | 95.7 | 1 | 2.3 |
| 41D12 | 92.4 | 98.9 | 95.9 | 4 | 2.3 |
| 41H8 | 94.9 | 97.0 | 96.0 | 1 | 2.2 |
| 35G2 | 96.2 | 96.6 | 96.4 | 1 | 1.7 |
| 40F1 | 94.9 | 98.0 | 96.6 | 1 | 1.6 |
| 39C3 | 97.5 | 97.7 | 97.6 | 6 | 2.5 |

TABLE 14A

VH amino acid sequences of germlined 27B3 clones with more than 94% total human identity, with sequence identifiers broken down by FR and CDR. Humanizing mutations are shaded and primer-introduced mutations ar bolded.

| HEAVY CHAIN CLONE | FRAMEWORK 1 | CDR1 | FRAMEWORK 2 |
|---|---|---|---|
| 27BE | EVQLVESGGGLVQPGGSLRLSCAASGFTFS SEQ ID NO: 2 | VYYMN SEQ ID NO: 11 | WVRQAPGKGLEWVS SEQ ID NO: 22 |
| 36A9 | EVQLVESGGGLVQPGGSLRLSCAASGFTFS SEQ ID NO: 2 | VYYMN SEQ ID NO: 11 | WVRQAPGKGLEWVS SEQ ID NO: 22 |
| 53F1 | EVQLVESGGGLVQPGGSLRLSCAASGFTFS SEQ ID NO: 2 | VYYMN SEQ ID NO: 11 | WVRQAPGKGLEWVS SEQ ID NO: 22 |
| 36D6 | EVQLVESGGGLVQPGGSLRLSCAASGFTFS SEQ ID NO: 2 | VYYMN SEQ ID NO: 11 | WVRQAPGKGLEWVS SEQ ID NO: 22 |
| 53G1 | EVQLVESGGGLVQPGGSLRLSCAASGFTFS SEQ ID NO: 2 | VYYMN SEQ ID NO: 11 | WVRQAPGKGLEWVS SEQ ID NO: 22 |
| 35G3 | EVQLVESGGGLVQPGGSLRLSCAASGFTFS SEQ ID NO: 2 | VYYMN SEQ ID NO: 11 | WVRQAPGKGLEWVS SEQ ID NO: 22 |
| 53C1 | EVQLVESGGGLVQPGGSLRLSCAASGFTFS SEQ ID NO: 2 | VYYMN SEQ ID NO: 11 | WVRQAPGKGLEWVS SEQ ID NO: 22 |
| 35F6 | EVQLVESGGGLVQPGGSLRLSCASSGFTFS SEQ ID NO: 274 | VYYMN SEQ ID NO: 11 | WVRQAPGKGLEWVS SEQ ID NO: 22 |
| 36G2 | EVQLVESGGGLVQPGGSLRLSCAASGFTFS SEQ ID NO: 2 | VYYMN SEQ ID NO: 11 | WVRQAPGKGLEWVS SEQ ID NO: 22 |
| 39D5 | EVQLVESGGGLVQPGGSLRLSCAASGFTFS SEQ ID NO: 2 | GYYMN SEQ ID NO: 248 | WVRQAPGKGLEWVS SEQ ID NO: 22 |
| 42D12 | EVQLVESGGGLVQPGGSLRLSCAASGFTFS SEQ ID NO: 2 | VYYMN SEQ ID NO: 11 | WVRQAPGKGLEWVS SEQ ID NO: 22 |
| 35G1 | EVQLVESGGGLVQPGGSVRLSCAASGFTFS SEQ ID NO: 2 | VYYMN SEQ ID NO: 11 | WVRQAPGKGLEWVS SEQ ID NO: 22 |
| 41D12 | EVQLVESGGGLVQPGGSLRLSCAASGFTFS SEQ ID NO: 2 | VYYMN SEQ ID NO: 11 | WVRQAPGKGLEWVS SEQ ID NO: 22 |
| 41H8 | EVQLVESGGGLVQPGGSLRLSCAASGFTFS SEQ ID NO: 2 | VYYMN SEQ ID NO: 11 | WVRQAPGKGLEWVS SEQ ID NO: 22 |

TABLE 14A -continued

VH amino acid sequences of germlined 27B3 clones with more than 94%
total human identity, with sequence identifiers broken down by FR and CDR.
Humanizing mutations are shaded and primer-introduced mutations ar bolded.

| | | | |
|---|---|---|---|
| 35G2 | EVQLVESGGGLVQPGGSLRLSCAASGFTFS<br>SEQ ID NO: 2 | VYYMN<br>SEQ ID NO: 11 | WVRQAPGKGLEWVS<br>SEQ ID NO: 22 |
| 40F1 | EVQLVESGGGLVQPGGSLRLSCAASGFTFS<br>SEQ ID NO: 2 | VYYMN<br>SEQ ID NO: 11 | WVRQAPGKGLEWVS<br>SEQ ID NO: 22 |
| 53B1 | EVQLVESGGGLVQPGGSLRLSCAASGFTFS<br>SEQ ID NO: 2 | VYYMN<br>SEQ ID NO: 11 | WVRQAPGKGLEWVS<br>SEQ ID NO: 22 |
| 39C3 | EVQLVASGGGLVQPGGSLRLSCAASGFTFS<br>SEQ ID NO: 275 | VYYMN<br>SEQ ID NO: 11 | WVRQAPGKGLEWVS<br>SEQ ID NO: 22 |
| 53E1 | EVQLVASGGGLVQPGGSLRLSCAASGFTFS<br>SEQ ID NO: 275 | VYYMN<br>SEQ ID NO: 11 | WVRQAPGKGLEWVS<br>SEQ ID NO: 22 |
| 53H1 | EVQLVESGGGLVQPGGSLRLSCAASGFTFS<br>SEQ ID NO: 2 | VYYMN<br>SEQ ID NO: 11 | WVRQAPGKGLEWVS<br>SEQ ID NO: 22 |
| 53A2 | EVQLVESGGGLVQPGGSLRLSCAASGFTFS<br>SEQ ID NO: 2 | VYYMN<br>SEQ ID NO: 11 | WVRQAPGKGLEWVS<br>SEQ ID NO: 22 |

| HEAVY<br>CHAIN<br>CLONE | CDR2 | FRAMEWORK 3 | CDR3 | FRAMEWORK 4 |
|---|---|---|---|---|
| 27B3 | DINNEGGTTYYADSVKC<br>SEQ ID NO: 27 | RFTISRDNAKNTLTLQMNSLKPEDTALYYCVR<br>SEQ ID NO: 39 | DACYSNHVPIFDS<br>SEQ ID NO: 50 | WGQGTQVIVAS<br>SEQ ID NO: 61 |
| 36A9 | DINNEGGTTYYADSVKG<br>SEQ ID NO: 27 | RFTISRDNSKNTLTLQMNSLKPEDTAVYYCVR<br>SEQ ID NO: 350 | DAGYSNHVPIFDS<br>SEQ ID NO: 50 | WGQGTQVIVSS<br>SEQ ID NO: 287 |
| 53F1 | DINNEGGTTYYADSVKG<br>SEQ ID NO: 27 | RFTISRDNAKNTLTLQMNSLKPEDTAVYYCVR<br>SEQ ID NO: 351 | DAGYSNHVPIFDS<br>SEQ ID NO: 50 | WGQGTQVTVAS<br>SEQ ID NO: 288 |
| 36D6 | DINNEGGTTYYADSVKG<br>SEQ ID NO: 27 | RFTISRDNAKNTLVLQMNSLKPEDTALYYCVR<br>SEQ ID NO: 278 | DAGYSNHVPIFDS<br>SEQ ID NO: 50 | WGQGTTVTVSS<br>SEQ ID NO: 289 |
| 53G1 | DINNEGGTTYYADSVKG<br>SEQ ID NO: 27 | RFTISRDNAKNTLVLQMNSLKPEDTAVYYCVR<br>SEQ ID NO: 279 | DAGYSNHVPIFDS<br>SEQ ID NO: 50 | WGQGTTVIVSS<br>SEQ ID NO: 290 |
| 35G3 | DINNEGGTTYYADSVKG<br>SEQ ID NO: 27 | RFTISRDNSKNSLTLQMNSLKPEDTAVYYCAR<br>SEQ ID NO: 280 | DAGYSNHVPIFDS<br>SEQ ID NO: 50 | WGQGTLVTVSS<br>SEQ ID NO: 293 |
| 53C1 | DINNEGGTTYYADSVKG<br>SEQ ID NO: 27 | RFTISRDNSKNSLTLQMNSLKPEDTAVYYCAR<br>SEQ ID NO: 280 | DAGYSNHVPIFDS<br>SEQ ID NO: 50 | WGQGTLVTVSS<br>SEQ ID NO: 293 |
| 35F6 | DINNEGGTTYYADSVKG<br>SEQ ID NO: 27 | RFTISRDNSKNTLVLQMNSLRAEDTAVYYCVR<br>SEQ ID NO: 281 | DAGYSNHVPIFDS<br>SEQ ID NO: 50 | WGQGTTVTVAS<br>SEQ ID NO: 291 |
| 36G2 | DINNEGGTTYYADSVKG<br>SEQ ID NO: 27 | RFTISRDNAKNSLTLQMNSLRAEDTAVYYCVR<br>SEQ ID NO: 282 | DAGYSNHVPIFDS<br>SEQ ID NO: 50 | WGQGTQVTVSS<br>SEQ ID NO: 292 |
| 39D5 | DINNEGGTTYYADSVKG<br>SEQ ID NO: 27 | RFTISRDNAKNTLVLQMNSLRAEDTAVYYCVR<br>SEQ ID NO: 283 | DAGYSNHVPIFDS<br>SEQ ID NO: 50 | WGQGTTVTVAS<br>SEQ ID NO: 291 |
| 42D12 | DINNEGGTTYYADSVKG<br>SEQ ID NO: 27 | RFTISRDNSKNTLVLQMNSLRAEDTAVYYCVR<br>SEQ ID NO: 281 | DAGYSNHVPIFDS<br>SEQ ID NO: 50 | WGQGTQVTVSS<br>SEQ ID NO: 292 |
| 35G1 | DINNEGGTTYYADSVKG<br>SEQ ID NO: 27 | RFTISRDNAKNTLVLQMNSLKPEDTAVYYCAR<br>SEQ ID NO: 284 | DAGYSNHVPIFDS<br>SEQ ID NO: 50 | WGQGTLVTVAS<br>SEQ ID NO: 294 |
| 41D12 | DINNEGGTTYYADSVKG<br>SEQ ID NO: 27 | RFTISRDNSKNSLVLQMNSLRAEDTAVYYCAR<br>SEQ ID NO: 285 | DAGYSNHVPIFDS<br>SEQ ID NO: 50 | WGQGTLVTVSS<br>SEQ ID NO: 293 |

TABLE 14A -continued

VH amino acid sequences of germlined 27B3 clones with more than 94%
total human identity, with sequence identifiers broken down by FR and CDR.
Humanizing mutations are shaded and primer-introduced mutations ar bolded.

| | | | | |
|---|---|---|---|---|
| 41H8 | DINNEGGTTYYADSVKG | RFTISRDNSKNTLYLQMNSLRAEDTAVYYCAR | DAGYSNHVPIFDS | WGQGTQVTVAS |
| | SEQ ID NO: 27 | SEQ ID NO: 286 | SEQ ID NO: 50 | SEQ ID NO: 288 |
| 35G2 | DINNEGGTTYYADSVKG | RFTISRDNAKNTLYLQMNSLKPEDTAVYYCAR | DAGYSNHVPIFDS | WGQGTLVTVSS |
| | SEQ ID NO: 27 | SEQ ID NO: 284 | SEQ ID NO: 50 | SEQ ID NO: 293 |
| 40F1 | DINNEGGATYYADSVKG | RFTISRDNSKNSLYLQMNSLRAEDTAVYYCAR | DAGYSNHVPIFDS | WGQGTQVTVSS |
| | SEQ ID NO: 249 | SEQ ID NO: 285 | SEQ ID NO: 50 | SEQ ID NO: 292 |
| 53B1 | DINNEGGATYYADSVKG | RFTISRDNSKNSLYLQMNSLRAEDTAVYYCAR | DAGYSNHVPIFDS | WGQGTQVTVSS |
| | SEQ ID NO: 249 | SEQ ID NO: 285 | SEQ ID NO: 50 | SEQ ID NO: 292 |
| 39C3 | DINNEGGTTYYADSVKG | RFTISRDNSKNTLYLQMNSLRAEDTAVYYCAR | DAGYSNHVPIFDS | WGQGTTVTVSS |
| | SEQ ID NO: 27 | SEQ ID NO: 286 | SEQ ID NO: 50 | SEQ ID NO: 289 |
| 53E1 | DINNEGGTTYYADSVKG | RFTISRDNSKNTLYLQMNSLRAEDTAVYYCAR | DAGYSNHVPIFDS | WGQGTTVTVSS |
| | SEQ ID NO: 27 | SEQ ID NO: 286 | SEQ ID NO: 50 | SEQ ID NO: 289 |
| 53H1 | DINNEGGTTYYADSVKG | RFTISRDNSKNTLYLQMNSLRAEDTAVYYCAR | DAGYSNHVPIFDS | WGQGTLVTVSS |
| | SEQ ID NO: 27 | SEQ ID NO: 286 | SEQ ID NO: 50 | SEQ ID NO: 293 |
| 53A2 | DINNEGGTTYYADSVKG | RFTISRDNSKNSLYLQMNSLRAEDTAVYYCAR | DAGYSNHVPIFDS | WGQGTLVTVSS |
| | SEQ ID NO: 27 | SEQ ID NO: 285 | SEQ ID NO: 50 | SEQ ID NO: 293 |

TABLE 14B

VH amino acid sequences of germlined 27B3 clones with more than 94%
total human identity, with sequence identifiers for the full VH amino acid sequence.

| SEQ ID NO: | HEAVY CHAIN CLONE | FULL VH SEQUENCE |
|---|---|---|
| 178 | 27B3 | EVQLVESGGGLVQPGGSLRLSCAASGFTFSVYYMNWVRQAPGKGLEWVSDINNEGGTTYYADSVKG RFTISRDNAKNTLTLQMNSLKPEDTALYYCVRDAGYSNHVPIFDSWGQGTQVIVAS |
| 212 | 36A9 | EVQLVESGGGLVQPGGSLRLSCAASGFTFSVYYMNWVRQAPGKGLEWVSDINNEGGTTYYADSVKG RFTISRDNSKNTLTLQMNSLKPEDTAVYYCVRDAGYSNHVPIFDSWGQGTQVIVSS |
| 213 | 53F1 | EVQLVESGGGLVQPGGSLRLSCAASGFTFSVYYMNWVRQAPGKGLEWVSDINNEGGTTYYADSVKG RFTISRDNAKNTLTLQMNSLKPEDTAVYYCVRDAGYSNHVPIFDSWGQGTQVTVAS |
| 214 | 36D6 | EVQLVESGGGLVQPGGSLRLSCAASGFTFSVYYMNWVRQAPGKGLEWVSDINNEGGTTYYADSVKG RFTISRDNAKNTLYLQMNSLKPEDTALYYCVRDAGYSNHVPIFDSWGQGTTVTVSS |
| 215 | 53G1 | EVQLVESGGGLVQPGGSLRLSCAASGFTFSVYYMNWVRQAPGKGLEWVSDINNEGGTTYYADSVKG RFTISRDNAKNTLYLQMNSLKPEDTAVYYCVRDAGYSNHVPIFDSWGQGTTVIVSS |
| 216 | 35G3 | EVQLVESGGGLVQPGGSLRLSCAASGFTFSVYYMNWVRQAPGKGLEWVSDINNEGGTTYYADSVKG RFTISRDNSKNSLTLQMNSLKPEDTAVYYCARDAGYSNHVPIFDSWGQGTLVTVSS |
| 217 | 53C1 | EVQLVESGGGLVQPGGSLRLSCAASGFTFSVYYMNWVRQAPGKGLEWVSDINNEGGTTYYADSVKG RFTISRDNSKNSLTLQMNSLKPEDTAVYYCARDAGYSNHVPIFDSWGQGTLVTVSS |
| 218 | 35F6 | EVQLVESGGGLVQPGGSLRLSCASSGFTFSVYYMNWVRQAPGKGLEWVSDINNEGGTTYYADSVKG RFTISRDNSKNTLYLQMNSLRAEDTAVYYCVRDAGYSNHVPIFDSWGQGTTVTVAS |
| 219 | 36G2 | EVQLVESGGGLVQPGGSLRLSCAASGFTFSVYYMNWVRQAPGKGLEWVSDINNEGGTTYYADSVKG RFTISRDNAKNSLTLQMNSLRAEDTAVYYCVRDAGYSNHVPIFDSWGQGTQVTVSS |

TABLE 14B-continued

VH amino acid sequences of germlined 27B3 clones with more than 94%
total human identity, with sequence identifiers for the full VH amino acid sequence.

| SEQ ID NO: | HEAVY CHAIN CLONE | FULL VH SEQUENCE |
|---|---|---|
| 220 | 39D5 | EVQLVESGGGLVQPGGSLRLSCAASGFTFSGYYMNWVRQAPGKGLEWVSDINNEGGTTYYADSVKG RFTISRDNAKNTLYLQMNSLRAEDTAVYYCVRDAGYSNHVPIFDSWGQGTTVTVAS |
| 221 | 42D12 | EVQLVESGGGLVQPGGSLRLSCAASGFTFSVYYMNWVRQAPGKGLEWVSDINNEGGTTYYADSVKG RFTISRDNSKNTLYLQMNSLRAEDTAVYYCVRDAGYSNHVPIFDSWGQGTQVTVSS |
| 222 | 35G1 | EVQLVESGGGLVQPGGSVRLSCAASGFTFSVYYMNWVRQAPGKGLEWVSDINNEGGTTYYADSVKG RFTISRDNAKNTLYLQMNSLKPEDTAVYYCARDAGYSNHVPIFDSWGQGTLVTVAS |
| 223 | 41D12 | EVQLVESGGGLVQPGGSLRLSCAASGFTFSVYYMNWVRQAPGKGLEWVSDINNEGGTTYYADSVKG RFTISRDNSKNSLYLQMNSLRAEDTAVYYCARDAGYSNHVPIFDSWGQGTLVTVSS |
| 224 | 41H8 | EVQLVESGGGLVQPGGSLRLSCAASGFTFSVYYMNWVRQAPGKGLEWVSDINNEGGTTYYADSVKG RFTISRDNSKNTLYLQMNSLRAEDTAVYYCARDAGYSNHVPIFDSWGQGTQVTVAS |
| 225 | 35G2 | EVQLVESGGGLVQPGGSLRLSCAASGFTFSVYYMNWVRQAPGKGLEWVSDINNEGGTTYYADSVKG RFTISRDNAKNTLYLQMNSLKPEDTAVYYCARDAGYSNHVPIFDSWGQGTLVTVSS |
| 226 | 40F1 | EVQLVESGGGLVQPGGSLRLSCAASGFTFSVYYMNWVRQAPGKGLEWVSDINNEGGATYYADSVKG RFTISRDNSKNSLYLQMNSLRAEDTAVYYCARDAGYSNHVPIFDSWGQGTQVTVSS |
| 227 | 53B1 | EVQLVESGGGLVQPGGSLRLSCAASGFTFSVYYMNWVRQAPGKGLEWVSDINNEGGATYYADSVKG RFTISRDNSKNSLYLQMNSLRAEDTAVYYCARDAGYSNHVPIFDSWGQGTQVTVSS |
| 228 | 39C3 | EVQLVASGGGLVQPGGSLRLSCAASGFTFSVYYMNWVRQAPGKGLEWVSDINNEGGTTYYADSVKG RFTISRDNSKNTLYLQMNSLRAEDTAVYYCARDAGYSNHVPIFDSWGQGTTVTVSS |
| 229 | 53E1 | EVQLVASGGGLVQPGGSLRLSCAASGFTFSVYYMNWVRQAPGKGLEWVSDINNEGGTTYYADSVKG RFTISRDNSKNTLYLQMNSLRAEDTAVYYCARDAGYSNHVPIFDSWGQGTTVTVSS |
| 223 | 53H1 | EVQLVESGGGLVQPGGSLRLSCAASGFTFSVYYMNWVRQAPGKGLEWVSDINNEGGTTYYADSVKG RFTISRDNSKNSLYLQMNSLRAEDTAVYYCARDAGYSNHVPIFDSWGQGTLVTVSS |
| 223 | 53A2 | EVQLVESGGGLVQPGGSLRLSCAASGFTFSVYYMNWVRQAPGKGLEWVSDINNEGGTTYYADSVKG RFTISRDNSKNSLYLQMNSLRAEDTAVYYCARDAGYSNHVPIFDSWGQGTLVTVSS |

TABLE 15A

VL amino acid sequences of germlined 27B3 clones with more than 94%
total human identity, with sequence identifiers broken down by FR and CDR.
Humanizing mutations are shaded and primer-introduced mutations are bolded.

| LIGHT CHAIN CLONE | FRAMEWORK 1 | CDR1 | FRAMEWORK 2 |
|---|---|---|---|
| 27B3 | QAVVTQEPSLTVSPGGTVTLTC SEQ ID NO: 71 | GLKSGSVTSTNFPT SEQ ID NO: 87 | WYQQTPGQAPRLLIY SEQ ID NO: 99 |
| 36A9 | QTVVTQEPSFSVSPGGTVTLTC SEQ ID NO: 294 | GLKSGSVTSDNFPT SEQ ID NO: 250 | WYQQTPGQAPRLLIY SEQ ID NO: 99 |
| 53F1 | QAVVTQEPSFSVSPGGTVTLTC SEQ ID NO: 295 | GLKSGSVTSDNFPT SEQ ID NO: 250 | WYQQTPGQAPRLLIY SEQ ID NO: 99 |
| 36D6 | QTVVTQEPSLTVSPGGTVTLTC SEQ ID NO: 296 | GLKSGSVTSTNFPT SEQ ID NO: 87 | WYQQTPGQAPRLLIY SEQ ID NO: 99 |
| 53G1 | QTVVTQEPSFSVSPGGTVTLTC SEQ ID NO: 294 | GLTSGSVTSTNFPT SEQ ID NO: 251 | WYQQTPGQAPRLLIY SEQ ID NO: 99 |
| 35G3 | QAVVTQEPSFSVSPGGTVTLTC SEQ ID NO: 295 | GLKSGSVTSDNFPT SEQ ID NO: 250 | WYQQTPGQAPRLLIY SEQ ID NO: 99 |

TABLE 15A -continued

VL amino acid sequences of germlined 27B3 clones with more than 94%
total human identity, with sequence identifiers broken down by FR and CDR.
Humanizing mutations are shaded and primer-introduced mutations are bolded.

| Clone | FR1 | CDR1 | FR2 |
|---|---|---|---|
| 53C1 | QTVVTQEPSESVSPGGTVTLTC<br>SEQ ID NO: 294 | GLKSGSVTSENFPT<br>SEQ ID NO: 250 | WYQQTPGQAPRLLIY<br>SEQ ID NO: 99 |
| 35F6 | QTVVTQEPSESVSPGGTVTLTC<br>SEQ ID NO: 294 | GLTSGSVTSENFPT<br>SEQ ID NO: 252 | WYQQTPGQAPRLLIY<br>SEQ ID NO: 99 |
| 36G2 | QAVVTQEPSLTVSPGGTVTLTC<br>SEQ ID NO: 71 | GLKSGSVTSDNFPT<br>SEQ ID NO: 250 | WYQQTPGQAPRLLIY<br>SEQ ID NO: 99 |
| 39D5 | QTVVTQEPSLTVSPGGTVTLTC<br>SEQ ID NO: 296 | GVTSGSVTSDNFPT<br>SEQ ID NO: 253 | WYQQTPGQAPRLLIY<br>SEQ ID NO: 99 |
| 42D12 | QAVVTQEPSESVSPGGTVTLTC<br>SEQ ID NO: 295 | GLTSGSVTSTNFPT<br>SEQ ID NO: 251 | WYQQTPGQAPRLLIY<br>SEQ ID NO: 99 |
| 35G1 | QTVVTQEPSESVSPGGTVTLTC<br>SEQ ID NO: 294 | GLKSGSVTSENFPT<br>SEQ ID NO: 250 | WYQQTPGQAPRLLIY<br>SEQ ID NO: 99 |
| 41D12 | QAVVTQEPSLTVSPGGTVTLTC<br>SEQ ID NO: 71 | GLKSGSVTSDNFPT<br>SEQ ID NO: 250 | WYQQTPGQAPRLLIY<br>SEQ ID NO: 99 |
| 41H8 | QAVVTQEPSESVSPGGTVTLTC<br>SEQ ID NO: 295 | GLTSGSVTSTNFPT<br>SEQ ID NO: 251 | WYQQTPGQAPRLLIY<br>SEQ ID NO: 99 |
| 35G2 | QTVVTQEPSESVSPGGTVTLTC<br>SEQ ID NO: 294 | GLKSGSVTSTNFPT<br>SEQ ID NO: 87 | WYQQTPGQAPRLLIY<br>SEQ ID NO: 99 |
| 40F1 | QAVVTQEPSESVSPGGTVTLTC<br>SEQ ID NO: 295 | GLKSGSVTSDNFPT<br>SEQ ID NO: 250 | WYQQTPGQAPRLLIY<br>SEQ ID NO: 99 |
| 53B1 | QTVVTQEPSESVSPGGTVTLTC<br>SEQ ID NO: 294 | GLKSGSVTSDNFPT<br>SEQ ID NO: 250 | WYQQTPGQAPRLLIY<br>SEQ ID NO: 99 |
| 39C3 | QAVVTQEPSESVSPGGTVTLTC<br>SEQ ID NO: 295 | GLKSGSVTSDNFPT<br>SEQ ID NO: 250 | WYQQTPGQAPRLLIY<br>SEQ ID NO: 99 |
| 53E1 | QTVVTQEPSESVSPGGTVTLTC<br>SEQ ID NO: 294 | GLKSGSVTSDNFPT<br>SEQ ID NO: 250 | WYQQTPGQAPRLLIY<br>SEQ ID NO: 99 |
| 53H1 | QTVVTQEPSESVSPGGTVTLTC<br>SEQ ID NO: 294 | GLKSGSVTSDNFPT<br>SEQ ID NO: 250 | WYQQTPGQAPRLLIY<br>SEQ ID NO: 99 |
| 53A2 | QAVVTQEPSESVSPGGTVTLTC<br>SEQ ID NO: 295 | GLKSGSVTSDNFPT<br>SEQ ID NO: 250 | WYQQTPGQAPRLLIY<br>SEQ ID NO: 99 |

| LIGHT<br>CHAIN<br>CLONE | CDR2 | FRAMEWORK 3 | CDR3 | FRAMEWORK 4 |
|---|---|---|---|---|
| 27B3 | NTNTRHS<br>SEQ ID NO: 119 | GVPSRFSGSISENKAALTITGAQPEDEAEYFC<br>SEQ ID NO: 139 | ALFISNPSVE<br>SEQ ID NO: 160 | FGGGTQLTVLS<br>SEQ ID NO: 174 |
| 36A9 | NTNTRHS<br>SEQ ID NO: 119 | GVPDRFSGSILGNKAALTITGAQADDESDYFC<br>SEQ ID NO: 297 | ALFISNPSVE<br>SEQ ID NO: 160 | FGGGTQLTVLG<br>SEQ ID NO: 309 |
| 53F1 | NTNTRHS<br>SEQ ID NO: 119 | GVPDRFSGSILGNKAALTITGAQADDESDYFC<br>SEQ ID NO: 297 | ALFISNPSVE<br>SEQ ID NO: 160 | FGGGTQLTVLG<br>SEQ ID NO: 309 |

TABLE 15A -continued

VL amino acid sequences of germlined 27B3 clones with more than 94%
total human identity, with sequence identifiers broken down by FR and CDR.
Humanizing mutations are shaded and primer-introduced mutations are bolded.

| Clone | FR | CDR | FR | CDR | FR |
|---|---|---|---|---|---|
| 36D6 | NTNSRHS | | GVPDRFSGSILGNKAALTITGAQADDESDYFC | ALFISNPSVE | FGGGTQLTVLG |
| | SEQ ID NO: 110 | | SEQ ID NO: 297 | SEQ ID NO: 160 | SEQ ID NO: 309 |
| 53G1 | NTNSRHS | | GVPSRFSGSILGNKAALTITGAQADDESDYFC | ALFISNPSVE | FGGGTQLTVLG |
| | SEQ ID NO: 110 | | SEQ ID NO: 298 | SEQ ID NO: 160 | SEQ ID NO: 309 |
| 53G3 | NTNSRHS | | GVPDRFSGSILGNKAALTIRGAQADDEAEYYC | ALFISNPSVE | FGGGTQLTVLG |
| | SEQ ID NO: 110 | | SEQ ID NO: 299 | SEQ ID NO: 160 | SEQ ID NO: 309 |
| 53C1 | NTNSRHS | | GVPDRFSGSILGNKAALTIRGAQADDEAEYYC | ALFISNPSVE | FGGGTQLTVLG |
| | SEQ ID NO: 110 | | SEQ ID NO: 299 | SEQ ID NO: 160 | SEQ ID NO: 309 |
| 35F6 | NTNSRHS | | GVPDRFSGSILGNKAALTITGAQPEDESDYFC | ALFISNPSVE | FGGGTQLTVLG |
| | SEQ ID NO: 110 | | SEQ ID NO: 300 | SEQ ID NO: 160 | SEQ ID NO: 309 |
| 36G2 | NTNTRHS | | GVPDRFSGSILGNKAALTITGAQPEDESDYYC | ALFISNPSVE | FGGGTQLTVLG |
| | SEQ ID NO: 119 | | SEQ ID NO: 301 | SEQ ID NO: 160 | SEQ ID NO: 309 |
| 39D5 | NTNTRHS | | GVPDRFSGSILGNKAALTITGAQPEDESDYYC | ALFISNPSVE | FGGGTQLTVLG |
| | SEQ ID NO: 119 | | SEQ ID NO: 301 | SEQ ID NO: 160 | SEQ ID NO: 309 |
| 42D12 | NTNTRHS | | GVPSRFSGSILGNKAALTTTGAQADDEAEYFC | ALFISNPSVE | FGGGTQLTVLG |
| | SEQ ID NO: 119 | | SEQ ID NO: 302 | SEQ ID NO: 160 | SEQ ID NO: 309 |
| 35G1 | NTNSRHS | | GVPDRFSGSILGNKAALTITGAQADDESDYFC | ALFISNPSVE | FGGGTQLTVLG |
| | SEQ ID NO: 110 | | SEQ ID NO: 297 | SEQ ID NO: 160 | SEQ ID NO: 309 |
| 41D12 | NTNTRHS | | GVPDRFSGSILGNKAALTITGAQADDEAEYFC | ALFISNPSVE | FGGGTQLTVLG |
| | SEQ ID NO: 119 | | SEQ ID NO: 303 | SEQ ID NO: 160 | SEQ ID NO: 309 |
| 41H8 | NTNSRHS | | GVPDRFSGSILGNKAALTITGAQPEDESDYFC | ALFISNPSVE | FGGGTQLTVLG |
| | SEQ ID NO: 110 | | SEQ ID NO: 300 | SEQ ID NO: 160 | SEQ ID NO: 309 |
| 35G2 | NTNSRHS | | GVPDRFSGSILGNKAALTITGAQADDEADYFC | ALFISNPSVE | FGGGTQLTVLG |
| | SEQ ID NO: 110 | | SEQ ID NO: 304 | SEQ ID NO: 160 | SEQ ID NO: 309 |
| 40F1 | NTNTRHS | | GVPDRFSGSILGNKAALTITGAQADDEAEYFC | ALFISNPSVE | FGGGTQLTVLG |
| | SEQ ID NO: 119 | | SEQ ID NO: 303 | SEQ ID NO: 160 | SEQ ID NO: 309 |
| 53B1 | NTNTRHS | | GVPDRFSGSILGNKAALTITGAQADDEAEYFC | ALFISNPSVE | FGGGTQLTVLG |
| | SEQ ID NO: 119 | | SEQ ID NO: 303 | SEQ ID NO: 160 | SEQ ID NO: 309 |
| 39C3 | NTNTRHS | | GVPSRFSGSILGNKAALTITGAQADDESDYYC | ALFISNPSVE | FGGGTQLTVLG |
| | SEQ ID NO: 119 | | SEQ ID NO: 305 | SEQ ID NO: 160 | SEQ ID NO: 309 |
| 53E1 | NTNTRHS | | GVPSRFSGSILGNKAALTITGAQADDESDYYC | ALFISNPSVE | FGGGTQLTVLG |
| | SEQ ID NO: 119 | | SEQ ID NO: 305 | SEQ ID NO: 160 | SEQ ID NO: 309 |
| 53H1 | NTNTRHS | | GVPDRFSGSILGNKAALTITGAQADDEAEYFC | ALFISNPSVE | FGGGTQLTVLG |
| | SEQ ID NO: 119 | | SEQ ID NO: 303 | SEQ ID NO: 160 | SEQ ID NO: 309 |
| 53A2 | NTNTRHS | | GVPDRFSGSILGNKAALTITGAQADDEAEYFC | ALFISNPSVE | FGGGTQLTVLG |
| | SEQ ID NO: 119 | | SEQ ID NO: 303 | SEQ ID NO: 160 | SEQ ID NO: 309 |

TABLE 15B

VL amino acid sequences of germlined 27B3 clones with more than 94% total human identity, with sequence identifiers for the full VL sequence. Humanizing mutations are shaded and primer-introduced mutations are bolded.

| SEQ ID NO: | LIGHT CHAIN CLONE | FULL VL SEQUENCE |
|---|---|---|
| 201 | 27B3 | QAVVTQEPSLTVSPGGTVTLTCGLKSGSVTSTNFPTWYQQTPGQAPRLLIYNTNTRHSGVPSRFSGSISENKAALTITGAQPEDEAEYFCALFISNPSVEFGGGTQLTVLS |
| 230 | 36A9 | QTVVTQEPSFSVSPGGTVTLTCGLKSGSVTSDNFPTWYQQTPGQAPRLLIYNTNTRHSGVPDRFSGSILGNKAALTITGAQADDESDYFCALFISNPSVEFGGGTQLTVLG |
| 231 | 53F1 | QAVVTQEPSFSVSPGGTVTLTCGLKSGSVTSDNFPTWYQQTPGQAPRLLIYNTNTRHSGVPDRFSGSILGNKAALTITGAQADDESDYFCALFISNPSVEFGGGTQLTVLG |
| 232 | 36D6 | QTVVTQEPSLTVSPGGTVTLTCGLKSGSVTSTNFPTWYQQTPGQAPRLLIYNTNSRHSGVPDRFSGSILGNKAALTITGAQADDESDYFCALFISNPSVEFGGGTQLTVLG |
| 233 | 53G1 | QTVVTQEPSFSVSPGGTVTLTCGLTSGSVTSTNFPTWYQQTPGQAPRLLIYNTNSRHSGVPSRFSGSILGNKAALTITGAQADDESDYFCALFISNPSVEFGGGTQLTVLG |
| 234 | 35G3 | QAVVTQEPSFSVSPGGTVTLTCGLKSGSVTSDNFPTWYQQTPGQAPRLLIYNTNSRHSGVPDRFSGSILGNKAALTIRGAQADDEAEYYCALFISNPSVEFGGGTQLTVLG |
| 235 | 53C1 | QTVVTQEPSFSVSPGGTVTLTCGLKSGSVTSDNFPTWYQQTPGQAPRLLIYNTNSRHSGVPDRFSGSILGNKAALTIRGAQADDEAEYYCALFISNPSVEFGGGTQLTVLG |
| 236 | 35F6 | QTVVTQEPSFSVSPGGTVTLTCGLTSGSVTSDNFPTWYQQTPGQAPRLLIYNTNSRHSGVPDRFSGSILGNKAALTITGAQPEDESDYFCALFISNPSVEFGGGTQLTVLG |
| 237 | 36G2 | QAVVTQEPSLTVSPGGTVTLTCGLKSGSVTSTNFPTWYQQTPGQAPRLLIYNTNTRHSGVPDRFSGSILGNKAALTITGAQPEDESDYYCALFISNPSVEFGGGTQLTVLG |
| 238 | 39D5 | QTVVTQEPSLTVSPGGTVTLTCGVTSGSVTSDNFPTWYQQTPGQAPRLLIYNTNTRHSGVPDRFSGSILGNKAALTITGAQPEDESDYYCALFISNPSVEFGGGTQLTVLG |
| 239 | 42D12 | QAVVTQEPSFSVSPGGTVTLTCGLTSGSVTSTNFPTWYQQTPGQAPRLLIYNTNTRHSGVPSRFSGSILGNKAALTITGAQADDEAEYFCALFISNPSVEFGGGTQLTVLG |
| 240 | 35G1 | QTVVTQEPSFSVSPGGTVTLTCGLKSGSVTSDNFPTWYQQTPGQAPRLLIYNTNSRHSGVPDRFSGSILGNKAALTITGAQADDESDYFCALFISNPSVEFGGGTQLTVLG |
| 241 | 41D12 | QAVVTQEPSLTVSPGGTVTLTCGLKSGSVTSDNFPTWYQQTPGQAPRLLIYNTNTRHSGVPDRFSGSILGNKAALTITGAQADDEAEYFCALFISNPSVEFGGGTQLTVLG |
| 242 | 41H8 | QAVVTQEPSFSVSPGGTVTLTCGLTSGSVTSTNFPTWYQQTPGQAPRLLIYNTNSRHSGVPDRFSGSILGNKAALTITGAQPEDESDYFCALFISNPSVEFGGGTQLTVLG |
| 243 | 35G2 | QTVVTQEPSFSVSPGGTVTLTCGLKSGSVTSTNFPTWYQQTPGQAPRLLIYNTNSRHSGVPDRFSGSILGNKAALTITGAQADDEADYFCALFISNPSVEFGGGTQLTVLG |
| 244 | 40F1 | QAVVTQEPSFSVSPGGTVTLTCGLKSGSVTSDNFPTWYQQTPGQAPRLLIYNTNTRHSGVPDRFSGSILGNKAALTITGAQADDEAEYFCALFISNPSVEFGGGTQLTVLG |
| 245 | 53B1 | QTVVTQEPSFSVSPGGTVTLTCGLKSGSVTSDNFPTWYQQTPGQAPRLLIYNTNTRHSGVPDRFSGSILGNKAALTITGAQADDEAEYFCALFISNPSVEFGGGTQLTVLG |
| 246 | 39C3 | QAVVTQEPSFSVSPGGTVTLTCGLKSGSVTSDNFPTWYQQTPGQAPRLLIYNTNTRHSGVPSRFSGSILGNKAALTITGAQADDESDYYCALFISNPSVEFGGGTQLTVLG |
| 247 | 53E1 | QTVVTQEPSFSVSPGGTVTLTCGLKSGSVTSDNFPTWYQQTPGQAPRLLIYNTNTRHSGVPSRFSGSILGNKAALTITGAQADDESDYYCALFISNPSVEFGGGTQLTVLG |
| 244 | 53H1 | QTVVTQEPSFSVSPGGTVTLTCGLKSGSVTSDNFPTWYQQTPGQAPRLLIYNTNTRHSGVPDRFSGSILGNKAALTITGAQADDEAEYFCALFISNPSVEFGGGTQLTVLG |
| 245 | 53A2 | QAVVTQEPSFSVSPGGTVTLTCGLKSGSVTSDNFPTWYQQTPGQAPRLLIYNTNTRHSGVPDRFSGSILGNKAALTITGAQADDEAEYFCALFISNPSVEFGGGTQLTVLG |

Example 15: Temperature Stability of Germlined 27B3 mAbs

Several germlined 27B3 mAb variants were expressed in HEK293 cells as full-length human IgG1 molecules. After protein A purification, the temperature stability of the germlined 27B3 mAb clones was assessed. Specifically, each mAb was incubated at various temperatures (2 or 5° C. intervals apart) for 1 hour at a concentration of 100 µg/ml in PBS buffer. The temperature of the mAbs was then decreased in a controlled manner (reduction to 25° C. over 2 hours, followed by overnight incubation at 4° C.) and centrifugation was used to remove aggregates. The amount of active mAb (as percentage of the total mAb concentration) in the supernatant was measured by Biacore.

The results (set forth in Table 17) demonstrate that most clones have a similar melting temperature ($T_m$) as wild type 27B3 has. Surprisingly, clones 41D12 and 35G2 show to have an increased thermostability as compared to 27B3.

TABLE 17

Temperature stability of germlined 27B3 mAbs

| mAb Clone | $T_m$ [° C.] | |
|---|---|---|
| 27B3 (WT) | 64.7 | 64.6 |
| 35G1 | 63.7 | |
| 35G3 | 61.7 | |
| 53A2 | 62.2 | 62.2 |
| 41D12 | 65.9 | 65.9 |

TABLE 17-continued

Temperature stability of germlined 27B3 mAbs

| mAb Clone | $T_m$ [° C.] | |
|---|---|---|
| 35G2 | 65.6 | 66.0 |
| 40F1 | 63.5 | |
| 53H1 | 64.1 | |

The temperature stability of germlined 27B3 mAbs: 41D12, 35G2 and 40F1 was further studied using a variety of techniques. Aliquots (1 ml) of the test mAbs at a concentration of 100 µg/ml were prepared in Delbucco's PBS containing 0.02% Tween. A negative control aliquot consisting of buffer only (Delbucco's PBS containing 0.02% Tween) and a positive control aliquot consisting of mAb in Delbucco's PBS containing 0.02% Tween were also prepared. For each mAb preparation, aliquots were stored at 4° C., at RT and at 37° C. for a period of 0-8 weeks. 50 µl samples were removed from the aliquots on days 1, 7, 14, 21, 28, 35, 56 and 92 for analysis. A sample was stored at −20° C. and used as reference.

15.1 Gelfiltration Analysis of Samples

Samples taken at each time point were also analysed by gelfiltration using a Superdex200 10/300 GL column. The 50 µl test sample was added to 200 µl PBS+0.02% Tween-20. A sample (125 µl) was taken for gelfiltration analysis. Samples were centrifuged before analysis to remove larger aggregates. The % of monomeric peak and area of monomeric peak was measured, as well as the retention volume. The results are shown in Tables 19, 20 and 21.

TABLE 19

Results of PBS stability study - % monomeric peak

| | | d 1 | d 7 | d 14 | d 21 | d 28 | d 35 | d 56 | d 92 |
|---|---|---|---|---|---|---|---|---|---|
| 35G2 | Reference | 99.82 | 99.84 | 99.81 | 99.81 | 99.80 | 99.87 | | |
| 40F1 | | 99.85 | 99.83 | 99.83 | 99.83 | 99.87 | 99.86 | | |
| 41D12 | | 99.84 | 99.81 | 99.84 | 99.75 | 99.73 | 99.23 | 99.82 | 99.84 |
| 35G2 | 4° C. | 99.85 | 99.75 | 99.74 | 99.83 | 99.66 | 99.84 | | |
| 40F1 | | 99.65 | 99.29 | 99.73 | 99.77 | 99.72 | | | |
| 41D12 | | 99.88 | 99.76 | 99.83 | 99.8 | 99.84 | | 99.81 | 99.49 |
| 35G2 | RT | 99.78 | 99.83 | 99.81 | 99.87 | 99.83 | | | |
| 40F1 | | 99.87 | 99.83 | 99.84 | 99.77 | 99.77 | | | |
| 41D12 | | 99.88 | 99.86 | 99.87 | 99.78 | 99.73 | | 99.80 | 99.71 |
| 35G2 | 37° C. | 99.86 | 99.80 | 99.72 | 99.68 | 99.48 | 99.32 | | |
| 40F1 | | 99.83 | 99.78 | 99.78 | 99.77 | 99.40 | 99.27 | | |
| 41D12 | | 99.89 | 99.77 | 99.61 | 99.71 | 99.45 | 99.02 | 98.66 | 97.46 |

TABLE 20

Results of PBS stability study - area under curve of the monomeric peak (mAU*ml)

| | | d 1 | d 7 | d 14 | d 21 | d 28 | d 35 | d 56 | d 92 |
|---|---|---|---|---|---|---|---|---|---|
| 35G2 | Reference | 67.34 | 68.46 | 64.92 | 66.70 | 66.69 | 66.37 | | |
| 40F1 | | 67.04 | 67.96 | 70.36 | 69.62 | 69.53 | 67.23 | | |
| 41D12 | | 66.41 | 67.64 | 61.17 | 68.53 | 68.60 | 66.08 | 67.48 | 67.06 |
| 35G2 | 4° C. | 68.41 | 67.58 | 62.55 | 68.64 | 68.12 | 68.42 | | |
| 40F1 | | 69.86 | 67.31 | 65.55 | 66.76 | 68.99 | | | |
| 41D12 | | 68.38 | 69.87 | 65.61 | 68.98 | 69.99 | | 68.85 | 67.33 |
| 35G2 | RT | 66.76 | 67.23 | 71.40 | 68.55 | 68.45 | | | |
| 40F1 | | 68.42 | 69.53 | 69.17 | 68.02 | 70.32 | | | |
| 41D12 | | 66.47 | 69.01 | 64.32 | 69.72 | 71.56 | | 69.36 | 67.16 |
| 35G2 | 37° C. | 67.52 | 67.14 | 64.49 | 61.89 | 66.51 | 65.64 | | |
| 40F1 | | 66.48 | 67.69 | 67.35 | 68.02 | 68.61 | 67.23 | | |
| 41D12 | | 67.09 | 68.13 | 61.51 | 68.97 | 68.37 | 68.25 | 67.78 | 66.51 |

TABLE 21

Results of PBS stability study - retention volume (ml)

|  |  | d 1 | d 7 | d 14 | d 21 | d 28 | d 35 | d 56 | d 92 |
|---|---|---|---|---|---|---|---|---|---|
| 35G2 | Reference | 12.17 | 12.13 | 12.13 | 12.15 | 12.17 | 12.20 | | |
| 40F1 | | 12.14 | 12.09 | 12.11 | 12.12 | 12.14 | 12.16 | | |
| 41D12 | | 12.12 | 12.08 | 12.10 | 12.10 | 12.12 | 12.14 | 12.10 | 12.13 |
| 35G2 | 4° C. | 12.16 | 12.12 | 12.14 | 12.16 | 12.17 | 12.20 | | |
| 40F1 | | 12.13 | 12.09 | 12.11 | 12.12 | 12.14 | | | |
| 41D12 | | 12.12 | 12.08 | 12.10 | 12.10 | 12.13 | | 12.10 | 12.13 |
| 35G2 | RT | 12.16 | 12.12 | 12.14 | 12.16 | 12.17 | | | |
| 40F1 | | 12.14 | 12.09 | 12.10 | 12.12 | 12.13 | | | |
| 41D12 | | 12.12 | 12.07 | 12.10 | 12.10 | 12.28 | | 12.09 | 12.13 |
| 35G2 | 37° C. | 12.16 | 12.12 | 12.13 | 12.14 | 12.16 | 12.17 | | |
| 40F1 | | 12.13 | 12.09 | 12.09 | 12.12 | 12.12 | 12.14 | | |
| 41D12 | | 12.12 | 12.08 | 12.08 | 12.09 | 12.10 | 12.12 | 12.06 | 12.08 |

Figure 13:
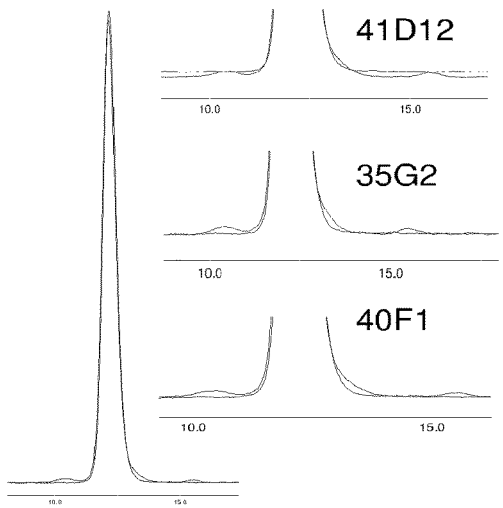
FIG. 13: shows gelfiltration analysis of samples of germlined 27B3 mAb variants taken after 5 weeks incubation at 37° C.
Figure 14:
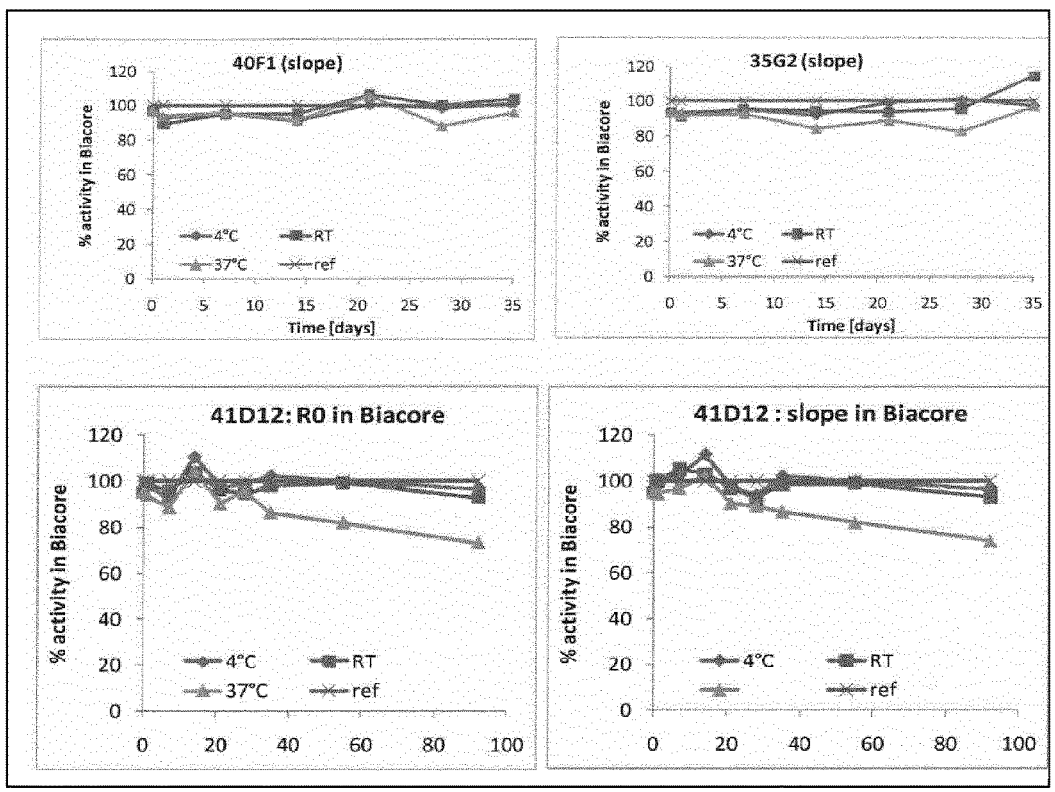
FIG. 14: shows the potency in CD70 binding, as measured using Biacore, of samples of germlined CD70 mAbs taken at various time points after incubation at various temperatures.

The results of gelfiltration analysis of 35G2, 40F1 and 41D12 samples taken after 5 weeks incubation at 37° C. are shown in FIG. 13. Two minor peaks are visible at a higher retention time (indicating the presence of some aggregates) and lower retention time (indicating the presence of some degradation product). The results demonstrate that the majority of the protein is intact and does not aggregate.

Analysis of Samples by BIACORE

Figure 16:
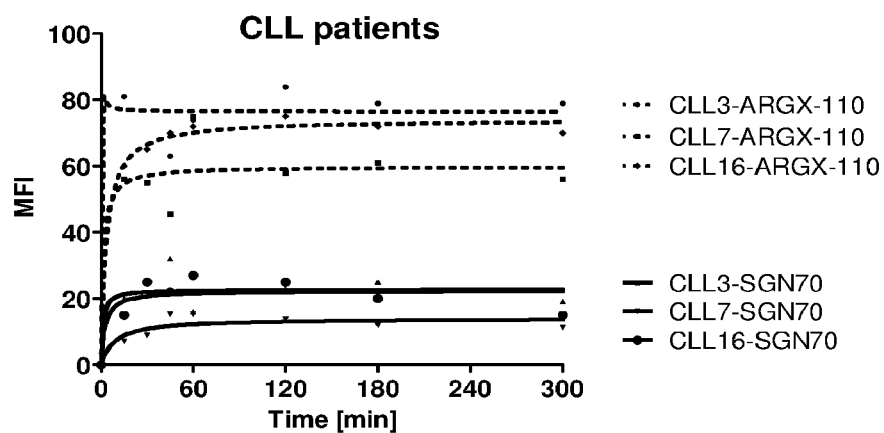
FIG. 16: shows the affinity of CD70 mAbs for CLL patient cells expressing CD70.

Samples taken at certain time points were tested for potency in CD70 binding using Biacore. The 50 µl sample was added to 200 µl PBS+0.02% Tween, and diluted 1/400 as follows: 5 µl of sample (1 mg/ml)+195 µl HBS-EP+ (Biacore buffer), further diluted 10 µl+90 µl HVS-EP+=2.5 Biacore analysis was performed using a highly CD70 coated CM5 chip (4000 RU). The results for mAbs 40F1, 35G2 and 41D12 are shown in FIG. 16. The reference sample is the 100% sample.

The results demonstrate that the mAbs loose some potency (affinity for the antigen CD70) over time when incubated at 37° C. For 41D12, both the slope and the maximal signal (R0) are plotted (see FIGS. 16C and D).

Next, the freeze-thaw stability of germlined 27B3 mAbs: 41D12, 35G2 and 40F1 was studied. Therefore, a 0.7 ml aliquot of the mAbs (at 5 mg/ml) was frozen for at least 6 hours at −20° C. and thawed for 1 hour at RT. This cycle was repeated 9× (so 10 freeze-thaw cycles in total) and samples were analyzed by gelfiltration as above. The results demonstrate that the mAbs are stable upon freeze thawing for 10 cycles: no degradation products or aggregates were observed in gelfiltration.

TABLE 22

Results of gelfiltration stability study PBS
(left = value after 10 F/T cycles, right is value for reference sample)

| | Gel Filtration | | |
|---|---|---|---|
| | 35G2 10/ref | 40F1 10/ref | 41D12 10/ref |
| % monomeric peak | 99.9/99.8 | 99.8/99.7 | 99.8/99.8 |
| Area monomeric peak | 67.5/64.7 | 65.9/67.2 | 68.2/67.8 |
| Retention time | 12.20/12.21 | 12.15/12.15 | 12.12/12.12 |

Samples were also tested for potency in Biacore as described above. The results demonstrate that after 10 freeze-thaw cycles the mAb still has 97% of its potency (for all three mAbs tested.

TABLE 23

Potency in Biacore upon 10 freeze-thaw cycles (%)

| | 35G2 | 40F1 | 41D12 |
|---|---|---|---|
| Reference | 100 | 100 | 100 |
| 10xFT | 97.35 | 96.96 | 97.02 |

Example 16: ADCC Potency of Germlined 27B3 mAbs

Several germlined 27B3 variants were expressed in HEK293 cells as full-length human IgG1 molecules. After protein A purification, the ADCC potency of the germlined 27B3 mAbs was assessed. ADCC was measured using as described above in example 7.

The relative IC50's for the germlined 27B3 mAbs compared to the parental 27B3 are given in table 18 for both ADCC potency and CD70/CD27 blocking potency in the Raji co-culture assay (as described in example 6). A figure of <1.0 denotes improved IC50 for germlined variant relative to parental 27B3. From these data it can be concluded that germlined variant 41D12 maintained the ADCC potency as well as the CD70/CD27 blocking potency combined with the best $T_m$.

TABLE 18

Relative IC50's of germlined 27B3 variants in the 786-O based ADCC assay and neutralization in Raji based bioassay compared to that of parental mAb clone

| mAb clone | Raji co-culture assay IC50 relative to 27B3 | ADCC IC50 of germlined mAb relative to 27B3 | | | | | |
|---|---|---|---|---|---|---|---|
| 27B3 | 1.0 | 1.0 | 1.0 | 1.0 | 1.0 | 1.0 | 1.0 |
| 53A2 | 0.8 | 1.5 | | 1.9 | 1.5 | 4.6 | 0.7 |
| 41D12 | 1.2 | 1.7 | 1.1 | 2.2 | 1.4 | 2.0 | 2.0 |
| 35G2 | 1.4 | 1.7 | 2.1 | 4.4 | 1.4 | 1.9 | 2.3 |
| 40F1 | 1.8 | 1.0 | 1.5 | 1.3 | 1.5 | 2.1 | 1.6 |
| 53H1 | 1.6 | 0.9 | 1.8 | 3.4 | 2.1 | 1.9 | 1.7 |

Example 17: Construction and Selection of Cell Lines Expressing the Non-Fucosylated CD70 mAb, ARGX-110

A double gene vector encoding the VH and VL amino acid sequences of germlined 27B3 clone 41D12 was produced (za allotype). Nucleotide sequences encoding the heavy chain (SEQ ID NO:344) and light chain (SEQ ID NO:345) of 41D12 are given in Table 30 below.

Potelligent® CHOK1SV cells were stably transfected with the double gene vector by electroporation. Six rounds of transfection were performed. In each round, the cells from each electroporation were added to 200 mL of chemically defined animal component free (CDACF) medium CM63 and plated out over forty 96-well plates at 50 μL per well. The day after transfection, 150 μL of the CM63 medium containing the selective agent L-methionine sulphoximine (MSX) was added to each well to give a final MSX concentration of 50 After approximately 3, 4 and 5 weeks of incubation the plates were screened for the presence of colonies using a cloning mirror. Any colonies identified were examined further using a microscope to evaluate if the colony had arisen from a single or multiple cells. Two hundred and forty-five colonies were identified and screened for antibody production using an Octet based method. Antibody concentrations ranged from 0 to 172 μg/mL. Of the 245 cell lines screened, 214 were positive for antibody production. The cell lines were ranked based on productivity and the top 70 cell lines were selected. Cultures of these 70 cell lines were initially expanded in static culture and subsequently into suspension culture. Thirty cell lines that exhibited acceptable growth were selected and evaluated further in a batch shake-flask culture productivity screen. Cultures were gassed on days 4, 6, 8 and 10 and harvested on day 12. The concentration of antibody in the harvest supernatant samples was determined in HPLC using Protein A containing column. The antibody concentrations in the samples from the 30 cell lines ranged from 109 to 877 mg/L. The results of the batch shake-flask assessment were used to rank the cell lines, based on productivity. The top 20 cell lines were selected for further evaluation.

The growth and productivity data for these 20 selected cell lines expressing the ARGX-110 antibody was studied in fed-batch shake-flask cultures using CDACF medium and the results are shown in Table 24. Antibody concentrations at harvest ranged from 857 to 3922 mg/L, as determined on a Protein A HPLC column. Cell line F13 was selected to inoculate a disposable 10 L cell bag bioreactor. A harvest antibody concentration of 4327 mg/L was achieved. This cell line achieved an antibody concentration at harvest of 2711 mg/L in fed-batch shake-flask culture and had the second highest specific production rate (2.22 pg/cell/h) of all 6 cell lines assessed (B1, D4, D5, F1, F13 and F18). This cell line also exhibited acceptable growth characteristics.

TABLE 24

Summary of growth and productivity data for 20 selected cell lines, expressing the ARGX-110 antibody, grown in CDACF fed-batch shake-flask cultures.

| Cell Line | Maximum Viable Cell Concentration ($10^6$/mL) | IVC at Harvest[1] ($10^9$ cell · h/L) | Viability at Harvest (%) | Antibody Concentration at Harvest[2] (mg/L) | Specific Production Rate ($q_P$)[3] (pg/cell/h) |
|---|---|---|---|---|---|
| A1  | 8.55  | 1276 | 47.1 | 1536 | 1.204 |
| A9  | 4.01  | 1039 | 71.5 | 1033 | 0.994 |
| B1  | 8.60  | 1777 | 69.9 | 3922 | 2.206 |
| B2  | 5.22  | 1277 | 59.7 | 2938 | 2.301 |
| D4  | 9.10  | 1957 | 79.5 | 3346 | 1.709 |
| D5  | 7.84  | 1791 | 78.5 | 3258 | 1.819 |
| D12 | 7.76  | 1635 | 91.2 | 1424 | 0.871 |
| D20 | 7.66  | 1525 | 60.6 | 3130 | 2.052 |
| D24 | 4.25  | 973  | 28.3 | 1133 | 1.164 |
| D30 | 7.58  | 1492 | 93.4 | 2095 | 1.405 |
| F1  | 8.55  | 1717 | 41.0 | 3704 | 2.157 |
| F13 | 6.14  | 1224 | 46.0 | 2711 | 2.215 |
| F18 | 7.80  | 1641 | 50.0 | 3301 | 2.011 |
| F20 | 7.76  | 1812 | 68.2 | 2095 | 1.156 |
| F21 | 7.95  | 1693 | 39.7 | 2008 | 1.186 |
| F22 | 8.13  | 1953 | 87.9 | 1572 | 0.805 |
| F29 | 9.16  | 1944 | 88.3 | 1435 | 0.738 |
| F31 | 7.27  | 1453 | 73.9 | 1540 | 1.060 |
| F33 | 5.67  | 1409 | 7.2  | 857  | 0.608 |
| F34 | 10.04 | 2049 | 93.4 | 1328 | 0.648 |

[1]Time integral of the viable cell concentration at harvest.
[2]Determined by Protein A HPLC.
[3]Calculated by linear regression analysis of the antibody concentration against the time integral of the viable cell concentration.

Example 18: Affinity of CD70 mAbs 18.1 Affinity for Cancer Cell Lines Expressing CD70

Several cancer cell lines were tested by FACS analysis for binding of ARGX-110 and SGN70 (described in US2010/0129362) at saturating mAb concentrations (at least 2 μg/ml). This was either done at 4° C. (1 hour incubation of cells with mAbs) or at 37° C. (15 minutes incubation of cells with mAbs). Binding was detected using anti-hIgG1-Fc-FITC (AF006, Binding Site) or anti-hIgG1-Fc-PE antibody (eBioscience, 12-4998). Fluorescence was measured using a flow cytometer. The results are summarized in Table 25. The third column of the table shows whether ARGX-110 binds with low (+), medium (++) or high (+++) affinity to the various cell lines tested.

In the right-hand column, the FACS signal (MFI) for ARGX-110 is divided by the FACS signal (MFI) for SGN70 for the experiment carried out at 37° C. These results demonstrate that ARGX-110 binds with higher affinity to the cells than SGN70, particularly for lower copy-number cell lines where it can be expected that high affinity binding of an antibody can be picked up more easily.

TABLE 25

Binding of CD70 mAbs ARGX-110 and SGN70 to cancer cell lines

| Type | Cell line | ARGX-110 | Signal in FACS of ARGX-110/ signal in FACS of SGN70 |
|---|---|---|---|
| Burkitt lymphoma | Raji | +++ | 1.2 |
| Large B cell lymphoma | SU-DHL-6 | + | 2.4 |
| Hodgkin lymphoma | L428 | +++ | 1.4 |
| Non Hodgkin lymphoma | MHHPREB1 | +++ | 1.2 |
| Mantle Cell Lymphoma | Mino | +++ | 1.0 |
|  | Jeko | +++ |  |
|  | Granta 519 | ++ | 0.9 |
|  | Rec-1 | + |  |
| Chronic lymphocytic leukemia | Mec1 | +++ | 1.2 |
|  | JVM-3 | ++ |  |
|  | JVM-2 | + | 2.4 |
| Cutaneous T cell lymphoma | HUT78 | +++ | 1.0 |
|  | HH | + | 1.7 |
| Multiple Myeloma | U266 | +++ | 0.8 |
|  | JNN-3 | +++ |  |
|  | LP1 | ++ |  |
|  | AMO-1 | +++ |  |
|  | RPMI8226 | +++ |  |
|  | MM1.S | ++ |  |
|  | KMS11 | +++ |  |
|  | KMS12MB | +++ |  |
| Renal cell carcinoma | 786-O | +++ | 2.1 |
|  | Caki-1 | ++ | 1.9 |
|  | A498 | ++ | 1.0 |
| Astrocytoma | U251 | +++ |  |
| Gastric carcinoma | MKN-45 | + | 10.6 |
| Lung carcinoma | A549 | + | 3.8 |
|  | EBC-1 | + | 8.9 |
| Melanoma | WM1205-Lu | +++ |  |
|  | WM852 | + |  |
|  | WM3248 | +++ |  |
|  | WM793 | + |  |
|  | WM1552C | ++ |  |
|  | WM115 | +++ |  |
| Glioblastoma | GaMG | + |  |
|  | U87MG | ++ | 2.0 |
|  | U343 | ++ |  |
| Ovarian carcinoma | OAW-42 | + |  |
|  | SKOV3 | + |  |
|  | OVCAR3 | + |  |
| Pancreatic carcinoma | PANC-1 | ++ | 2.9 |
|  | PANC-89 | + |  |

Figure 15:
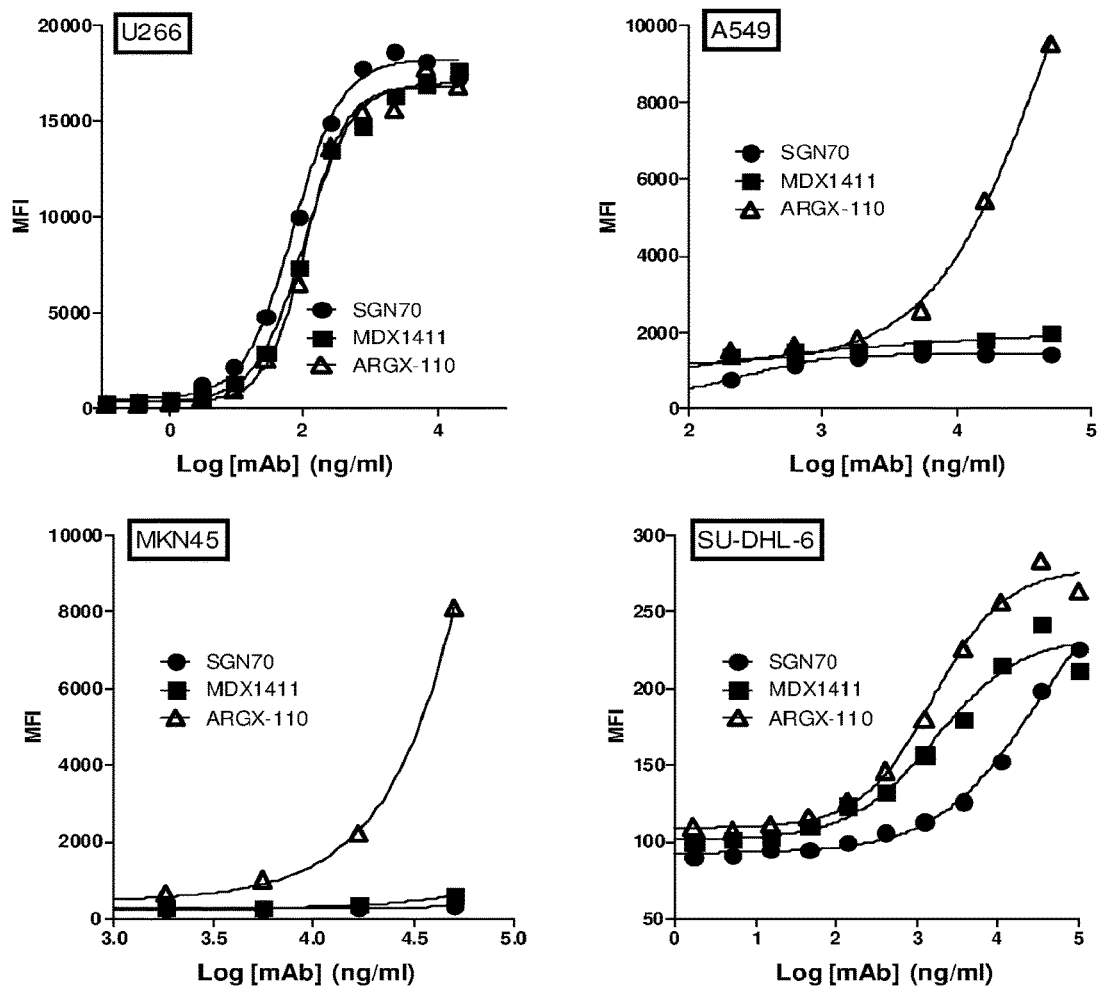
FIG. 15: shows the binding affinity of CD70 mAbs for CD70-expressing cancer cell lines.

In a further experiment, the apparent binding affinity of CD70 mAbs, ARGX-110, SGN70 and MDX1411 [see above], across a range of concentrations was determined for different cell lines. Cells were incubated for 1 hour at 4° C. with a dilution series of CD70 binding mAbs and binding was detected using anti-hIgG1-Fc-FITC or anti-hIgG-Fc-PE antibody. Fluorescence was measured using a flow cytometer and the median fluorescence was plotted. The results are shown in FIG. 15.

The results demonstrate that the affinity of the three different mAbs for CD70 on cells is comparable, but for some cell lines, SU-DHL-6, A549 and MKN45, binding of ARGX-110 is superior as compared to MDX1411 and SGN70. The EC50 for binding to SU-DHL-6, A549 and MKN45 is much higher for all mAbs as compared to EC50 on the other cell lines like U266 and many others, which probably indicates that the mAb is binding only with one arm (Fab), no longer allowing for avidity and thus resulting in lower affinities. Indeed, when tested in Biacore, the affinity of the Fab of ARGX-110 versus SGN70 and MDX1411 is much higher (see below).

18.2 Affinity for Patient Cells Expressing CD70

Primary cells taken from chronic lymphocytic leukaemia (CLL) patients (2 high risk patients, 1 low risk patient) were plated at 250,000 cells/well in round bottom 96 well plates in RPMI 1640+10% FBS and mAbs at a concentration of 5 µg/ml in RPMI+10% FBS were added. After incubation for up to 5 hours at 37° C., cells were washed twice with ice-cold PBS. Alexa Fluor 647 labelled goat Anti-Human IgG (Invitrogen Cat#21445) was diluted 1/500 in PBS/1% BSA and incubated for 20 minutes at 4° C. The plate was washed twice with ice-cold PBS and 4% paraformaldehyde was added for 15 minutes at room temperature to fix the cells. Signals were measured by FACS. The results are shown in FIG. 16. The results demonstrate that ARGX-110 binds well to the cells from the CLL patients whereas SGN70 almost gave no binding signals.

18.3 Affinity of CD70 Fabs for Recombinant CD70 in Biacore

Recombinant human CD70 was immobilized on a CM5 Biacore chip. The immobilization was performed in accordance with a method provided by Biacore and by using the NHS/EDC kit (Biacore AB): after activation of the chip, a solution of 50 µg/ml of recombinant CD70 in 10 mM acetate buffer with pH of 5 was prepared and 1 µl of this solution (50 ng) was injected resulting in a surface density of approximately 1000 RU.

Fabs were prepared for the CD70 mAbs ARGX-110, MDX1411 and SGN70 by papain digestion. These Fabs, at a concentration of approximately 100-400 µg/ml, were diluted 6-fold in HEPES-buffered saline (0.1M HEPES, 1.5M NaCl, 30 mM EDTA, 0.5% v/v surfactant P20). They were injected (30 µl) and passed through the flow cells at a flow rate of 30 µl/min. After binding of the Fab to CD70, the off-rate was monitored for a period of 10 minutes. After dissociation, the flow cell surfaces were regenerated by injecting 5 µl of 10 mM NaOH. Sometimes multiple injections of NaOH were needed to regenerate the surfaces depending on the affinity of the Fabs. Off-rate analysis was done by applying the BIAevaluation software. First, the sensogram of the blank runs were subtracted from those obtained with the coated flow cell. Then the off-rate was determined for a time range of 10 minutes using the Fit kinetics application and the Kd value was calculated. The off rates are summarized in Table 26.

TABLE 26

"off rate" of Fabs for binding to human CD70

| | Off rate [$10^{-4}$ s$^{-1}$] |
|---|---|
| ARGX-110 | 1.4 |
| SGN70 | 7 |
| MDX1411 | 17 |

18.4 Spiking Experiments to Assess Lysis of SU-DHL-6 Cells Bound by CD70 mAbs

Figure 17:
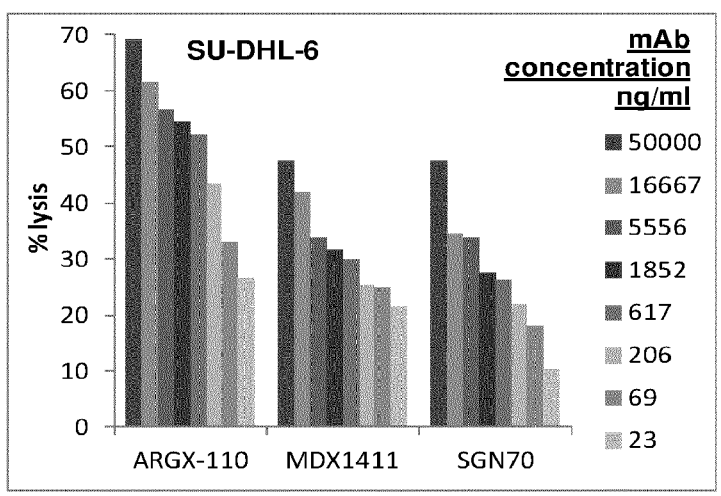
FIG. 17: shows lysis of SU-DHL-6 cells bound by CD70 mAbs.

SU-DHL-6 cells (a diffuse large B cell lymphoma cell line) were piped into wells at 50,000 cells/well which were spiked then into 300,000 freshly isolated PBMCs/well from healthy donors and mAbs were added at different concentrations. The samples were incubated for 2 days and analysed by FACS for the depletion of the cell line (as measured with anti-human CD19 APC (eBioscience 17-0199-42)). The best potency in cell killing was obtained with ARGX-110, which also gives the highest % of lysis. The results are shown in FIG. 17.

Example 19: CD27-CD70 Blocking Activity of CD70 mAbs

The interaction between CD70 and CD27 may contribute to tumour cell survival, proliferation and/or immune suppression within the tumour microenvironment. The ability of CD70 mAbs to block the interaction between CD70 and CD27 was therefore assessed by ELISA.

In this assay, a microtiter plate (Nunc Maxisorb) was first coated with 100 µl anti-FLAG M2 monoclonal antibody (Sigma Aldrich, F3165) at 1250-fold dilution in PBS (to achieve a final concentration of approximately 3.5 µg/ml) overnight at 4° C. The plate was washed once with PBS-Tween and incubated at RT for 2 hours with 300 µl PBS-1% casein. The plate was washed a further three times with PBS-Tween. 100 µl of 5 ng/ml (80 pM) Flag-TNC-CD70 (The Journal of Immunology, 2009, 183: 1851-1861) diluted in PBS-0.1% casein was added to the plate and incubated at RT for 1 hour while shaking. The plate was washed five times with PBS-Tween. The CD70 mAb to be tested was added to the plate; various concentrations were achieved by diluting the stock antibody solution in PBS-0.1% casein. Immediately thereafter, 50 µl of 1 µg/ml (final concentration 6.5 nM) recombinant human CD27 Fc chimera (R&D systems 382-CD, MW=46.5 kDa) was added, and incubated at RT for 1 hour while shaking. The plate was washed five times with PBS Tween. 100 µl of biotinylated anti-CD27 (eBioscience 13-0271), diluted 500-fold in PBS-0.1% casein, was added, and the plate incubated at RT for a further hour, while shaking. The plate was washed five times with PBS Tween. 100 µl of Strep-HRP (Jackson Immunoresearch 016-030-084) diluted 5000 fold in PBS-0.1% casein was added, and the plate incubated at RT for a further hour, while shaking. The plate was washed five times with PBS-Tween. 100 µl TMB was added to the plate and the OD at 620 nm was measured.

Using this assay, the blocking potency of ARGX-110 was compared to the potency of SGN70 and MDX1411. As shown in FIG. 18, ARGX-110 is much more potent (about 100-fold) in blocking the interaction between CD70 and CD27 than the two benchmark mAbs (IC50 ARGX-110=67 ng/ml, MDX1411=5500 ng/ml and SGN70=4972 ng/ml).

Example 20: Binding Properties of CD70 mAbs 20.1 Cross-Reactivity with CD70 of Non-Human Species
Determining the animal cross-reactivity of CD70 mAbs is useful for the purposes of assessing which animal models can be used for in vivo proof of concept studies, and which species are most suited for toxicology studies. Rhesus CD70 is 94% identical to human CD70 and Cynomolgus monkey CD70 is 95% identical to human CD70. An alignment of the sequences from the different species is shown in FIG. 19. The mouse and rat CD70 sequences are also included so as to highlight the differences as compared with the human sequence.

CD70 mAbs ARGX-110, SGN70 and MDX1411 were tested for binding to U266 (a human multiple myeloma cell line), LCL8664 cells (rhesus B cell lymphoma cell line, ATCC-CRL-1805) and to HSC-F cells (*cynomolgus* monkey T-cell line, fetal spleen-derived lymphocytes, Japanese health science foundation) cells in a dilution series starting at a concentration of 10-20 µg/ml.

Figure 20:
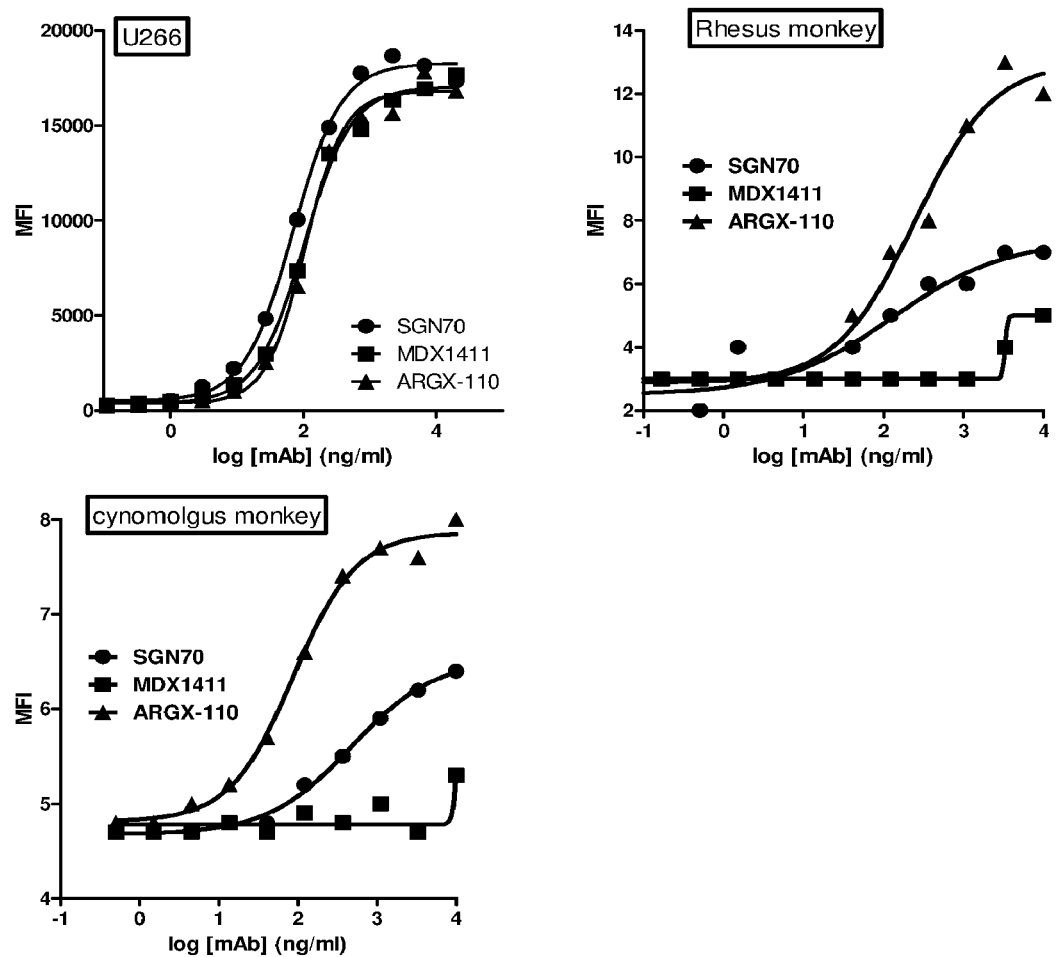
FIG. 20: shows the binding affinity of CD70 mAbs for human U266 cells, rhesus monkey LCL8864 cells and cynomologus monkey HSC-F cells.

Detection was performed using goat anti human IgG1 FITC. Samples were analysed by FACS. The results are shown in FIG. 20. The copy-number of CD70 on both monkey cell lines is very low (low signals in FACS). However, ARGX-110 has a high affinity for *cynomolgus* and rhesus CD70 as compared to the affinity of SGN70 and MDX1411 for CD70 of these species.

20.2 Blocking Potency of CD70 mAbs
The ability of CD70 mAbs (ARGX-110, SGN70 and MDX1411) to block the interaction between CD70 and CD27 was tested using the blocking ELISA described in Example 19 above. The assay was adapted such to measure the blocking potency of each antibody for human, rhesus and *cynomolgus* monkey Flag-TNC-CD70 (Wyzgol, et al., J. Immunol., 2009, 183: 1851-1861).

Figure 21:
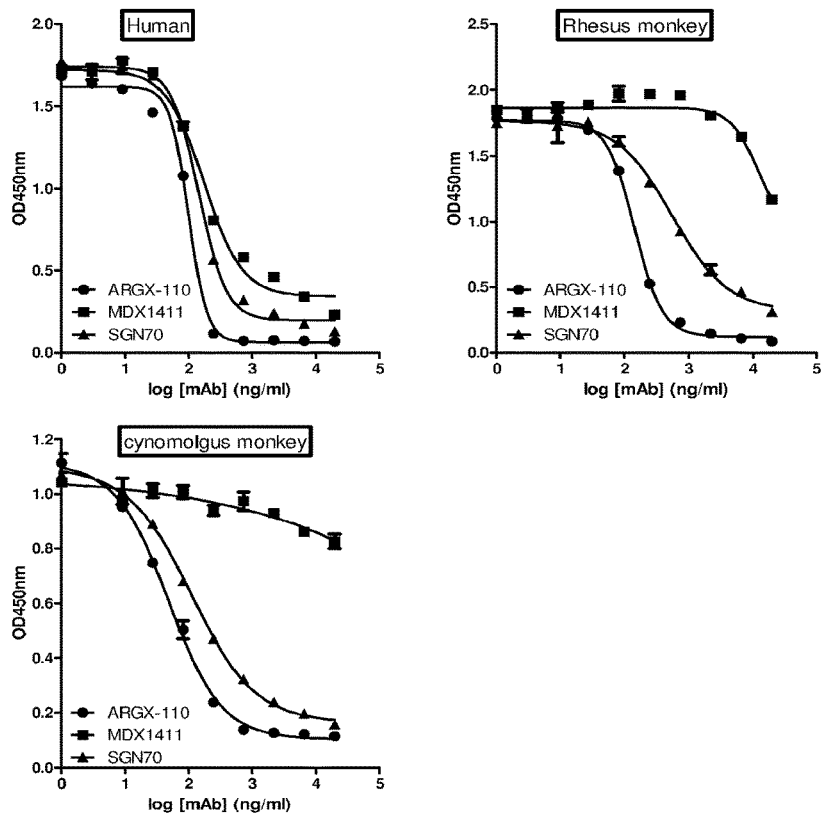
FIG. 21: shows inhibition of binding of CD27 to CD70 of human, rhesus monkey and cynomologus monkey by CD70 mAbs as determined by ELISA.

In the ELISA, exactly the same conditions were used for CD70 from the different species so that the IC50 values between the different species could be compared directly. The results are shown in FIG. 21 and support the results seen using cells from humans, rhesus monkeys and *cynomolgus* monkeys. ARGX-110 has an unaltered potency and therefore an unaltered affinity for CD70 of monkeys as compared to human, whereas SGN70 and especially MDX1411 have a lower affinity for monkey than for human CD70. IC50 values are summarized in Table 27.

TABLE 27

IC50 for blocking of the CD27-CD70 interaction in ELISA for CD70 from different species

| | IC50 [ng/ml] in inhibition ELISA | | |
|---|---|---|---|
| Cells | Human | Rhesus monkey | Cynomolgus monkey |
| ARGX-110 | 39 | 75 | 48 |
| SGN70 | 54 | 178 | 112 |
| MDX1411 | 44 | >10000 | >10000 |

Figure 22:
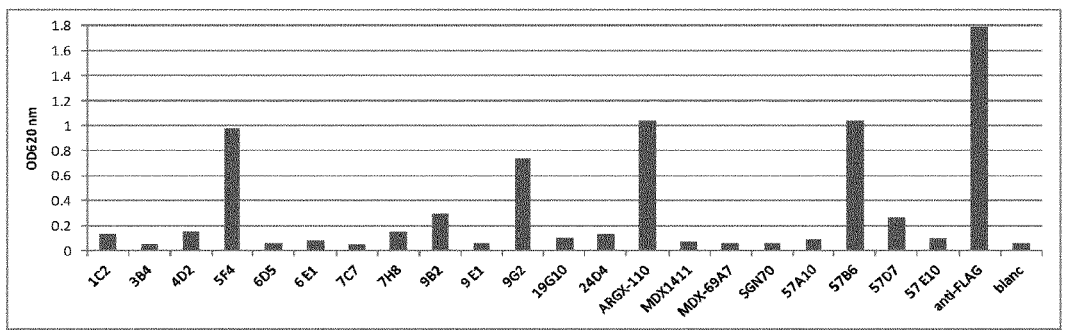
FIG. 22: shows binding of CD70 mAbs to denatured recombinant CD70, assessed by ELISA.

20.3 Binding to Denatured CD70
The binding of CD70 mAbs to denatured recombinant CD70 was assessed by ELISA. Recombinant CD70 was denatured by heating for 5 minutes at 95° C., followed by immediate cooling on ice for 5 minutes. A microtiter plate was coated with 5 µg/ml CD70 with or without denaturation. The plate was blocked and the CD70 mAbs for testing were applied at 10 µg/ml. After washing, binding of the mAbs was detected using anti-human IgG-HRP. As a positive control for the coating, instead of using the CD70 mAbs, an anti-Flag mouse-derived mAb was applied and detection was with anti-mouse-HRP. TMB was used as a substrate and OD at 620 nm was measured. The results from this ELISA are shown in FIG. 22. The results demonstrate that ARGX-110 binds to a different epitope than SGN70, MDX1411 (MDX2H5) and MDX69A7 as ARGX-110 still binds to denatured CD70 whereas the other mAbs don't. Amongst the other mAbs, some are also binding to denatured CD70 (fc 5F4, 9G2, 57B6).

20.4 Epitope Mapping Using Mouse-Human Chimeras
Human-mouse CD70 ECD fusion proteins were constructed by exchanging domains of human and mouse CD70 in order to map the domain recognition of the mAbs. The construction was done using standard recombinant DNA and PCR methodologies. The mouse and human chimeras were cloned into a eukaryote expression vector with a Flag tag for capturing in ELISA and a TNC for trimerisation of the protein (Flag-TNC-CD70). Proteins were expressed as soluble proteins in HEK293 cells. The sequence of the different chimeras is shown in FIG. 23.

A Maxisorb (Nunc) microtiter plate was coated with 3.5 µg/ml mouse M2 anti-Flag mAb (Sigma Aldrich, F3165) and the different chimeras were captured. A dilution series of the CD70 mAbs to be tested was applied starting at a concentration of 10 µg/ml and making 3-fold dilutions. After 2 hours, binding was detected using anti-human-Fc-HRP at a 16000-fold dilution. Staining was done with ABTS and OD at 405 nm was measured. As a positive control, CD27-Fc was applied which is able to bind to both human and mouse CD70 with good affinity as well as to the chimeric human-mouse CD70 variants. The EC50 values for binding are summarized in Table 28.

TABLE 28

Binding of ARGX-110 to human-mouse CD70 chimeras shown in FIG. 23.

| EC50 [ng/ml] | ARGX-110 | CD27 |
| --- | --- | --- |
| human | 22 | 79 |
| chim-1 | 27 | 159 |
| chim-2.1 | 15 | 51 |
| chim-2.2 | 16 | 56 |
| chim-2.3 | 15 | |
| chim-2.4 | 14 | 76 |
| chim-2 | NB | 99 |
| chim-3 | NB | 94 |
| chim-4 | NB | 51 |
| mouse | NB | 41 |

NB = no binding

The results demonstrate that ARGX-110 can bind to human Flag-TNC-CD70 and to chimeras 1, 2.1, 2.2, 2.3 and 2.4 but does not bind to chimeras 2, 3 and 4 and mouse Flag-TNC-CD70. This indicates that the epitope for ARGX-110 is within the following amino acid sequence: HIQVTLAICSS (SEQ ID NO:342).

Figure 24:
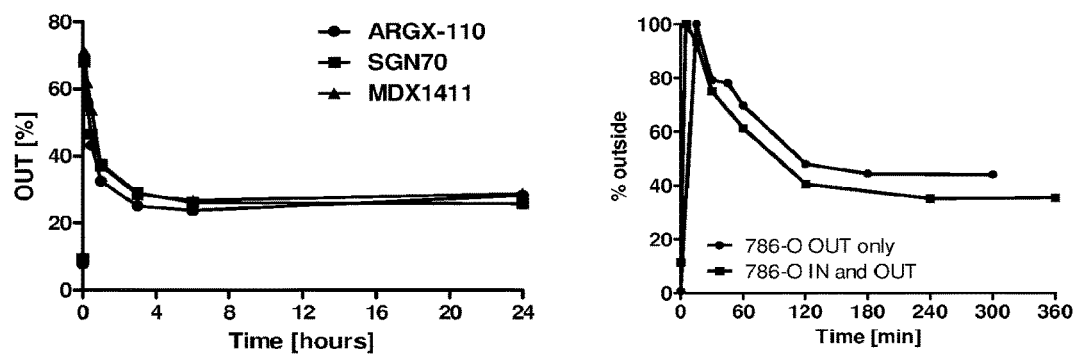
FIG. 24: illustrates antibody internalisation for CD70 mAbs as a function of time on 786-O cells.

Example 21: CD70 Internalization of Different Tumor Cell Lines and Primary Tumor Cells It has been demonstrated that binding of CD70 antibodies to the renal carcinoma derived cell lines 786-O and A498 results in the rapid (within 1 hour) internalization of the antibody-receptor complex (Adam et al., Br. J. Cancer (2006) 95: 298-306). In order to test for internalization of mAbs ARGX-110, SGN70 and MDX1411, 786-0 cells were cultured in a 96-well microtiter plate and incubated overnight at 37° C. 2.5 µg/ml mAb was added and incubated with the cells for 0-24 hours at 37° C. Plates were washed 3 times 5' with stripping buffer (150 mM NaCl, 100 mM Glycine, pH=2.5; coded "IN" representing the amount of mAb internalized via CD70) or PBS (coded "OUT" and representing the amount of mAb bound to the receptor at the outside of the cell). Subsequently, cells were fixed with 4% paraformaldehyde for 30' at RT, washed with PBS, and incubated 5' with 0.2% Triton-X-100 ("IN") or PBS ("OUT"). Next, cells were washed twice and incubated at RT for 10' with 100 mM glycine followed by 30 mins incubation with PBS-1% BSA. Finally cells were stained with goat anti-human Fc (Jackson immunoresearch 109-005-098) and anti-goat IRDYE800 (Li-cor 926-32214) before analysis on the Li-Cor Odyssey infrared scanner. The % of mAb OUT as a function of time is shown in FIG. 24.

The results demonstrate that internalization for all mAbs is comparable and that none of the mAbs internalizes completely. Initially, between 0 and 2 hours, the mAb internalization goes very fast, but then it seems that a steady state is reached where about 30% of the mAb remains at the outside of the cell, even after 24 hours of incubation at 37° C.

The internalization of CD70-bound mAbs was also assessed using other cell lines. In these experiments, only the signal of the mAb outside the cell was measured as a function of time using FACS analysis according to the protocol described below. This alternative protocol was determined to be a reliable readout as compared with the method described above (see FIG. 24, right-hand panel).

For suspension cells, cells were centrifuged, counted and the pellet resuspended in medium to a density of $5 \times 10^5$ cells/ml, and 1000 of this suspension was added per well of a 96-well V-bottom plate. For adherent cells, cells were seeded in a 96-well plate and grown ON at 37° C., 5% $CO_2$ until cells were fully attached. Cells were plated at a density which allowed linear cell growth for an additional 48 h period.

The mAbs for testing were diluted and incubated with the cells at 37° C., 5% $CO_2$ for varying time periods: 24 h, 8 h, 6 h, 4 h, 2 h, 1 h, 30 min, 15 min, 5 min, 0 min (=no mAb). Following incubation, the plates were washed on ice with cold FACS buffer to stop the internalization reaction. At this stage, adherent cells were detached from the plate using cell dissociation solution (Sigma) and transferred to a V-bottom 96-well plate. Next, cells were spun down at 4° C. The supernatant was removed by gently inverting the plate. The cells were washed twice by gently re-suspending the cell pellet in 100 µl cold FACS buffer. After washing, the cell pellet was resuspended in 100 µl anti-hu IgG-FITC, diluted 1/500 in FACS buffer. The plate was incubated for 30 min at 4° C., while shaking, and the cells were washed a further three times with cold FACS buffer. The cells were resuspended in 100 µl FACS buffer and fluorescence was measured immediately. The median mean fluorescence intensity (MFI) was plotted versus time.

Several of the experiments were repeated two or more times. Results from two experiments were very comparable. In some experiments, using U266, SU-DHL-6 and Raji cells, a concentration range (20 ng/ml-5 µg/ml) was used to see if there was an effect of mAb concentration on internalization rate. No such effect was observed (data not shown).

The results for different cell lines tested are shown in Table 29 and demonstrate that internalization is not a common phenomenon, actually it is quite a rare event. Table 29 summarizes the percentage of internalization after 6 hours for the different cell lines. These results show that most of ARGX-110 remains bound to the outside of the cells making the cells more susceptible to ADCC, CDC and ADCP.

TABLE 29

% internalization of CD70 mAbs on different cell lines after 6 hours.

| Type | Cell line | % internalization after 6 hours | Average % per indication |
| --- | --- | --- | --- |
| Burkitt lymphoma | Raji | 2 | 2 |
| Large B cell lymphoma | SU-DHL-6 | 3 | 3 |
| Hodgkin lymphoma | L428 | 15 | 15 |
| Non Hodgkin lymphoma | MHHPREB1 | 19 | 19 |
| Mantle Cell Lymphoma | Mino | 12 | 7 |
| | Granta 519 | 7 | |
| | Rec-1 | 2 | |
| Chronic lymphocytic leukemia | Mec1 | 3 | 7 |
| | JVM-2 | 8 | |
| | JVM-3 | 11 | |
| | Patient HR | 5 | |
| | Patient HR | 7 | |
| | Patient LR | 8 | |
| Cutaneous T cell lymphoma | HUT78 | 35 | 33 |
| | HH | 31 | |
| Multiple Myeloma | U266 | 38 | 34 |
| | AMO-1 | 36 | |
| | RPMI8226 | 38 | |
| | MM1.S | 35 | |
| | KMS12MB | 49 | |

TABLE 29-continued

% internalization of CD70 mAbs on different cell lines after 6 hours.

| Type | Cell line | % internalization after 6 hours | Average % per indication |
|---|---|---|---|
| Renal cell carcinoma | 786-O | 58 | 54 |
| | Caki-1 | 37 | |
| | A498 | 66 | |
| Astrocytoma | U251 | 52 | 52 |
| Gastric carcinoma | MKN-45 | 0 | 0 |
| Lung carcinoma | A549 | 0 | 3 |
| | EBC-1 | 6 | |
| Melanoma | WM1205-Lu | 45 | 44 |
| | WM3248 | 34 | |
| | WM115 | 52 | |
| Glioblastoma | U87MG | 10 | 21 |
| | U343 | 32 | |
| Ovarian carcinoma | SKOV3 | 51 | 51 |
| Pancreatic carcinoma | PANC-1 | 29 | 25 |
| | PANC-89 | 20 | |

TABLE 30 nucleotide sequences encoding selected CD70 antibodies

| mAb | | |
|---|---|---|
| 41D12 | Heavy chain SEQ ID NO: 344 | gccgccaccATGGGCTGGTCCTGCATCATCCTGTTTCTGGTGGCCAC<br>CGCCACAGGCGTCCACTCTGAGGTGCAGCTCGTGGAGTCTGGG<br>GGAGGCTTGGTGCAGCCTGGGGGGTCTCTGAGACTCTCCTGTG<br>CAGCCTCTGGATTCACCTTCAGTGTCTACTACATGAACTGGGTC<br>CGCCAGGCTCCAGGGAAGGGGCTCGAGTGGGTCTCAGATATTA<br>ATAATGAAGGTGGTACTACATACTATGCAGACTCCGTGAAGGGC<br>CGATTCACCATCTCCAGAGACAACTCTAAGAACAGCCTGTATCT<br>GCAAATGAACAGCCTGCGCGCCGAGGACACGGCCGTGTACTAC<br>TGCGCGAGAGATGCCGGATATAGCAACCATGTACCCATCTTTGA<br>TTCTTGGGGCCAGGGGACCCTGGTCACTGTCTCCTCAGCCAGTA<br>CAAAAGGTCCAAGTGTGTTCCCTCTTGCTCCCTCATCCAAGAGTA<br>CCAGTGGAGGCACCGCCGCTCTTGGCTGCTTGGTTAAGGATTAT<br>TTCCCAGAGCCTGTCACTGTTTCATGGAACTCCGGCGCCTTGACA<br>TCTGGTGTGCATACCTTTCCAGCCGTGCTGCAGTCAAGTGGCCTC<br>TACAGCCTCAGTAGCGTGGTCACTGTGCCCAGCAGCTCTCTCGG<br>CACACAAACTTATATCTGTAATGTGAATCATAAGCCTTCAAATACC<br>AAGGTGGATAAGAAAGTGGAACCAAAATCATGTGACAAGACACAC<br>ACCTGCCCTCCTTGTCCAGCCCCCGAACTGCTGGGTGGGCCCAG<br>CGTGTTCCTGTTTCCTCCTAAACCCAAAGACACTCTGATGATTAGT<br>AGGACCCCAGAAGTCACTTGCGTGGTGGTTGACGTGTCACATGA<br>AGATCCCGAGGTCAAGTTCAATTGGTATGTTGACGGGGTCGAAGT<br>TCACAACGCTAAAACTAAACCAAGAGAGGAACAGTATAACTCTAC<br>CTACCGGGTGGTGAGTGTTCTGACTGTCCTCCATCAAGACTGGCT<br>GAATGGCAAAGAATACAAGTGTAAGGTGAGCAACAAAGCCCTGC<br>CCGCTCCTATAGAGAAAACAATATCCAAAGCCAAAGGTCAACCTC<br>GCGAGCCACAGGTGTACACCCTCCCACCAAGCCGCGATGAACTT<br>ACTAAGAACCAAGTCTCTCTTACTTGCCTGGTTAAGGGGTTCTAT<br>CCATCCGACATTGCAGTCGAGTGGGAGTCTAATGGACAGCCTGA<br>GAACAACTACAAAACCACCCCTCCTGTTCTGGATTCTGACGGATC<br>TTTCTTCCTTTATTCTAAACTCACCGTGGATAAAAGCAGGTGGCAG<br>CAGGGCAACGTGTTCAGCTGTTCCGTTATGCATGAGGCCCTGCA<br>TAACCATTATACCCAGAAGTCTTTGTCCCTCAGTCCAGGAAAGTGA<br>kozak<br>LEADER<br>VARIABLE REGION<br>LAMBDA CONSTANT REGION |
| | Light chain SEQ ID NO: 345 | gccgccaccATGGGCTGGTCCTGCATCATCCTGTTTCTGGTGGCCAC<br>CGCCACAGGCGTCCACTCTCAGGCAGTGGTGACCCAGGAGCCT<br>TCCCTGACAGTGTCTCCAGGAGGGACGGTCACGCTCACCTGCG<br>GCCTCAAATCTGGGTCTGTCACTTCCGATAACTTCCCCACTTGGT<br>ACCAGCAGACACCAGGCCAGGCTCCCCGATTGCTTATCTACAA<br>CACAAACACCCGTCACTCTGGCGTCCCCGACCGCTTCTCCGGAT<br>CCATCCTGGGCAACAAAGCCGCCCTCACCATCACGGGGGCCCA<br>GGCCGACGACGAGGCCGAATATTTCTGTGCTCTGTTCATAAGTA<br>ATCCTAGTGTTGAGTTCGGCGGAGGGACCCAACTGACCGTCCTA<br>GGTCAACCTAAAGCAGCACCTTCAGTTACTCTGTTTCCACCCTAGT<br>TCAGAGGAACTGCAGGCCAATAAAGCCACACTCGTCTGCCTCAT<br>CAGTGACTTCTACCCAGGAGCCGTGACCGTGGCCTGGAAAGCCG<br>ACAGTAGCCCCGTGAAGGCCGGGGTGGAGACAACAACTCCTAGT<br>AAACAGAGTAATAACAAATATGCCGCTAGTAGTTATCTCTCCCTCA<br>CTCCCGAGCAGTGGAAGTCTCACAGAAGTTACTCTTGTCAGGTTA<br>CTCACGAGGGTTCCACAGTGGAAAAGACTGTGGCCCCTACTGAA<br>TGTAGTTGA<br>kozak<br>LEADER<br>VARIABLE REGION<br>LAMBDA CONSTANT REGION |

TABLE 30-continued nucleotide sequences encoding selected CD70 antibodies mAb

| 57B6 | Heavy chain<br>SEQ ID NO:<br>346 | CAGTTGCAGCTGGTGGAGTCTGGGGGAGGCTTGGTGCAGCCTG<br>GGGGGTCTCTGAGACTC<br>TCTTGTGCAGCCTCTGGATTCAGCTTCAGTCACTATGCCATGAGC<br>TGGGTCCGCCAGGCT<br>CCAGGAAAGGGGCTAGAGTGGGTCTCAGGTGATAATACCTACGA<br>TGGTGGTACAAGGTAT<br>CAAGACTCCGTGAAGGGCCGATTCACCATCTCCAGAGACAATGG<br>CAAGAACACGCTGTAT<br>CTGCAAATGAACAGCCTGAAACCTGAGGACACGGCCGTGTATTA<br>CTGTGCAAAAGATACT<br>GGTAGAGGCATTATGGGGGAGTACGGCATGGACTACTGGGGCAA<br>AGGGACCCTGGTCACC<br>GTCTCCTCA |
|---|---|---|
| | Light chain<br>SEQ ID NO:<br>347 | CAGACTGTGGTGACCCAGGAGCCGTCCCTGTCAGTGTCTCCAGG<br>AGGGACGGTCACACTC<br>ACCTGCGGCCTCAAGTCTGGGTCTGTCACTTCCAGTAACTACCCT<br>GCTTGGTACCAGCAG<br>ACACCAGGCCAGGCTCCCCGATTGCTTATCTACAACACAAACAGC<br>CGTCACTCTGGGGTC<br>CCCAGTCGCTTCTCCGGATCCATCTCTGGGAACAAAGCCGCCCT<br>CACCATCACGGGGGCC<br>CAGCCCGAGGACGAGGCCGACTATTACTGTGCTCTGTACATGGG<br>TAGTGGTAGTGCCAAT<br>GCTATGTTCGGCGGAGGGACCCATCTGACCGTCCTGGGTCA |
| 59D10 | Heavy chain<br>SEQ ID NO:<br>348 | GAGGTGCAGCTGGTGGAGTCTGGGGGAGGCTTGGTGCAGCCTG<br>GGGGGTCTCTGAGACTC<br>TCCTGTGCAGCGTCCGAATTGTCCTTCAGTATTTCTGAGATGACC<br>TGGGTCCGCCAGGCT<br>CCAGGAAAGGGGCTCGAGTGGGTCTCAGGTATTAGTGGTGTAAC<br>TGGTGGTAGTAGTACA<br>AGTTATGCAGACTCCGTGAAGGGCCGATTCACCATCTCCAGAGA<br>CAACGACAAGAACACG<br>TTGTATCTACAAATGAACAGCCTGATACCCGAGGACACGGCCGTA<br>TATTACTGTGCAACA<br>ACTAGTGGTACTTACTACTTCATCCCCGAGTATGAGTACTGGGGC<br>CAGGGGACCCAGGTC<br>ACCGTCTCCTCA |
| | Light chain<br>SEQ ID NO:<br>349 | CAGTCTGTGCTGACCCAGCCTCCCTCCGTGTCTGGGTCTCCAGG<br>AAAGACGGTCACCATC<br>TCCTGTGCAGGAACCAGCAGTGATGTTGGGTATGGATACTATGTC<br>TCCTGGTATCAACAG<br>TTCCCAGGAATGGCCCCCAAACTCCTGATATATGACGTCAATAAA<br>CGGGCCTCAGGGATC<br>GCTGATCGCTTCTCTGGCTCCAAGGCCGGCAACACTGCCTCCCT<br>GACCATCTCTGGGCTC<br>CAGTCTGAGGACGAGGCTGATTATTACTGTGCCTCATATAGAAGT<br>AGCGCCAATGCTGTG<br>TTCGGCGGAGGGACCCATCTGACCGTCCTGGGT |

The invention claimed is:

1. A method of treating a CD70-expressing cancer in a human patient, comprising administering to a human patient in need thereof a therapeutically effective amount of a monoclonal antibody, or antigen binding fragment thereof, which specifically binds to human CD70, wherein the monoclonal antibody or antigen binding fragment thereof comprises: a heavy chain variable (VH) domain comprising HCDR3, HCDR2, and HCDR1 regions, and a light chain variable (VL) domain comprising LCDR3, LCDR2, and LCDR1 regions, wherein
the HCDR3 region comprises the amino acid sequence set forth in SEQ ID NO:50 (DAGYSNHVPIFDS);
the HCDR2 region comprises the amino acid sequence set forth in SEQ ID NO:27 (DINNEGGTTYYADSVKG);
the HCDR1 region comprises the amino acid sequence set forth in SEQ ID NO:11 (VYYMN),
the CDRL3 region comprises the amino acid sequence set forth in SEQ ID NO:160 (ALFISNPSVE),
the CDRL2 region comprises the amino acid sequence set forth in SEQ ID NO:119 (NTNTRHS), and
the CDRL1 region comprises the amino acid sequence set forth in SEQ ID NO:250 (GLKSGSVTSDNFPT),
wherein the cancer is chronic lymphocytic leukemia.

2. The method of claim 1, wherein the heavy chain variable (VH) domain and the light chain variable (VL) domain are derived from a camelid species.

3. The method of claim 2, wherein the VH and VL domains are derived from llama (Lama glama).

4. The method of claim 1, wherein the monoclonal antibody is a chimeric antibody, wherein the chimeric antibody comprises a constant domain derived from a human immunoglobulin.

5. The method of claim 4, wherein the constant domain is derived from a human immunoglobulin selected from the group consisting of IgG1, IgG2, IgG3, and IgG4.

6. The method of claim 5, wherein the constant domain is derived from human IgG1.

7. The method of claim 6, wherein the constant domain derived from human IgG1 is non-fucosylated.

8. The method of claim 1, wherein the monoclonal antibody or antigen binding fragment thereof is capable of directing immune effector function against a cell expressing human CD70 on its surface, wherein the immune effector function is selected from the group consisting of antibody-dependent cellular cytotoxicity (ADCC), complement-dependent cytotoxicity (CDC), antibody-dependent cellular phagocytosis (ADCP), and any combination thereof.

9. A method of treating acute myeloid leukemia in a human patient, comprising administering to a human patient in need thereof a therapeutically effective amount of a monoclonal antibody, or antigen binding fragment thereof, which specifically binds to human CD70, wherein the monoclonal antibody or antigen binding fragment thereof comprises: a heavy chain variable (VH) domain comprising HCDR3, 9 2, and HCDR1 regions, and a light chain variable (VL) domain comprising LCDR3, LCDR2, and LCDR1 regions, wherein the HCDR3 region comprises the amino acid sequence set forth in SEQ ID NO:50 (DAGYSNHVPIFDS);
the HCDR2 region comprises the amino acid sequence set forth in SEQ ID NO:27 (DINNEGGTTYYADSVKG);
the HCDR1 region comprises the amino acid sequence set forth in SEQ ID NO: 11 (VYYMN);
the LCDR3 region comprises the amino acid sequence set forth in SEQ ID NO: 160 (ALFISNPSVE);
the LCDR2 region comprises the amino acid sequence set forth in SEQ ID NO: 119 (NTNTRHS); and
the LCDR1 region comprises the amino acid sequence set forth in SEQ ID NO: 250 (GLKSGSVTSDNFPT).

10. The method of claim 9, wherein the heavy chain variable (VH) domain and the light chain variable (VL) domain are derived from a camelid species.

11. The method of claim 10, wherein the VH and VL domains are derived from llama (Lama glama).

12. The method of claim 9, wherein the monoclonal antibody is a chimeric antibody, wherein the chimeric antibody comprises a constant domain derived from a human immunoglobulin.

13. The method of claim 12, wherein the constant domain is derived from a human immunoglobulin selected from the group consisting of IgG1, IgG2, IgG3, and IgG4.

14. The method of claim 13, wherein the constant domain is derived from human IgG1.

15. The method of claim 14, wherein the constant domain derived from human IgG1 is non-fucosylated.

16. The method of claim 9, wherein the monoclonal antibody or antigen binding fragment thereof is capable of directing immune effector function against a cell expressing human CD70 on its surface, wherein the immune effector function is selected from the group consisting of antibody-dependent cellular cytotoxicity (ADCC), complement-dependent cytotoxicity (CDC), antibody-dependent cellular phagocytosis (ADCP), and any combination thereof.

17. A method of treating acute myeloid leukemia in a human patient, comprising administering to a human patient in need thereof a therapeutically effective amount of a monoclonal antibody, or antigen binding fragment thereof, which specifically binds to human CD70, wherein the monoclonal antibody or antigen binding fragment thereof comprises:

a heavy chain variable domain comprising the amino acid sequence set forth as SEQ ID NO:223, and a light chain variable domain comprising the amino acid sequence set forth as SEQ ID NO:241.

18. The method of claim 17, wherein the monoclonal antibody is a chimeric antibody, wherein the chimeric antibody comprises a constant domain derived from a human immunoglobulin.

19. The method of claim 18, wherein the constant domain is derived from a human immunoglobulin selected from the group consisting of IgG1, IgG2, IgG3, and IgG4.

20. The method of claim 19, wherein the constant domain is derived from human IgG1.

21. The method of claim 20 wherein the constant domain derived from human IgG1 is non-fucosylated.

22. The method of claim 17, wherein the monoclonal antibody or antigen binding fragment thereof is capable of directing immune effector function against a cell expressing human CD70 on its surface, wherein the immune effector function is selected from the group consisting of antibody-dependent cellular cytotoxicity (ADCC), complement-dependent cytotoxicity (CDC), antibody-dependent cellular phagocytosis (ADCP), and any combination thereof.

23. A method of treating a CD70-expressing cancer in a human patient, comprising administering to a human patient in need thereof a therapeutically effective amount of a monoclonal antibody, or antigen binding fragment thereof, which specifically binds to human CD70, wherein the monoclonal antibody or antigen binding fragment thereof comprises: a heavy chain variable (VH) domain comprising HCDR3, HCDR2, and HCDR1 regions, and a light chain variable (VL) domain comprising LCDR3, LCDR2, and LCDR1 regions, wherein the HCDR3 region comprises the amino acid sequence set forth in SEQ ID NO:50 (DAGYSNHVPIFDS);
the HCDR2 region comprises the amino acid sequence set forth in SEQ ID NO:27 (DINNEGGTTYYADSVKG);
the HCDR1 region comprises the amino acid sequence set forth in SEQ ID NO:11 (VYYMN);
the LCDR3 region comprises the amino acid sequence set forth in SEQ ID NO:160 (ALFISNPSVE);
the LCDR2 region comprises the amino acid sequence set forth in SEQ ID NO:119 (NTNTRHS); and
the LCDR1 region comprises the amino acid sequence set forth in SEQ ID NO:250 (GLKSGSVTSDNFPT),
wherein the cancer is selected from the group consisting of Burkitt lymphoma, large B cell lymphoma, Hodgkin lymphoma, non-Hodgkin lymphoma, mantle cell lymphoma, chronic lymphocytic leukemia, pancreatic carcinoma, glioblastoma, and lung carcinoma.

24. The method of claim 23, wherein the cancer is selected from the group consisting of Burkitt lymphoma, Hodgkin lymphoma, non-Hodgkin lymphoma, mantle cell lymphoma, and pancreatic carcinoma.

25. The method of claim 24, wherein the cancer is selected from the group consisting of: Burkitt lymphoma, Hodgkin lymphoma, non-Hodgkin lymphoma, and mantle cell lymphoma.

26. The method of claim 24, wherein the cancer is pancreatic carcinoma.

27. A method of treating a CD70-expressing cancer in a human patient, comprising administering to a human patient in need thereof a therapeutically effective amount of a monoclonal antibody, or antigen binding fragment thereof, which specifically binds to human CD70, wherein the monoclonal antibody or antigen binding fragment thereof comprises: a heavy chain variable (VH) domain comprising HCDR3, HCDR2, and HCDR1 regions, and a light chain variable (VL) domain comprising LCDR3, LCDR2, and LCDR1 regions, wherein the HCDR3 region comprises the amino acid sequence set forth in SEQ ID NO:50 (DAGYSNHVPIFDS),
the HCDR2 region comprises the amino acid sequence set forth in SEQ ID NO:27 (DINNEGGTTYYADSVKG);
the HCDR1 region comprises the amino acid sequence set forth in SEQ ID NO:11 (VYYMN);
the LCDR3 region comprises the amino acid sequence set forth in SEQ ID NO:160 (ALFISNPSVE);
the LCDR2 region comprises the amino acid sequence set forth in SEQ ID NO:119 (NTNTRHS), and
the LCDR1 region comprises the amino acid sequence set forth in SEQ ID NO:250 (GLKSGSVTSDNFPT),
wherein the cancer is ovarian cancer.

28. A method of treating a CD70-expressing cancer in a human patient, comprising administering to a human patient in need thereof a therapeutically effective amount of a monoclonal antibody, or antigen binding fragment thereof, which specifically binds to human CD70, wherein the monoclonal antibody or antigen binding fragment thereof comprises: a heavy chain variable (VH) domain comprising HCDR3, HCDR2, and HCDR1 regions, and a light chain variable (VL) domain comprising LCDR3, LCDR2, and LCDR1 regions, wherein
   the HCDR3 region comprises the amino acid sequence set forth in SEQ ID NO:50 (DAGYSNHVPIFDS),
   the HCDR2 region comprises the amino acid sequence set forth in SEQ ID NO:27 (DINNEGGTTYYADSVKG);
   the HCDR1 region comprises the amino acid sequence set forth in SEQ ID NO:11 (VYYMN);
   the LCDR3 region comprises the amino acid sequence set forth in SEQ ID NO:160 (ALFISNPSVE);
   the LCDR2 region comprises the amino acid sequence set forth in SEQ ID NO:119 (NTNTRHS), and
   the LCDR1 region comprises the amino acid sequence set forth in SEQ ID NO:250 (GLKSGSVTSDNFPT),
   wherein the cancer is a leukemia selected from the group consisting of acute myeloid leukemia, chronic myeloid leukemia, acute lymphoblastic leukemia, and chronic lymphocytic leukemia.

29. A method of treating a CD70-expressing cancer in a human patient, comprising administering to a human patient in need thereof a therapeutically effective amount of a monoclonal antibody, or antigen binding fragment thereof, which specifically binds to human CD70, wherein the monoclonal antibody or antigen binding fragment thereof comprises: a heavy chain variable (VH) domain comprising HCDR3, HCDR2, and HCDR1 regions, and a light chain variable (VL) domain comprising LCDR3, LCDR2, and LCDR1 regions, wherein
   the HCDR3 region comprises the amino acid sequence set forth in SEQ ID NO:50 (DAGYSNHVPIFDS),
   the HCDR2 region comprises the amino acid sequence set forth in SEQ ID NO:27 (DINNEGGTTYYADSVKG);
   the HCDR1 region comprises the amino acid sequence set forth in SEQ ID NO:11 (VYYMN);
   the LCDR3 region comprises the amino acid sequence set forth in SEQ ID NO:160 (ALFISNPSVE);
   the LCDR2 region comprises the amino acid sequence set forth in SEQ ID NO:119 (NTNTRHS), and
   the LCDR1 region comprises the amino acid sequence set forth in SEQ ID NO:250 (GLKSGSVTSDNFPT),
   wherein the cancer is a lymphoma selected from the group consisting of Hodgkin lymphoma, non-Hodgkin lymphoma, lymphocytic lymphoma, primary central nervous system (CNS) lymphoma, and T-cell lymphoma.

30. A method of treating a CD70-expressing cancer in a human patient, comprising administering to a human patient in need thereof a therapeutically effective amount of a monoclonal antibody, or antigen binding fragment thereof, which specifically binds to human CD70, wherein the monoclonal antibody or antigen binding fragment thereof comprises: a heavy chain variable (VH) domain comprising HCDR3, HCDR2, and HCDR1 regions, and a light chain variable (VL) domain comprising LCDR3, LCDR2, and LCDR1 regions, wherein
   the HCDR3 region comprises the amino acid sequence set forth in SEQ ID NO:50 (DAGYSNHVPIFDS),
   the HCDR2 region comprises the amino acid sequence set forth in SEQ ID NO:27 (DINNEGGTTYYADSVKG);
   the HCDR1 region comprises the amino acid sequence set forth in SEQ ID NO:11 (VYYMN);
   the LCDR3 region comprises the amino acid sequence set forth in SEQ ID NO:160 (ALFISNPSVE);
   the LCDR2 region comprises the amino acid sequence set forth in SEQ ID NO:119 (NTNTRHS), and
   the LCDR1 region comprises the amino acid sequence set forth in SEQ ID NO:250 (GLKSGSVTSDNFPT),
   wherein the cancer is a melanoma selected from the group consisting of melanoma, metastatic malignant melanoma, cutaneous malignant melanoma, and intraocular malignant melanoma.

31. A method of treating a CD70-expressing cancer in a human patient, comprising administering to a human patient in need thereof a therapeutically effective amount of a monoclonal antibody, or antigen binding fragment thereof, which specifically binds to human CD70, wherein the monoclonal antibody or antigen binding fragment thereof comprises: a heavy chain variable (VH) domain comprising HCDR3, HCDR2, and HCDR1 regions, and a light chain variable (VL) domain comprising LCDR3, LCDR2, and LCDR1 regions, wherein
   the HCDR3 region comprises the amino acid sequence set forth in SEQ ID NO:50 (DAGYSNHVPIFDS),
   the HCDR2 region comprises the amino acid sequence set forth in SEQ ID NO:27 (DINNEGGTTYYADSVKG);
   the HCDR1 region comprises the amino acid sequence set forth in SEQ ID NO:11 (VYYMN);
   the LCDR3 region comprises the amino acid sequence set forth in SEQ ID NO:160 (ALFISNPSVE);
   the LCDR2 region comprises the amino acid sequence set forth in SEQ ID NO:119 (NTNTRHS), and
   the LCDR1 region comprises the amino acid sequence set forth in SEQ ID NO:250 (GLKSGSVTSDNFPT),
   wherein the cancer is selected from the group consisting of renal cell carcinomas (RCC), clear cell RCC, glioblastoma, brain tumors, nasopharyngeal carcinomas, non-Hodgkin lymphoma (NHL), acute lymphocytic leukemia (ALL), chronic lymphocytic leukemia (CLL), Burkitt lymphoma, anaplastic large-cell lymphomas (ALCL), multiple myeloma, cutaneous T-cell lymphomas, nodular small cleaved-cell lymphomas, lymphocytic lymphomas, peripheral T-cell lymphomas, Lennert's lymphomas, immunoblastic lymphomas, T-cell leukemia/lymphomas (ATLL), adult T-cell leukemia (T-ALL), centroblastic/centrocytic (cb/cc) follicular lymphomas, diffuse large cell lymphomas of B lineage, angioimmunoblastic lymphadenopathy (AILD)-like T-cell lymphoma, HIV-associated body cavity-based lymphomas, undifferentiated carcinomas of the rhinopharynx, mantle cell lymphoma, and other B-cell lymphomas.

32. The method of claim 1, wherein the monoclonal antibody or antigen binding fragment thereof comprises a heavy chain variable domain comprising the amino acid sequence set forth as SEQ ID NO:223, and a light chain variable domain comprising the amino acid sequence set forth as SEQ ID NO:241.

33. The method of claim 9, wherein the monoclonal antibody or antigen binding fragment thereof comprises a heavy chain variable domain comprising the amino acid sequence set forth as SEQ ID NO:223, and a light chain variable domain comprising the amino acid sequence set forth as SEQ ID NO:241.

34. The method of claim 23, wherein the monoclonal antibody or antigen binding fragment thereof comprises a heavy chain variable domain comprising the amino acid sequence set forth as SEQ ID NO:223, and a light chain variable domain comprising the amino acid sequence set forth as SEQ ID NO:241.

35. The method of claim 27, wherein the monoclonal antibody or antigen binding fragment thereof comprises a heavy chain variable domain comprising the amino acid sequence set forth as SEQ ID NO:223, and a light chain variable domain comprising the amino acid sequence set forth as SEQ ID NO:241.

36. The method of claim 28, wherein the monoclonal antibody or antigen binding fragment thereof comprises a heavy chain variable domain comprising the amino acid sequence set forth as SEQ ID NO:223, and a light chain variable domain comprising the amino acid sequence set forth as SEQ ID NO:241.

37. The method of claim 29, wherein the monoclonal antibody or antigen binding fragment thereof comprises a heavy chain variable domain comprising the amino acid sequence set forth as SEQ ID NO:223, and a light chain variable domain comprising the amino acid sequence set forth as SEQ ID NO:241.

38. The method of claim 30, wherein the monoclonal antibody or antigen binding fragment thereof comprises a heavy chain variable domain comprising the amino acid sequence set forth as SEQ ID NO:223, and a light chain variable domain comprising the amino acid sequence set forth as SEQ ID NO:241.

39. The method of claim 31, wherein the monoclonal antibody or antigen binding fragment thereof comprises a heavy chain variable domain comprising the amino acid sequence set forth as SEQ ID NO:223, and a light chain variable domain comprising the amino acid sequence set forth as SEQ ID NO:241.

\* \* \* \* \*

UNITED STATES PATENT AND TRADEMARK OFFICE
CERTIFICATE OF CORRECTION

| | |
|---|---|
| PATENT NO. | : 11,072,665 B2 |
| APPLICATION NO. | : 14/626038 |
| DATED | : July 27, 2021 |
| INVENTOR(S) | : Silence et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 884 days.

Signed and Sealed this
Twenty-ninth Day of November, 2022

Katherine Kelly Vidal
*Director of the United States Patent and Trademark Office*

SEQUENCE LISTING

<160> NUMBER OF SEQ ID NOS: 351

<210> SEQ ID NO 1
<211> LENGTH: 30
<212> TYPE: PRT
<213> ORGANISM: Llama glama

<400> SEQUENCE: 1

Glu Leu Gln Val Val Glu Ser Gly Gly Gly Leu Val Gln Pro Gly Gly
1               5                   10                  15

Ser Leu Arg Leu Ser Cys Ala Ala Ser Gly Phe Thr Leu Ser
            20                  25                  30

<210> SEQ ID NO 2

```
<211> LENGTH: 30
<212> TYPE: PRT
<213> ORGANISM: Llama glama

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 3
<211> LENGTH: 30
<212> TYPE: PRT
<213> ORGANISM: Llama glama

<400> SEQUENCE: 3

Glu Val Gln Leu Gln Glu Ser Gly Gly Gly Val Val Gln Pro Gly Gly
1               5                   10                  15

Ser Leu Arg Leu Ser Cys Ala Ala Ser Gly Phe Thr Phe Asp
            20                  25                  30

<210> SEQ ID NO 4
<211> LENGTH: 30
<212> TYPE: PRT
<213> ORGANISM: Llama glama

<400> SEQUENCE: 4

Glu Val Gln Val Gln Glu Ser Gly Gly Gly Leu Val His Pro Gly Gly
1               5                   10                  15

Ser Leu Lys Leu Ser Cys Ala Ala Ser Gly Phe Thr Phe Asp
            20                  25                  30

<210> SEQ ID NO 5
<211> LENGTH: 30
<212> TYPE: PRT
<213> ORGANISM: Llama glama

<400> SEQUENCE: 5

Gln Val Gln Leu Val Glu Ser Gly Gly Asp Leu Val Gln Pro Gly Gly
1               5                   10                  15

Ser Leu Arg Leu Ser Cys Ala Ala Ser Gly Phe Thr Val Ser
            20                  25                  30

<210> SEQ ID NO 6
<211> LENGTH: 30
<212> TYPE: PRT
<213> ORGANISM: Llama glama

<400> SEQUENCE: 6

Glu Val Gln Leu Val Gln Pro Gly Ala Glu Leu Arg Lys Pro Gly Ala
1               5                   10                  15

Ser Val Lys Val Ser Cys Lys Ala Ser Gly Tyr Thr Phe Thr
            20                  25                  30

<210> SEQ ID NO 7
<211> LENGTH: 30
<212> TYPE: PRT
<213> ORGANISM: Llama glama

<400> SEQUENCE: 7

Gln Val Gln Leu Gln Glu Ser Gly Pro Gly Leu Val Lys Pro Ser Gln
1               5                   10                  15
```

```
Thr Leu Ser Leu Ala Cys Thr Val Ser Gly Gly Ser Ile Thr
            20                  25                  30

<210> SEQ ID NO 8
<211> LENGTH: 30
<212> TYPE: PRT
<213> ORGANISM: Llama glama

<400> SEQUENCE: 8

Gln Val Gln Leu Val Glu Ser Gly Gly Gly Leu Met Gln Pro Gly Gly
1               5                   10                  15

Ser Leu Arg Leu Ser Cys Ala Ala Ser Gly Phe Thr Phe Ser
            20                  25                  30

<210> SEQ ID NO 9
<211> LENGTH: 30
<212> TYPE: PRT
<213> ORGANISM: Llama glama

<400> SEQUENCE: 9

Gln Leu Gln Val Val Glu Ser Gly Gly Gly Leu Met Gln Pro Gly Gly
1               5                   10                  15

Ser Leu Arg Leu Ser Cys Ala Ala Ser Gly Phe Thr Phe Ser
            20                  25                  30

<210> SEQ ID NO 10
<211> LENGTH: 5
<212> TYPE: PRT
<213> ORGANISM: Llama glama

<400> SEQUENCE: 10

Asn Tyr Trp Met His
1               5

<210> SEQ ID NO 11
<211> LENGTH: 5
<212> TYPE: PRT
<213> ORGANISM: Llama glama

<400> SEQUENCE: 11

Val Tyr Tyr Met Asn
1               5

<210> SEQ ID NO 12
<211> LENGTH: 5
<212> TYPE: PRT
<213> ORGANISM: Llama glama

<400> SEQUENCE: 12

Asp Tyr Ala Met Ser
1               5

<210> SEQ ID NO 13
<211> LENGTH: 5
<212> TYPE: PRT
<213> ORGANISM: Llama glama

<400> SEQUENCE: 13

Thr Tyr Ala Met Ser
1               5

<210> SEQ ID NO 14
<211> LENGTH: 5
<212> TYPE: PRT
```

```
<213> ORGANISM: Llama glama

<400> SEQUENCE: 14

Asn Pro Ala Met Ser
1               5

<210> SEQ ID NO 15
<211> LENGTH: 5
<212> TYPE: PRT
<213> ORGANISM: Llama glama

<400> SEQUENCE: 15

Ser Tyr Tyr Ile Asp
1               5

<210> SEQ ID NO 16
<211> LENGTH: 7
<212> TYPE: PRT
<213> ORGANISM: Llama glama

<400> SEQUENCE: 16

Thr Ser Tyr Tyr Tyr Trp Ser
1               5

<210> SEQ ID NO 17
<211> LENGTH: 5
<212> TYPE: PRT
<213> ORGANISM: Llama glama

<400> SEQUENCE: 17

Ser Tyr Ala Met Ser
1               5

<210> SEQ ID NO 18
<211> LENGTH: 5
<212> TYPE: PRT
<213> ORGANISM: Llama glama

<400> SEQUENCE: 18

Ser Ser Ala Met Ser
1               5

<210> SEQ ID NO 19
<211> LENGTH: 5
<212> TYPE: PRT
<213> ORGANISM: Llama glama

<400> SEQUENCE: 19

Gly Ser Ala Met Ser
1               5

<210> SEQ ID NO 20
<211> LENGTH: 5
<212> TYPE: PRT
<213> ORGANISM: Llama glama

<400> SEQUENCE: 20

Ala Tyr Tyr Met Asn
1               5

<210> SEQ ID NO 21
<211> LENGTH: 14
<212> TYPE: PRT
<213> ORGANISM: Llama glama
```

```
<400> SEQUENCE: 21

Trp Val Arg Gln Ala Pro Arg Lys Gly Leu Glu Trp Val Ser
1               5                   10

<210> SEQ ID NO 22
<211> LENGTH: 14
<212> TYPE: PRT
<213> ORGANISM: Llama glama

<400> SEQUENCE: 22

Trp Val Arg Gln Ala Pro Gly Lys Gly Leu Glu Trp Val Ser
1               5                   10

<210> SEQ ID NO 23
<211> LENGTH: 14
<212> TYPE: PRT
<213> ORGANISM: Llama glama

<400> SEQUENCE: 23

Trp Val Arg Gln Ala Pro Gly Gln Gly Leu Glu Trp Met Gly
1               5                   10

<210> SEQ ID NO 24
<211> LENGTH: 14
<212> TYPE: PRT
<213> ORGANISM: Llama glama

<400> SEQUENCE: 24

Trp Ile Arg Gln Pro Pro Gly Lys Gly Leu Glu Trp Met Gly
1               5                   10

<210> SEQ ID NO 25
<211> LENGTH: 14
<212> TYPE: PRT
<213> ORGANISM: Llama glama

<400> SEQUENCE: 25

Trp Val Arg Gln Ala Pro Gly Lys Gly Leu Glu Trp Ile Ser
1               5                   10

<210> SEQ ID NO 26
<211> LENGTH: 17
<212> TYPE: PRT
<213> ORGANISM: Llama glama

<400> SEQUENCE: 26

Thr Ile Ser Thr Asp Asn Ser Arg Thr Tyr Tyr Ala Asp Ser Val Lys
1               5                   10                  15

Gly

<210> SEQ ID NO 27
<211> LENGTH: 17
<212> TYPE: PRT
<213> ORGANISM: Llama glama

<400> SEQUENCE: 27

Asp Ile Asn Asn Glu Gly Gly Thr Thr Tyr Tyr Ala Asp Ser Val Lys
1               5                   10                  15

Gly

<210> SEQ ID NO 28
<211> LENGTH: 17
<212> TYPE: PRT
```

<213> ORGANISM: Llama glama

<400> SEQUENCE: 28

Asp Ile Asn Asn Glu Gly Asp Thr Thr Tyr Tyr Ala Asp Ser Val Lys
1               5                   10                  15

Gly

<210> SEQ ID NO 29
<211> LENGTH: 17
<212> TYPE: PRT
<213> ORGANISM: Llama glama

<400> SEQUENCE: 29

Ser Ile Tyr Met Tyr Asp Ser Ser Thr Tyr Tyr Ala Asp Ser Val Lys
1               5                   10                  15

Gly

<210> SEQ ID NO 30
<211> LENGTH: 17
<212> TYPE: PRT
<213> ORGANISM: Llama glama

<400> SEQUENCE: 30

Ala Ile Ser Trp Ser Gly Gly Glu Thr Phe Tyr Ala Glu Ser Met Lys
1               5                   10                  15

Gly

<210> SEQ ID NO 31
<211> LENGTH: 17
<212> TYPE: PRT
<213> ORGANISM: Llama glama

<400> SEQUENCE: 31

Glu Ile Thr Asn Tyr Gly Tyr Asn Arg Tyr Tyr Ala Asp Ser Val Lys
1               5                   10                  15

Gly

<210> SEQ ID NO 32
<211> LENGTH: 17
<212> TYPE: PRT
<213> ORGANISM: Llama glama

<400> SEQUENCE: 32

Arg Ile Asp Pro Glu Asp Gly Gly Thr Lys Tyr Ala Gln Lys Phe Gln
1               5                   10                  15

Gly

<210> SEQ ID NO 33
<211> LENGTH: 16
<212> TYPE: PRT
<213> ORGANISM: Llama glama

<400> SEQUENCE: 33

Ala Ile Gly Ser Arg Gly Ser Thr Tyr Tyr Ser Pro Ser Leu Lys Thr
1               5                   10                  15

<210> SEQ ID NO 34
<211> LENGTH: 17
<212> TYPE: PRT
<213> ORGANISM: Llama glama

<400> SEQUENCE: 34

```
Asp Ile Asn Ser Gly Gly Ser Thr Lys Tyr Asn Asp Ser Val Lys
1               5                   10                  15

Gly

<210> SEQ ID NO 35
<211> LENGTH: 17
<212> TYPE: PRT
<213> ORGANISM: Llama glama

<400> SEQUENCE: 35

Ser Ile Tyr Ser Asp Ser Ser Tyr Thr Tyr Tyr Ala Asp Ser Val Lys
1               5                   10                  15

Ser

<210> SEQ ID NO 36
<211> LENGTH: 17
<212> TYPE: PRT
<213> ORGANISM: Llama glama

<400> SEQUENCE: 36

Ser Ile Tyr Ser His Ser Met Tyr Thr Tyr Tyr Ala Asp Ser Val Lys
1               5                   10                  15

Ser

<210> SEQ ID NO 37
<211> LENGTH: 17
<212> TYPE: PRT
<213> ORGANISM: Llama glama

<400> SEQUENCE: 37

Asp Ile Asn Asn Glu Gly Tyr Glu Thr Tyr Tyr Ala Asp Ser Val Lys
1               5                   10                  15

Gly

<210> SEQ ID NO 38
<211> LENGTH: 32
<212> TYPE: PRT
<213> ORGANISM: Llama glama

<400> SEQUENCE: 38

Arg Phe Thr Ile Ser Arg Asp His Ala Lys Asn Thr Leu Ile Leu Gln
1               5                   10                  15

Met Asn Ser Leu Lys Ser Glu Asp Thr Ala Val Tyr Tyr Cys Ile Arg
                20                  25                  30

<210> SEQ ID NO 39
<211> LENGTH: 32
<212> TYPE: PRT
<213> ORGANISM: Llama glama

<400> SEQUENCE: 39

Arg Phe Thr Ile Ser Arg Asp Asn Ala Lys Asn Thr Leu Thr Leu Gln
1               5                   10                  15

Met Asn Ser Leu Lys Pro Glu Asp Thr Ala Leu Tyr Tyr Cys Val Arg
                20                  25                  30

<210> SEQ ID NO 40
<211> LENGTH: 32
<212> TYPE: PRT
<213> ORGANISM: Llama glama
```

```
<400> SEQUENCE: 40

Arg Phe Thr Ile Ser Arg Asp Asn Ala Lys Asn Thr Leu Thr Leu Gln
1               5                   10                  15

Met Asp Ser Leu Lys Pro Glu Asp Thr Ala Leu Tyr Tyr Cys Val Arg
            20                  25                  30

<210> SEQ ID NO 41
<211> LENGTH: 32
<212> TYPE: PRT
<213> ORGANISM: Llama glama

<400> SEQUENCE: 41

Arg Phe Thr Ile Ser Thr Asp Asn Ala Lys Asn Thr Val Tyr Leu Gln
1               5                   10                  15

Met Asn Ser Leu Lys Ser Glu Asp Thr Ala Val Tyr Tyr Cys Ala Lys
            20                  25                  30

<210> SEQ ID NO 42
<211> LENGTH: 32
<212> TYPE: PRT
<213> ORGANISM: Llama glama

<400> SEQUENCE: 42

Arg Phe Thr Ile Ser Arg Asn Asn Ala Lys Asn Thr Leu Tyr Leu Gln
1               5                   10                  15

Met Asn Ser Leu Lys Ser Glu Asp Thr Ala Val Tyr Tyr Cys Ala Arg
            20                  25                  30

<210> SEQ ID NO 43
<211> LENGTH: 32
<212> TYPE: PRT
<213> ORGANISM: Llama glama

<400> SEQUENCE: 43

Arg Phe Thr Ile Ser Thr Asp Asn Ala Lys Asn Thr Leu Tyr Leu Gln
1               5                   10                  15

Met Asn Ser Leu Arg Ser Glu Asp Ser Ala Val Tyr Tyr Cys Thr Ala
            20                  25                  30

<210> SEQ ID NO 44
<211> LENGTH: 32
<212> TYPE: PRT
<213> ORGANISM: Llama glama

<400> SEQUENCE: 44

Arg Val Thr Phe Thr Ala Asp Ala Ser Thr Ser Thr Ala Tyr Val Glu
1               5                   10                  15

Leu Ser Ser Leu Arg Ser Glu Asp Thr Ala Val Tyr Tyr Cys Ala Ser
            20                  25                  30

<210> SEQ ID NO 45
<211> LENGTH: 32
<212> TYPE: PRT
<213> ORGANISM: Llama glama

<400> SEQUENCE: 45

Arg Thr Ser Ile Ser Arg Asp Thr Ser Lys Asn Gln Phe Thr Leu Gln
1               5                   10                  15

Leu Ser Ser Val Thr Pro Glu Asp Thr Ala Val Tyr Tyr Cys Ala Arg
            20                  25                  30
```

-continued

```
<210> SEQ ID NO 46
<211> LENGTH: 32
<212> TYPE: PRT
<213> ORGANISM: Llama glama

<400> SEQUENCE: 46

Arg Phe Ala Ile Ser Arg Asp Asn Ala Lys Asn Thr Leu Tyr Leu Gln
1               5                   10                  15

Met Asn Ser Leu Lys Pro Glu Asp Thr Ala Val Tyr Tyr Cys Ala Lys
            20                  25                  30

<210> SEQ ID NO 47
<211> LENGTH: 32
<212> TYPE: PRT
<213> ORGANISM: Llama glama

<400> SEQUENCE: 47

Arg Phe Thr Ile Ser Thr Asp Asn Ala Lys Asn Thr Leu Tyr Leu Gln
1               5                   10                  15

Met Asn Ser Leu Lys Pro Asp Asp Thr Ala Val Tyr Tyr Cys Ala Gly
            20                  25                  30

<210> SEQ ID NO 48
<211> LENGTH: 32
<212> TYPE: PRT
<213> ORGANISM: Llama glama

<400> SEQUENCE: 48

Arg Phe Thr Ile Ser Arg Asp Asn Ala Lys Asn Thr Leu Thr Leu Gln
1               5                   10                  15

Met Asp Ser Leu Lys Pro Glu Asp Thr Ala Arg Tyr Tyr Cys Val Arg
            20                  25                  30

<210> SEQ ID NO 49
<211> LENGTH: 6
<212> TYPE: PRT
<213> ORGANISM: Llama glama

<400> SEQUENCE: 49

Gly Ser Asp Tyr Glu His
1               5

<210> SEQ ID NO 50
<211> LENGTH: 13
<212> TYPE: PRT
<213> ORGANISM: Llama glama

<400> SEQUENCE: 50

Asp Ala Gly Tyr Ser Asn His Val Pro Ile Phe Asp Ser
1               5                   10

<210> SEQ ID NO 51
<211> LENGTH: 19
<212> TYPE: PRT
<213> ORGANISM: Llama glama

<400> SEQUENCE: 51

Asp Ile Asn Arg Ser Tyr Gly Ser Ser Trp Ser His Phe Gly Pro Ile
1               5                   10                  15

Phe Ser Ser

<210> SEQ ID NO 52
<211> LENGTH: 10
```

```
<212> TYPE: PRT
<213> ORGANISM: Llama glama

<400> SEQUENCE: 52

Gly Met Gly Leu Ala Glu Gly Leu Thr Asp
1               5                   10

<210> SEQ ID NO 53
<211> LENGTH: 10
<212> TYPE: PRT
<213> ORGANISM: Llama glama

<400> SEQUENCE: 53

Ser Leu Gly Leu Glu Tyr Gly Tyr Gly Asp
1               5                   10

<210> SEQ ID NO 54
<211> LENGTH: 7
<212> TYPE: PRT
<213> ORGANISM: Llama glama

<400> SEQUENCE: 54

Arg Arg Arg Asp Phe Asp Tyr
1               5

<210> SEQ ID NO 55
<211> LENGTH: 21
<212> TYPE: PRT
<213> ORGANISM: Llama glama

<400> SEQUENCE: 55

Val Thr Gly Glu Ile Thr Tyr Asn Ser Gly Ser Tyr Tyr Thr Leu
1               5                   10                  15

Asn Leu Phe Asp Tyr
            20

<210> SEQ ID NO 56
<211> LENGTH: 14
<212> TYPE: PRT
<213> ORGANISM: Llama glama

<400> SEQUENCE: 56

Glu Gly Gly Ser Gly Arg Tyr Trp Thr Asn Glu Tyr Asp Tyr
1               5                   10

<210> SEQ ID NO 57
<211> LENGTH: 10
<212> TYPE: PRT
<213> ORGANISM: Llama glama

<400> SEQUENCE: 57

Ser Ser Asp Tyr Glu Gly Ser Phe Ala Ser
1               5                   10

<210> SEQ ID NO 58
<211> LENGTH: 10
<212> TYPE: PRT
<213> ORGANISM: Llama glama

<400> SEQUENCE: 58

Ser Ser Asp Tyr Glu Gly Leu Phe Val Ser
1               5                   10

<210> SEQ ID NO 59
```

```
<211> LENGTH: 13
<212> TYPE: PRT
<213> ORGANISM: Llama glama

<400> SEQUENCE: 59

Asp Ala Gly Tyr Ser Asn His Val Gln Ile Phe Asp Ser
1               5                   10

<210> SEQ ID NO 60
<211> LENGTH: 11
<212> TYPE: PRT
<213> ORGANISM: Llama glama

<400> SEQUENCE: 60

Trp Gly Gln Gly Thr Gln Val Thr Val Ser Ser
1               5                   10

<210> SEQ ID NO 61
<211> LENGTH: 11
<212> TYPE: PRT
<213> ORGANISM: Llama glama

<400> SEQUENCE: 61

Trp Gly Gln Gly Thr Gln Val Ile Val Ala Ser
1               5                   10

<210> SEQ ID NO 62
<211> LENGTH: 22
<212> TYPE: PRT
<213> ORGANISM: Llama glama

<400> SEQUENCE: 62

Gln Thr Val Val Thr Gln Glu Pro Ser Leu Ser Val Ser Pro Gly Gly
1               5                   10                  15

Thr Val Thr Leu Thr Cys
            20

<210> SEQ ID NO 63
<211> LENGTH: 22
<212> TYPE: PRT
<213> ORGANISM: Llama glama

<400> SEQUENCE: 63

Gln Ala Val Val Thr Gln Glu Pro Ser Leu Ser Val Ser Pro Gly Gly
1               5                   10                  15

Thr Val Thr Leu Thr Cys
            20

<210> SEQ ID NO 64
<211> LENGTH: 22
<212> TYPE: PRT
<213> ORGANISM: Llama glama

<400> SEQUENCE: 64

Gln Ala Val Val Thr His Pro Pro Ser Leu Ser Ala Ser Pro Gly Ser
1               5                   10                  15

Ser Val Arg Leu Thr Cys
            20

<210> SEQ ID NO 65
<211> LENGTH: 22
<212> TYPE: PRT
<213> ORGANISM: Llama glama
```

```
<400> SEQUENCE: 65

Gln Ser Ala Leu Thr Gln Pro Pro Ser Val Ser Gly Thr Leu Gly Lys
1               5                   10                  15

Thr Leu Thr Ile Ser Cys
            20

<210> SEQ ID NO 66
<211> LENGTH: 22
<212> TYPE: PRT
<213> ORGANISM: Llama glama

<400> SEQUENCE: 66

Gln Ser Ala Leu Thr Gln Pro Ser Ala Val Ser Val Ser Leu Gly Gln
1               5                   10                  15

Thr Ala Arg Ile Thr Cys
            20

<210> SEQ ID NO 67
<211> LENGTH: 22
<212> TYPE: PRT
<213> ORGANISM: Llama glama

<400> SEQUENCE: 67

Gln Ser Val Leu Thr Gln Pro Pro Ser Leu Ser Ala Ser Pro Gly Ser
1               5                   10                  15

Ser Val Arg Leu Thr Cys
            20

<210> SEQ ID NO 68
<211> LENGTH: 22
<212> TYPE: PRT
<213> ORGANISM: Llama glama

<400> SEQUENCE: 68

Gln Ser Ala Leu Thr Gln Pro Ser Ala Leu Ser Val Thr Leu Gly Gln
1               5                   10                  15

Thr Ala Lys Ile Thr Cys
            20

<210> SEQ ID NO 69
<211> LENGTH: 22
<212> TYPE: PRT
<213> ORGANISM: Llama glama

<400> SEQUENCE: 69

Gln Ser Val Val Thr Gln Pro Pro Ser Leu Ser Ala Ser Pro Gly Ser
1               5                   10                  15

Ser Val Arg Leu Thr Cys
            20

<210> SEQ ID NO 70
<211> LENGTH: 22
<212> TYPE: PRT
<213> ORGANISM: Llama glama

<400> SEQUENCE: 70

Gln Ala Val Leu Thr Gln Pro Pro Ser Leu Ser Ala Ser Pro Gly Ser
1               5                   10                  15

Ser Val Arg Leu Thr Cys
            20
```

```
<210> SEQ ID NO 71
<211> LENGTH: 22
<212> TYPE: PRT
<213> ORGANISM: Llama glama

<400> SEQUENCE: 71

Gln Ala Val Val Thr Gln Glu Pro Ser Leu Thr Val Ser Pro Gly Gly
1               5                   10                  15

Thr Val Thr Leu Thr Cys
            20

<210> SEQ ID NO 72
<211> LENGTH: 22
<212> TYPE: PRT
<213> ORGANISM: Llama glama

<400> SEQUENCE: 72

Gln Ser Ala Leu Thr Gln Pro Ser Thr Val Ser Val Ser Leu Gly Gln
1               5                   10                  15

Thr Ala Arg Ile Thr Cys
            20

<210> SEQ ID NO 73
<211> LENGTH: 22
<212> TYPE: PRT
<213> ORGANISM: Llama glama

<400> SEQUENCE: 73

Gln Pro Val Leu Thr Gln Pro Ser Ala Val Ser Val Ser Leu Gly Gln
1               5                   10                  15

Thr Ala Arg Ile Thr Cys
            20

<210> SEQ ID NO 74
<211> LENGTH: 22
<212> TYPE: PRT
<213> ORGANISM: Llama glama

<400> SEQUENCE: 74

Asn Phe Met Leu Thr Gln Pro Ser Ala Val Ser Val Ser Leu Gly Gln
1               5                   10                  15

Thr Ala Arg Ile Thr Cys
            20

<210> SEQ ID NO 75
<211> LENGTH: 22
<212> TYPE: PRT
<213> ORGANISM: Llama glama

<400> SEQUENCE: 75

Gln Ala Val Leu Thr Gln Pro Ser Ser Val Ser Val Ser Leu Gly Gln
1               5                   10                  15

Thr Ala Lys Ile Thr Cys
            20

<210> SEQ ID NO 76
<211> LENGTH: 22
<212> TYPE: PRT
<213> ORGANISM: Llama glama

<400> SEQUENCE: 76

Gln Ala Val Leu Thr Gln Pro Ser Ser Val Ser Val Ser Leu Gly Gln
1               5                   10                  15
```

Thr Ala Asn Ile Thr Cys
            20

<210> SEQ ID NO 77
<211> LENGTH: 14
<212> TYPE: PRT
<213> ORGANISM: Llama glama

<400> SEQUENCE: 77

Gly Leu Ser Ser Gly Ser Val Thr Thr Thr Asn Tyr Pro Gly
1               5                   10

<210> SEQ ID NO 78
<211> LENGTH: 14
<212> TYPE: PRT
<213> ORGANISM: Llama glama

<400> SEQUENCE: 78

Gly Leu Ser Ser Gly Ser Val Thr Ser Ser His Tyr Pro Gly
1               5                   10

<210> SEQ ID NO 79
<211> LENGTH: 14
<212> TYPE: PRT
<213> ORGANISM: Llama glama

<400> SEQUENCE: 79

Gly Leu Ser Ser Gly Ser Val Thr Ser Ser Asn Tyr Pro Gly
1               5                   10

<210> SEQ ID NO 80
<211> LENGTH: 14
<212> TYPE: PRT
<213> ORGANISM: Llama glama

<400> SEQUENCE: 80

Gly Leu Thr Ser Gly Ser Val Thr Ser Ser Asn Tyr Pro Asp
1               5                   10

<210> SEQ ID NO 81
<211> LENGTH: 14
<212> TYPE: PRT
<213> ORGANISM: Llama glama

<400> SEQUENCE: 81

Thr Leu Ile Ser Gly Asp Asn Ile Gly Gly Tyr Asp Ile Ser
1               5                   10

<210> SEQ ID NO 82
<211> LENGTH: 14
<212> TYPE: PRT
<213> ORGANISM: Llama glama

<400> SEQUENCE: 82

Ala Gly Thr Ser Ser Asp Val Gly Tyr Gly Asn Tyr Val Ser
1               5                   10

<210> SEQ ID NO 83
<211> LENGTH: 11
<212> TYPE: PRT
<213> ORGANISM: Llama glama

<400> SEQUENCE: 83

Gln Gly Gly Asn Ala Arg Phe Ser Ser Phe Ala

```
1               5                   10
```

<210> SEQ ID NO 84
<211> LENGTH: 14
<212> TYPE: PRT
<213> ORGANISM: Llama glama

<400> SEQUENCE: 84

```
Thr Leu Ser Ser Gly Asn Ser Val Gly Asn Tyr Asp Ile Ser
1               5                   10
```

<210> SEQ ID NO 85
<211> LENGTH: 11
<212> TYPE: PRT
<213> ORGANISM: Llama glama

<400> SEQUENCE: 85

```
Gln Gly Gly Arg Leu Gly Ser Ser Tyr Ala His
1               5                   10
```

<210> SEQ ID NO 86
<211> LENGTH: 14
<212> TYPE: PRT
<213> ORGANISM: Llama glama

<400> SEQUENCE: 86

```
Thr Leu Asn Ser Ala Asn Ser Val Gly Ser Tyr Asp Ile Ser
1               5                   10
```

<210> SEQ ID NO 87
<211> LENGTH: 14
<212> TYPE: PRT
<213> ORGANISM: Llama glama

<400> SEQUENCE: 87

```
Gly Leu Lys Ser Gly Ser Val Thr Ser Thr Asn Phe Pro Thr
1               5                   10
```

<210> SEQ ID NO 88
<211> LENGTH: 14
<212> TYPE: PRT
<213> ORGANISM: Llama glama

<400> SEQUENCE: 88

```
Gly Leu Thr Ser Gly Ser Val Thr Ser Asp Asn Phe Pro Val
1               5                   10
```

<210> SEQ ID NO 89
<211> LENGTH: 11
<212> TYPE: PRT
<213> ORGANISM: Llama glama

<400> SEQUENCE: 89

```
Arg Gly Asp Ser Leu Glu Arg Tyr Gly Thr Asn
1               5                   10
```

<210> SEQ ID NO 90
<211> LENGTH: 11
<212> TYPE: PRT
<213> ORGANISM: Llama glama

<400> SEQUENCE: 90

```
Arg Gly Asp Thr Leu Arg Asn Tyr His Ala Asn
1               5                   10
```

<210> SEQ ID NO 91
<211> LENGTH: 7
<212> TYPE: PRT
<213> ORGANISM: Llama glama

<400> SEQUENCE: 91

Gln Gly Gly Tyr Tyr Thr His
1               5

<210> SEQ ID NO 92
<211> LENGTH: 11
<212> TYPE: PRT
<213> ORGANISM: Llama glama

<400> SEQUENCE: 92

Gln Gly Gly Asn Leu Gly Leu Tyr Gly Ala Asn
1               5                   10

<210> SEQ ID NO 93
<211> LENGTH: 11
<212> TYPE: PRT
<213> ORGANISM: Llama glama

<400> SEQUENCE: 93

Gln Gly Gly Asn Leu Trp Leu Tyr Gly Ala Asn
1               5                   10

<210> SEQ ID NO 94
<211> LENGTH: 14
<212> TYPE: PRT
<213> ORGANISM: Llama glama

<400> SEQUENCE: 94

Gly Leu Ser Ser Gly Ser Ala Thr Ser Gly Asn Tyr Pro Glu
1               5                   10

<210> SEQ ID NO 95
<211> LENGTH: 14
<212> TYPE: PRT
<213> ORGANISM: Llama glama

<400> SEQUENCE: 95

Gly Leu Ser Ser Gly Ser Val Thr Ser Ser Asn Tyr Pro Asp
1               5                   10

<210> SEQ ID NO 96
<211> LENGTH: 15
<212> TYPE: PRT
<213> ORGANISM: Llama glama

<400> SEQUENCE: 96

Trp Phe Gln Gln Thr Pro Gly Gln Ala Pro Arg Thr Leu Ile Tyr
1               5                   10                  15

<210> SEQ ID NO 97
<211> LENGTH: 15
<212> TYPE: PRT
<213> ORGANISM: Llama glama

<400> SEQUENCE: 97

Trp Tyr Gln Gln Thr Pro Gly Gln Ala Pro Arg Leu Leu Ile Phe
1               5                   10                  15

<210> SEQ ID NO 98

```
<211> LENGTH: 15
<212> TYPE: PRT
<213> ORGANISM: Llama glama

<400> SEQUENCE: 98

Trp Tyr Gln Gln Thr Pro Gly Gln Ala Pro Arg Val Leu Ile Tyr
1               5                   10                  15

<210> SEQ ID NO 99
<211> LENGTH: 15
<212> TYPE: PRT
<213> ORGANISM: Llama glama

<400> SEQUENCE: 99

Trp Tyr Gln Gln Thr Pro Gly Gln Ala Pro Arg Leu Leu Ile Tyr
1               5                   10                  15

<210> SEQ ID NO 100
<211> LENGTH: 15
<212> TYPE: PRT
<213> ORGANISM: Llama glama

<400> SEQUENCE: 100

Trp Tyr Gln Gln Lys Thr Gly Ser Pro Arg Tyr Leu Leu Tyr
1               5                   10                  15

<210> SEQ ID NO 101
<211> LENGTH: 15
<212> TYPE: PRT
<213> ORGANISM: Llama glama

<400> SEQUENCE: 101

Trp Tyr Gln Gln Leu Pro Gly Thr Ala Pro Lys Leu Leu Ile Tyr
1               5                   10                  15

<210> SEQ ID NO 102
<211> LENGTH: 15
<212> TYPE: PRT
<213> ORGANISM: Llama glama

<400> SEQUENCE: 102

Trp Tyr Gln Gln Lys Pro Gly Gln Ala Pro Val Gln Val Ile Tyr
1               5                   10                  15

<210> SEQ ID NO 103
<211> LENGTH: 15
<212> TYPE: PRT
<213> ORGANISM: Llama glama

<400> SEQUENCE: 103

Trp Tyr Gln Gln Lys Ala Gly Ser Pro Arg Tyr Leu Leu Tyr
1               5                   10                  15

<210> SEQ ID NO 104
<211> LENGTH: 15
<212> TYPE: PRT
<213> ORGANISM: Llama glama

<400> SEQUENCE: 104

Trp Tyr Gln Gln Lys Pro Gly Gln Ala Pro Val Leu Val Ile Tyr
1               5                   10                  15

<210> SEQ ID NO 105
<211> LENGTH: 15
<212> TYPE: PRT
```

<213> ORGANISM: Llama glama

<400> SEQUENCE: 105

Trp Tyr Arg Gln Lys Pro Gly Gln Ala Pro Val Leu Val Ile Tyr
1               5                   10                  15

<210> SEQ ID NO 106
<211> LENGTH: 15
<212> TYPE: PRT
<213> ORGANISM: Llama glama

<400> SEQUENCE: 106

Trp Tyr Gln Gln Asn Pro Gly Arg Ala Pro Ile Leu Leu Ile Tyr
1               5                   10                  15

<210> SEQ ID NO 107
<211> LENGTH: 15
<212> TYPE: PRT
<213> ORGANISM: Llama glama

<400> SEQUENCE: 107

Trp Tyr Gln Gln Asn Pro Gly Arg Ala Pro Ile Leu Leu Phe Tyr
1               5                   10                  15

<210> SEQ ID NO 108
<211> LENGTH: 15
<212> TYPE: PRT
<213> ORGANISM: Llama glama

<400> SEQUENCE: 108

Trp Tyr Gln Gln Thr Pro Gly Gln Ala Pro Arg Leu Ile Ile Tyr
1               5                   10                  15

<210> SEQ ID NO 109
<211> LENGTH: 7
<212> TYPE: PRT
<213> ORGANISM: Llama glama

<400> SEQUENCE: 109

Ser Thr Ser Ser Arg His Ser
1               5

<210> SEQ ID NO 110
<211> LENGTH: 7
<212> TYPE: PRT
<213> ORGANISM: Llama glama

<400> SEQUENCE: 110

Asn Thr Asn Ser Arg His Ser
1               5

<210> SEQ ID NO 111
<211> LENGTH: 7
<212> TYPE: PRT
<213> ORGANISM: Llama glama

<400> SEQUENCE: 111

Asn Thr Asn Asn Arg His Ser
1               5

<210> SEQ ID NO 112
<211> LENGTH: 11
<212> TYPE: PRT
<213> ORGANISM: Llama glama

```
<400> SEQUENCE: 112

Tyr Tyr Ser Asp Ser Tyr Lys His Gln Ser Ser
1               5                   10

<210> SEQ ID NO 113
<211> LENGTH: 7
<212> TYPE: PRT
<213> ORGANISM: Llama glama

<400> SEQUENCE: 113

Arg Val Ser Thr Arg Ala Ser
1               5

<210> SEQ ID NO 114
<211> LENGTH: 7
<212> TYPE: PRT
<213> ORGANISM: Llama glama

<400> SEQUENCE: 114

Tyr Asn Thr Asn Arg Pro Ser
1               5

<210> SEQ ID NO 115
<211> LENGTH: 11
<212> TYPE: PRT
<213> ORGANISM: Llama glama

<400> SEQUENCE: 115

Tyr Tyr Ser Asp Ser Tyr Lys Asn Gln Gly Ser
1               5                   10

<210> SEQ ID NO 116
<211> LENGTH: 7
<212> TYPE: PRT
<213> ORGANISM: Llama glama

<400> SEQUENCE: 116

Gly Asn Asn Tyr Arg Pro Ser
1               5

<210> SEQ ID NO 117
<211> LENGTH: 11
<212> TYPE: PRT
<213> ORGANISM: Llama glama

<400> SEQUENCE: 117

Tyr Tyr Ser Asp Ser Val Lys His Gln Gly Ser
1               5                   10

<210> SEQ ID NO 118
<211> LENGTH: 11
<212> TYPE: PRT
<213> ORGANISM: Llama glama

<400> SEQUENCE: 118

Tyr Tyr Ser Asp Ser Leu Ser His Gln Gly Ser
1               5                   10

<210> SEQ ID NO 119
<211> LENGTH: 7
<212> TYPE: PRT
<213> ORGANISM: Llama glama

<400> SEQUENCE: 119
```

Asn Thr Asn Thr Arg His Ser
1               5

<210> SEQ ID NO 120
<211> LENGTH: 7
<212> TYPE: PRT
<213> ORGANISM: Llama glama

<400> SEQUENCE: 120

Thr Ile Asn Ser Arg His Ser
1               5

<210> SEQ ID NO 121
<211> LENGTH: 7
<212> TYPE: PRT
<213> ORGANISM: Llama glama

<400> SEQUENCE: 121

Asp Asp Asp Ser Arg Pro Ser
1               5

<210> SEQ ID NO 122
<211> LENGTH: 7
<212> TYPE: PRT
<213> ORGANISM: Llama glama

<400> SEQUENCE: 122

Gly Asp Asp Ile Arg Pro Ser
1               5

<210> SEQ ID NO 123
<211> LENGTH: 7
<212> TYPE: PRT
<213> ORGANISM: Llama glama

<400> SEQUENCE: 123

Ile Asn Asn Asn Arg Pro Ser
1               5

<210> SEQ ID NO 124
<211> LENGTH: 7
<212> TYPE: PRT
<213> ORGANISM: Llama glama

<400> SEQUENCE: 124

Val Asn Asn Asn Arg Pro Ser
1               5

<210> SEQ ID NO 125
<211> LENGTH: 7
<212> TYPE: PRT
<213> ORGANISM: Llama glama

<400> SEQUENCE: 125

Gly Asp Asn Tyr Arg Pro Leu
1               5

<210> SEQ ID NO 126
<211> LENGTH: 7
<212> TYPE: PRT
<213> ORGANISM: Llama glama

<400> SEQUENCE: 126

Gly Asp Asn Gln Arg Pro Leu
1               5

<210> SEQ ID NO 127
<211> LENGTH: 7
<212> TYPE: PRT
<213> ORGANISM: Llama glama

<400> SEQUENCE: 127

Gly Asp Asn Tyr Met Pro Leu
1               5

<210> SEQ ID NO 128
<211> LENGTH: 7
<212> TYPE: PRT
<213> ORGANISM: Llama glama

<400> SEQUENCE: 128

Asn Thr Ala Ser Arg His Ser
1               5

<210> SEQ ID NO 129
<211> LENGTH: 32
<212> TYPE: PRT
<213> ORGANISM: Llama glama

<400> SEQUENCE: 129

Gly Val Pro Ser Arg Phe Ser Gly Ser Ile Ser Gly Asn Lys Ala Ala
1               5                   10                  15

Leu Thr Ile Thr Gly Ala Gln Pro Glu Asp Glu Ala Asp Tyr Tyr Cys
            20                  25                  30

<210> SEQ ID NO 130
<211> LENGTH: 32
<212> TYPE: PRT
<213> ORGANISM: Llama glama

<400> SEQUENCE: 130

Gly Val Pro Ser Arg Tyr Ser Gly Ser Ile Ser Gly Asn Lys Ala Ala
1               5                   10                  15

Leu Thr Ile Thr Gly Ala Glu Pro Glu Asp Glu Ala Asp Tyr Tyr Cys
            20                  25                  30

<210> SEQ ID NO 131
<211> LENGTH: 32
<212> TYPE: PRT
<213> ORGANISM: Llama glama

<400> SEQUENCE: 131

Gly Val Pro Ser Arg Phe Ser Gly Ser Ile Ser Gly Asn Lys Ala Ala
1               5                   10                  15

Leu Thr Ile Thr Gly Ala Gln Pro Glu Asp Glu Ala Asp Tyr Tyr Cys
            20                  25                  30

<210> SEQ ID NO 132
<211> LENGTH: 34
<212> TYPE: PRT
<213> ORGANISM: Llama glama

<400> SEQUENCE: 132

Gly Val Pro Ser Arg Phe Ser Gly Ser Lys Asp Ala Ser Ala Asn Ala
1               5                   10                  15

Gly Leu Leu Leu Ile Ser Gly Leu Gln Ser Glu Asp Glu Ala Asp Tyr
            20                  25                  30

Tyr Cys

<210> SEQ ID NO 133
<211> LENGTH: 32
<212> TYPE: PRT
<213> ORGANISM: Llama glama

<400> SEQUENCE: 133

Gly Met Pro Asp Arg Phe Ser Gly Ser Lys Ser Gly Asn Thr Ala Ser
1               5                   10                  15

Leu Thr Ile Ser Gly Leu Gln Ser Glu Asp Glu Ala Asp Tyr Tyr Cys
            20                  25                  30

<210> SEQ ID NO 134
<211> LENGTH: 32
<212> TYPE: PRT
<213> ORGANISM: Llama glama

<400> SEQUENCE: 134

Gly Ile Pro Ala Arg Phe Ser Gly Ser Ser Ser Gly Gly Ala Ala Thr
1               5                   10                  15

Leu Thr Ile Ser Gly Ala Gln Ala Glu Asp Glu Ala Asp Tyr Tyr Cys
            20                  25                  30

<210> SEQ ID NO 135
<211> LENGTH: 34
<212> TYPE: PRT
<213> ORGANISM: Llama glama

<400> SEQUENCE: 135

Gly Val Pro Ser Arg Phe Ser Gly Ser Lys Asp Pro Ser Ala Asn Ala
1               5                   10                  15

Gly Leu Leu Leu Ile Ser Gly Leu Gln Ala Glu Asp Glu Ala Asp Tyr
            20                  25                  30

Tyr Cys

<210> SEQ ID NO 136
<211> LENGTH: 32
<212> TYPE: PRT
<213> ORGANISM: Llama glama

<400> SEQUENCE: 136

Gly Ile Pro Glu Arg Phe Ser Gly Ser Ser Ser Gly Asp Thr Ala Thr
1               5                   10                  15

Leu Thr Ile Ser Gly Ala Gln Ala Glu Asp Glu Ala Val Tyr Tyr Cys
            20                  25                  30

<210> SEQ ID NO 137
<211> LENGTH: 34
<212> TYPE: PRT
<213> ORGANISM: Llama glama

<400> SEQUENCE: 137

Gly Val Pro Ser Arg Phe Ser Gly Ser Ser Asp Ala Ser Ala Asn Ala
1               5                   10                  15

Gly Leu Leu Leu Ile Ser Gly Leu Gln Pro Glu Asp Glu Ala Asp Tyr
            20                  25                  30

Tyr Cys

<210> SEQ ID NO 138
<211> LENGTH: 34

<212> TYPE: PRT
<213> ORGANISM: Llama glama

<400> SEQUENCE: 138

Gly Val Pro Ser Arg Phe Ser Gly Ser Thr Asp Ala Ser Ala Asn Ala
1               5                   10                  15

Gly Leu Leu Leu Ile Ser Gly Leu Gln Pro Glu Asp Glu Ala Asp Tyr
            20                  25                  30

Tyr Cys

<210> SEQ ID NO 139
<211> LENGTH: 32
<212> TYPE: PRT
<213> ORGANISM: Llama glama

<400> SEQUENCE: 139

Gly Val Pro Ser Arg Phe Ser Gly Ser Ile Ser Glu Asn Lys Ala Ala
1               5                   10                  15

Leu Thr Ile Thr Gly Ala Gln Pro Glu Asp Glu Ala Glu Tyr Phe Cys
            20                  25                  30

<210> SEQ ID NO 140
<211> LENGTH: 32
<212> TYPE: PRT
<213> ORGANISM: Llama glama

<400> SEQUENCE: 140

Gly Val Pro Ser Arg Phe Ser Gly Ser Ile Thr Gly Asn Lys Ala Ile
1               5                   10                  15

Leu Thr Ile Thr Gly Ala Gln Pro Glu Asp Glu Ala Asp Tyr Tyr Cys
            20                  25                  30

<210> SEQ ID NO 141
<211> LENGTH: 32
<212> TYPE: PRT
<213> ORGANISM: Llama glama

<400> SEQUENCE: 141

Gly Ile Pro Glu Arg Phe Ser Gly Ser Ser Ser Gly Ala Thr Ala Ala
1               5                   10                  15

Leu Thr Ile Ser Gly Ala Gln Ala Glu Asp Glu Gly Asp Tyr Tyr Cys
            20                  25                  30

<210> SEQ ID NO 142
<211> LENGTH: 32
<212> TYPE: PRT
<213> ORGANISM: Llama glama

<400> SEQUENCE: 142

Gly Ile Pro Glu Arg Phe Ser Gly Ser Arg Leu Gly Gly Thr Ala Thr
1               5                   10                  15

Leu Thr Val Ser Gly Ala Gln Ala Glu Asp Glu Ala Asp Tyr Tyr Cys
            20                  25                  30

<210> SEQ ID NO 143
<211> LENGTH: 32
<212> TYPE: PRT
<213> ORGANISM: Llama glama

<400> SEQUENCE: 143

Gly Ile Pro Glu Arg Phe Ser Gly Ser Ile Ser Gly Asn Thr Ala Thr
1               5                   10                  15

Leu Thr Ile Ser Gly Ala Gln Val Glu Asp Glu Ala Asp Tyr Tyr Cys
            20                  25                  30

<210> SEQ ID NO 144
<211> LENGTH: 32
<212> TYPE: PRT
<213> ORGANISM: Llama glama

<400> SEQUENCE: 144

Gly Ile Pro Glu Arg Phe Ser Gly Ser Ser Gly Asn Thr Ala Thr
1               5                   10                  15

Leu Thr Ile Ser Gly Ala Gln Ala Glu Asp Glu Ala Ala Tyr Tyr Cys
            20                  25                  30

<210> SEQ ID NO 145
<211> LENGTH: 32
<212> TYPE: PRT
<213> ORGANISM: Llama glama

<400> SEQUENCE: 145

Gly Ile Pro Glu Arg Phe Thr Ile Ser Lys Ser Gly Gly Thr Ala Thr
1               5                   10                  15

Leu Thr Ile Asp Gly Ala Gln Ala Glu Asp Glu Ser Asp Tyr Tyr Cys
            20                  25                  30

<210> SEQ ID NO 146
<211> LENGTH: 32
<212> TYPE: PRT
<213> ORGANISM: Llama glama

<400> SEQUENCE: 146

Gly Ile Pro Glu Arg Phe Thr Ile Ser Lys Ser Gly Gly Thr Ala Thr
1               5                   10                  15

Leu Thr Ile Asp Gly Ala Gln Ala Glu Asn Glu Ser Asp Tyr Tyr Cys
            20                  25                  30

<210> SEQ ID NO 147
<211> LENGTH: 32
<212> TYPE: PRT
<213> ORGANISM: Llama glama

<400> SEQUENCE: 147

Gly Val Pro Gly Arg Phe Ser Gly Ser Ile Ser Gly Asn Lys Ala Ala
1               5                   10                  15

Leu Thr Ile Thr Gly Ala Gln Pro Glu Asp Glu Ala Asp Tyr Tyr Cys
            20                  25                  30

<210> SEQ ID NO 148
<211> LENGTH: 11
<212> TYPE: PRT
<213> ORGANISM: Llama glama

<400> SEQUENCE: 148

Ala Leu Glu Glu Ile Gly Ser Tyr Thr Tyr Met
1               5                   10

<210> SEQ ID NO 149
<211> LENGTH: 11
<212> TYPE: PRT
<213> ORGANISM: Llama glama

<400> SEQUENCE: 149

```
Ala Leu Leu Asn Ile Asp Asp Gly Ser Thr Met
1               5                  10

<210> SEQ ID NO 150
<211> LENGTH: 10
<212> TYPE: PRT
<213> ORGANISM: Llama glama

<400> SEQUENCE: 150

Asn Leu His Leu Gly Ser Tyr Thr Pro Met
1               5                  10

<210> SEQ ID NO 151
<211> LENGTH: 12
<212> TYPE: PRT
<213> ORGANISM: Llama glama

<400> SEQUENCE: 151

Ala Leu Tyr Trp Gly Tyr Gly Thr Asn Val Asp Val
1               5                  10

<210> SEQ ID NO 152
<211> LENGTH: 11
<212> TYPE: PRT
<213> ORGANISM: Llama glama

<400> SEQUENCE: 152

Asn Leu Tyr Met Gly Ser Gly Gly Ser Lys Val
1               5                  10

<210> SEQ ID NO 153
<211> LENGTH: 12
<212> TYPE: PRT
<213> ORGANISM: Llama glama

<400> SEQUENCE: 153

Ser Ala Tyr Lys Ser Gly Ser Tyr Lys Ala Pro Val
1               5                  10

<210> SEQ ID NO 154
<211> LENGTH: 10
<212> TYPE: PRT
<213> ORGANISM: Llama glama

<400> SEQUENCE: 154

Ala Ser Tyr Thr Thr Asn Asn Lys Pro Val
1               5                  10

<210> SEQ ID NO 155
<211> LENGTH: 9
<212> TYPE: PRT
<213> ORGANISM: Llama glama

<400> SEQUENCE: 155

Gln Ser Tyr Glu Ser Gly Asn Tyr Val
1               5

<210> SEQ ID NO 156
<211> LENGTH: 11
<212> TYPE: PRT
<213> ORGANISM: Llama glama

<400> SEQUENCE: 156

Ser Val Ser Asn Ser Gly Thr Tyr Lys Pro Val
1               5                  10
```

```
<210> SEQ ID NO 157
<211> LENGTH: 10
<212> TYPE: PRT
<213> ORGANISM: Llama glama

<400> SEQUENCE: 157

Gln Ser Gly Ser Ser Asn Thr Asn Val Met
1               5                   10

<210> SEQ ID NO 158
<211> LENGTH: 9
<212> TYPE: PRT
<213> ORGANISM: Llama glama

<400> SEQUENCE: 158

Ser Ala Tyr Lys Ser Gly Ser His Val
1               5

<210> SEQ ID NO 159
<211> LENGTH: 9
<212> TYPE: PRT
<213> ORGANISM: Llama glama

<400> SEQUENCE: 159

Ser Ala Tyr Asn Arg Gly Ser His Val
1               5

<210> SEQ ID NO 160
<211> LENGTH: 10
<212> TYPE: PRT
<213> ORGANISM: Llama glama

<400> SEQUENCE: 160

Ala Leu Phe Ile Ser Asn Pro Ser Val Glu
1               5                   10

<210> SEQ ID NO 161
<211> LENGTH: 10
<212> TYPE: PRT
<213> ORGANISM: Llama glama

<400> SEQUENCE: 161

Ala Leu Tyr Leu Glu Asn Phe Ala Asn Glu
1               5                   10

<210> SEQ ID NO 162
<211> LENGTH: 10
<212> TYPE: PRT
<213> ORGANISM: Llama glama

<400> SEQUENCE: 162

Gln Ser Ala Asp Ser Ser Gly Asn Ala Val
1               5                   10

<210> SEQ ID NO 163
<211> LENGTH: 11
<212> TYPE: PRT
<213> ORGANISM: Llama glama

<400> SEQUENCE: 163

Gln Ser Ser Asp Ser Ser Gly Tyr Arg Val Val
1               5                   10
```

```
<210> SEQ ID NO 164
<211> LENGTH: 10
<212> TYPE: PRT
<213> ORGANISM: Llama glama

<400> SEQUENCE: 164

Gln Ser Gly Ser Ser Thr Ile Pro Val
1               5                   10

<210> SEQ ID NO 165
<211> LENGTH: 10
<212> TYPE: PRT
<213> ORGANISM: Llama glama

<400> SEQUENCE: 165

Gln Ser Ala Asp Tyr Ser Gly Asn Ser Val
1               5                   10

<210> SEQ ID NO 166
<211> LENGTH: 10
<212> TYPE: PRT
<213> ORGANISM: Llama glama

<400> SEQUENCE: 166

Gln Ser Ala Asp Tyr Ser Gly Asn Ser Val
1               5                   10

<210> SEQ ID NO 167
<211> LENGTH: 10
<212> TYPE: PRT
<213> ORGANISM: Llama glama

<400> SEQUENCE: 167

Gln Ser Ser Asp Tyr Pro Gly Asn Ser Val
1               5                   10

<210> SEQ ID NO 168
<211> LENGTH: 12
<212> TYPE: PRT
<213> ORGANISM: Llama glama

<400> SEQUENCE: 168

Leu Leu Tyr Met Gly Gly Ser Asp Phe Asn Phe Val
1               5                   10

<210> SEQ ID NO 169
<211> LENGTH: 11
<212> TYPE: PRT
<213> ORGANISM: Llama glama

<400> SEQUENCE: 169

Phe Gly Gly Gly Thr His Leu Thr Val Leu Gly
1               5                   10

<210> SEQ ID NO 170
<211> LENGTH: 11
<212> TYPE: PRT
<213> ORGANISM: Llama glama

<400> SEQUENCE: 170

Phe Gly Gly Gly Thr Lys Leu Thr Val Leu Gly
1               5                   10

<210> SEQ ID NO 171
<211> LENGTH: 11
```

```
<212> TYPE: PRT
<213> ORGANISM: Llama glama

<400> SEQUENCE: 171

Phe Gly Gly Gly Thr Thr Leu Thr Val Leu Gly
1               5                   10

<210> SEQ ID NO 172
<211> LENGTH: 11
<212> TYPE: PRT
<213> ORGANISM: Llama glama

<400> SEQUENCE: 172

Phe Gly Gly Gly Ser Lys Leu Thr Val Leu Gly
1               5                   10

<210> SEQ ID NO 173
<211> LENGTH: 11
<212> TYPE: PRT
<213> ORGANISM: Llama glama

<400> SEQUENCE: 173

Phe Gly Gly Gly Thr His Leu Thr Val Leu Ser
1               5                   10

<210> SEQ ID NO 174
<211> LENGTH: 11
<212> TYPE: PRT
<213> ORGANISM: Llama glama

<400> SEQUENCE: 174

Phe Gly Gly Gly Thr Gln Leu Thr Val Leu Ser
1               5                   10

<210> SEQ ID NO 175
<211> LENGTH: 11
<212> TYPE: PRT
<213> ORGANISM: Llama glama

<400> SEQUENCE: 175

Phe Gly Gly Gly Thr Arg Leu Thr Val Leu Gly
1               5                   10

<210> SEQ ID NO 176
<211> LENGTH: 11
<212> TYPE: PRT
<213> ORGANISM: Llama glama

<400> SEQUENCE: 176

Phe Gly Gly Gly Thr Glu Leu Thr Val Leu Gly
1               5                   10

<210> SEQ ID NO 177
<211> LENGTH: 115
<212> TYPE: PRT
<213> ORGANISM: Llama glama

<400> SEQUENCE: 177

Glu Leu Gln Val Val Glu Ser Gly Gly Gly Leu Val Gln Pro Gly Gly
1               5                   10                  15

Ser Leu Arg Leu Ser Cys Ala Ala Ser Gly Phe Thr Leu Ser Asn Tyr
            20                  25                  30

Trp Met His Trp Val Arg Gln Ala Pro Arg Lys Gly Leu Glu Trp Val
        35                  40                  45
```

```
Ser Thr Ile Ser Thr Asp Asn Ser Arg Thr Tyr Tyr Ala Asp Ser Val
        50                  55                  60

Lys Gly Arg Phe Thr Ile Ser Arg Asp His Ala Lys Asn Thr Leu Ile
 65                  70                  75                  80

Leu Gln Met Asn Ser Leu Lys Ser Glu Asp Thr Ala Val Tyr Tyr Cys
                85                  90                  95

Ile Arg Gly Ser Asp Tyr Glu His Trp Gly Gln Gly Thr Gln Val Thr
            100                 105                 110

Val Ser Ser
        115
```

<210> SEQ ID NO 178
<211> LENGTH: 122
<212> TYPE: PRT
<213> ORGANISM: Llama glama

<400> SEQUENCE: 178

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Val Tyr
                20                  25                  30

Tyr Met Asn Trp Val Arg Gln Ala Pro Gly Lys Gly Leu Glu Trp Val
                35                  40                  45

Ser Asp Ile Asn Asn Glu Gly Gly Thr Thr Tyr Tyr Ala Asp Ser Val
        50                  55                  60

Lys Gly Arg Phe Thr Ile Ser Arg Asp Asn Ala Lys Asn Thr Leu Thr
 65                  70                  75                  80

Leu Gln Met Asn Ser Leu Lys Pro Glu Asp Thr Ala Leu Tyr Tyr Cys
                85                  90                  95

Val Arg Asp Ala Gly Tyr Ser Asn His Val Pro Ile Phe Asp Ser Trp
            100                 105                 110

Gly Gln Gly Thr Gln Val Ile Val Ala Ser
            115                 120
```

<210> SEQ ID NO 179
<211> LENGTH: 122
<212> TYPE: PRT
<213> ORGANISM: Llama glama

<400> SEQUENCE: 179

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Val Tyr
                20                  25                  30

Tyr Met Asn Trp Val Arg Gln Ala Pro Gly Lys Gly Leu Glu Trp Val
                35                  40                  45

Ser Asp Ile Asn Asn Glu Gly Asp Thr Thr Tyr Tyr Ala Asp Ser Val
        50                  55                  60

Lys Gly Arg Phe Thr Ile Ser Arg Asp Asn Ala Lys Asn Thr Leu Thr
 65                  70                  75                  80

Leu Gln Met Asp Ser Leu Lys Pro Glu Asp Thr Ala Leu Tyr Tyr Cys
                85                  90                  95

Val Arg Asp Ala Gly Tyr Ser Asn His Val Pro Ile Phe Asp Ser Trp
            100                 105                 110

Gly Gln Gly Thr Gln Val Ile Val Ala Ser
            115                 120
```

<210> SEQ ID NO 180
<211> LENGTH: 128
<212> TYPE: PRT
<213> ORGANISM: Llama glama

<400> SEQUENCE: 180

Glu Val Gln Leu Gln Glu Ser Gly Gly Gly Val Val Gln Pro Gly Gly
1               5                   10                  15

Ser Leu Arg Leu Ser Cys Ala Ala Ser Gly Phe Thr Phe Asp Asp Tyr
            20                  25                  30

Ala Met Ser Trp Val Arg Gln Ala Pro Gly Lys Gly Leu Glu Trp Val
        35                  40                  45

Ser Ser Ile Tyr Met Tyr Asp Ser Ser Thr Tyr Tyr Ala Asp Ser Val
    50                  55                  60

Lys Gly Arg Phe Thr Ile Ser Thr Asp Asn Ala Lys Asn Thr Val Tyr
65                  70                  75                  80

Leu Gln Met Asn Ser Leu Lys Ser Glu Asp Thr Ala Val Tyr Tyr Cys
                85                  90                  95

Ala Lys Asp Ile Asn Arg Ser Tyr Gly Ser Ser Trp Ser His Phe Gly
            100                 105                 110

Pro Ile Phe Ser Ser Trp Gly Gln Gly Thr Gln Val Thr Val Ser Ser
        115                 120                 125

<210> SEQ ID NO 181
<211> LENGTH: 119
<212> TYPE: PRT
<213> ORGANISM: Llama glama

<400> SEQUENCE: 181

Glu Val Gln Val Gln Glu Ser Gly Gly Gly Leu Val His Pro Gly Gly
1               5                   10                  15

Ser Leu Lys Leu Ser Cys Ala Ala Ser Gly Phe Thr Phe Asp Thr Tyr
            20                  25                  30

Ala Met Ser Trp Val Arg Gln Ala Pro Gly Lys Gly Leu Glu Trp Val
        35                  40                  45

Ser Ala Ile Ser Trp Ser Gly Gly Glu Thr Phe Tyr Ala Glu Ser Met
    50                  55                  60

Lys Gly Arg Phe Thr Ile Ser Arg Asn Asn Ala Lys Asn Thr Leu Tyr
65                  70                  75                  80

Leu Gln Met Asn Ser Leu Lys Ser Glu Asp Thr Ala Val Tyr Tyr Cys
                85                  90                  95

Ala Arg Gly Met Gly Leu Ala Glu Gly Leu Thr Asp Trp Gly Gln Gly
            100                 105                 110

Thr Gln Val Thr Val Ser Ser
        115

<210> SEQ ID NO 182
<211> LENGTH: 119
<212> TYPE: PRT
<213> ORGANISM: Llama glama

<400> SEQUENCE: 182

Gln Val Gln Leu Val Glu Ser Gly Gly Asp Leu Val Gln Pro Gly Gly
1               5                   10                  15

Ser Leu Arg Leu Ser Cys Ala Ala Ser Gly Phe Thr Val Ser Asn Pro
            20                  25                  30

Ala Met Ser Trp Val Arg Gln Ala Pro Gly Lys Gly Leu Glu Trp Val
            35                  40                  45

Ser Glu Ile Thr Asn Tyr Gly Tyr Asn Arg Tyr Tyr Ala Asp Ser Val
 50                  55                  60

Lys Gly Arg Phe Thr Ile Ser Thr Asp Asn Ala Lys Asn Thr Leu Tyr
 65                  70                  75                  80

Leu Gln Met Asn Ser Leu Arg Ser Glu Asp Ser Ala Val Tyr Tyr Cys
                 85                  90                  95

Thr Ala Ser Leu Gly Leu Glu Tyr Gly Tyr Gly Asp Trp Gly Gln Gly
            100                 105                 110

Thr Gln Val Thr Val Ser Ser
            115

<210> SEQ ID NO 183
<211> LENGTH: 116
<212> TYPE: PRT
<213> ORGANISM: Llama glama

<400> SEQUENCE: 183

Glu Val Gln Leu Val Gln Pro Gly Ala Glu Leu Arg Lys Pro Gly Ala
 1               5                  10                  15

Ser Val Lys Val Ser Cys Lys Ala Ser Gly Tyr Thr Phe Thr Ser Tyr
                 20                  25                  30

Tyr Ile Asp Trp Val Arg Gln Ala Pro Gly Gln Gly Leu Glu Trp Met
            35                  40                  45

Gly Arg Ile Asp Pro Glu Asp Gly Gly Thr Lys Tyr Ala Gln Lys Phe
 50                  55                  60

Gln Gly Arg Val Thr Phe Thr Ala Asp Ala Ser Thr Ser Thr Ala Tyr
 65                  70                  75                  80

Val Glu Leu Ser Ser Leu Arg Ser Glu Asp Thr Ala Val Tyr Tyr Cys
                 85                  90                  95

Ala Ser Arg Arg Arg Asp Phe Asp Tyr Trp Gly Gln Gly Thr Gln Val
            100                 105                 110

Thr Val Ser Ser
            115

<210> SEQ ID NO 184
<211> LENGTH: 131
<212> TYPE: PRT
<213> ORGANISM: Llama glama

<400> SEQUENCE: 184

Gln Val Gln Leu Gln Glu Ser Gly Pro Gly Leu Val Lys Pro Ser Gln
 1               5                  10                  15

Thr Leu Ser Leu Ala Cys Thr Val Ser Gly Gly Ser Ile Thr Thr Ser
                 20                  25                  30

Tyr Tyr Tyr Trp Ser Trp Ile Arg Gln Pro Pro Gly Lys Gly Leu Glu
            35                  40                  45

Trp Met Gly Ala Ile Gly Ser Arg Gly Ser Thr Tyr Tyr Ser Pro Ser
 50                  55                  60

Leu Lys Thr Arg Thr Ser Ile Ser Arg Asp Thr Ser Lys Asn Gln Phe
 65                  70                  75                  80

Thr Leu Gln Leu Ser Ser Val Thr Pro Glu Asp Thr Ala Val Tyr Tyr
                 85                  90                  95

Cys Ala Arg Val Thr Gly Glu Ile Thr Tyr Asn Ser Gly Ser Tyr Tyr
            100                 105                 110

Tyr Thr Leu Asn Leu Phe Asp Tyr Trp Gly Gln Gly Thr Gln Val Thr
            115                 120                 125

Val Ser Ser
    130

<210> SEQ ID NO 185
<211> LENGTH: 123
<212> TYPE: PRT
<213> ORGANISM: Llama glama

<400> SEQUENCE: 185

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Asp Ile Asn Ser Gly Gly Gly Ser Thr Lys Tyr Asn Asp Ser Val
    50                  55                  60

Lys Gly Arg Phe Ala Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Lys Glu Gly Gly Ser Gly Arg Tyr Trp Thr Asn Gly Tyr Asp Tyr
            100                 105                 110

Trp Gly Gln Gly Thr Gln Val Thr Val Ser Ser
            115                 120

<210> SEQ ID NO 186
<211> LENGTH: 119
<212> TYPE: PRT
<213> ORGANISM: Llama glama

<400> SEQUENCE: 186

Gln Val Gln Leu Val Glu Ser Gly Gly Gly Leu Met Gln Pro Gly Gly
1               5                   10                  15

Ser Leu Arg Leu Ser Cys Ala Ala Ser Gly Phe Thr Phe Ser Ser Ser
            20                  25                  30

Ala Met Ser Trp Val Arg Gln Ala Pro Gly Lys Gly Leu Glu Trp Val
        35                  40                  45

Ser Ser Ile Tyr Ser Asp Ser Ser Tyr Thr Tyr Tyr Ala Asp Ser Val
    50                  55                  60

Lys Ser Arg Phe Thr Ile Ser Thr Asp Asn Ala Lys Asn Thr Leu Tyr
65                  70                  75                  80

Leu Gln Met Asn Ser Leu Lys Pro Asp Asp Thr Ala Val Tyr Tyr Cys
                85                  90                  95

Ala Gly Ser Ser Asp Tyr Glu Gly Ser Phe Ala Ser Trp Gly Gln Gly
            100                 105                 110

Thr Gln Val Thr Val Ser Ser
        115

<210> SEQ ID NO 187
<211> LENGTH: 119
<212> TYPE: PRT
<213> ORGANISM: Llama glama

<400> SEQUENCE: 187

Gln Leu Gln Val Val Glu Ser Gly Gly Gly Leu Met Gln Pro Gly Gly

```
1               5                   10                  15
Ser Leu Arg Leu Ser Cys Ala Ala Ser Gly Phe Thr Phe Ser Gly Ser
            20                  25                  30
Ala Met Ser Trp Val Arg Gln Ala Pro Gly Lys Gly Leu Glu Trp Val
            35                  40                  45
Ser Ser Ile Tyr Ser His Ser Met Tyr Thr Tyr Tyr Ala Asp Ser Val
            50                  55                  60
Lys Ser Arg Phe Thr Ile Ser Thr Asp Asn Ala Lys Asn Thr Leu Tyr
65                  70                  75                  80
Leu Gln Met Asn Ser Leu Lys Pro Asp Asp Thr Ala Val Tyr Tyr Cys
            85                  90                  95
Ala Ala Ser Ser Asp Tyr Glu Gly Leu Phe Val Ser Trp Gly Gln Gly
            100                 105                 110
Thr Gln Val Thr Val Ser Ser
            115
```

<210> SEQ ID NO 188
<211> LENGTH: 122
<212> TYPE: PRT
<213> ORGANISM: Llama glama

<400> SEQUENCE: 188

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Ala Tyr
            20                  25                  30
Tyr Met Asn Trp Val Arg Gln Ala Pro Gly Lys Gly Leu Glu Trp Ile
            35                  40                  45
Ser Asp Ile Asn Asn Glu Gly Tyr Glu Thr Tyr Tyr Ala Asp Ser Val
            50                  55                  60
Lys Gly Arg Phe Thr Ile Ser Arg Asp Asn Ala Lys Asn Thr Leu Thr
65                  70                  75                  80
Leu Gln Met Asp Ser Leu Lys Pro Glu Asp Thr Ala Arg Tyr Tyr Cys
            85                  90                  95
Val Arg Asp Ala Gly Tyr Ser Asn His Val Gln Ile Phe Asp Ser Trp
            100                 105                 110
Gly Gln Gly Thr Gln Val Ile Val Ala Ser
            115                 120
```

<210> SEQ ID NO 189
<211> LENGTH: 112
<212> TYPE: PRT
<213> ORGANISM: Llama glama

<400> SEQUENCE: 189

```
Gln Thr Val Val Thr Gln Glu Pro Ser Leu Ser Val Ser Pro Gly Gly
1               5                   10                  15
Thr Val Thr Leu Thr Cys Gly Leu Ser Ser Gly Ser Val Thr Thr Thr
            20                  25                  30
Asn Tyr Pro Gly Trp Phe Gln Gln Thr Pro Gly Gln Ala Pro Arg Thr
            35                  40                  45
Leu Ile Tyr Ser Thr Ser Arg His Ser Gly Val Pro Ser Arg Phe
            50                  55                  60
Ser Gly Ser Ile Ser Gly Asn Lys Ala Ala Leu Thr Ile Thr Gly Ala
65                  70                  75                  80
Gln Pro Glu Asp Glu Ala Asp Tyr Tyr Cys Ala Leu Glu Glu Ile Gly
```

```
                    85                  90                  95

Ser Tyr Thr Tyr Met Phe Gly Gly Thr His Leu Thr Val Leu Gly
            100                 105                 110

<210> SEQ ID NO 190
<211> LENGTH: 112
<212> TYPE: PRT
<213> ORGANISM: Llama glama

<400> SEQUENCE: 190

Gln Ala Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Ser Ser
            20                  25                  30

His Tyr Pro Gly Trp Tyr Gln Gln Thr Pro Gly Gln Ala Pro Arg Leu
        35                  40                  45

Leu Ile Phe Asn Thr Asn Ser Arg His Ser Gly Val Pro Ser Arg Phe
    50                  55                  60

Ser Gly Ser Ile Ser Gly Asn Lys Ala Ala Leu Thr Ile Thr Gly Ala
65                  70                  75                  80

Gln Pro Glu Asp Glu Ala Asp Tyr Tyr Cys Ala Leu Leu Asn Ile Asp
                85                  90                  95

Asp Gly Ser Thr Met Phe Gly Gly Gly Thr His Leu Thr Val Leu Gly
            100                 105                 110

<210> SEQ ID NO 191
<211> LENGTH: 111
<212> TYPE: PRT
<213> ORGANISM: Llama glama

<400> SEQUENCE: 191

Gln Thr Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Ser Ser
            20                  25                  30

Asn Tyr Pro Gly Trp Tyr Gln Gln Thr Pro Gly Gln Ala Pro Arg Val
        35                  40                  45

Leu Ile Tyr Asn Thr Asn Asn Arg His Ser Gly Val Pro Ser Arg Tyr
    50                  55                  60

Ser Gly Ser Ile Ser Gly Asn Lys Ala Ala Leu Thr Ile Thr Gly Ala
65                  70                  75                  80

Glu Pro Glu Asp Glu Ala Asp Tyr Tyr Cys Asn Leu His Leu Gly Ser
                85                  90                  95

Tyr Thr Pro Met Phe Gly Gly Gly Thr Lys Leu Thr Val Leu Gly
            100                 105                 110

<210> SEQ ID NO 192
<211> LENGTH: 113
<212> TYPE: PRT
<213> ORGANISM: Llama glama

<400> SEQUENCE: 192

Gln Ala Val Val Thr Gln Glu Pro Ser Leu Ser Val Ser Pro Gly Gly
1               5                   10                  15

Thr Val Thr Leu Thr Cys Gly Leu Thr Ser Gly Ser Val Thr Ser Ser
            20                  25                  30

Asn Tyr Pro Asp Trp Tyr Gln Gln Thr Pro Gly Gln Ala Pro Arg Leu
        35                  40                  45
```

```
Leu Ile Tyr Asn Thr Asn Ser Arg His Ser Gly Val Pro Ser Arg Phe
        50                  55                  60

Ser Gly Ser Ile Ser Gly Asn Lys Ala Ala Leu Thr Ile Thr Gly Ala
 65                  70                  75                  80

Gln Pro Glu Asp Glu Ala Asp Tyr Tyr Cys Ala Leu Tyr Trp Gly Tyr
                 85                  90                  95

Gly Thr Asn Val Asp Val Phe Gly Gly Gly Thr Lys Leu Thr Val Leu
            100                 105                 110

Gly

<210> SEQ ID NO 193
<211> LENGTH: 112
<212> TYPE: PRT
<213> ORGANISM: Llama glama

<400> SEQUENCE: 193

Gln Ala Val Val Thr Gln Glu Pro Ser Leu Ser Val Ser Pro Gly Gly
 1               5                  10                  15

Thr Val Thr Leu Thr Cys Gly Leu Thr Ser Gly Ser Val Thr Ser Ser
            20                  25                  30

Asn Tyr Pro Asp Trp Tyr Gln Gln Thr Pro Gly Gln Ala Pro Arg Leu
        35                  40                  45

Leu Ile Tyr Asn Thr Asn Ser Arg His Ser Gly Val Pro Ser Arg Phe
    50                  55                  60

Ser Gly Ser Ile Ser Gly Asn Lys Ala Ala Leu Thr Ile Thr Gly Ala
 65                  70                  75                  80

Gln Pro Glu Asp Glu Ala Asp Tyr Tyr Cys Asn Leu Tyr Met Gly Ser
                 85                  90                  95

Gly Gly Ser Lys Val Phe Gly Gly Gly Thr Lys Leu Thr Val Leu Gly
            100                 105                 110

<210> SEQ ID NO 194
<211> LENGTH: 119
<212> TYPE: PRT
<213> ORGANISM: Llama glama

<400> SEQUENCE: 194

Gln Ala Val Val Thr His Pro Pro Ser Leu Ser Ala Ser Pro Gly Ser
 1               5                  10                  15

Ser Val Arg Leu Thr Cys Thr Leu Ile Ser Gly Asp Asn Ile Gly Gly
            20                  25                  30

Tyr Asp Ile Ser Trp Tyr Gln Gln Lys Thr Gly Ser Pro Arg Tyr
        35                  40                  45

Leu Leu Tyr Tyr Tyr Ser Asp Ser Tyr Lys His Gln Ser Ser Gly Val
    50                  55                  60

Pro Ser Arg Phe Ser Gly Ser Lys Asp Ala Ser Ala Asn Ala Gly Leu
 65                  70                  75                  80

Leu Leu Ile Ser Gly Leu Gln Ser Glu Asp Glu Ala Asp Tyr Tyr Cys
                 85                  90                  95

Ser Ala Tyr Lys Ser Gly Ser Tyr Lys Ala Pro Val Phe Gly Gly Gly
            100                 105                 110

Thr His Leu Thr Val Leu Gly
        115

<210> SEQ ID NO 195
<211> LENGTH: 111
```

<212> TYPE: PRT
<213> ORGANISM: Llama glama

<400> SEQUENCE: 195

Gln Ser Ala Leu Thr Gln Pro Pro Ser Val Ser Gly Thr Leu Gly Lys
1               5                   10                  15

Thr Leu Thr Ile Ser Cys Ala Gly Thr Ser Ser Asp Val Gly Tyr Gly
            20                  25                  30

Asn Tyr Val Ser Trp Tyr Gln Gln Leu Pro Gly Thr Ala Pro Lys Leu
        35                  40                  45

Leu Ile Tyr Arg Val Ser Thr Arg Ala Ser Gly Met Pro Asp Arg Phe
    50                  55                  60

Ser Gly Ser Lys Ser Gly Asn Thr Ala Ser Leu Thr Ile Ser Gly Leu
65                  70                  75                  80

Gln Ser Glu Asp Glu Ala Asp Tyr Tyr Cys Ala Ser Tyr Thr Thr Asn
                85                  90                  95

Asn Lys Pro Val Phe Gly Gly Gly Thr His Leu Thr Val Leu Gly
            100                 105                 110

<210> SEQ ID NO 196
<211> LENGTH: 107
<212> TYPE: PRT
<213> ORGANISM: Llama glama

<400> SEQUENCE: 196

Gln Ser Ala Leu Thr Gln Pro Ser Ala Val Ser Val Ser Leu Gly Gln
1               5                   10                  15

Thr Ala Arg Ile Thr Cys Gln Gly Gly Asn Ala Arg Phe Ser Ser Phe
            20                  25                  30

Ala Trp Tyr Gln Gln Lys Pro Gly Gln Ala Pro Val Gln Val Ile Tyr
        35                  40                  45

Tyr Asn Thr Asn Arg Pro Ser Gly Ile Pro Ala Arg Phe Ser Gly Ser
    50                  55                  60

Ser Ser Gly Gly Ala Ala Thr Leu Thr Ile Ser Gly Ala Gln Ala Glu
65                  70                  75                  80

Asp Glu Ala Asp Tyr Tyr Cys Gln Ser Tyr Glu Ser Gly Asn Tyr Val
                85                  90                  95

Phe Gly Gly Gly Thr Thr Leu Thr Val Leu Gly
            100                 105

<210> SEQ ID NO 197
<211> LENGTH: 118
<212> TYPE: PRT
<213> ORGANISM: Llama glama

<400> SEQUENCE: 197

Gln Ser Val Leu Thr Gln Pro Pro Ser Leu Ser Ala Ser Pro Gly Ser
1               5                   10                  15

Ser Val Arg Leu Thr Cys Thr Leu Ser Ser Gly Asn Ser Val Gly Asn
            20                  25                  30

Tyr Asp Ile Ser Trp Tyr Gln Gln Lys Ala Gly Ser Pro Pro Arg Tyr
        35                  40                  45

Leu Leu Tyr Tyr Tyr Ser Asp Ser Tyr Lys Asn Gln Gly Ser Gly Val
    50                  55                  60

Pro Ser Arg Phe Ser Gly Ser Lys Asp Pro Ser Ala Asn Ala Gly Leu
65                  70                  75                  80

Leu Leu Ile Ser Gly Leu Gln Ala Glu Asp Glu Ala Asp Tyr Tyr Cys

```
                    85                  90                  95
Ser Val Ser Asn Ser Gly Thr Tyr Lys Pro Val Phe Gly Gly Gly Ser
                100                 105                 110
Lys Leu Thr Val Leu Gly
            115

<210> SEQ ID NO 198
<211> LENGTH: 108
<212> TYPE: PRT
<213> ORGANISM: Llama glama

<400> SEQUENCE: 198

Gln Ser Ala Leu Thr Gln Pro Ser Ala Leu Ser Val Thr Leu Gly Gln
1               5                   10                  15

Thr Ala Lys Ile Thr Cys Gln Gly Gly Arg Leu Gly Ser Ser Tyr Ala
            20                  25                  30

His Trp Tyr Gln Gln Lys Pro Gly Gln Ala Pro Val Leu Val Ile Tyr
        35                  40                  45

Gly Asn Asn Tyr Arg Pro Ser Gly Ile Pro Glu Arg Phe Ser Gly Ser
    50                  55                  60

Ser Ser Gly Asp Thr Ala Thr Leu Thr Ile Ser Gly Ala Gln Ala Glu
65                  70                  75                  80

Asp Glu Ala Val Tyr Tyr Cys Gln Ser Gly Ser Ser Asn Thr Asn Val
                85                  90                  95

Met Phe Gly Gly Gly Thr His Leu Thr Val Leu Ser
                100                 105

<210> SEQ ID NO 199
<211> LENGTH: 116
<212> TYPE: PRT
<213> ORGANISM: Llama glama

<400> SEQUENCE: 199

Gln Ser Val Val Thr Gln Pro Pro Ser Leu Ser Ala Ser Pro Gly Ser
1               5                   10                  15

Ser Val Arg Leu Thr Cys Thr Leu Ser Ser Gly Asn Ser Val Gly Asn
            20                  25                  30

Tyr Asp Ile Ser Trp Tyr Gln Gln Lys Ala Gly Ser Pro Pro Arg Tyr
        35                  40                  45

Leu Leu Tyr Tyr Tyr Ser Asp Ser Val Lys His Gln Gly Ser Gly Val
    50                  55                  60

Pro Ser Arg Phe Ser Gly Ser Ser Asp Ala Ser Ala Asn Ala Gly Leu
65                  70                  75                  80

Leu Leu Ile Ser Gly Leu Gln Pro Glu Asp Glu Ala Asp Tyr Tyr Cys
                85                  90                  95

Ser Ala Tyr Lys Ser Gly Ser His Val Phe Gly Gly Gly Thr Lys Leu
                100                 105                 110

Thr Val Leu Gly
            115

<210> SEQ ID NO 200
<211> LENGTH: 116
<212> TYPE: PRT
<213> ORGANISM: Llama glama

<400> SEQUENCE: 200

Gln Ala Val Leu Thr Gln Pro Pro Ser Leu Ser Ala Ser Pro Gly Ser
1               5                   10                  15
```

```
Ser Val Arg Leu Thr Cys Thr Leu Asn Ser Ala Asn Ser Val Gly Ser
            20                  25                  30

Tyr Asp Ile Ser Trp Tyr Gln Gln Lys Ala Gly Ser Pro Pro Arg Tyr
        35                  40                  45

Leu Leu Tyr Tyr Tyr Ser Asp Ser Leu Ser His Gln Gly Ser Gly Val
50                  55                  60

Pro Ser Arg Phe Ser Gly Ser Thr Asp Ala Ser Ala Asn Ala Gly Leu
65                  70                  75                  80

Leu Leu Ile Ser Gly Leu Gln Pro Glu Asp Glu Ala Asp Tyr Tyr Cys
                85                  90                  95

Ser Ala Tyr Asn Arg Gly Ser His Val Phe Gly Gly Gly Thr Lys Leu
            100                 105                 110

Thr Val Leu Gly
        115
```

<210> SEQ ID NO 201
<211> LENGTH: 111
<212> TYPE: PRT
<213> ORGANISM: Llama glama

<400> SEQUENCE: 201

```
Gln Ala Val Val Thr Gln Glu Pro Ser Leu Thr Val Ser Pro Gly Gly
1               5                   10                  15

Thr Val Thr Leu Thr Cys Gly Leu Lys Ser Gly Ser Val Thr Ser Thr
            20                  25                  30

Asn Phe Pro Thr Trp Tyr Gln Gln Thr Pro Gly Gln Ala Pro Arg Leu
        35                  40                  45

Leu Ile Tyr Asn Thr Asn Thr Arg His Ser Gly Val Pro Ser Arg Phe
50                  55                  60

Ser Gly Ser Ile Ser Glu Asn Lys Ala Ala Leu Thr Ile Thr Gly Ala
65                  70                  75                  80

Gln Pro Glu Asp Glu Ala Glu Tyr Phe Cys Ala Leu Phe Ile Ser Asn
                85                  90                  95

Pro Ser Val Glu Phe Gly Gly Gly Thr Gln Leu Thr Val Leu Ser
            100                 105                 110
```

<210> SEQ ID NO 202
<211> LENGTH: 111
<212> TYPE: PRT
<213> ORGANISM: Llama glama

<400> SEQUENCE: 202

```
Gln Ala Val Val Thr Gln Glu Pro Ser Leu Ser Val Ser Pro Gly Gly
1               5                   10                  15

Thr Val Thr Leu Thr Cys Gly Leu Thr Ser Gly Ser Val Thr Ser Asp
            20                  25                  30

Asn Phe Pro Val Trp Tyr Gln Gln Thr Pro Gly Gln Ala Pro Arg Leu
        35                  40                  45

Leu Ile Tyr Thr Ile Asn Ser Arg His Ser Gly Val Pro Ser Arg Phe
50                  55                  60

Ser Gly Ser Ile Thr Gly Asn Lys Ala Ile Leu Thr Ile Thr Gly Ala
65                  70                  75                  80

Gln Pro Glu Asp Glu Ala Asp Tyr Tyr Cys Ala Leu Tyr Leu Glu Asn
                85                  90                  95

Phe Ala Asn Glu Phe Gly Gly Gly Thr Arg Leu Thr Val Leu Gly
            100                 105                 110
```

```
<210> SEQ ID NO 203
<211> LENGTH: 108
<212> TYPE: PRT
<213> ORGANISM: Llama glama

<400> SEQUENCE: 203

Gln Ser Ala Leu Thr Gln Pro Ser Thr Val Ser Val Ser Leu Gly Gln
1               5                   10                  15

Thr Ala Arg Ile Thr Cys Arg Gly Asp Ser Leu Glu Arg Tyr Gly Thr
            20                  25                  30

Asn Trp Tyr Gln Gln Lys Pro Gly Gln Ala Pro Val Leu Val Ile Tyr
        35                  40                  45

Asp Asp Asp Ser Arg Pro Ser Gly Ile Pro Glu Arg Phe Ser Gly Ser
    50                  55                  60

Ser Ser Gly Ala Thr Ala Ala Leu Thr Ile Ser Gly Ala Gln Ala Glu
65                  70                  75                  80

Asp Glu Gly Asp Tyr Tyr Cys Gln Ser Ala Asp Ser Ser Gly Asn Ala
                85                  90                  95

Val Phe Gly Gly Gly Thr His Leu Thr Val Leu Gly
            100                 105

<210> SEQ ID NO 204
<211> LENGTH: 109
<212> TYPE: PRT
<213> ORGANISM: Llama glama

<400> SEQUENCE: 204

Gln Ser Ala Leu Thr Gln Pro Ser Ala Val Ser Val Ser Leu Gly Gln
1               5                   10                  15

Thr Ala Arg Ile Thr Cys Arg Gly Asp Thr Leu Arg Asn Tyr His Ala
            20                  25                  30

Asn Trp Tyr Arg Gln Lys Pro Gly Gln Ala Pro Val Leu Val Ile Tyr
        35                  40                  45

Gly Asp Asp Ile Arg Pro Ser Gly Ile Pro Glu Arg Phe Ser Gly Ser
    50                  55                  60

Arg Leu Gly Gly Thr Ala Thr Leu Thr Val Ser Gly Ala Gln Ala Glu
65                  70                  75                  80

Asp Glu Ala Asp Tyr Tyr Cys Gln Ser Ser Asp Ser Ser Gly Tyr Arg
                85                  90                  95

Val Val Phe Gly Gly Gly Thr Lys Leu Thr Val Leu Gly
            100                 105

<210> SEQ ID NO 205
<211> LENGTH: 104
<212> TYPE: PRT
<213> ORGANISM: Llama glama

<400> SEQUENCE: 205

Gln Pro Val Leu Thr Gln Pro Ser Ala Val Ser Val Ser Leu Gly Gln
1               5                   10                  15

Thr Ala Arg Ile Thr Cys Gln Gly Gly Tyr Tyr Thr His Trp Tyr Gln
            20                  25                  30

Gln Lys Pro Gly Gln Ala Pro Val Leu Val Ile Tyr Ile Asn Asn Asn
        35                  40                  45

Arg Pro Ser Gly Ile Pro Glu Arg Phe Ser Gly Ser Ile Ser Gly Asn
    50                  55                  60
```

Thr Ala Thr Leu Thr Ile Ser Gly Ala Gln Val Glu Asp Glu Ala Asp
65                  70                  75                  80

Tyr Tyr Cys Gln Ser Gly Ser Ser Ser Thr Ile Pro Val Phe Gly Gly
                85                  90                  95

Gly Thr Lys Leu Thr Val Leu Gly
            100

<210> SEQ ID NO 206
<211> LENGTH: 104
<212> TYPE: PRT
<213> ORGANISM: Llama glama

<400> SEQUENCE: 206

Asn Phe Met Leu Thr Gln Pro Ser Ala Val Ser Val Ser Leu Gly Gln
1               5                   10                  15

Thr Ala Arg Ile Thr Cys Gln Gly Gly Tyr Tyr Thr His Trp Tyr Gln
            20                  25                  30

Gln Lys Pro Gly Gln Ala Pro Val Leu Val Ile Tyr Val Asn Asn Asn
        35                  40                  45

Arg Pro Ser Gly Ile Pro Glu Arg Phe Ser Gly Ser Ser Ser Gly Asn
    50                  55                  60

Thr Ala Thr Leu Thr Ile Ser Gly Ala Gln Ala Glu Asp Glu Ala Ala
65                  70                  75                  80

Tyr Tyr Cys Gln Ser Gly Ser Ser Thr Ile Pro Val Phe Gly Gly
                85                  90                  95

Gly Thr Lys Leu Thr Val Leu Gly
            100

<210> SEQ ID NO 207
<211> LENGTH: 108
<212> TYPE: PRT
<213> ORGANISM: Llama glama

<400> SEQUENCE: 207

Gln Ala Val Leu Thr Gln Pro Ser Ser Val Ser Val Ser Leu Gly Gln
1               5                   10                  15

Thr Ala Lys Ile Thr Cys Gln Gly Gly Asn Leu Gly Leu Tyr Gly Ala
            20                  25                  30

Asn Trp Tyr Gln Gln Asn Pro Gly Arg Ala Pro Ile Leu Leu Ile Tyr
        35                  40                  45

Gly Asp Asn Tyr Arg Pro Leu Gly Ile Pro Glu Arg Phe Thr Ile Ser
    50                  55                  60

Lys Ser Gly Gly Thr Ala Thr Leu Thr Ile Asp Gly Ala Gln Ala Glu
65                  70                  75                  80

Asp Glu Ser Asp Tyr Tyr Cys Gln Ser Ala Asp Tyr Ser Gly Asn Ser
                85                  90                  95

Val Phe Gly Gly Gly Thr Lys Leu Thr Val Leu Gly
            100                 105

<210> SEQ ID NO 208
<211> LENGTH: 108
<212> TYPE: PRT
<213> ORGANISM: Llama glama

<400> SEQUENCE: 208

Gln Ala Val Leu Thr Gln Pro Ser Ser Val Ser Val Ser Leu Gly Gln
1               5                   10                  15

Thr Ala Lys Ile Thr Cys Gln Gly Gly Asn Leu Trp Leu Tyr Gly Ala

```
                 20                  25                  30

Asn Trp Tyr Gln Gln Asn Pro Gly Arg Ala Pro Ile Leu Leu Ile Tyr
            35                  40                  45

Gly Asp Asn Gln Arg Pro Leu Gly Ile Pro Glu Arg Phe Thr Ile Ser
        50                  55                  60

Lys Ser Gly Gly Thr Ala Thr Leu Thr Ile Asp Gly Ala Gln Ala Glu
 65                  70                  75                  80

Asp Glu Ser Asp Tyr Tyr Cys Gln Ser Ala Asp Tyr Ser Gly Asn Ser
                    85                  90                  95

Val Phe Gly Gly Gly Thr Lys Leu Thr Val Leu Gly
                100                 105
```

<210> SEQ ID NO 209
<211> LENGTH: 108
<212> TYPE: PRT
<213> ORGANISM: Llama glama

<400> SEQUENCE: 209

```
Gln Ala Val Leu Thr Gln Pro Ser Ser Val Ser Leu Gly Gln
 1               5                  10                  15

Thr Ala Asn Ile Thr Cys Gln Gly Gly Asn Leu Gly Leu Tyr Gly Ala
            20                  25                  30

Asn Trp Tyr Gln Gln Asn Pro Gly Arg Ala Pro Ile Leu Leu Phe Tyr
            35                  40                  45

Gly Asp Asn Tyr Met Pro Leu Gly Ile Pro Glu Arg Phe Thr Ile Ser
        50                  55                  60

Lys Ser Gly Gly Thr Ala Thr Leu Thr Ile Asp Gly Ala Gln Ala Glu
 65                  70                  75                  80

Asn Glu Ser Asp Tyr Tyr Cys Gln Ser Ser Asp Tyr Pro Gly Asn Ser
                    85                  90                  95

Val Phe Gly Gly Gly Thr Lys Leu Thr Val Leu Gly
                100                 105
```

<210> SEQ ID NO 210
<211> LENGTH: 113
<212> TYPE: PRT
<213> ORGANISM: Llama glama

<400> SEQUENCE: 210

```
Gln Ala Val Val Thr Gln Glu Pro Ser Leu Ser Val Ser Pro Gly Gly
 1               5                  10                  15

Thr Val Thr Leu Thr Cys Gly Leu Ser Ser Gly Ser Ala Thr Ser Gly
            20                  25                  30

Asn Tyr Pro Glu Trp Tyr Gln Gln Thr Pro Gly Gln Ala Pro Arg Leu
            35                  40                  45

Ile Ile Tyr Asn Thr Ala Ser Arg His Ser Gly Val Pro Gly Arg Phe
        50                  55                  60

Ser Gly Ser Ile Ser Gly Asn Lys Ala Ala Leu Thr Ile Thr Gly Ala
 65                  70                  75                  80

Gln Pro Glu Asp Glu Ala Asp Tyr Tyr Cys Leu Leu Tyr Met Gly Gly
                    85                  90                  95

Ser Asp Phe Asn Phe Val Phe Gly Gly Gly Thr Lys Leu Thr Val Leu
                100                 105                 110

Gly
```

<210> SEQ ID NO 211

```
<211> LENGTH: 113
<212> TYPE: PRT
<213> ORGANISM: Llama glama

<400> SEQUENCE: 211

Gln Ala Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Ser Ser
            20                  25                  30

Asn Tyr Pro Asp Trp Tyr Gln Gln Thr Pro Gly Gln Ala Pro Arg Leu
        35                  40                  45

Leu Ile Tyr Asn Thr Asn Ser Arg His Ser Gly Val Pro Ser Arg Phe
50                  55                  60

Ser Gly Ser Ile Ser Gly Asn Lys Ala Ala Leu Thr Ile Thr Gly Ala
65                  70                  75                  80

Gln Pro Glu Asp Glu Ala Asp Tyr Tyr Cys Ala Leu Tyr Met Gly Ser
                85                  90                  95

Gly Ser Asn Asn Val Val Phe Gly Gly Gly Thr Glu Leu Thr Val Leu
            100                 105                 110

Gly

<210> SEQ ID NO 212
<211> LENGTH: 122
<212> TYPE: PRT
<213> ORGANISM: Artificial
<220> FEATURE:
<223> OTHER INFORMATION: Germlined Antibody Sequence

<400> SEQUENCE: 212

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Val Tyr
            20                  25                  30

Tyr Met Asn Trp Val Arg Gln Ala Pro Gly Lys Gly Leu Glu Trp Val
        35                  40                  45

Ser Asp Ile Asn Asn Glu Gly Gly Thr Thr Tyr Tyr Ala Asp Ser Val
50                  55                  60

Lys Gly Arg Phe Thr Ile Ser Arg Asp Asn Ser Lys Asn Thr Leu Thr
65                  70                  75                  80

Leu Gln Met Asn Ser Leu Lys Pro Glu Asp Thr Ala Val Tyr Tyr Cys
                85                  90                  95

Val Arg Asp Ala Gly Tyr Ser Asn His Val Pro Ile Phe Asp Ser Trp
            100                 105                 110

Gly Gln Gly Thr Gln Val Ile Val Ser Ser
        115                 120

<210> SEQ ID NO 213
<211> LENGTH: 122
<212> TYPE: PRT
<213> ORGANISM: Artificial
<220> FEATURE:
<223> OTHER INFORMATION: Germlined Antibody Sequence

<400> SEQUENCE: 213

Glu Val Gln Leu Val Glu Ser Gly Gly Gly Leu Val Gln Pro Gly Gly
1               5                   10                  15

Ser Leu Arg Leu Ser Cys Ala Ser Gly Phe Thr Phe Ser Val Tyr
            20                  25                  30
```

```
Tyr Met Asn Trp Val Arg Gln Ala Pro Gly Lys Gly Leu Glu Trp Val
            35                  40                  45

Ser Asp Ile Asn Asn Glu Gly Gly Thr Thr Tyr Tyr Ala Asp Ser Val
 50                  55                  60

Lys Gly Arg Phe Thr Ile Ser Arg Asp Asn Ala Lys Asn Thr Leu Thr
 65                  70                  75                  80

Leu Gln Met Asn Ser Leu Lys Pro Glu Asp Thr Ala Val Tyr Tyr Cys
                85                  90                  95

Val Arg Asp Ala Gly Tyr Ser Asn His Val Pro Ile Phe Asp Ser Trp
            100                 105                 110

Gly Gln Gly Thr Gln Val Thr Val Ala Ser
            115                 120

<210> SEQ ID NO 214
<211> LENGTH: 122
<212> TYPE: PRT
<213> ORGANISM: Artificial
<220> FEATURE:
<223> OTHER INFORMATION: Germlined Antibody Sequence

<400> SEQUENCE: 214

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Val Tyr
            20                  25                  30

Tyr Met Asn Trp Val Arg Gln Ala Pro Gly Lys Gly Leu Glu Trp Val
            35                  40                  45

Ser Asp Ile Asn Asn Glu Gly Gly Thr Thr Tyr Tyr Ala Asp Ser Val
 50                  55                  60

Lys Gly Arg Phe Thr Ile Ser Arg Asp Asn Ala Lys Asn Thr Leu Tyr
 65                  70                  75                  80

Leu Gln Met Asn Ser Leu Lys Pro Glu Asp Thr Ala Leu Tyr Tyr Cys
                85                  90                  95

Val Arg Asp Ala Gly Tyr Ser Asn His Val Pro Ile Phe Asp Ser Trp
            100                 105                 110

Gly Gln Gly Thr Thr Val Thr Val Ser Ser
            115                 120

<210> SEQ ID NO 215
<211> LENGTH: 122
<212> TYPE: PRT
<213> ORGANISM: Artificial
<220> FEATURE:
<223> OTHER INFORMATION: Germlined Antibody Sequence

<400> SEQUENCE: 215

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Val Tyr
            20                  25                  30

Tyr Met Asn Trp Val Arg Gln Ala Pro Gly Lys Gly Leu Glu Trp Val
            35                  40                  45

Ser Asp Ile Asn Asn Glu Gly Gly Thr Thr Tyr Tyr Ala Asp Ser Val
 50                  55                  60

Lys Gly Arg Phe Thr Ile Ser Arg Asp Asn Ala Lys Asn Thr Leu Tyr
 65                  70                  75                  80

Leu Gln Met Asn Ser Leu Lys Pro Glu Asp Thr Ala Val Tyr Tyr Cys
                85                  90                  95
```

Val Arg Asp Ala Gly Tyr Ser Asn His Val Pro Ile Phe Asp Ser Trp
            100                 105                 110

Gly Gln Gly Thr Thr Val Ile Val Ser Ser
            115                 120

<210> SEQ ID NO 216
<211> LENGTH: 122
<212> TYPE: PRT
<213> ORGANISM: Artificial
<220> FEATURE:
<223> OTHER INFORMATION: Germlined Antibody Sequence

<400> SEQUENCE: 216

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Val Tyr
            20                  25                  30

Tyr Met Asn Trp Val Arg Gln Ala Pro Gly Lys Gly Leu Glu Trp Val
            35                  40                  45

Ser Asp Ile Asn Asn Glu Gly Gly Thr Thr Tyr Tyr Ala Asp Ser Val
        50                  55                  60

Lys Gly Arg Phe Thr Ile Ser Arg Asp Asn Ser Lys Asn Ser Leu Thr
65                  70                  75                  80

Leu Gln Met Asn Ser Leu Lys Pro Glu Asp Thr Ala Val Tyr Tyr Cys
            85                  90                  95

Ala Arg Asp Ala Gly Tyr Ser Asn His Val Pro Ile Phe Asp Ser Trp
            100                 105                 110

Gly Gln Gly Thr Leu Val Thr Val Ser Ser
            115                 120

<210> SEQ ID NO 217
<211> LENGTH: 122
<212> TYPE: PRT
<213> ORGANISM: Artificial
<220> FEATURE:
<223> OTHER INFORMATION: Germlined Antibody Sequence

<400> SEQUENCE: 217

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Val Tyr
            20                  25                  30

Tyr Met Asn Trp Val Arg Gln Ala Pro Gly Lys Gly Leu Glu Trp Val
            35                  40                  45

Ser Asp Ile Asn Asn Glu Gly Gly Thr Thr Tyr Tyr Ala Asp Ser Val
        50                  55                  60

Lys Gly Arg Phe Thr Ile Ser Arg Asp Asn Ser Lys Asn Ser Leu Thr
65                  70                  75                  80

Leu Gln Met Asn Ser Leu Lys Pro Glu Asp Thr Ala Val Tyr Tyr Cys
            85                  90                  95

Ala Arg Asp Ala Gly Tyr Ser Asn His Val Pro Ile Phe Asp Ser Trp
            100                 105                 110

Gly Gln Gly Thr Leu Val Thr Val Ser Ser
            115                 120

<210> SEQ ID NO 218
<211> LENGTH: 122
<212> TYPE: PRT

```
<213> ORGANISM: Artificial
<220> FEATURE:
<223> OTHER INFORMATION: Germlined Antibody Sequence

<400> SEQUENCE: 218

Glu Val Gln Leu Val Glu Ser Gly Gly Gly Leu Val Gln Pro Gly Gly
1               5                   10                  15

Ser Leu Arg Leu Ser Cys Ala Ser Ser Gly Phe Thr Phe Ser Val Tyr
            20                  25                  30

Tyr Met Asn Trp Val Arg Gln Ala Pro Gly Lys Gly Leu Glu Trp Val
        35                  40                  45

Ser Asp Ile Asn Asn Glu Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Asp Ala Gly Tyr Ser Asn His Val Pro Ile Phe Asp Ser Trp
            100                 105                 110

Gly Gln Gly Thr Thr Val Thr Val Ala Ser
        115                 120

<210> SEQ ID NO 219
<211> LENGTH: 122
<212> TYPE: PRT
<213> ORGANISM: Artificial
<220> FEATURE:
<223> OTHER INFORMATION: Germlined Antibody Sequence

<400> SEQUENCE: 219

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Val Tyr
            20                  25                  30

Tyr Met Asn Trp Val Arg Gln Ala Pro Gly Lys Gly Leu Glu Trp Val
        35                  40                  45

Ser Asp Ile Asn Asn Glu Gly Gly Thr Thr Tyr Tyr Ala Asp Ser Val
    50                  55                  60

Lys Gly Arg Phe Thr Ile Ser Arg Asp Asn Ala Lys Asn Ser Leu Thr
65                  70                  75                  80

Leu Gln Met Asn Ser Leu Arg Ala Glu Asp Thr Ala Val Tyr Tyr Cys
                85                  90                  95

Val Arg Asp Ala Gly Tyr Ser Asn His Val Pro Ile Phe Asp Ser Trp
            100                 105                 110

Gly Gln Gly Thr Gln Val Thr Val Ser Ser
        115                 120

<210> SEQ ID NO 220
<211> LENGTH: 122
<212> TYPE: PRT
<213> ORGANISM: Artificial
<220> FEATURE:
<223> OTHER INFORMATION: Germlined Antibody Sequence

<400> SEQUENCE: 220

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30
```

```
Tyr Met Asn Trp Val Arg Gln Ala Pro Gly Lys Gly Leu Glu Trp Val
        35                  40                  45

Ser Asp Ile Asn Asn Glu Gly Gly Thr Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Asp Ala Gly Tyr Ser Asn His Val Pro Ile Phe Asp Ser Trp
            100                 105                 110

Gly Gln Gly Thr Thr Val Thr Val Ala Ser
            115                 120

<210> SEQ ID NO 221
<211> LENGTH: 122
<212> TYPE: PRT
<213> ORGANISM: Artificial
<220> FEATURE:
<223> OTHER INFORMATION: Germlined Antibody Sequence

<400> SEQUENCE: 221

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Val Tyr
            20                  25                  30

Tyr Met Asn Trp Val Arg Gln Ala Pro Gly Lys Gly Leu Glu Trp Val
        35                  40                  45

Ser Asp Ile Asn Asn Glu Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Asp Ala Gly Tyr Ser Asn His Val Pro Ile Phe Asp Ser Trp
            100                 105                 110

Gly Gln Gly Thr Gln Val Thr Val Ser Ser
            115                 120

<210> SEQ ID NO 222
<211> LENGTH: 122
<212> TYPE: PRT
<213> ORGANISM: Artificial
<220> FEATURE:
<223> OTHER INFORMATION: Germlined Antibody Sequence

<400> SEQUENCE: 222

Glu Val Gln Leu Val Glu Ser Gly Gly Gly Leu Val Gln Pro Gly Gly
1               5                   10                  15

Ser Val Arg Leu Ser Cys Ala Ala Ser Gly Phe Thr Phe Ser Val Tyr
            20                  25                  30

Tyr Met Asn Trp Val Arg Gln Ala Pro Gly Lys Gly Leu Glu Trp Val
        35                  40                  45

Ser Asp Ile Asn Asn Glu Gly Gly Thr Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
```

85                  90                  95

Ala Arg Asp Ala Gly Tyr Ser Asn His Val Pro Ile Phe Asp Ser Trp
                100                 105                 110

Gly Gln Gly Thr Leu Val Thr Val Ala Ser
        115                 120

<210> SEQ ID NO 223
<211> LENGTH: 122
<212> TYPE: PRT
<213> ORGANISM: Artificial
<220> FEATURE:
<223> OTHER INFORMATION: Germlined Antibody Sequence

<400> SEQUENCE: 223

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Val Tyr
            20                  25                  30

Tyr Met Asn Trp Val Arg Gln Ala Pro Gly Lys Gly Leu Glu Trp Val
        35                  40                  45

Ser Asp Ile Asn Asn Glu Gly Gly Thr Thr Tyr Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Gly Tyr Ser Asn His Val Pro Ile Phe Asp Ser Trp
                100                 105                 110

Gly Gln Gly Thr Leu Val Thr Val Ser Ser
        115                 120

<210> SEQ ID NO 224
<211> LENGTH: 122
<212> TYPE: PRT
<213> ORGANISM: Artificial
<220> FEATURE:
<223> OTHER INFORMATION: Germlined Antibody Sequence

<400> SEQUENCE: 224

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Val Tyr
            20                  25                  30

Tyr Met Asn Trp Val Arg Gln Ala Pro Gly Lys Gly Leu Glu Trp Val
        35                  40                  45

Ser Asp Ile Asn Asn Glu Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Gly Tyr Ser Asn His Val Pro Ile Phe Asp Ser Trp
                100                 105                 110

Gly Gln Gly Thr Gln Val Thr Val Ala Ser
        115                 120

<210> SEQ ID NO 225
<211> LENGTH: 122

<212> TYPE: PRT
<213> ORGANISM: Artificial
<220> FEATURE:
<223> OTHER INFORMATION: Germlined Antibody Sequence

<400> SEQUENCE: 225

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Val Tyr
            20                  25                  30

Tyr Met Asn Trp Val Arg Gln Ala Pro Gly Lys Gly Leu Glu Trp Val
        35                  40                  45

Ser Asp Ile Asn Asn Glu Gly Gly Thr Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Arg Asp Ala Gly Tyr Ser Asn His Val Pro Ile Phe Asp Ser Trp
            100                 105                 110

Gly Gln Gly Thr Leu Val Thr Val Ser Ser
        115                 120

<210> SEQ ID NO 226
<211> LENGTH: 122
<212> TYPE: PRT
<213> ORGANISM: Artificial
<220> FEATURE:
<223> OTHER INFORMATION: Germlined Antibody Sequence

<400> SEQUENCE: 226

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Val Tyr
            20                  25                  30

Tyr Met Asn Trp Val Arg Gln Ala Pro Gly Lys Gly Leu Glu Trp Val
        35                  40                  45

Ser Asp Ile Asn Asn Glu Gly Gly Ala Thr Tyr Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Gly Tyr Ser Asn His Val Pro Ile Phe Asp Ser Trp
            100                 105                 110

Gly Gln Gly Thr Gln Val Thr Val Ser Ser
        115                 120

<210> SEQ ID NO 227
<211> LENGTH: 122
<212> TYPE: PRT
<213> ORGANISM: Artificial
<220> FEATURE:
<223> OTHER INFORMATION: Germlined Antibody Sequence

<400> SEQUENCE: 227

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Val Tyr

```
                    20                  25                  30

Tyr Met Asn Trp Val Arg Gln Ala Pro Gly Lys Gly Leu Glu Trp Val
            35                  40                  45

Ser Asp Ile Asn Asn Glu Gly Gly Ala Thr Tyr Tyr Ala Asp Ser Val
        50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Gly Tyr Ser Asn His Val Pro Ile Phe Asp Ser Trp
            100                 105                 110

Gly Gln Gly Thr Gln Val Thr Val Ser Ser
            115                 120

<210> SEQ ID NO 228
<211> LENGTH: 122
<212> TYPE: PRT
<213> ORGANISM: Artificial
<220> FEATURE:
<223> OTHER INFORMATION: Germlined Antibody Sequence

<400> SEQUENCE: 228

Glu Val Gln Leu Val Ala Ser Gly Gly Gly Leu Val Gln Pro Gly Gly
1               5                   10                  15

Ser Leu Arg Leu Ser Cys Ala Ala Ser Gly Phe Thr Phe Ser Val Tyr
            20                  25                  30

Tyr Met Asn Trp Val Arg Gln Ala Pro Gly Lys Gly Leu Glu Trp Val
            35                  40                  45

Ser Asp Ile Asn Asn Glu Gly Gly Thr Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Gly Tyr Ser Asn His Val Pro Ile Phe Asp Ser Trp
            100                 105                 110

Gly Gln Gly Thr Thr Val Thr Val Ser Ser
            115                 120

<210> SEQ ID NO 229
<211> LENGTH: 122
<212> TYPE: PRT
<213> ORGANISM: Artificial
<220> FEATURE:
<223> OTHER INFORMATION: Germlined Antibody Sequence

<400> SEQUENCE: 229

Glu Val Gln Leu Val Ala Ser Gly Gly Gly Leu Val Gln Pro Gly Gly
1               5                   10                  15

Ser Leu Arg Leu Ser Cys Ala Ala Ser Gly Phe Thr Phe Ser Val Tyr
            20                  25                  30

Tyr Met Asn Trp Val Arg Gln Ala Pro Gly Lys Gly Leu Glu Trp Val
            35                  40                  45

Ser Asp Ile Asn Asn Glu Gly Gly Thr Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80
```

Leu Gln Met Asn Ser Leu Arg Ala Glu Asp Thr Ala Val Tyr Tyr Cys
                85                  90                  95

Ala Arg Asp Ala Gly Tyr Ser Asn His Val Pro Ile Phe Asp Ser Trp
            100                 105                 110

Gly Gln Gly Thr Thr Val Thr Val Ser Ser
        115                 120

<210> SEQ ID NO 230
<211> LENGTH: 111
<212> TYPE: PRT
<213> ORGANISM: Artificial
<220> FEATURE:
<223> OTHER INFORMATION: Germlined Antibody Sequence

<400> SEQUENCE: 230

Gln Thr Val Val Thr Gln Glu Pro Ser Phe Ser Val Ser Pro Gly Gly
1               5                   10                  15

Thr Val Thr Leu Thr Cys Gly Leu Lys Ser Gly Ser Val Thr Ser Asp
            20                  25                  30

Asn Phe Pro Thr Trp Tyr Gln Gln Thr Pro Gly Gln Ala Pro Arg Leu
        35                  40                  45

Leu Ile Tyr Asn Thr Asn Thr Arg His Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Phe Cys Ala Leu Phe Ile Ser Asn
                85                  90                  95

Pro Ser Val Glu Phe Gly Gly Gly Thr Gln Leu Thr Val Leu Gly
            100                 105                 110

<210> SEQ ID NO 231
<211> LENGTH: 111
<212> TYPE: PRT
<213> ORGANISM: Artificial
<220> FEATURE:
<223> OTHER INFORMATION: Germlined Antibody Sequence

<400> SEQUENCE: 231

Gln Ala Val Val Thr Gln Glu Pro Ser Phe Ser Val Ser Pro Gly Gly
1               5                   10                  15

Thr Val Thr Leu Thr Cys Gly Leu Lys Ser Gly Ser Val Thr Ser Asp
            20                  25                  30

Asn Phe Pro Thr Trp Tyr Gln Gln Thr Pro Gly Gln Ala Pro Arg Leu
        35                  40                  45

Leu Ile Tyr Asn Thr Asn Thr Arg His Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Phe Cys Ala Leu Phe Ile Ser Asn
                85                  90                  95

Pro Ser Val Glu Phe Gly Gly Gly Thr Gln Leu Thr Val Leu Gly
            100                 105                 110

<210> SEQ ID NO 232
<211> LENGTH: 111
<212> TYPE: PRT
<213> ORGANISM: Artificial
<220> FEATURE:
<223> OTHER INFORMATION: Germlined Antibody Sequence -continued

<400> SEQUENCE: 232

Gln Thr Val Val Thr Gln Glu Pro Ser Leu Thr Val Ser Pro Gly Gly
1               5                   10                  15

Thr Val Thr Leu Thr Cys Gly Leu Lys Ser Gly Ser Val Thr Ser Thr
            20                  25                  30

Asn Phe Pro Thr Trp Tyr Gln Gln Thr Pro Gly Gln Ala Pro Arg Leu
        35                  40                  45

Leu Ile Tyr Asn Thr Asn Ser Arg His Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Phe Cys Ala Leu Phe Ile Ser Asn
                85                  90                  95

Pro Ser Val Glu Phe Gly Gly Gly Thr Gln Leu Thr Val Leu Gly
            100                 105                 110

<210> SEQ ID NO 233
<211> LENGTH: 111
<212> TYPE: PRT
<213> ORGANISM: Artificial
<220> FEATURE:
<223> OTHER INFORMATION: Germlined Antibody Sequence

<400> SEQUENCE: 233

Gln Thr Val Val Thr Gln Glu Pro Ser Phe Ser Val Ser Pro Gly Gly
1               5                   10                  15

Thr Val Thr Leu Thr Cys Gly Leu Thr Ser Gly Ser Val Thr Ser Thr
            20                  25                  30

Asn Phe Pro Thr Trp Tyr Gln Gln Thr Pro Gly Gln Ala Pro Arg Leu
        35                  40                  45

Leu Ile Tyr Asn Thr Asn Ser Arg His Ser Gly Val Pro Ser Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Phe Cys Ala Leu Phe Ile Ser Asn
                85                  90                  95

Pro Ser Val Glu Phe Gly Gly Gly Thr Gln Leu Thr Val Leu Gly
            100                 105                 110

<210> SEQ ID NO 234
<211> LENGTH: 111
<212> TYPE: PRT
<213> ORGANISM: Artificial
<220> FEATURE:
<223> OTHER INFORMATION: Germlined Antibody Sequence

<400> SEQUENCE: 234

Gln Ala Val Val Thr Gln Glu Pro Ser Phe Ser Val Ser Pro Gly Gly
1               5                   10                  15

Thr Val Thr Leu Thr Cys Gly Leu Lys Ser Gly Ser Val Thr Ser Asp
            20                  25                  30

Asn Phe Pro Thr Trp Tyr Gln Gln Thr Pro Gly Gln Ala Pro Arg Leu
        35                  40                  45

Leu Ile Tyr Asn Thr Asn Ser Arg His Ser Gly Val Pro Asp Arg Phe
    50                  55                  60

Ser Gly Ser Ile Leu Gly Asn Lys Ala Ala Leu Thr Ile Arg Gly Ala
65                  70                  75                  80

Gln Ala Asp Asp Glu Ala Glu Tyr Tyr Cys Ala Leu Phe Ile Ser Asn
                85                  90                  95

Pro Ser Val Glu Phe Gly Gly Gly Thr Gln Leu Thr Val Leu Gly
            100                 105                 110

<210> SEQ ID NO 235
<211> LENGTH: 111
<212> TYPE: PRT
<213> ORGANISM: Artificial
<220> FEATURE:
<223> OTHER INFORMATION: Germlined Antibody Sequence

<400> SEQUENCE: 235

Gln Thr Val Val Thr Gln Glu Pro Ser Phe Ser Val Ser Pro Gly Gly
1               5                   10                  15

Thr Val Thr Leu Thr Cys Gly Leu Lys Ser Gly Ser Val Thr Ser Asp
            20                  25                  30

Asn Phe Pro Thr Trp Tyr Gln Gln Thr Pro Gly Gln Ala Pro Arg Leu
        35                  40                  45

Leu Ile Tyr Asn Thr Asn Ser Arg His Ser Gly Val Pro Asp Arg Phe
    50                  55                  60

Ser Gly Ser Ile Leu Gly Asn Lys Ala Ala Leu Thr Ile Arg Gly Ala
65                  70                  75                  80

Gln Ala Asp Asp Glu Ala Glu Tyr Tyr Cys Ala Leu Phe Ile Ser Asn
                85                  90                  95

Pro Ser Val Glu Phe Gly Gly Gly Thr Gln Leu Thr Val Leu Gly
            100                 105                 110

<210> SEQ ID NO 236
<211> LENGTH: 111
<212> TYPE: PRT
<213> ORGANISM: Artificial
<220> FEATURE:
<223> OTHER INFORMATION: Germlined Antibody Sequence

<400> SEQUENCE: 236

Gln Thr Val Val Thr Gln Glu Pro Ser Phe Ser Val Ser Pro Gly Gly
1               5                   10                  15

Thr Val Thr Leu Thr Cys Gly Leu Thr Ser Gly Ser Val Thr Ser Asp
            20                  25                  30

Asn Phe Pro Thr Trp Tyr Gln Gln Thr Pro Gly Gln Ala Pro Arg Leu
        35                  40                  45

Leu Ile Tyr Asn Thr Asn Ser Arg His Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Pro Glu Asp Glu Ser Asp Tyr Phe Cys Ala Leu Phe Ile Ser Asn
                85                  90                  95

Pro Ser Val Glu Phe Gly Gly Gly Thr Gln Leu Thr Val Leu Gly
            100                 105                 110

<210> SEQ ID NO 237
<211> LENGTH: 111
<212> TYPE: PRT
<213> ORGANISM: Artificial
<220> FEATURE:
<223> OTHER INFORMATION: Germlined Antibody Sequence

<400> SEQUENCE: 237

Gln Ala Val Val Thr Gln Glu Pro Ser Leu Thr Val Ser Pro Gly Gly

```
                1               5                   10                  15
            Thr Val Thr Leu Thr Cys Gly Leu Lys Ser Gly Ser Val Thr Ser Asp
                            20                  25                  30

Asn Phe Pro Thr Trp Tyr Gln Gln Thr Pro Gly Gln Ala Pro Arg Leu
                        35                  40                  45

Leu Ile Tyr Asn Thr Asn Thr Arg His Ser Gly Val Pro Asp Arg Phe
                    50                  55                  60

Ser Gly Ser Ile Leu Gly Asn Lys Ala Ala Leu Thr Ile Thr Gly Ala
            65                  70                  75                  80

Gln Pro Glu Asp Glu Ser Asp Tyr Tyr Cys Ala Leu Phe Ile Ser Asn
                            85                  90                  95

Pro Ser Val Glu Phe Gly Gly Gly Thr Gln Leu Thr Val Leu Gly
                        100                 105                 110

<210> SEQ ID NO 238
<211> LENGTH: 111
<212> TYPE: PRT
<213> ORGANISM: Artificial
<220> FEATURE:
<223> OTHER INFORMATION: Germlined Antibody Sequence

<400> SEQUENCE: 238

Gln Thr Val Val Thr Gln Glu Pro Ser Leu Thr Val Ser Pro Gly Gly
            1               5                   10                  15

Thr Val Thr Leu Thr Cys Gly Val Thr Ser Gly Ser Val Thr Ser Asp
                            20                  25                  30

Asn Phe Pro Thr Trp Tyr Gln Gln Thr Pro Gly Gln Ala Pro Arg Leu
                        35                  40                  45

Leu Ile Tyr Asn Thr Asn Thr Arg His Ser Gly Val Pro Asp Arg Phe
                    50                  55                  60

Ser Gly Ser Ile Leu Gly Asn Lys Ala Ala Leu Thr Ile Thr Gly Ala
            65                  70                  75                  80

Gln Pro Glu Asp Glu Ser Asp Tyr Tyr Cys Ala Leu Phe Ile Ser Asn
                            85                  90                  95

Pro Ser Val Glu Phe Gly Gly Gly Thr Gln Leu Thr Val Leu Gly
                        100                 105                 110

<210> SEQ ID NO 239
<211> LENGTH: 111
<212> TYPE: PRT
<213> ORGANISM: Artificial
<220> FEATURE:
<223> OTHER INFORMATION: Germlined Antibody Sequence

<400> SEQUENCE: 239

Gln Ala Val Val Thr Gln Glu Pro Ser Phe Ser Val Ser Pro Gly Gly
            1               5                   10                  15

Thr Val Thr Leu Thr Cys Gly Leu Thr Ser Gly Ser Val Thr Ser Thr
                            20                  25                  30

Asn Phe Pro Thr Trp Tyr Gln Gln Thr Pro Gly Gln Ala Pro Arg Leu
                        35                  40                  45

Leu Ile Tyr Asn Thr Asn Thr Arg His Ser Gly Val Pro Ser Arg Phe
                    50                  55                  60

Ser Gly Ser Ile Leu Gly Asn Lys Ala Ala Leu Thr Ile Thr Gly Ala
            65                  70                  75                  80

Gln Ala Asp Asp Glu Ala Glu Tyr Phe Cys Ala Leu Phe Ile Ser Asn
                            85                  90                  95
```

-continued

Pro Ser Val Glu Phe Gly Gly Gly Thr Gln Leu Thr Val Leu Gly
            100                 105                 110

<210> SEQ ID NO 240
<211> LENGTH: 111
<212> TYPE: PRT
<213> ORGANISM: Artificial
<220> FEATURE:
<223> OTHER INFORMATION: Germlined Antibody Sequence

<400> SEQUENCE: 240

Gln Thr Val Val Thr Gln Glu Pro Ser Phe Ser Val Ser Pro Gly Gly
1               5                   10                  15

Thr Val Thr Leu Thr Cys Gly Leu Lys Ser Gly Ser Val Thr Ser Asp
            20                  25                  30

Asn Phe Pro Thr Trp Tyr Gln Gln Thr Pro Gly Gln Ala Pro Arg Leu
        35                  40                  45

Leu Ile Tyr Asn Thr Asn Ser Arg His Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Phe Cys Ala Leu Phe Ile Ser Asn
                85                  90                  95

Pro Ser Val Glu Phe Gly Gly Gly Thr Gln Leu Thr Val Leu Gly
            100                 105                 110

<210> SEQ ID NO 241
<211> LENGTH: 111
<212> TYPE: PRT
<213> ORGANISM: Artificial
<220> FEATURE:
<223> OTHER INFORMATION: Germlined Antibody Sequence

<400> SEQUENCE: 241

Gln Ala Val Val Thr Gln Glu Pro Ser Leu Thr Val Ser Pro Gly Gly
1               5                   10                  15

Thr Val Thr Leu Thr Cys Gly Leu Lys Ser Gly Ser Val Thr Ser Asp
            20                  25                  30

Asn Phe Pro Thr Trp Tyr Gln Gln Thr Pro Gly Gln Ala Pro Arg Leu
        35                  40                  45

Leu Ile Tyr Asn Thr Asn Thr Arg His Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ala Glu Tyr Phe Cys Ala Leu Phe Ile Ser Asn
                85                  90                  95

Pro Ser Val Glu Phe Gly Gly Gly Thr Gln Leu Thr Val Leu Gly
            100                 105                 110

<210> SEQ ID NO 242
<211> LENGTH: 111
<212> TYPE: PRT
<213> ORGANISM: Artificial
<220> FEATURE:
<223> OTHER INFORMATION: Germlined Antibody Sequence

<400> SEQUENCE: 242

Gln Ala Val Val Thr Gln Glu Pro Ser Phe Ser Val Ser Pro Gly Gly
1               5                   10                  15

Thr Val Thr Leu Thr Cys Gly Leu Thr Ser Gly Ser Val Thr Ser Thr

```
                    20                  25                  30

Asn Phe Pro Thr Trp Tyr Gln Gln Thr Pro Gly Gln Ala Pro Arg Leu
                35                  40                  45

Leu Ile Tyr Asn Thr Asn Ser Arg His Ser Gly Val Pro Asp Arg Phe
         50                  55                  60

Ser Gly Ser Ile Leu Gly Asn Lys Ala Ala Leu Thr Ile Thr Gly Ala
 65                  70                  75                  80

Gln Pro Glu Asp Glu Ser Asp Tyr Phe Cys Ala Leu Phe Ile Ser Asn
                 85                  90                  95

Pro Ser Val Glu Phe Gly Gly Gly Thr Gln Leu Thr Val Leu Gly
                100                 105                 110

<210> SEQ ID NO 243
<211> LENGTH: 111
<212> TYPE: PRT
<213> ORGANISM: Artificial
<220> FEATURE:
<223> OTHER INFORMATION: Germlined Antibody Sequence

<400> SEQUENCE: 243

Gln Thr Val Val Thr Gln Glu Pro Ser Phe Ser Val Ser Pro Gly Gly
 1               5                  10                  15

Thr Val Thr Leu Thr Cys Gly Leu Lys Ser Gly Ser Val Thr Ser Thr
                20                  25                  30

Asn Phe Pro Thr Trp Tyr Gln Gln Thr Pro Gly Gln Ala Pro Arg Leu
                35                  40                  45

Leu Ile Tyr Asn Thr Asn Ser Arg His Ser Gly Val Pro Asp Arg Phe
         50                  55                  60

Ser Gly Ser Ile Leu Gly Asn Lys Ala Ala Leu Thr Ile Thr Gly Ala
 65                  70                  75                  80

Gln Ala Asp Asp Glu Ala Asp Tyr Phe Cys Ala Leu Phe Ile Ser Asn
                 85                  90                  95

Pro Ser Val Glu Phe Gly Gly Gly Thr Gln Leu Thr Val Leu Gly
                100                 105                 110

<210> SEQ ID NO 244
<211> LENGTH: 111
<212> TYPE: PRT
<213> ORGANISM: Artificial
<220> FEATURE:
<223> OTHER INFORMATION: Germlined Antibody Sequence

<400> SEQUENCE: 244

Gln Ala Val Val Thr Gln Glu Pro Ser Phe Ser Val Ser Pro Gly Gly
 1               5                  10                  15

Thr Val Thr Leu Thr Cys Gly Leu Lys Ser Gly Ser Val Thr Ser Asp
                20                  25                  30

Asn Phe Pro Thr Trp Tyr Gln Gln Thr Pro Gly Gln Ala Pro Arg Leu
                35                  40                  45

Leu Ile Tyr Asn Thr Asn Thr Arg His Ser Gly Val Pro Asp Arg Phe
         50                  55                  60

Ser Gly Ser Ile Leu Gly Asn Lys Ala Ala Leu Thr Ile Thr Gly Ala
 65                  70                  75                  80

Gln Ala Asp Asp Glu Ala Glu Tyr Phe Cys Ala Leu Phe Ile Ser Asn
                 85                  90                  95

Pro Ser Val Glu Phe Gly Gly Gly Thr Gln Leu Thr Val Leu Gly
                100                 105                 110
```

<210> SEQ ID NO 245
<211> LENGTH: 111
<212> TYPE: PRT
<213> ORGANISM: Artificial
<220> FEATURE:
<223> OTHER INFORMATION: Germlined Antibody Sequence

<400> SEQUENCE: 245

Gln Thr Val Val Thr Gln Glu Pro Ser Phe Ser Val Ser Pro Gly Gly
1               5                   10                  15

Thr Val Thr Leu Thr Cys Gly Leu Lys Ser Gly Ser Val Thr Ser Asp
            20                  25                  30

Asn Phe Pro Thr Trp Tyr Gln Gln Thr Pro Gly Gln Ala Pro Arg Leu
        35                  40                  45

Leu Ile Tyr Asn Thr Asn Thr Arg His Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ala Glu Tyr Phe Cys Ala Leu Phe Ile Ser Asn
                85                  90                  95

Pro Ser Val Glu Phe Gly Gly Gly Thr Gln Leu Thr Val Leu Gly
            100                 105                 110

<210> SEQ ID NO 246
<211> LENGTH: 111
<212> TYPE: PRT
<213> ORGANISM: Artificial
<220> FEATURE:
<223> OTHER INFORMATION: Germlined Antibody Sequence

<400> SEQUENCE: 246

Gln Ala Val Val Thr Gln Glu Pro Ser Phe Ser Val Ser Pro Gly Gly
1               5                   10                  15

Thr Val Thr Leu Thr Cys Gly Leu Lys Ser Gly Ser Val Thr Ser Asp
            20                  25                  30

Asn Phe Pro Thr Trp Tyr Gln Gln Thr Pro Gly Gln Ala Pro Arg Leu
        35                  40                  45

Leu Ile Tyr Asn Thr Asn Thr Arg His Ser Gly Val Pro Ser Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Ala Leu Phe Ile Ser Asn
                85                  90                  95

Pro Ser Val Glu Phe Gly Gly Gly Thr Gln Leu Thr Val Leu Gly
            100                 105                 110

<210> SEQ ID NO 247
<211> LENGTH: 111
<212> TYPE: PRT
<213> ORGANISM: Artificial
<220> FEATURE:
<223> OTHER INFORMATION: Germlined Antibody Sequence

<400> SEQUENCE: 247

Gln Thr Val Val Thr Gln Glu Pro Ser Phe Ser Val Ser Pro Gly Gly
1               5                   10                  15

Thr Val Thr Leu Thr Cys Gly Leu Lys Ser Gly Ser Val Thr Ser Asp
            20                  25                  30

Asn Phe Pro Thr Trp Tyr Gln Gln Thr Pro Gly Gln Ala Pro Arg Leu

```
            35                  40                  45
Leu Ile Tyr Asn Thr Asn Thr Arg His Ser Gly Val Pro Ser Arg Phe
         50                  55                  60
Ser Gly Ser Ile Leu Gly Asn Lys Ala Ala Leu Thr Ile Thr Gly Ala
 65                  70                  75                  80
Gln Ala Asp Asp Glu Ser Asp Tyr Tyr Cys Ala Leu Phe Ile Ser Asn
                 85                  90                  95
Pro Ser Val Glu Phe Gly Gly Gly Thr Gln Leu Thr Val Leu Gly
            100                 105                 110

<210> SEQ ID NO 248
<211> LENGTH: 5
<212> TYPE: PRT
<213> ORGANISM: Artificial
<220> FEATURE:
<223> OTHER INFORMATION: Germlined Antibody Sequence

<400> SEQUENCE: 248

Gly Tyr Tyr Met Asn
1               5

<210> SEQ ID NO 249
<211> LENGTH: 17
<212> TYPE: PRT
<213> ORGANISM: Artificial
<220> FEATURE:
<223> OTHER INFORMATION: Germlined Antibody Sequence

<400> SEQUENCE: 249

Asp Ile Asn Asn Glu Gly Gly Ala Thr Tyr Tyr Ala Asp Ser Val Lys
1               5                   10                  15

Gly

<210> SEQ ID NO 250
<211> LENGTH: 14
<212> TYPE: PRT
<213> ORGANISM: Artificial
<220> FEATURE:
<223> OTHER INFORMATION: Germlined Antibody Sequence

<400> SEQUENCE: 250

Gly Leu Lys Ser Gly Ser Val Thr Ser Asp Asn Phe Pro Thr
1               5                   10

<210> SEQ ID NO 251
<211> LENGTH: 14
<212> TYPE: PRT
<213> ORGANISM: Artificial
<220> FEATURE:
<223> OTHER INFORMATION: Germlined Antibody Sequence

<400> SEQUENCE: 251

Gly Leu Thr Ser Gly Ser Val Thr Ser Thr Asn Phe Pro Thr
1               5                   10

<210> SEQ ID NO 252
<211> LENGTH: 14
<212> TYPE: PRT
<213> ORGANISM: Artificial
<220> FEATURE:
<223> OTHER INFORMATION: Germlined Antibody Sequence

<400> SEQUENCE: 252

Gly Leu Thr Ser Gly Ser Val Thr Ser Asp Asn Phe Pro Thr
```

```
                    1               5                   10

<210> SEQ ID NO 253
<211> LENGTH: 14
<212> TYPE: PRT
<213> ORGANISM: Artificial
<220> FEATURE:
<223> OTHER INFORMATION: Germlined Antibody Sequence

<400> SEQUENCE: 253

Gly Val Thr Ser Gly Ser Val Thr Ser Asp Asn Phe Pro Thr
1               5                   10

<210> SEQ ID NO 254
<211> LENGTH: 30
<212> TYPE: PRT
<213> ORGANISM: Llama glama

<400> SEQUENCE: 254

Gln Leu Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser
            20                  25                  30

<210> SEQ ID NO 255
<211> LENGTH: 30
<212> TYPE: PRT
<213> ORGANISM: Llama glama

<400> SEQUENCE: 255

Glu Val Gln Leu Val Glu Ser Gly Gly Gly Leu Val Gln Pro Gly Gly
1               5                   10                  15

Ser Leu Arg Leu Ser Cys Ala Ala Ser Glu Leu Ser Phe Ser
            20                  25                  30

<210> SEQ ID NO 256
<211> LENGTH: 5
<212> TYPE: PRT
<213> ORGANISM: Llama glama

<400> SEQUENCE: 256

His Tyr Ala Met Ser
1               5

<210> SEQ ID NO 257
<211> LENGTH: 5
<212> TYPE: PRT
<213> ORGANISM: Llama glama

<400> SEQUENCE: 257

Ile Ser Glu Met Thr
1               5

<210> SEQ ID NO 258
<211> LENGTH: 17
<212> TYPE: PRT
<213> ORGANISM: Llama glama

<400> SEQUENCE: 258

Gly Asp Asn Thr Tyr Asp Gly Gly Thr Arg Tyr Gln Asp Ser Val Lys
1               5                   10                  15

Gly
```

-continued

```
<210> SEQ ID NO 259
<211> LENGTH: 19
<212> TYPE: PRT
<213> ORGANISM: Llama glama

<400> SEQUENCE: 259

Gly Ile Ser Gly Val Thr Gly Gly Ser Ser Thr Ser Tyr Ala Asp Ser
1               5                   10                  15

Val Lys Gly

<210> SEQ ID NO 260
<211> LENGTH: 32
<212> TYPE: PRT
<213> ORGANISM: Llama glama

<400> SEQUENCE: 260

Arg Phe Thr Ile Ser Arg Asp Asn Gly Lys Asn Thr Leu Tyr Leu Gln
1               5                   10                  15

Met Asn Ser Leu Lys Pro Glu Asp Thr Ala Val Tyr Tyr Cys Ala Lys
            20                  25                  30

<210> SEQ ID NO 261
<211> LENGTH: 32
<212> TYPE: PRT
<213> ORGANISM: Llama glama

<400> SEQUENCE: 261

Arg Phe Thr Ile Ser Arg Asp Asn Asp Lys Asn Thr Leu Tyr Leu Gln
1               5                   10                  15

Met Asn Ser Leu Ile Pro Glu Asp Thr Ala Val Tyr Tyr Cys Ala Thr
            20                  25                  30

<210> SEQ ID NO 262
<211> LENGTH: 14
<212> TYPE: PRT
<213> ORGANISM: Llama glama

<400> SEQUENCE: 262

Asp Thr Gly Arg Gly Ile Met Gly Glu Tyr Gly Met Asp Tyr
1               5                   10

<210> SEQ ID NO 263
<211> LENGTH: 13
<212> TYPE: PRT
<213> ORGANISM: Llama glama

<400> SEQUENCE: 263

Thr Ser Gly Thr Tyr Tyr Phe Ile Pro Glu Tyr Glu Tyr
1               5                   10

<210> SEQ ID NO 264
<211> LENGTH: 11
<212> TYPE: PRT
<213> ORGANISM: Llama glama

<400> SEQUENCE: 264

Trp Gly Lys Gly Thr Leu Val Thr Val Ser Ser
1               5                   10

<210> SEQ ID NO 265
<211> LENGTH: 22
<212> TYPE: PRT
<213> ORGANISM: Llama glama
```

<400> SEQUENCE: 265

Gln Thr Val Val Thr Gln Glu Pro Ser Leu Ser Val Ser Pro Gly Gly
1               5                   10                  15

Thr Val Thr Leu Thr Cys
            20

<210> SEQ ID NO 266
<211> LENGTH: 22
<212> TYPE: PRT
<213> ORGANISM: Llama glama

<400> SEQUENCE: 266

Gln Ser Val Leu Thr Gln Pro Pro Ser Val Ser Gly Ser Pro Gly Lys
1               5                   10                  15

Thr Val Thr Ile Ser Cys
            20

<210> SEQ ID NO 267
<211> LENGTH: 14
<212> TYPE: PRT
<213> ORGANISM: Llama glama

<400> SEQUENCE: 267

Gly Leu Lys Ser Gly Ser Val Thr Ser Ser Asn Tyr Pro Ala
1               5                   10

<210> SEQ ID NO 268
<211> LENGTH: 14
<212> TYPE: PRT
<213> ORGANISM: Llama glama

<400> SEQUENCE: 268

Ala Gly Thr Ser Ser Asp Val Gly Tyr Gly Tyr Tyr Val Ser
1               5                   10

<210> SEQ ID NO 269
<211> LENGTH: 15
<212> TYPE: PRT
<213> ORGANISM: Llama glama

<400> SEQUENCE: 269

Trp Tyr Gln Gln Phe Pro Gly Met Ala Pro Lys Leu Leu Ile Tyr
1               5                   10                  15

<210> SEQ ID NO 270
<211> LENGTH: 7
<212> TYPE: PRT
<213> ORGANISM: Llama glama

<400> SEQUENCE: 270

Asp Val Asn Lys Arg Ala Ser
1               5

<210> SEQ ID NO 271
<211> LENGTH: 12
<212> TYPE: PRT
<213> ORGANISM: Llama glama

<400> SEQUENCE: 271

Ala Leu Tyr Met Gly Ser Gly Ser Ala Asn Ala Met
1               5                   10

<210> SEQ ID NO 272

```
<211> LENGTH: 32
<212> TYPE: PRT
<213> ORGANISM: Llama glama

<400> SEQUENCE: 272

Gly Ile Ala Asp Arg Phe Ser Gly Ser Lys Ala Gly Asn Thr Ala Ser
1               5                   10                  15

Leu Thr Ile Ser Gly Leu Gln Ser Glu Asp Glu Ala Asp Tyr Tyr Cys
            20                  25                  30

<210> SEQ ID NO 273
<211> LENGTH: 10
<212> TYPE: PRT
<213> ORGANISM: Llama glama

<400> SEQUENCE: 273

Ala Ser Tyr Arg Ser Ser Ala Asn Ala Val
1               5                   10

<210> SEQ ID NO 274
<211> LENGTH: 123
<212> TYPE: PRT
<213> ORGANISM: Artificial
<220> FEATURE:
<223> OTHER INFORMATION: Germlined antibody sequence

<400> SEQUENCE: 274

Gln Leu Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser His Tyr
            20                  25                  30

Ala Met Ser Trp Val Arg Gln Ala Pro Gly Lys Gly Leu Glu Trp Val
        35                  40                  45

Ser Gly Asp Asn Thr Tyr Asp Gly Gly Thr Arg Tyr Gln Asp Ser Val
    50                  55                  60

Lys Gly Arg Phe Thr Ile Ser Arg Asp Asn Gly Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Lys Asp Thr Gly Arg Gly Ile Met Gly Glu Tyr Gly Met Asp Tyr
            100                 105                 110

Trp Gly Lys Gly Thr Leu Val Thr Val Ser Ser
        115                 120

<210> SEQ ID NO 275
<211> LENGTH: 124
<212> TYPE: PRT
<213> ORGANISM: Artificial
<220> FEATURE:
<223> OTHER INFORMATION: Germlined antibody sequence

<400> SEQUENCE: 275

Glu Val Gln Leu Val Glu Ser Gly Gly Gly Leu Val Gln Pro Gly Gly
1               5                   10                  15

Ser Leu Arg Leu Ser Cys Ala Ala Ser Glu Leu Ser Phe Ser Ile Ser
            20                  25                  30

Glu Met Thr Trp Val Arg Gln Ala Pro Gly Lys Gly Leu Glu Trp Val
        35                  40                  45

Ser Gly Ile Ser Gly Val Thr Gly Gly Ser Ser Thr Ser Tyr Ala Asp
    50                  55                  60
```

```
Ser Val Lys Gly Arg Phe Thr Ile Ser Arg Asp Asn Asp Lys Asn Thr
 65                  70                  75                  80

Leu Tyr Leu Gln Met Asn Ser Leu Ile Pro Glu Asp Thr Ala Val Tyr
                 85                  90                  95

Tyr Cys Ala Thr Thr Ser Gly Thr Tyr Tyr Phe Ile Pro Glu Tyr Glu
            100                 105                 110

Tyr Trp Gly Gln Gly Thr Gln Val Thr Val Ser Ser
            115                 120

<210> SEQ ID NO 276
<211> LENGTH: 113
<212> TYPE: PRT
<213> ORGANISM: Artificial
<220> FEATURE:
<223> OTHER INFORMATION: Germlined antibody sequence

<400> SEQUENCE: 276

Gln Thr Val Val Thr Gln Glu Pro Ser Leu Ser Val Ser Pro Gly Gly
  1               5                  10                  15

Thr Val Thr Leu Thr Cys Gly Leu Lys Ser Gly Ser Val Thr Ser Ser
                 20                  25                  30

Asn Tyr Pro Ala Trp Tyr Gln Gln Thr Pro Gly Gln Ala Pro Arg Leu
             35                  40                  45

Leu Ile Tyr Asn Thr Asn Ser Arg His Ser Gly Val Pro Ser Arg Phe
 50                  55                  60

Ser Gly Ser Ile Ser Gly Asn Lys Ala Ala Leu Thr Ile Thr Gly Ala
 65                  70                  75                  80

Gln Pro Glu Asp Glu Ala Asp Tyr Tyr Cys Ala Leu Tyr Met Gly Ser
                 85                  90                  95

Gly Ser Ala Asn Ala Met Phe Gly Gly Gly Thr His Leu Thr Val Leu
            100                 105                 110

Gly

<210> SEQ ID NO 277
<211> LENGTH: 111
<212> TYPE: PRT
<213> ORGANISM: Artificial
<220> FEATURE:
<223> OTHER INFORMATION: Germlined antibody sequence

<400> SEQUENCE: 277

Gln Ser Val Leu Thr Gln Pro Pro Ser Val Ser Gly Ser Pro Gly Lys
  1               5                  10                  15

Thr Val Thr Ile Ser Cys Ala Gly Thr Ser Ser Asp Val Gly Tyr Gly
                 20                  25                  30

Tyr Tyr Val Ser Trp Tyr Gln Gln Phe Pro Gly Met Ala Pro Lys Leu
             35                  40                  45

Leu Ile Tyr Asp Val Asn Lys Arg Ala Ser Gly Ile Ala Asp Arg Phe
 50                  55                  60

Ser Gly Ser Lys Ala Gly Asn Thr Ala Ser Leu Thr Ile Ser Gly Leu
 65                  70                  75                  80

Gln Ser Glu Asp Glu Ala Asp Tyr Tyr Cys Ala Ser Tyr Arg Ser Ser
                 85                  90                  95

Ala Asn Ala Val Phe Gly Gly Gly Thr His Leu Thr Val Leu Gly
            100                 105                 110

<210> SEQ ID NO 278
<211> LENGTH: 32
```

<212> TYPE: PRT
<213> ORGANISM: Artificial
<220> FEATURE:
<223> OTHER INFORMATION: Germlined Antibody Sequence

<400> SEQUENCE: 278

Arg Phe Thr Ile Ser Arg Asp Asn Ala Lys Asn Thr Leu Tyr Leu Gln
1               5                   10                  15

Met Asn Ser Leu Lys Pro Glu Asp Thr Ala Leu Tyr Tyr Cys Val Arg
            20                  25                  30

<210> SEQ ID NO 279
<211> LENGTH: 32
<212> TYPE: PRT
<213> ORGANISM: Artificial
<220> FEATURE:
<223> OTHER INFORMATION: Germlined Antibody Sequence

<400> SEQUENCE: 279

Arg Phe Thr Ile Ser Arg Asp Asn Ala Lys Asn Thr Leu Tyr Leu Gln
1               5                   10                  15

Met Asn Ser Leu Lys Pro Glu Asp Thr Ala Leu Tyr Tyr Cys Val Arg
            20                  25                  30

<210> SEQ ID NO 280
<211> LENGTH: 32
<212> TYPE: PRT
<213> ORGANISM: Artificial
<220> FEATURE:
<223> OTHER INFORMATION: Germlined Antibody Sequence

<400> SEQUENCE: 280

Arg Phe Thr Ile Ser Arg Asp Asn Ser Lys Asn Ser Leu Thr Leu Gln
1               5                   10                  15

Met Asn Ser Leu Lys Pro Glu Asp Thr Ala Val Tyr Tyr Cys Ala Arg
            20                  25                  30

<210> SEQ ID NO 281
<211> LENGTH: 32
<212> TYPE: PRT
<213> ORGANISM: Artificial
<220> FEATURE:
<223> OTHER INFORMATION: Germlined Antibody Sequence

<400> SEQUENCE: 281

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Val Arg
            20                  25                  30

<210> SEQ ID NO 282
<211> LENGTH: 32
<212> TYPE: PRT
<213> ORGANISM: Artificial
<220> FEATURE:
<223> OTHER INFORMATION: Germlined Antibody Sequence

<400> SEQUENCE: 282

Arg Phe Thr Ile Ser Arg Asp Asn Ala Lys Asn Ser Leu Thr Leu Gln
1               5                   10                  15

Met Asn Ser Leu Arg Ala Glu Asp Thr Ala Val Tyr Tyr Cys Val Arg
            20                  25                  30

<210> SEQ ID NO 283

<211> LENGTH: 32
<212> TYPE: PRT
<213> ORGANISM: Artificial
<220> FEATURE:
<223> OTHER INFORMATION: Germlined Antibody Sequence

<400> SEQUENCE: 283

Arg Phe Thr Ile Ser Arg Asp Asn Ala Lys Asn Thr Leu Tyr Leu Gln
1               5                   10                  15
Met Asn Ser Leu Arg Ala Glu Asp Thr Ala Val Tyr Tyr Cys Val Arg
            20                  25                  30

<210> SEQ ID NO 284
<211> LENGTH: 32
<212> TYPE: PRT
<213> ORGANISM: Artificial
<220> FEATURE:
<223> OTHER INFORMATION: Germlined Antibody Sequence

<400> SEQUENCE: 284

Arg Phe Thr Ile Ser Arg Asp Asn Ala Lys Asn Thr Leu Tyr Leu Gln
1               5                   10                  15
Met Asn Ser Leu Lys Pro Glu Asp Thr Ala Val Tyr Tyr Cys Ala Arg
            20                  25                  30

<210> SEQ ID NO 285
<211> LENGTH: 32
<212> TYPE: PRT
<213> ORGANISM: Artificial
<220> FEATURE:
<223> OTHER INFORMATION: Germlined Antibody Sequence

<400> SEQUENCE: 285

Arg Phe Thr Ile Ser Arg Asp Asn Ser Lys Asn Ser Leu Tyr Leu Gln
1               5                   10                  15
Met Asn Ser Leu Arg Ala Glu Asp Thr Ala Val Tyr Tyr Cys Ala Arg
            20                  25                  30

<210> SEQ ID NO 286
<211> LENGTH: 32
<212> TYPE: PRT
<213> ORGANISM: Artificial
<220> FEATURE:
<223> OTHER INFORMATION: Germlined Antibody Sequence

<400> SEQUENCE: 286

Arg Phe Thr Ile Ser Arg Asp Asn Ser Lys Asn Thr Leu Tyr Leu Gln
1               5                   10                  15
Met Asn Ser Leu Arg Ala Glu Asp Thr Ala Val Tyr Tyr Cys Ala Arg
            20                  25                  30

<210> SEQ ID NO 287
<211> LENGTH: 11
<212> TYPE: PRT
<213> ORGANISM: Artificial
<220> FEATURE:
<223> OTHER INFORMATION: Germlined Antibody Sequence

<400> SEQUENCE: 287

Trp Gly Gln Gly Thr Gln Val Ile Val Ser Ser
1               5                   10

<210> SEQ ID NO 288
<211> LENGTH: 11
<212> TYPE: PRT

<213> ORGANISM: Artificial
<220> FEATURE:
<223> OTHER INFORMATION: Germlined Antibody Sequence

<400> SEQUENCE: 288

Trp Gly Gln Gly Thr Gln Val Thr Val Ala Ser
1               5                   10

<210> SEQ ID NO 289
<211> LENGTH: 11
<212> TYPE: PRT
<213> ORGANISM: Artificial
<220> FEATURE:
<223> OTHER INFORMATION: Germlined Antibody Sequence

<400> SEQUENCE: 289

Trp Gly Gln Gly Thr Thr Val Thr Val Ser Ser
1               5                   10

<210> SEQ ID NO 290
<211> LENGTH: 11
<212> TYPE: PRT
<213> ORGANISM: Artificial
<220> FEATURE:
<223> OTHER INFORMATION: Germlined Antibody Sequence

<400> SEQUENCE: 290

Trp Gly Gln Gly Thr Thr Val Ile Val Ser Ser
1               5                   10

<210> SEQ ID NO 291
<211> LENGTH: 11
<212> TYPE: PRT
<213> ORGANISM: Artificial
<220> FEATURE:
<223> OTHER INFORMATION: Germlined Antibody Sequence

<400> SEQUENCE: 291

Trp Gly Gln Gly Thr Thr Val Thr Val Ala Ser
1               5                   10

<210> SEQ ID NO 292
<211> LENGTH: 11
<212> TYPE: PRT
<213> ORGANISM: Artificial
<220> FEATURE:
<223> OTHER INFORMATION: Germlined Antibody Sequence

<400> SEQUENCE: 292

Trp Gly Gln Gly Thr Gln Val Thr Val Ser Ser
1               5                   10

<210> SEQ ID NO 293
<211> LENGTH: 11
<212> TYPE: PRT
<213> ORGANISM: Artificial
<220> FEATURE:
<223> OTHER INFORMATION: Germlined Antibody Sequence

<400> SEQUENCE: 293

Trp Gly Gln Gly Thr Leu Val Thr Val Ser Ser
1               5                   10

<210> SEQ ID NO 294
<211> LENGTH: 22
<212> TYPE: PRT
<213> ORGANISM: Artificial

```
<220> FEATURE:
<223> OTHER INFORMATION: Germlined Antibody Sequence

<400> SEQUENCE: 294

Gln Thr Val Val Thr Gln Glu Pro Ser Phe Ser Val Ser Pro Gly Gly
1               5                   10                  15

Thr Val Thr Leu Thr Cys
            20

<210> SEQ ID NO 295
<211> LENGTH: 22
<212> TYPE: PRT
<213> ORGANISM: Artificial
<220> FEATURE:
<223> OTHER INFORMATION: Germlined Antibody Sequence

<400> SEQUENCE: 295

Gln Ala Val Val Thr Gln Glu Pro Ser Phe Ser Val Ser Pro Gly Gly
1               5                   10                  15

Thr Val Thr Leu Thr Cys
            20

<210> SEQ ID NO 296
<211> LENGTH: 22
<212> TYPE: PRT
<213> ORGANISM: Artificial
<220> FEATURE:
<223> OTHER INFORMATION: Germlined Antibody Sequence

<400> SEQUENCE: 296

Gln Thr Val Val Thr Gln Glu Pro Ser Leu Thr Val Ser Pro Gly Gly
1               5                   10                  15

Thr Val Thr Leu Thr Cys
            20

<210> SEQ ID NO 297
<211> LENGTH: 32
<212> TYPE: PRT
<213> ORGANISM: Artificial
<220> FEATURE:
<223> OTHER INFORMATION: Germlined Antibody Sequence

<400> SEQUENCE: 297

Gly Val Pro Asp Arg Phe Ser Gly Ser Ile Leu Gly Asn Lys Ala Ala
1               5                   10                  15

Leu Thr Ile Thr Gly Ala Gln Ala Asp Asp Glu Ser Asp Tyr Phe Cys
            20                  25                  30

<210> SEQ ID NO 298
<211> LENGTH: 32
<212> TYPE: PRT
<213> ORGANISM: Artificial
<220> FEATURE:
<223> OTHER INFORMATION: Germlined Antibody Sequence

<400> SEQUENCE: 298

Gly Val Pro Ser Arg Phe Ser Gly Ser Ile Leu Gly Asn Lys Ala Ala
1               5                   10                  15

Leu Thr Ile Thr Gly Ala Gln Ala Asp Asp Glu Ser Asp Tyr Phe Cys
            20                  25                  30

<210> SEQ ID NO 299
<211> LENGTH: 32
<212> TYPE: PRT
```

```
<213> ORGANISM: Artificial
<220> FEATURE:
<223> OTHER INFORMATION: Germlined Antibody Sequence

<400> SEQUENCE: 299

Gly Val Pro Asp Arg Phe Ser Gly Ser Ile Leu Gly Asn Lys Ala Ala
1               5                   10                  15

Leu Thr Ile Arg Gly Ala Gln Ala Asp Asp Glu Ala Glu Tyr Tyr Cys
            20                  25                  30

<210> SEQ ID NO 300
<211> LENGTH: 32
<212> TYPE: PRT
<213> ORGANISM: Artificial
<220> FEATURE:
<223> OTHER INFORMATION: Germlined Antibody Sequence

<400> SEQUENCE: 300

Gly Val Pro Asp Arg Phe Ser Gly Ser Ile Leu Gly Asn Lys Ala Ala
1               5                   10                  15

Leu Thr Ile Thr Gly Ala Gln Pro Glu Asp Glu Ser Asp Tyr Phe Cys
            20                  25                  30

<210> SEQ ID NO 301
<211> LENGTH: 32
<212> TYPE: PRT
<213> ORGANISM: Artificial
<220> FEATURE:
<223> OTHER INFORMATION: Germlined Antibody Sequence

<400> SEQUENCE: 301

Gly Val Pro Asp Arg Phe Ser Gly Ser Ile Leu Gly Asn Lys Ala Ala
1               5                   10                  15

Leu Thr Ile Thr Gly Ala Gln Pro Glu Asp Glu Ser Asp Tyr Tyr Cys
            20                  25                  30

<210> SEQ ID NO 302
<211> LENGTH: 32
<212> TYPE: PRT
<213> ORGANISM: Artificial
<220> FEATURE:
<223> OTHER INFORMATION: Germlined Antibody Sequence

<400> SEQUENCE: 302

Gly Val Pro Ser Arg Phe Ser Gly Ser Ile Leu Gly Asn Lys Ala Ala
1               5                   10                  15

Leu Thr Ile Thr Gly Ala Gln Ala Asp Asp Glu Ala Glu Tyr Phe Cys
            20                  25                  30

<210> SEQ ID NO 303
<211> LENGTH: 32
<212> TYPE: PRT
<213> ORGANISM: Artificial
<220> FEATURE:
<223> OTHER INFORMATION: Germlined Antibody Sequence

<400> SEQUENCE: 303

Gly Val Pro Asp Arg Phe Ser Gly Ser Ile Leu Gly Asn Lys Ala Ala
1               5                   10                  15

Leu Thr Ile Thr Gly Ala Gln Ala Asp Asp Glu Ala Glu Tyr Phe Cys
            20                  25                  30

<210> SEQ ID NO 304
<211> LENGTH: 32
```

```
<212> TYPE: PRT
<213> ORGANISM: Artificial
<220> FEATURE:
<223> OTHER INFORMATION: Germlined Antibody Sequence

<400> SEQUENCE: 304

Gly Val Pro Asp Arg Phe Ser Gly Ser Ile Leu Gly Asn Lys Ala Ala
1               5                   10                  15

Leu Thr Ile Thr Gly Ala Gln Ala Asp Asp Glu Ala Asp Tyr Phe Cys
            20                  25                  30

<210> SEQ ID NO 305
<211> LENGTH: 32
<212> TYPE: PRT
<213> ORGANISM: Artificial
<220> FEATURE:
<223> OTHER INFORMATION: Germlined Antibody Sequence

<400> SEQUENCE: 305

Gly Val Pro Ser Arg Phe Ser Gly Ser Ile Leu Gly Asn Lys Ala Ala
1               5                   10                  15

Leu Thr Ile Thr Gly Ala Gln Ala Asp Asp Glu Ser Asp Tyr Tyr Cys
            20                  25                  30

<210> SEQ ID NO 306
<211> LENGTH: 17
<212> TYPE: PRT
<213> ORGANISM: Artificial
<220> FEATURE:
<223> OTHER INFORMATION: Germlined Antibody Sequence
<220> FEATURE:
<221> NAME/KEY: MISC_FEATURE
<222> LOCATION: (1)..(1)
<223> OTHER INFORMATION: X is any amino acid, preferably D, T, S or E
<220> FEATURE:
<221> NAME/KEY: MISC_FEATURE
<222> LOCATION: (2)..(2)
<223> OTHER INFORMATION: X is any amino acid, preferably I
<220> FEATURE:
<221> NAME/KEY: MISC_FEATURE
<222> LOCATION: (3)..(3)
<223> OTHER INFORMATION: X is any amino acid, preferably N, S, T or Y
<220> FEATURE:
<221> NAME/KEY: MISC_FEATURE
<222> LOCATION: (4)..(4)
<223> OTHER INFORMATION: X is any amino acid, preferably N, M, S or T
<220> FEATURE:
<221> NAME/KEY: MISC_FEATURE
<222> LOCATION: (5)..(5)
<223> OTHER INFORMATION: X is any amino acid, preferably E, D, Y or H
<220> FEATURE:
<221> NAME/KEY: MISC_FEATURE
<222> LOCATION: (6)..(6)
<223> OTHER INFORMATION: X is any amino acid, preferably G, D, S or N
<220> FEATURE:
<221> NAME/KEY: MISC_FEATURE
<222> LOCATION: (7)..(7)
<223> OTHER INFORMATION: X is any amino acid, preferably G, Y, S, D or M
<220> FEATURE:
<221> NAME/KEY: MISC_FEATURE
<222> LOCATION: (8)..(8)
<223> OTHER INFORMATION: X is any amino acid, preferably T, E, S, N, Y
    or R
<220> FEATURE:
<221> NAME/KEY: MISC_FEATURE
<222> LOCATION: (9)..(9)
<223> OTHER INFORMATION: X is any amino acid, preferably T, A or R
<220> FEATURE:
<221> NAME/KEY: MISC_FEATURE
<222> LOCATION: (17)..(17)
<223> OTHER INFORMATION: X is any amino acid, preferably G or S

<400> SEQUENCE: 306
```

```
Xaa Xaa Xaa Xaa Xaa Xaa Xaa Xaa Xaa Tyr Tyr Ala Asp Ser Val Lys
1               5                   10                  15

Xaa

<210> SEQ ID NO 307
<211> LENGTH: 5
<212> TYPE: PRT
<213> ORGANISM: Artificial
<220> FEATURE:
<223> OTHER INFORMATION: Germlined Antibody Sequence
<220> FEATURE:
<221> NAME/KEY: MISC_FEATURE
<222> LOCATION: (1)..(1)
<223> OTHER INFORMATION: X is any amino acid, preferably V, G or A

<400> SEQUENCE: 307

Xaa Tyr Tyr Met Asn
1               5

<210> SEQ ID NO 308
<211> LENGTH: 5
<212> TYPE: PRT
<213> ORGANISM: Artificial
<220> FEATURE:
<223> OTHER INFORMATION: Germlined Antibody Sequence
<220> FEATURE:
<221> NAME/KEY: MISC_FEATURE
<222> LOCATION: (1)..(1)
<223> OTHER INFORMATION: X is any amino acid, preferably D, T, S, N or G
<220> FEATURE:
<221> NAME/KEY: MISC_FEATURE
<222> LOCATION: (2)..(2)
<223> OTHER INFORMATION: X is any amino acid, preferably Y, S or P

<400> SEQUENCE: 308

Xaa Xaa Ala Met Ser
1               5

<210> SEQ ID NO 309
<211> LENGTH: 11
<212> TYPE: PRT
<213> ORGANISM: Artificial
<220> FEATURE:
<223> OTHER INFORMATION: Germlined Antibody Sequence

<400> SEQUENCE: 309

Phe Gly Gly Gly Thr Gln Leu Thr Val Leu Gly
1               5                   10

<210> SEQ ID NO 310
<211> LENGTH: 7
<212> TYPE: PRT
<213> ORGANISM: Artificial
<220> FEATURE:
<223> OTHER INFORMATION: Germlined Antibody Sequence
<220> FEATURE:
<221> NAME/KEY: MISC_FEATURE
<222> LOCATION: (1)..(1)
<223> OTHER INFORMATION: X is any amino acid, preferably N or S
<220> FEATURE:
<221> NAME/KEY: MISC_FEATURE
<222> LOCATION: (3)..(3)
<223> OTHER INFORMATION: X is any amino acid, preferably N, S or A
<220> FEATURE:
<221> NAME/KEY: MISC_FEATURE
<222> LOCATION: (4)..(4)
<223> OTHER INFORMATION: X is any amino acid, preferably S, N or T

<400> SEQUENCE: 310
```

```
Xaa Thr Xaa Xaa Arg His Ser
1               5

<210> SEQ ID NO 311
<211> LENGTH: 11
<212> TYPE: PRT
<213> ORGANISM: Artificial
<220> FEATURE:
<223> OTHER INFORMATION: Germlined Antibody Sequence
<220> FEATURE:
<221> NAME/KEY: MISC_FEATURE
<222> LOCATION: (6)..(6)
<223> OTHER INFORMATION: X is any amino acid, preferably Y, V or L
<220> FEATURE:
<221> NAME/KEY: MISC_FEATURE
<222> LOCATION: (7)..(7)
<223> OTHER INFORMATION: X is any amino acid, preferably K or S
<220> FEATURE:
<221> NAME/KEY: MISC_FEATURE
<222> LOCATION: (8)..(8)
<223> OTHER INFORMATION: X is any amino acid, preferably H or N
<220> FEATURE:
<221> NAME/KEY: MISC_FEATURE
<222> LOCATION: (10)..(10)
<223> OTHER INFORMATION: X is any amino acid, preferably G or S

<400> SEQUENCE: 311

Tyr Tyr Ser Asp Ser Xaa Xaa Xaa Gln Xaa Ser
1               5                   10

<210> SEQ ID NO 312
<211> LENGTH: 7
<212> TYPE: PRT
<213> ORGANISM: Artificial
<220> FEATURE:
<223> OTHER INFORMATION: Germlined Antibody Sequence
<220> FEATURE:
<221> NAME/KEY: MISC_FEATURE
<222> LOCATION: (1)..(1)
<223> OTHER INFORMATION: X is any amino acid, preferably V, I or Y
<220> FEATURE:
<221> NAME/KEY: MISC_FEATURE
<222> LOCATION: (3)..(3)
<223> OTHER INFORMATION: X is any amino acid, preferably N or T

<400> SEQUENCE: 312

Xaa Asn Xaa Asn Arg Pro Ser
1               5

<210> SEQ ID NO 313
<211> LENGTH: 7
<212> TYPE: PRT
<213> ORGANISM: Artificial
<220> FEATURE:
<223> OTHER INFORMATION: Germlined Antibody Sequence
<220> FEATURE:
<221> NAME/KEY: MISC_FEATURE
<222> LOCATION: (4)..(4)
<223> OTHER INFORMATION: X is any amino acid, preferably Y
<220> FEATURE:
<221> NAME/KEY: MISC_FEATURE
<222> LOCATION: (5)..(5)
<223> OTHER INFORMATION: X is any amino acid, preferably R or M

<400> SEQUENCE: 313

Gly Asp Asn Xaa Xaa Pro Leu
1               5

<210> SEQ ID NO 314
<211> LENGTH: 7
<212> TYPE: PRT
<213> ORGANISM: Artificial
```

-continued

```
<220> FEATURE:
<223> OTHER INFORMATION: Germlined Antibody Sequence
<220> FEATURE:
<221> NAME/KEY: MISC_FEATURE
<222> LOCATION: (1)..(1)
<223> OTHER INFORMATION: X is any amino acid, preferably D or G
<220> FEATURE:
<221> NAME/KEY: MISC_FEATURE
<222> LOCATION: (4)..(4)
<223> OTHER INFORMATION: X is any amino acid, preferably S or I

<400> SEQUENCE: 314

Xaa Asp Asp Xaa Arg Pro Ser
1               5

<210> SEQ ID NO 315
<211> LENGTH: 14
<212> TYPE: PRT
<213> ORGANISM: Artificial
<220> FEATURE:
<223> OTHER INFORMATION: Germlined Antibody Sequence
<220> FEATURE:
<221> NAME/KEY: MISC_FEATURE
<222> LOCATION: (3)..(3)
<223> OTHER INFORMATION: X is any amino acid, preferably S or T
<220> FEATURE:
<221> NAME/KEY: MISC_FEATURE
<222> LOCATION: (7)..(7)
<223> OTHER INFORMATION: X is any amino acid, preferably V or A
<220> FEATURE:
<221> NAME/KEY: MISC_FEATURE
<222> LOCATION: (9)..(9)
<223> OTHER INFORMATION: X is any amino acid, preferably S or T
<220> FEATURE:
<221> NAME/KEY: MISC_FEATURE
<222> LOCATION: (10)..(10)
<223> OTHER INFORMATION: X is any amino acid, preferably S, T or G
<220> FEATURE:
<221> NAME/KEY: MISC_FEATURE
<222> LOCATION: (11)..(11)
<223> OTHER INFORMATION: X is any amino acid, preferably N or H
<220> FEATURE:
<221> NAME/KEY: MISC_FEATURE
<222> LOCATION: (14)..(14)
<223> OTHER INFORMATION: X is any amino acid, preferably G, D or E

<400> SEQUENCE: 315

Gly Leu Xaa Ser Gly Ser Xaa Thr Xaa Xaa Xaa Tyr Pro Xaa
1               5                   10

<210> SEQ ID NO 316
<211> LENGTH: 14
<212> TYPE: PRT
<213> ORGANISM: Artificial
<220> FEATURE:
<223> OTHER INFORMATION: Germlined Antibody Sequence
<220> FEATURE:
<221> NAME/KEY: MISC_FEATURE
<222> LOCATION: (3)..(3)
<223> OTHER INFORMATION: X is any amino acid, preferably S, N or I
<220> FEATURE:
<221> NAME/KEY: MISC_FEATURE
<222> LOCATION: (5)..(5)
<223> OTHER INFORMATION: X is any amino acid, preferably G or A
<220> FEATURE:
<221> NAME/KEY: MISC_FEATURE
<222> LOCATION: (6)..(6)
<223> OTHER INFORMATION: X is any amino acid, preferably N or D
<220> FEATURE:
<221> NAME/KEY: MISC_FEATURE
<222> LOCATION: (7)..(7)
<223> OTHER INFORMATION: X is any amino acid, preferably N or S
<220> FEATURE:
<221> NAME/KEY: MISC_FEATURE
<222> LOCATION: (8)..(8)
```

```
<223> OTHER INFORMATION: X is any amino acid, preferably V or I
<220> FEATURE:
<221> NAME/KEY: MISC_FEATURE
<222> LOCATION: (10)..(10)
<223> OTHER INFORMATION: X is any amino acid, preferably N or S

<400> SEQUENCE: 316

Thr Leu Xaa Ser Xaa Xaa Xaa Xaa Gly Xaa Tyr Asp Ile Ser
1               5                   10

<210> SEQ ID NO 317
<211> LENGTH: 11
<212> TYPE: PRT
<213> ORGANISM: Artificial
<220> FEATURE:
<223> OTHER INFORMATION: Germlined Antibody Sequence
<220> FEATURE:
<221> NAME/KEY: MISC_FEATURE
<222> LOCATION: (6)..(6)
<223> OTHER INFORMATION: X is any amino acid, preferably G or W

<400> SEQUENCE: 317

Gln Gly Gly Asn Leu Xaa Leu Tyr Gly Ala Asn
1               5                   10

<210> SEQ ID NO 318
<211> LENGTH: 11
<212> TYPE: PRT
<213> ORGANISM: Artificial
<220> FEATURE:
<223> OTHER INFORMATION: Germlined Antibody Sequence
<220> FEATURE:
<221> NAME/KEY: MISC_FEATURE
<222> LOCATION: (4)..(4)
<223> OTHER INFORMATION: X is any amino acid, preferably S or T
<220> FEATURE:
<221> NAME/KEY: MISC_FEATURE
<222> LOCATION: (6)..(6)
<223> OTHER INFORMATION: X is any amino acid, preferably E or R
<220> FEATURE:
<221> NAME/KEY: MISC_FEATURE
<222> LOCATION: (7)..(7)
<223> OTHER INFORMATION: X is any amino acid, preferably R or N
<220> FEATURE:
<221> NAME/KEY: MISC_FEATURE
<222> LOCATION: (9)..(9)
<223> OTHER INFORMATION: X is any amino acid, preferably G or H
<220> FEATURE:
<221> NAME/KEY: MISC_FEATURE
<222> LOCATION: (10)..(10)
<223> OTHER INFORMATION: X is any amino acid, preferably T or A

<400> SEQUENCE: 318

Arg Gly Asp Xaa Leu Xaa Xaa Tyr Xaa Xaa Asn
1               5                   10

<210> SEQ ID NO 319
<211> LENGTH: 14
<212> TYPE: PRT
<213> ORGANISM: Artificial
<220> FEATURE:
<223> OTHER INFORMATION: Germlined Antibody Sequence
<220> FEATURE:
<221> NAME/KEY: MISC_FEATURE
<222> LOCATION: (2)..(2)
<223> OTHER INFORMATION: X is any amino acid, preferably V or L
<220> FEATURE:
<221> NAME/KEY: MISC_FEATURE
<222> LOCATION: (3)..(3)
<223> OTHER INFORMATION: X is any amino acid, preferably K or T
<220> FEATURE:
<221> NAME/KEY: MISC_FEATURE
<222> LOCATION: (10)..(10)
```

<223> OTHER INFORMATION: X is any amino acid, preferably T or D

<400> SEQUENCE: 319

Gly Xaa Xaa Ser Gly Ser Val Thr Ser Xaa Asn Phe Pro Thr
1               5                   10

<210> SEQ ID NO 320
<211> LENGTH: 10
<212> TYPE: PRT
<213> ORGANISM: Homo sapiens

<400> SEQUENCE: 320

Glu Pro Lys Ser Cys Asp Lys Thr His Thr
1               5                   10

<210> SEQ ID NO 321
<211> LENGTH: 5
<212> TYPE: PRT
<213> ORGANISM: Homo sapiens

<400> SEQUENCE: 321

Cys Pro Pro Cys Pro
1               5

<210> SEQ ID NO 322
<211> LENGTH: 8
<212> TYPE: PRT
<213> ORGANISM: Homo sapiens

<400> SEQUENCE: 322

Ala Pro Glu Leu Leu Gly Gly Pro
1               5

<210> SEQ ID NO 323
<211> LENGTH: 12
<212> TYPE: PRT
<213> ORGANISM: Homo sapiens

<400> SEQUENCE: 323

Glu Leu Lys Thr Pro Leu Gly Asp Thr Thr His Thr
1               5                   10

<210> SEQ ID NO 324
<211> LENGTH: 50
<212> TYPE: PRT
<213> ORGANISM: Homo sapiens

<400> SEQUENCE: 324

Cys Pro Arg Cys Pro Glu Pro Lys Ser Cys Asp Thr Pro Pro Cys
1               5                   10                  15

Pro Arg Cys Pro Glu Pro Lys Ser Cys Asp Thr Pro Pro Cys Pro
                20                  25                  30

Arg Cys Pro Glu Pro Lys Ser Cys Asp Thr Pro Pro Cys Pro Arg
                35                  40                  45

Cys Pro
    50

<210> SEQ ID NO 325
<211> LENGTH: 8
<212> TYPE: PRT
<213> ORGANISM: Homo sapiens

<400> SEQUENCE: 325

Ala Pro Glu Leu Leu Gly Gly Pro
1               5

<210> SEQ ID NO 326
<211> LENGTH: 7
<212> TYPE: PRT
<213> ORGANISM: Homo sapiens

<400> SEQUENCE: 326

Glu Ser Lys Tyr Gly Pro Pro
1               5

<210> SEQ ID NO 327
<211> LENGTH: 5
<212> TYPE: PRT
<213> ORGANISM: Homo sapiens

<400> SEQUENCE: 327

Cys Pro Ser Cys Pro
1               5

<210> SEQ ID NO 328
<211> LENGTH: 8
<212> TYPE: PRT
<213> ORGANISM: Homo sapiens

<400> SEQUENCE: 328

Ala Pro Glu Phe Leu Gly Gly Pro
1               5

<210> SEQ ID NO 329
<211> LENGTH: 3
<212> TYPE: PRT
<213> ORGANISM: Homo sapiens

<400> SEQUENCE: 329

Glu Arg Lys
1

<210> SEQ ID NO 330
<211> LENGTH: 10
<212> TYPE: PRT
<213> ORGANISM: Homo sapiens

<400> SEQUENCE: 330

Cys Cys Val Glu Cys Pro Pro Cys Pro
1               5                   10

<210> SEQ ID NO 331
<211> LENGTH: 7
<212> TYPE: PRT
<213> ORGANISM: Homo sapiens

<400> SEQUENCE: 331

Ala Pro Pro Val Ala Gly Pro
1               5

<210> SEQ ID NO 332
<211> LENGTH: 142
<212> TYPE: PRT
<213> ORGANISM: Homo sapiens

<400> SEQUENCE: 332

Ser Leu Gly Trp Asp Val Ala Glu Leu Gln Leu Asn His Thr Gly Pro
1               5                   10                  15

```
Gln Gln Asp Pro Arg Leu Tyr Trp Gln Gly Gly Pro Ala Leu Gly Arg
            20                  25                  30

Ser Phe Leu His Gly Pro Glu Leu Asp Lys Gly Gln Leu Arg Ile His
         35                  40                  45

Arg Asp Gly Ile Tyr Met Val His Ile Gln Val Thr Leu Ala Ile Cys
 50                  55                  60

Ser Ser Thr Thr Ala Ser Arg His His Pro Thr Leu Ala Val Gly
 65                  70                  75                  80

Ile Cys Ser Pro Ala Ser Arg Ser Ile Ser Leu Leu Arg Leu Ser Phe
                 85                  90                  95

His Gln Gly Cys Thr Ile Ala Ser Gln Arg Leu Thr Pro Leu Ala Arg
            100                 105                 110

Gly Asp Thr Leu Cys Thr Asn Leu Thr Gly Thr Leu Leu Pro Ser Arg
            115                 120                 125

Asn Thr Asp Glu Thr Phe Phe Gly Val Gln Trp Val Arg Pro
            130                 135                 140

<210> SEQ ID NO 333
<211> LENGTH: 142
<212> TYPE: PRT
<213> ORGANISM: Artificial
<220> FEATURE:
<223> OTHER INFORMATION: Chimeric Sequence

<400> SEQUENCE: 333

His Pro Glu Pro His Thr Ala Glu Leu Gln Leu Asn Leu Thr Val Pro
 1               5                  10                  15

Arg Lys Asp Pro Thr Leu Arg Trp Gly Ala Gly Pro Ala Leu Gly Arg
            20                  25                  30

Ser Phe Leu His Gly Pro Glu Leu Asp Lys Gly Gln Leu Arg Ile His
         35                  40                  45

Arg Asp Gly Ile Tyr Met Val His Ile Gln Val Thr Leu Ala Ile Cys
 50                  55                  60

Ser Ser Thr Thr Ala Ser Arg His His Pro Thr Leu Ala Val Gly
 65                  70                  75                  80

Ile Cys Ser Pro Ala Ser Arg Ser Ile Ser Leu Leu Arg Leu Ser Phe
                 85                  90                  95

His Gln Gly Cys Thr Ile Ala Ser Gln Arg Leu Thr Pro Leu Ala Arg
            100                 105                 110

Gly Asp Thr Leu Cys Thr Asn Leu Thr Gly Thr Leu Leu Pro Ser Arg
            115                 120                 125

Asn Thr Asp Glu Thr Phe Phe Gly Val Gln Trp Val Arg Pro
            130                 135                 140

<210> SEQ ID NO 334
<211> LENGTH: 142
<212> TYPE: PRT
<213> ORGANISM: Artificial
<220> FEATURE:
<223> OTHER INFORMATION: Chimeric sequence

<400> SEQUENCE: 334

His Pro Glu Pro His Thr Ala Glu Leu Gln Leu Asn Leu Thr Val Pro
 1               5                  10                  15

Arg Lys Asp Pro Thr Leu Arg Trp Gly Ala Gly Pro Ala Leu Gly Arg
            20                  25                  30

Ser Phe Thr His Gly Pro Glu Leu Asp Lys Gly Gln Leu Arg Ile His
```

```
                35                  40                  45
Arg Asp Gly Ile Tyr Met Val His Ile Gln Val Thr Leu Ala Ile Cys
 50                  55                  60

Ser Ser Thr Thr Ala Ser Arg His His Pro Thr Leu Ala Val Gly
 65                  70                  75                  80

Ile Cys Ser Pro Ala Ser Arg Ser Ile Ser Leu Leu Arg Leu Ser Phe
                85                  90                  95

His Gln Gly Cys Thr Ile Ala Ser Gln Arg Leu Thr Pro Leu Ala Arg
                100                 105                 110

Gly Asp Thr Leu Cys Thr Asn Leu Thr Gly Thr Leu Leu Pro Ser Arg
                115                 120                 125

Asn Thr Asp Glu Thr Phe Phe Gly Val Gln Trp Val Arg Pro
130                 135                 140

<210> SEQ ID NO 335
<211> LENGTH: 142
<212> TYPE: PRT
<213> ORGANISM: Artificial
<220> FEATURE:
<223> OTHER INFORMATION: Chimeric sequence

<400> SEQUENCE: 335

His Pro Glu Pro His Thr Ala Glu Leu Gln Leu Asn Leu Thr Val Pro
  1               5                  10                  15

Arg Lys Asp Pro Thr Leu Arg Trp Gly Ala Gly Pro Ala Leu Gly Arg
                20                  25                  30

Ser Phe Thr His Gly Pro Glu Leu Glu Glu Gly His Leu Arg Ile His
                35                  40                  45

Arg Asp Gly Ile Tyr Met Val His Ile Gln Val Thr Leu Ala Ile Cys
 50                  55                  60

Ser Ser Thr Thr Ala Ser Arg His His Pro Thr Leu Ala Val Gly
 65                  70                  75                  80

Ile Cys Ser Pro Ala Ser Arg Ser Ile Ser Leu Leu Arg Leu Ser Phe
                85                  90                  95

His Gln Gly Cys Thr Ile Ala Ser Gln Arg Leu Thr Pro Leu Ala Arg
                100                 105                 110

Gly Asp Thr Leu Cys Thr Asn Leu Thr Gly Thr Leu Leu Pro Ser Arg
                115                 120                 125

Asn Thr Asp Glu Thr Phe Phe Gly Val Gln Trp Val Arg Pro
130                 135                 140

<210> SEQ ID NO 336
<211> LENGTH: 142
<212> TYPE: PRT
<213> ORGANISM: Artificial
<220> FEATURE:
<223> OTHER INFORMATION: Chimeric sequence

<400> SEQUENCE: 336

His Pro Glu Pro His Thr Ala Glu Leu Gln Leu Asn Leu Thr Val Pro
  1               5                  10                  15

Arg Lys Asp Pro Thr Leu Arg Trp Gly Ala Gly Pro Ala Leu Gly Arg
                20                  25                  30

Ser Phe Thr His Gly Pro Glu Leu Glu Glu Gly His Leu Arg Ile His
                35                  40                  45

Gln Asp Gly Leu Tyr Arg Leu His Ile Gln Val Thr Leu Ala Ile Cys
 50                  55                  60
```

Ser Ser Thr Thr Ala Ser Arg His His Pro Thr Leu Ala Val Gly
65                  70                  75                  80

Ile Cys Ser Pro Ala Ser Arg Ser Ile Ser Leu Leu Arg Leu Ser Phe
                85                  90                  95

His Gln Gly Cys Thr Ile Ala Ser Gln Arg Leu Thr Pro Leu Ala Arg
            100                 105                 110

Gly Asp Thr Leu Cys Thr Asn Leu Thr Gly Thr Leu Leu Pro Ser Arg
            115                 120                 125

Asn Thr Asp Glu Thr Phe Phe Gly Val Gln Trp Val Arg Pro
130                 135                 140

<210> SEQ ID NO 337
<211> LENGTH: 142
<212> TYPE: PRT
<213> ORGANISM: Artificial
<220> FEATURE:
<223> OTHER INFORMATION: Chimeric sequence

<400> SEQUENCE: 337

His Pro Glu Pro His Thr Ala Glu Leu Gln Leu Asn Leu Thr Val Pro
1               5                   10                  15

Arg Lys Asp Pro Thr Leu Arg Trp Gly Ala Gly Pro Ala Leu Gly Arg
                20                  25                  30

Ser Phe Thr His Gly Pro Glu Leu Glu Glu Gly His Leu Arg Ile His
            35                  40                  45

Gln Asp Gly Leu Tyr Arg Leu His Ile Gln Val Thr Leu Ala Ile Cys
50                  55                  60

Ser Ser Thr Thr Ala Ser Arg His His Pro Thr Leu Ala Val Gly
65                  70                  75                  80

Ile Cys Ser Pro Ala Ser Arg Ser Ile Ser Leu Leu Arg Leu Ser Phe
                85                  90                  95

His Gln Gly Cys Thr Ile Ala Ser Gln Arg Leu Thr Pro Leu Ala Arg
            100                 105                 110

Gly Asp Thr Leu Cys Thr Asn Leu Thr Gly Thr Leu Leu Pro Ser Arg
            115                 120                 125

Asn Thr Asp Glu Thr Phe Phe Gly Val Gln Trp Val Arg Pro
130                 135                 140

<210> SEQ ID NO 338
<211> LENGTH: 142
<212> TYPE: PRT
<213> ORGANISM: Artificial
<220> FEATURE:
<223> OTHER INFORMATION: Chimeric sequence

<400> SEQUENCE: 338

His Pro Glu Pro His Thr Ala Glu Leu Gln Leu Asn Leu Thr Val Pro
1               5                   10                  15

Arg Lys Asp Pro Thr Leu Arg Trp Gly Ala Gly Pro Ala Leu Gly Arg
                20                  25                  30

Ser Phe Thr His Gly Pro Glu Leu Glu Glu Gly His Leu Arg Ile His
            35                  40                  45

Gln Asp Gly Leu Tyr Arg Leu His Ile Gln Val Thr Leu Ala Asn Cys
50                  55                  60

Ser Ser Thr Thr Ala Ser Arg His His Pro Thr Leu Ala Val Gly
65                  70                  75                  80

Ile Cys Ser Pro Ala Ser Arg Ser Ile Ser Leu Leu Arg Leu Ser Phe
                85                  90                  95

His Gln Gly Cys Thr Ile Ala Ser Gln Arg Leu Thr Pro Leu Ala Arg
            100                 105                 110

Gly Asp Thr Leu Cys Thr Asn Leu Thr Gly Thr Leu Leu Pro Ser Arg
            115                 120                 125

Asn Thr Asp Glu Thr Phe Phe Gly Val Gln Trp Val Arg Pro
            130                 135                 140

<210> SEQ ID NO 339
<211> LENGTH: 142
<212> TYPE: PRT
<213> ORGANISM: Artificial
<220> FEATURE:
<223> OTHER INFORMATION: Chimeric sequence

<400> SEQUENCE: 339

His Pro Glu Pro His Thr Ala Glu Leu Gln Leu Asn Leu Thr Val Pro
1               5                   10                  15

Arg Lys Asp Pro Thr Leu Arg Trp Gly Ala Gly Pro Ala Leu Gly Arg
            20                  25                  30

Ser Phe Thr His Gly Pro Glu Leu Glu Glu Gly His Leu Arg Ile His
            35                  40                  45

Gln Asp Gly Leu Tyr Arg Leu His Ile Gln Val Thr Leu Ala Asn Cys
    50                  55                  60

Ser Ser Pro Gly Ser Thr Leu Gln His Arg Ala Thr Leu Ala Val Gly
65                  70                  75                  80

Ile Cys Ser Pro Ala Ser Arg Ser Ile Ser Leu Leu Arg Leu Ser Phe
                85                  90                  95

His Gln Gly Cys Thr Ile Ala Ser Gln Arg Leu Thr Pro Leu Ala Arg
            100                 105                 110

Gly Asp Thr Leu Cys Thr Asn Leu Thr Gly Thr Leu Leu Pro Ser Arg
            115                 120                 125

Asn Thr Asp Glu Thr Phe Phe Gly Val Gln Trp Val Arg Pro
            130                 135                 140

<210> SEQ ID NO 340
<211> LENGTH: 142
<212> TYPE: PRT
<213> ORGANISM: Artificial
<220> FEATURE:
<223> OTHER INFORMATION: Chimeric sequence

<400> SEQUENCE: 340

His Pro Glu Pro His Thr Ala Glu Leu Gln Leu Asn Leu Thr Val Pro
1               5                   10                  15

Arg Lys Asp Pro Thr Leu Arg Trp Gly Ala Gly Pro Ala Leu Gly Arg
            20                  25                  30

Ser Phe Thr His Gly Pro Glu Leu Glu Glu Gly His Leu Arg Ile His
            35                  40                  45

Gln Asp Gly Leu Tyr Arg Leu His Ile Gln Val Thr Leu Ala Asn Cys
    50                  55                  60

Ser Ser Pro Gly Ser Thr Leu Gln His Arg Ala Thr Leu Ala Val Gly
65                  70                  75                  80

Ile Cys Ser Pro Ala Ala His Gly Ile Ser Leu Leu Arg Gly Arg Phe
                85                  90                  95

Gly Gln Asp Cys Thr Val Ala Leu Gln Arg Leu Thr Tyr Leu Val His
            100                 105                 110

Gly Asp Val Leu Cys Thr Asn Leu Thr Gly Thr Leu Leu Pro Ser Arg

```
                115                 120                 125
Asn Thr Asp Glu Thr Phe Phe Gly Val Gln Trp Val Arg Pro
    130                 135                 140

<210> SEQ ID NO 341
<211> LENGTH: 142
<212> TYPE: PRT
<213> ORGANISM: Mus musculus

<400> SEQUENCE: 341

His Pro Glu Pro His Thr Ala Glu Leu Gln Leu Asn Leu Thr Val Pro
1               5                   10                  15

Arg Lys Asp Pro Thr Leu Arg Trp Gly Ala Gly Pro Ala Leu Gly Arg
            20                  25                  30

Ser Phe Thr His Gly Pro Glu Leu Glu Glu Gly His Leu Arg Ile His
        35                  40                  45

Gln Asp Gly Leu Tyr Arg Leu His Ile Gln Val Thr Leu Ala Asn Cys
    50                  55                  60

Ser Ser Pro Gly Ser Thr Leu Gln His Arg Ala Thr Leu Ala Val Gly
65                  70                  75                  80

Ile Cys Ser Pro Ala Ala His Gly Ile Ser Leu Leu Arg Gly Arg Phe
                85                  90                  95

Gly Gln Asp Cys Thr Val Ala Leu Gln Arg Leu Thr Tyr Leu Val His
            100                 105                 110

Gly Asp Val Leu Cys Thr Asn Leu Thr Leu Pro Leu Pro Ser Arg
        115                 120                 125

Asn Ala Asp Glu Thr Phe Phe Gly Val Gln Trp Ile Cys Pro
    130                 135                 140

<210> SEQ ID NO 342
<211> LENGTH: 11
<212> TYPE: PRT
<213> ORGANISM: Artificial
<220> FEATURE:
<223> OTHER INFORMATION: CD70 Epitope

<400> SEQUENCE: 342

His Ile Gln Val Thr Leu Ala Ile Cys Ser Ser
1               5                   10

<210> SEQ ID NO 343
<211> LENGTH: 32
<212> TYPE: PRT
<213> ORGANISM: Llama glama

<400> SEQUENCE: 343

Arg Phe Thr Ile Ser Thr Asp Asn Ala Lys Asn Thr Leu Tyr Leu Gln
1               5                   10                  15

Met Asn Ser Leu Lys Pro Asp Asp Thr Ala Val Tyr Tyr Cys Ala Ala
            20                  25                  30

<210> SEQ ID NO 344
<211> LENGTH: 1425
<212> TYPE: DNA
<213> ORGANISM: Artificial
<220> FEATURE:
<223> OTHER INFORMATION: Germlined Nucleotide Sequence

<400> SEQUENCE: 344
gccgccacca tgggctggtc ctgcatcatc ctgtttctgg tggccaccgc cacaggcgtc    60
```

| | |
|---|---|
| cactctgagg tgcagctcgt ggagtctggg ggaggcttgg tgcagcctgg ggggtctctg | 120 |
| agactctcct gtgcagcctc tggattcacc ttcagtgtct actacatgaa ctgggtccgc | 180 |
| caggctccag ggaaggggct cgagtgggtc tcagatatta ataatgaagg tggtactaca | 240 |
| tactatgcag actccgtgaa gggccgattc accatctcca gagacaactc aaagaacagc | 300 |
| ctgtatctgc aaatgaacag cctgcgcgcc gaggacacgg ccgtgtacta ctgcgcgaga | 360 |
| gatgccggat atagcaacca tgtacccatc tttgattctt ggggccaggg gaccctggtc | 420 |
| actgtctcct cagccagtac aaaaggtcca agtgtgttcc ctcttgctcc ctcatccaag | 480 |
| agtaccagtg gaggcaccgc cgctcttggc tgcttggtta aggattattt cccagagcct | 540 |
| gtcactgttt catggaactc cggcgccttg acatctggtg tgcataccct tccagccgtg | 600 |
| ctgcagtcaa gtggcctcta cagcctcagt agcgtggtca ctgtgcccag cagctctctc | 660 |
| ggcacacaaa cttatatctg taatgtgaat cataagcctt caaataccaa ggtggataag | 720 |
| aaagtggaac caaatcatg tgacaagaca cacacctgcc ctccttgtcc agcccccgaa | 780 |
| ctgctgggtg ggcccagcgt gttcctgttt cctcctaaac ccaaagacac tctgatgatt | 840 |
| agtaggaccc cagaagtcac ttgcgtggtg gttgacgtgt cacatgaaga tcccgaggtc | 900 |
| aagttcaatt ggtatgttga cggggtcgaa gttcacaacg ctaaaactaa ccaagagag | 960 |
| gaacagtata actctaccta ccgggtggtg agtgttctga ctgtcctcca tcaagactgg | 1020 |
| ctgaatggca agaatacaa gtgtaaggtg agcaacaaag ccctgcccgc tcctatagag | 1080 |
| aaaacaatat ccaaagccaa aggtcaacct cgcgagccac aggtgtacac cctcccacca | 1140 |
| agccgcgatg aacttactaa gaaccaagtc tctcttactt gcctggttaa ggggttctat | 1200 |
| ccatccgaca ttgcagtcga gtgggagtct aatggacagc tgagaacaa ctacaaaacc | 1260 |
| accccctcctg ttctggattc tgacggatct ttcttccttt attctaaact caccgtggat | 1320 |
| aaaagcaggt ggcagcaggg caacgtgttc agctgttccg ttatgcatga ggccctgcat | 1380 |
| aaccattata cccagaagtc tttgtccctc agtccaggaa agtga | 1425 |

<210> SEQ ID NO 345
<211> LENGTH: 717
<212> TYPE: DNA
<213> ORGANISM: Artificial
<220> FEATURE:
<223> OTHER INFORMATION: Germlined Nucleotide Sequence

<400> SEQUENCE: 345

| | |
|---|---|
| gccgccacca tgggctggtc ctgcatcatc ctgtttctgg tggccaccgc cacaggcgtc | 60 |
| cactctcagg cagtggtgac ccaggagcct tccctgacag tgtctccagg agggacggtc | 120 |
| acgctcacct gcgcctcaa atctgggtct gtcacttccg ataacttccc cacttggtac | 180 |
| cagcagacac caggccaggc tccccgattg cttatctaca acacaaacac ccgtcactct | 240 |
| ggcgtccccg accgcttctc cggatccatc ctgggcaaca agccgccct caccatcacg | 300 |
| ggggcccagg ccgacgacga ggccgaatat ttctgtgctc tgttcataag taatcctagt | 360 |
| gttgagttcg gcggagggac ccaactgacc gtcctaggtc aacctaaagc agcaccttca | 420 |
| gttactctgt ttccacctag ttcagaggaa ctgcaggcca ataaagccac actcgtctgc | 480 |
| ctcatcagtg acttctaccc aggagccgtg accgtggcct ggaaagccga cagtagcccc | 540 |
| gtgaaggccg gggtggagac aacaactcct agtaaacaga gtaataacaa atatgccgct | 600 |
| agtagttatc tctcccctcac tcccgagcag tggaagtctc acagaagtta ctcttgtcag | 660 |
| gttactcacg agggttccac agtggaaaag actgtggccc ctactgaatg tagttga | 717 |

<210> SEQ ID NO 346
<211> LENGTH: 369
<212> TYPE: DNA
<213> ORGANISM: Artificial
<220> FEATURE:
<223> OTHER INFORMATION: Germlined Nucleotide Sequence

<400> SEQUENCE: 346

```
cagttgcagc tggtggagtc tgggggaggc ttggtgcagc ctgggggtc tctgagactc      60
tcttgtgcag cctctggatt cagcttcagt cactatgcca tgagctgggt ccgccaggct     120
ccaggaaagg ggctagagtg ggtctcaggt gataatacct acgatggtgg tacaaggtat     180
caagactccg tgaagggccg attcaccatc tccagagaca atggcaagaa cacgctgtat     240
ctgcaaatga acagcctgaa acctgaggac acggccgtgt attactgtgc aaaagatact     300
ggtagaggca ttatggggga gtacggcatg gactactggg gcaagggac cctggtcacc     360
gtctcctca                                                             369
```

<210> SEQ ID NO 347
<211> LENGTH: 341
<212> TYPE: DNA
<213> ORGANISM: Artificial
<220> FEATURE:
<223> OTHER INFORMATION: Germlined Nucleotide Sequence

<400> SEQUENCE: 347

```
cagactgtgg tgacccagga gccgtccctg tcagtgtctc caggagggac ggtcacactc      60
acctgcggcc tcaagtctgg gtctgtcact tccagtaact accctgcttg gtaccagcag     120
acaccaggcc aggctccccg attgcttatc tacaacacaa acagccgtca ctctggggtc     180
cccagtcgct tctccggatc catctctggg aacaaagccg ccctcaccat cacggggggcc    240
cagcccgagg acgaggccga ctattactgt gctctgtaca tgggtagtgg tagtgccaat     300
gctatgttcg gcggagggac ccatctgacc gtcctgggtc a                          341
```

<210> SEQ ID NO 348
<211> LENGTH: 372
<212> TYPE: DNA
<213> ORGANISM: Artificial
<220> FEATURE:
<223> OTHER INFORMATION: Germlined Nucleotide Sequence

<400> SEQUENCE: 348

```
gaggtgcagc tggtggagtc tgggggaggc ttggtgcagc ctgggggtc tctgagactc      60
tcctgtgcag cgtccgaatt gtccttcagt atttctgaga tgacctgggt ccgccaggct     120
ccaggaaagg ggctcgagtg ggtctcaggt attagtggtg taactggtgg tagtagtaca     180
agttatgcag actccgtgaa ggccgattc accatctcca gagacaacga caagaacacg     240
ttgtatctac aaatgaacag cctgataccc gaggacacgg ccgtatatta ctgtgcaaca     300
actagtggta cttactactt catccccgag tatgagtact ggggccaggg gacccaggtc     360
accgtctcct ca                                                          372
```

<210> SEQ ID NO 349
<211> LENGTH: 333
<212> TYPE: DNA
<213> ORGANISM: Artificial
<220> FEATURE:
<223> OTHER INFORMATION: Germlined Nucleotide Sequence

```
<400> SEQUENCE: 349
cagtctgtgc tgacccagcc tccctccgtg tctgggtctc caggaaagac ggtcaccatc      60
tcctgtgcag gaaccagcag tgatgttggg tatggatact atgtctcctg gtatcaacag     120
ttcccaggaa tggcccccaa actcctgata tatgacgtca ataaacgggc ctcagggatc     180
gctgatcgct tctctggctc caaggccggc aacactgcct ccctgaccat ctctgggctc     240
cagtctgagg acgaggctga ttattactgt gcctcatata gaagtagcgc caatgctgtg     300
ttcggcggag ggaccatct gaccgtcctg ggt                                    333

<210> SEQ ID NO 350
<211> LENGTH: 32
<212> TYPE: PRT
<213> ORGANISM: Artificial
<220> FEATURE:
<223> OTHER INFORMATION: Germlined Antibody Sequence

<400> SEQUENCE: 350

Arg Phe Thr Ile Ser Arg Asp Asn Ser Lys Asn Thr Leu Thr Leu Gln
1               5                   10                  15

Met Asn Ser Leu Lys Pro Glu Asp Thr Ala Val Tyr Tyr Cys Val Arg
            20                  25                  30

<210> SEQ ID NO 351
<211> LENGTH: 32
<212> TYPE: PRT
<213> ORGANISM: Artificial
<220> FEATURE:
<223> OTHER INFORMATION: Germlined Antibody Sequence

<400> SEQUENCE: 351

Arg Phe Thr Ile Ser Arg Asp Asn Ala Lys Asn Thr Leu Thr Leu Gln
1               5                   10                  15

Met Asn Ser Leu Lys Pro Glu Asp Thr Ala Val Tyr Tyr Cys Val Arg
            20                  25                  30
```